(12) United States Patent
Baldwin et al.

(10) Patent No.: US 8,658,635 B2
(45) Date of Patent: *Feb. 25, 2014

(54) BENZPYRAZOL DERIVATIVES AS INHIBITORS OF PI3 KINASES

(75) Inventors: Ian Robert Baldwin, Stevenage (GB); Kenneth David Down, Stevenage (GB); Paul Faulder, Stevenage (GB); Simon Gaines, Stevenage (GB); Julie Nicole Hamblin, Stevenage (GB); Joelle Le, Stevenage (GB); Christopher James Lunniss, Stevenage (GB); Nigel James Parr, Stevenage (GB); Timothy John Ritchie, Stevenage (GB); John Edward Robinson, Stevenage (GB); Juliet Kay Simpson, Stevenage (GB); Christian Alan Paul Smethurst, Harlow (GB)

(73) Assignee: GlaxoSmithKline Intellectual Property Development Limited, Brentford, Middlesex (GB)

(*) Notice: Subject to any disclaimer, the term of this patent is extended or adjusted under 35 U.S.C. 154(b) by 106 days.

This patent is subject to a terminal disclaimer.

(21) Appl. No.: 12/994,250

(22) PCT Filed: Jun. 3, 2009

(86) PCT No.: PCT/EP2009/056839
§ 371 (c)(1),
(2), (4) Date: Jan. 14, 2011

(87) PCT Pub. No.: WO2009/147188
PCT Pub. Date: Dec. 10, 2009

(65) Prior Publication Data
US 2011/0178063 A1    Jul. 21, 2011

Related U.S. Application Data

(60) Provisional application No. 61/158,425, filed on Mar. 9, 2009, provisional application No. 61/058,979, filed on Jun. 5, 2008.

(51) Int. Cl.
| | |
|---|---|
| A61K 31/55 | (2006.01) |
| A61K 31/5377 | (2006.01) |
| A61K 31/501 | (2006.01) |
| A61K 31/496 | (2006.01) |
| A61K 31/497 | (2006.01) |
| A61K 31/50 | (2006.01) |
| A61K 31/505 | (2006.01) |
| A61K 31/4523 | (2006.01) |
| A61K 31/4427 | (2006.01) |
| A61K 31/427 | (2006.01) |
| A61K 31/425 | (2006.01) |
| C07D 267/02 | (2006.01) |
| C07D 279/12 | (2006.01) |
| C07D 295/00 | (2006.01) |
| C07D 265/30 | (2006.01) |
| C07D 413/14 | (2006.01) |
| C07D 487/12 | (2006.01) |
| C07D 417/12 | (2006.01) |
| C07D 211/00 | (2006.01) |
| C07D 277/20 | (2006.01) |
| C07D 235/00 | (2006.01) |
| C07D 233/54 | (2006.01) |
| C07D 403/14 | (2006.01) |

(52) U.S. Cl.
USPC .............. 514/211.15; 514/228.2; 514/230.5; 514/234.5; 514/249; 514/254.02; 514/265.1; 514/322; 514/338; 514/365; 514/369; 540/544; 544/58.2; 544/71; 544/140; 544/280; 544/349; 544/369; 546/199; 546/269.7; 548/200; 548/304.4; 548/311.4; 548/364.7

(58) Field of Classification Search
USPC ........... 514/211.15, 228.2, 230.5, 234.5, 249, 514/254.02, 265.1, 322, 338, 365, 369; 540/544; 544/58.2, 71, 140, 280, 349, 544/369; 546/199, 269.7; 548/200, 304.4, 548/311.4, 364.7
See application file for complete search history.

(56) References Cited

U.S. PATENT DOCUMENTS 8,076,326 B2   12/2011  Haupt et al.
8,114,868 B2    2/2012  Himmelsbach
(Continued)

FOREIGN PATENT DOCUMENTS

EP    1679308 A    7/2006
WO    02067683 A1  9/2002
(Continued)

OTHER PUBLICATIONS

Centers for Disease Control and Prevention. Public Health Strategic Framework for COPD Prevention. Atlanta, GA: Centers for Disease Control and Prevention; 2011, URL: www.cdc.gov/copd.*

(Continued)

*Primary Examiner* — Samantha Shterengarts
(74) *Attorney, Agent, or Firm* — Robert J Smith

(57) ABSTRACT

The invention is directed to certain novel compounds of formula (I) and salts thereof. The compounds of the invention are inhibitors of PI3-kinase activity.

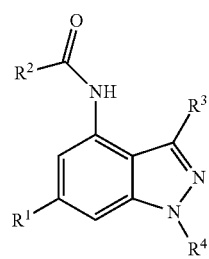

(I)

11 Claims, No Drawings

(56) References Cited

U.S. PATENT DOCUMENTS

| | | |
|---|---|---|
| 8,138,178 B2 | 3/2012 | Claremon et al. |
| 8,163,743 B2 | 4/2012 | Baldwin et al. |
| 8,242,111 B2 | 8/2012 | Claremon et al. |
| 2004/0009968 A1 | 1/2004 | Binch et al. |
| 2005/0090529 A1 | 4/2005 | McAlpine et al. |
| 2005/0288286 A1 | 12/2005 | Flynn et al. |
| 2006/0135540 A1 | 6/2006 | Lin et al. |
| 2006/0264433 A1 | 11/2006 | Backes et al. |
| 2007/0037820 A1 | 2/2007 | Edwards et al. |
| 2008/0032960 A1 | 2/2008 | Knight |
| 2008/0200523 A1 | 8/2008 | Murthi et al. |
| 2009/0203690 A1 | 8/2009 | Akritopoulou-Zanze et al. |
| 2010/0216792 A1 | 8/2010 | Gorgens et al. |
| 2010/0256363 A1 | 10/2010 | Xu |
| 2010/0280014 A1 | 11/2010 | Haupt et al. |
| 2010/0280029 A1 | 11/2010 | Hamblin et al. |
| 2010/0280045 A1 | 11/2010 | Hamblin et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0021512 A1 | 1/2011 | Claremon et al. |
| 2011/0067448 A1 | 3/2011 | Matsumoto et al. |
| 2011/0124635 A1 | 5/2011 | Claremon et al. |
| 2011/0183973 A1 | 7/2011 | Baldwin et al. |
| 2011/0263583 A1 | 10/2011 | Claremon et al. |
| 2011/0263584 A1 | 10/2011 | Claremon et al. |
| 2012/0040969 A1 | 2/2012 | Haupt et al. |
| 2012/0108579 A1 | 5/2012 | Renz et al. |
| 2012/0129854 A1 | 5/2012 | Mihara et al. |
| 2012/0178746 A1 | 7/2012 | Claremon et al. |
| 2012/0184549 A1 | 7/2012 | Himmelsbach |
| 2012/0238559 A1 | 9/2012 | Baldwin et al. |
| 2012/0238571 A1 | 9/2012 | Baldwin et al. |
| 2012/0245171 A1 | 9/2012 | Baldwin et al. |

FOREIGN PATENT DOCUMENTS

| | | |
|---|---|---|
| WO | 02083111 A2 | 10/2002 |
| WO | 03000257 A1 | 1/2003 |
| WO | 03051847 A1 | 6/2003 |
| WO | 03064397 A | 8/2003 |
| WO | 2004002480 A1 | 1/2004 |
| WO | 2004014370 A2 | 2/2004 |
| WO | 2004014881 A2 | 2/2004 |
| WO | 2004014902 A2 | 2/2004 |
| WO | WO 2005/016245 A | 2/2005 |
| WO | 2005075482 A1 | 8/2005 |
| WO | 2005077345 A1 | 8/2005 |
| WO | 2005077368 A2 | 8/2005 |
| WO | 2005077373 A2 | 8/2005 |
| WO | 2005082889 A1 | 9/2005 |
| WO | 2006012226 A2 | 2/2006 |
| WO | 2006014290 A2 | 2/2006 |
| WO | 2006055752 A2 | 5/2006 |
| WO | 2006060535 A2 | 6/2006 |
| WO | 2006089076 A2 | 8/2006 |
| WO | 2007017759 A2 | 2/2007 |
| WO | 2007021573 A1 | 2/2007 |
| WO | 2007022371 A2 | 2/2007 |
| WO | 2007105637 A1 | 9/2007 |
| WO | 2007/126841 A2 | 11/2007 |
| WO | 2007132171 A | 11/2007 |
| WO | 2008016123 A1 | 2/2008 |
| WO | 2008020229 A2 | 2/2008 |
| WO | 2008024945 A | 2/2008 |
| WO | 2008038136 A1 | 4/2008 |
| WO | WO 2008/037477 A | 4/2008 |
| WO | 2008057938 A1 | 5/2008 |
| WO | 2008090382 A1 | 7/2008 |
| WO | WO 2009/000832 A | 12/2008 |
| WO | 2009/017664 A1 | 2/2009 |
| WO | 2009/134400 A1 | 11/2009 |
| WO | 2009147187 A1 | 12/2009 |
| WO | 2009147188 A1 | 12/2009 |
| WO | 2009147189 A1 | 12/2009 |
| WO | 2009147190 A1 | 12/2009 |
| WO | 2010/011314 A1 | 1/2010 |
| WO | 2010/043315 A1 | 4/2010 |
| WO | 2010068287 A2 | 6/2010 |
| WO | 2010/125134 A1 | 11/2010 |
| WO | 2010/127237 A2 | 11/2010 |
| WO | 2010125082 A1 | 11/2010 |
| WO | 2012032065 A1 | 3/2012 |
| WO | 2012032067 A1 | 3/2012 |
| WO | 2012055846 A1 | 5/2012 |

OTHER PUBLICATIONS

U.S. Appl. No. 12/768,775, filed Apr. 28, 2010.
U.S. Appl. No. 12/768,777, filed Apr. 28, 2010.
U.S. Appl. No. 13/254,034, filed Aug. 31, 2011.
U.S. Appl. No. 13/266,254, filed Oct. 26, 2011.
Ameriks, et al., "Small Molecule Inhibitors of Phosphoinositide 3-Kinase (PI3K) delta and gamma" Current Topics in Medicinal Chemistry; 2009; vol. 9(8); pp. 738-753.
Folkes, et al., "The Identification of 2-(1H-indazol-4-y1)-6-(4-methanesulfonyl-piperazin-1-ylmethyl) -4-morpholin-4-yl-thieno [3,2-d] pyrimidine (GDC-0941) as a potent, selective, orally bioavailable inhibitor of class I PI3 kinase for the treatment of cancer" Journal of Medicinal Chemistry; 2008; vol. 51(18); pp. 5522-5532.
Verheijen, et al., "Phosphatidylinositol 3-kinase (PI3K) inhibitors as anticancer drugs" Drugs of the Future; Jun. 1, 2007; Prous Science; vol. 32(6); pp. 537-547.
Finan, et al., "PI3-kinase inhibition: a therapeutic target for respiratory disease"; Biochemical Society Transactions; 2004; vol. 32, part 2; pp. 378-382.
Horig, et al., "From bench to clinic and back: Perspective on the 1st IQPC Translational Research Conference"; Journal of Translational Medicine; 2004; vol. 2(44); pp. 1-8.
Schafer, et al., "Failure is an option: learning from unsuccessful proof-of-concept trials" Drug Discovery Today; 2008; vol. 13 (21/22); pp. 913-916.

* cited by examiner

BENZPYRAZOL DERIVATIVES AS INHIBITORS OF PI3 KINASES

This application is a 371 of International Application No. PCT/EP2009/056839, filed 03 Jun. 2009, which claims the benefit of U.S. Provisional Application Nos. 61/158,425, filed 09 Mar. 2009, and 61/058,979, filed 05 Jun. 2008, which are incorporated herein in their entireties.

FIELD OF THE INVENTION

The present invention is directed to certain novel compounds which are inhibitors of the activity or function of the phosphoinositide 3'OH kinase family (hereinafter PI3-kinases), processes for their preparation, pharmaceutical compositions comprising the compounds, and the use of the compounds or the compositions in the treatment of various disorders. More specifically, the compounds of the invention are inhibitors of the activity or function of, for example, PI3Kδ, PI3Kα, PI3Kβ and/or PI3Kγ. Compounds which are inhibitors of the activity or function of PI3-kinases may be useful in the treatment of disorders such as respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

BACKGROUND OF THE INVENTION

Cellular membranes represent a large store of second messengers that can be enlisted in a variety of signal transduction pathways. In relation to function and regulation of effector enzymes in phospholipids signaling pathways, class I PI3-kinases (e.g. PI3 Kdelta) generate second messengers from the membrane phospholipid pools. Class I PI3Ks convert the membrane phospholipid $PI(4,5)P_2$ into $PI(3,4,5)P_3$, which functions as a second messenger. PI and PI(4)P are also substrates of PI3K and can be phosphorylated and converted into PI3P and $PI(3,4)P_2$, respectively. In addition, these phosphoinositides can be converted into other phosphoinositides by 5'-specific and 3'-specific phosphatases. Thus, PI3K enzymatic activity results either directly or indirectly in the generation of two 3'-phosphoinositide subtypes which function as second messengers in intracellular signal transduction pathways (Trends Biochem. Sci. 22(7) p. 267-72 (1997) by Vanhaesebroeck et al.; Chem. Rev. 101(8) p. 2365-80 (2001) by Leslie et al.; Annu. Rev. Cell Dev. Biol. 17 p. 615-75 (2001) by Katso et al.; and Cell. Mol. Life Sci. 59(5) p. 761-79 (2002) by Toker). To date, eight mammalian PI3Ks have been identified, divided into three main classes (I, II, and III) on the basis of sequence homology, structure, binding partners, mode of activation, and substrate preference. In vitro, class I PI3Ks can phosphorylate phosphatidylinositol (PI), phosphatidylinositol-4-phosphate (PI4P), and phosphatidylinositol-4,5-bisphosphate $(PI(4,5)P_2)$ to produce phosphatidylinositol-3-phosphate (PI3P), phosphatidylinositol-3,4-bisphosphate $(PI(3,4)P_2$, and phosphatidylinositol-3,4,5-trisphosphate $(PI(3,4,5)P_3$, respectively. Class II PI3Ks can phosphorylate PI and PI4P. Class III PI3Ks can only phosphorylate PI (Vanhaesebroeck et al. (1997), above; Vanhaesebroeck et al., Exp. Cell Res. 253(1) p. 239-54 (1999); and Leslie et al. (2001), above).

Class I PI3K is a heterodimer consisting of a p110 catalytic subunit and a regulatory subunit, and the family is further divided into class Ia and class Ib enzymes on the basis of regulatory partners and mechanism of regulation. Class Ia enzymes consist of three distinct catalytic subunits (p110α, p110β, and p110δ) that dimerise with five distinct regulatory subunits (p85α, p55α, p50α, p85β, and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Small GTPases (ras as an example) are also involved in the activation of PI3K in conjunction with receptor tyrosine kinase activation. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor (GPCR) systems and its expression appears to be limited to leukocytes.

Scheme A: Conversion of PI(4,5)P$_2$ to PI(3,4,5)P$_3$

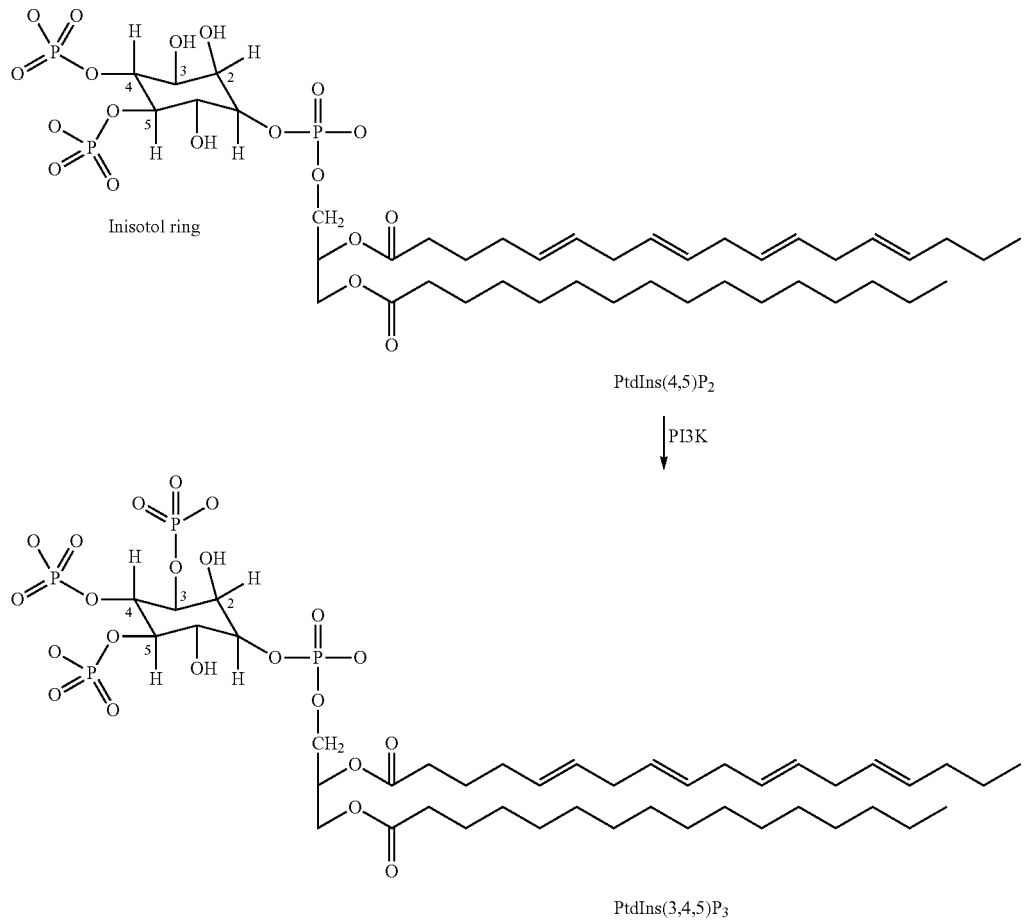

As illustrated in Scheme A above, phosphoinositide 3-kinases (PI3Ks) phosphorylate the hydroxyl of the third carbon of the inositol ring. The phosphorylation of phosphoinositides to generate PtdIns(3,4,5)P$_3$, PtdIns(3,4)P$_2$ and PtdIns(3) P, produces second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Katso et al. (2001), above; and Mol. Med. Today 6(9) p. 347-57 (2000) by Stein et al.).

The activity of PI3-kinases responsible for generating these phosphorylated signalling products was originally identified as being associated with viral oncoproteins and growth factor receptor tyrosine kinases that phosphorylate phosphatidylinositol (PI) and its phosphorylated derivatives at the 3'-hydroxyl of the inositol ring (Panayotou et al. Trends Cell Biol. 2 p. 358-60 (1992)). However, more recent biochemical studies have revealed that class I PI3-kinases (e.g. class IA isoform PI3Kδ) are dual-specific kinase enzymes, meaning they display both lipid kinase (phosphorylation of phosphoinositides) as well as protein kinase activity, and are capable of phosphorylation of other protein as substrates, including auto-phosphorylation as an intramolecular regulatory mechanism (EMBO J. 18(5) p. 1292-302 (1999) by Vanhaesebroeck et al.). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3-kinase activation is believed to be involved in a wide range of cellular responses including cell growth, differentiation, and apoptosis (Parker, Current Biology, 5(6) p. 577-79 (1995); and Yao et al. Science 267(5206) p. 2003-06 (1995)). PI3-kinase appears to be involved in a number of aspects of leukocyte activation. A p85-associated PI3-kinase has been shown to physically associate with the cytoplasmic domain of CD28, which is an important costimulatory molecule for the activation of T-cells in response to antigen (Pagès et al. Nature 369 p. 327-29 (1994); and Rudd, Immunity 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al. Science 251(4991) p. 313-16 (1991)).

PI3Kγ has been identified as a mediator of G beta-gamma-dependent regulation of JNK activity, and G beta-gamma are subunits of heterotrimeric G proteins (Lopez-Ilasaca et al. J. Biol. Chem. 273(5) p. 2505-8 (1998)). Recently, (Laffargue et al. Immunity 16(3) p. 441-51 (2002)) it has been described that PI3Kγ relays inflammatory signals through various G(i)-coupled receptors and is central to mast cell function, stimuli in the context of leukocytes, and immunology including cytokines, chemokines, adenosines, antibodies, integrins, aggregation factors, growth factors, viruses or hormones for example (J. Cell Sci. 114 (Pt 16) p. 2903-10 (2001) by Lawlor et al.; Laffargue et al. (2002), above; and Curr. Opinion Cell Biol. 14(2) p. 203-13 (2002) by Stephens et al.).

Specific inhibitors against individual members of a family of enzymes provide invaluable tools for deciphering functions of each enzyme. Two compounds, LY294002 and wortmannin (hereinafter), have been widely used as PI3-kinase inhibitors. These compounds are non-specific PI3K inhibitors, as they do not distinguish among the four members of Class I PI3-kinases. For example, the $IC_{50}$ values of wortmannin against each of the various Class I PI3-kinases are in the range of 1-10 nM. Similarly, the $IC_{50}$ values for LY294002 against each of these PI3-kinases is about 15-20 µM (Fruman et al. Ann. Rev. Biochem. 67 p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates subsequent cellular response to the extracellular factor. For example, neutrophils respond to the chemokine fMet-Leu-Phe (fMLP) by stimulating PI3K and synthesizing PtdIns (3, 4, 5)$P_3$. This synthesis correlates with activation of the respiratory burst involved in neutrophil destruction of invading microorganisms. Treatment of neutrophils with wortmannin prevents the fMLP-induced respiratory burst response (Thelen et al. Proc. Natl. Acad. Sci. USA 91 p. 4960-64 (1994)). Indeed, these experiments with wortmannin, as well as other experimental evidence, show that PI3K activity in cells of hematopoietic lineage, particularly neutrophils, monocytes, and other types of leukocytes, is involved in many of the non-memory immune response associated with acute and chronic inflammation.

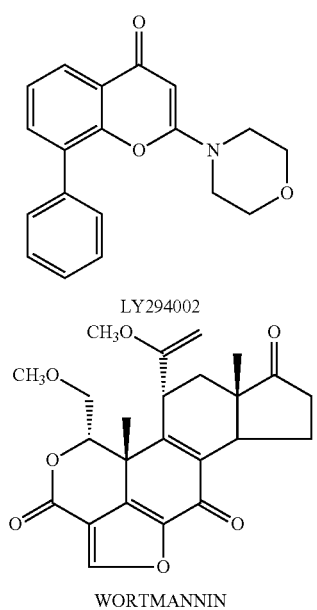

Based on studies using wortmannin, there is evidence that PI3-kinase function is also required for some aspects of leukocyte signaling through G-protein coupled receptors (Thelen et al. (1994), above). Moreover, it has been shown that wortmannin and LY294002 block neutrophil migration and superoxide release.

It is now well understood that deregulation of oncogenes and tumour suppressor genes contributes to the formation of malignant tumours, for example by way of increased cell growth and proliferation or increased cell survival. It is also now known that signaling pathways mediated by the PI3K family have a central role in a number of cell processes including proliferation and survival, and deregulation of these pathways is a causative factor a wide spectrum of human cancers and other diseases (Katso et al. Annual Rev. Cell Dev. Biol. (2001) 17 p. 615-675 and Foster et al. J. Cell Science (2003) 116(15) p. 3037-3040). PI3K effector proteins initiate signalling pathways and networks by translocating to the plasma membrane through a conserved Pleckstrin Homology (PH) domain, which specifically interacts with PtdIns(3,4,5)P3 (Vanhaesebroeck et al. Annu. Rev. Biochem. (2001) 70 p. 535-602). The effector proteins signalling through PtdIns(3,4,5)P3 and PH domains include Serine/Threonine (Ser/Thr) kinases, Tyrosine kinases, Rac or Arf GEFs (Guanine nucleotide exchange factors) and Arf GAPs (GTPase activating proteins).

In B and T cells PI3Ks have an important role through activation of the Tec family of protein tyrosine kinases which include Bruton's tyrosine kinase (BTK) in B cells and Interleukin-2-inducible T-cell kinase (ITK) in T cells. Upon PI3K activation, BTK or ITK translocate to the plasma membrane where they are subsequently phosphorylated by Src kinases. One of the major targets of activated ITK is phospholipase C-gamma (PLCγ1), which hydrolyses PtdIns(4,5)P2 into Ins (3,4,5)P3 and initiates an intracellular increase in calcium levels and diacylglycerol (DAG) which can activate Protein Kinases C in activated T cells.

Unlike the Class IA p110α and p110β, p110δ is expressed in a tissue restricted fashion. Its high expression level in lymphocytes and lymphoid tissues suggests a role in PI3K-mediated signalling in the immune system. The p110δ kinase dead knock-in mice are also viable and their phenotype is restricted to defects in immune signalling (Okkenhaug et al. Science (2002) 297 p. 1031-4). These transgenic mice have offered insight into the function of PI3Kδ in B-cell and T-cell signalling. In particular, p110δ is required for PtdIns(3,4,5) P3 formation downstream of CD28 and/or T cell Receptor (TCR) signalling. A key effect of PI3K signalling downstream of TCR is the activation of Akt, which phosphorylates anti-apoptotic factors as well as various transcription factors for cytokine production. As a consequence, T cells with inactive p110δ have defects in proliferation and Th1 and Th2 cytokine secretion. Activation of T cells through CD28 lowers the threshold for TCR activation by antigen and increases the magnitude and duration of the proliferative response. These effects are mediated by the PI3Kδ-dependent increase in the transcription of a number of genes including IL2, an important T cell growth factor.

Therefore, PI3K inhibitors are anticipated to provide therapeutic benefit via its role in modulating T-cell mediated inflammatory responses associated to respiratory diseases such as asthma, COPD and cystic fibrosis. In addition, there is indication that T-cell directed therapies may provide corticosteroid sparing properties (Alexander et al. Lancet (1992) 339 p. 324-8) suggesting that it may provide a useful therapy either as a standalone or in combination with inhaled or oral glucocorticosteroids in respiratory diseases. A PI3K inhibitor might also be used alongside other conventional therapies such as a long acting beta-agonist (LABA) in asthma.

In the vasculature, PI3Kδ is expressed by endothelial cells and participates in neutrophil trafficking by modulating the proadhesive state of these cells in response to TNFalpha (Puri et al. Blood (2004) 103(9) p. 3448-56). A role for PI3Kδ in TNFalpha-induced signalling of endothelial cells is demonstrated by the pharmacological inhibition of Akt phosphorylation and PDK1 activity. In addition, PI3Kδ is implicated in vascular permeability and airway tissue edema through the VEGF pathway (Lee et al. J. Allergy Clin. Immunol. (2006) 118(2) p. 403-9). These observations suggest additional benefits of PI3Kδ inhibition in asthma by the combined reduction of leukocyte extravasation and vascular permeability associated with asthma. In addition, PI3Kδ activity is required for mast cell function both in vitro and in vivo (Ali et al. Nature (2004) 431 p. 1007-11; and Ali et al. J. Immunol. (2008) 180(4) p. 2538-44) further suggesting that PI3K inhibition should be of therapeutic benefit for allergic indications such asthma, allergic rhinitis and atopic dermatitis.

The role of PI3Kδ in B cell proliferation, antibody secretion, B-cell antigen and IL-4 receptor signalling, B-cell antigen presenting function is also well established Okkenhaug et al. (2002), above; Al-Alwan et al. J. Immunol. (2007) 178(4) p. 2328-35; and Bilancio et al. Blood (2006) 107(2) p. 642-50) and indicates a role in autoimmune diseases such as rheumatoid arthritis or systemic lupus erythematosus. Therefore PI3K inhibitors may also be of benefit for these indications.

Pharmacological inhibition of PI3Kδ inhibits fMLP-dependent neutrophil chemotaxis on an ICAM coated agarose matrix integrin-dependent biased system (Sadhu et al. J. Immunol. (2003) 170(5) p. 2647-54). Inhibition of PI3Kδ regulates neutrophil activation, adhesion and migration without affecting neutrophil mediated phagocytosis and bactericidal activity over *Staphylococcus aureus* (Sadhu et al. Biochem. Biophys. Res. Commun. (2003) 308(4) p. 764-9). Overall, the data suggest that PI3Kδ inhibition should not globally inhibit neutrophil functions required for innate immune defence. PI3Kδ's role in neutrophils offers further scope for treating inflammatory diseases involving tissue remodeling such as COPD or rheumatoid arthritis.

In addition, there is also good evidence that class Ia PI3K enzymes also contribute to tumourigenesis in a wide variety of human cancers, either directly or indirectly (Vivanco and Sawyers, Nature Reviews Cancer (2002) 2(7) p. 489-501). For example, inhibition of PI3Kδ may have a therapeutic role for the treatment of malignant haematological disorders such as acute myeloid leukaemia (Billottet et al. Oncogene (2006) 25(50) p. 6648-59). Moreover, activating mutations within p110α (PIK3CA gene) have been associated with various other tumors such as those of the colon and of the breast and lung (Samuels et al. Science (2004) 304(5670) p. 554).

It has also been shown that PI3K is involved in the establishment of central sensitization in painful inflammatory conditions (Pezet et al. The J. of Neuroscience (2008) 28 (16) p. 4261-4270).

Attempts have been made to prepare compounds which inhibit PI3-kinase activity and a number of such compounds have been disclosed in the art. However, in view of the number of pathological responses which are mediated by PI3-kinases, there remains a continuing need for inhibitors of PI3-kinase which can be used in the treatment of a variety of conditions.

The present inventors have discovered novel compounds which are inhibitors of PI3-kinase activity. Compounds which are PI3-kinase inhibitors may be useful in the treatment of disorders associated with inappropriate PI3-kinase activity, for example in the treatment and prevention of disorders mediated by PI3-kinase mechanisms. Such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

In one embodiment, compounds of the invention may show selectivity for PI3-kinases over other kinases. For example, the compounds of the invention may show selectivity for PI3-kinases over DNA-dependent protein kinase (DNA-PK).

In one embodiment, compounds of the invention may show selectivity for PI3Kδ over other PI3-kinases. For example, the compounds of the invention may show selectivity for PI3Kδ over PI3Kα and/or PI3Kβ.

SUMMARY OF THE INVENTION

The invention is directed to certain novel compounds. Specifically, the invention is directed to compounds of formula (I)

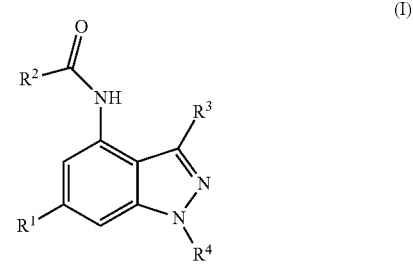

(I)

wherein $R^1$, $R^2$, $R^3$ and $R^4$ are as defined below, and salts thereof.

The compounds are inhibitors of PI3-kinase activity. Compounds which are PI3-kinase inhibitors may be useful in the treatment of disorders associated with inappropriate PI3-kinase activity, such as asthma and chronic obstructive pulmonary disease (COPD). Accordingly, the invention is further directed to pharmaceutical compositions comprising a compound of formula (I) or a pharmaceutically acceptable salt thereof. The invention is still further directed to methods of inhibiting PI3-kinase activity and treatment of disorders associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation for the compounds of the invention.

DETAILED DESCRIPTION OF THE INVENTION

In one embodiment, the invention is directed to compounds of formula (I)

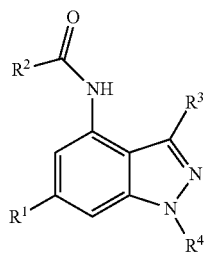

(I)

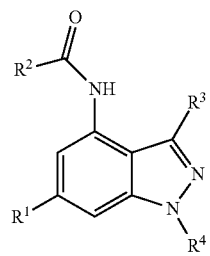

(IA)

wherein

R¹ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN, —OR¹³ or —NHSO₂R¹⁴; or phenyl fused to a 5-membered heterocyclyl wherein the 5-membered heterocyclyl contains one or two heteroatoms independently selected from oxygen and nitrogen and is substituted by oxo;

R² is 5-membered heteroaryl wherein the 5-membered heteroaryl contains from one to three heteroatoms independently selected from oxygen, nitrogen and sulphur and is optionally substituted by from one to three substituents independently selected from $C_{1-6}$alkyl optionally substituted by from one to three fluorine atoms; $C_{2-6}$alkenyl; $C_{3-6}$cycloalkyl; —OR⁵; halo; —COR⁶; —CO₂R⁷; —CONR⁸R⁹; —(CH₂)ₘNR¹⁰R¹¹; —CH(CH₃)NHCOphenyl; —NHCO₂R¹²; —(CH₂)ₙphenyl; and 5-membered heteroaryl wherein the second 5-membered heteroaryl contains one or two heteroatoms independently selected from oxygen, nitrogen and sulphur and is optionally substituted by $C_{1-6}$alkyl;

R³ is hydrogen or fluoro;

R⁴ is hydrogen or methyl;

R⁵, R⁷, R¹² and R¹³ are each independently hydrogen or $C_{1-6}$alkyl;

R⁶, R¹⁸ and R¹⁹ are each independently $C_{1-6}$alkyl;

R⁸ and R⁹ are each independently hydrogen or $C_{1-6}$alkyl, or R⁸ and R⁹, together with the nitrogen atom to which they are attached, are linked to form a 5- or 6-membered heterocyclyl optionally containing an oxygen atom;

R¹⁰ and R¹¹ are each independently hydrogen or $C_{1-6}$alkyl, or R¹⁰ and R¹¹, together with the nitrogen atom to which they are attached, are linked to form a 5-, 6- or 7-membered heterocyclyl or a 10-membered bicyclic heterocyclyl wherein the 5-, 6- or 7-membered heterocyclyl or the 10-membered bicyclic heterocyclyl optionally contains an oxygen atom, a sulphur atom or a further nitrogen atom and is optionally substituted by one or two substituents independently selected from $C_{1-6}$alkyl; $C_{3-6}$cycloalkyl; halo; oxo; phenyl optionally substituted by halo; pyridinyl; —(CH₂)ₚOR¹⁵; —(CH₂)_gNR¹⁶R¹⁷; —COR¹⁸; and —SO₂R¹⁹;

R¹⁴ is $C_{1-6}$alkyl or phenyl;

R¹⁵ is hydrogen, $C_{1-6}$alkyl or —(CH₂)ᵣphenyl;

R¹⁶ and R¹⁷, together with the nitrogen atom to which they are attached, are linked to form a 5- or 6-membered heterocyclyl optionally containing an oxygen atom; and m, n, p, q, r are each independently 0, 1 or 2;

and salts thereof (hereinafter "compounds of the invention").

In a further embodiment, the invention is directed to compounds of formula (IA)

wherein

R¹ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo or —CN, or phenyl fused to a 5-membered heterocyclyl wherein the heterocyclyl contains one or two heteroatoms independently selected from oxygen and nitrogen and is substituted by oxo;

R² is 5-membered heteroaryl wherein the 5-membered heteroaryl contains from one to three heteroatoms independently selected from oxygen, nitrogen and sulphur and is optionally substituted by from one to three substituents independently selected from $C_{1-6}$alkyl optionally substituted by from one to three fluorine atoms, $C_{2-6}$alkenyl, $C_{3-6}$cycloalkyl, —OR⁵, halo, —COR⁶, —CO₂R⁷, —CONR⁸R⁹, —(CH₂)ₘNR¹⁰R¹¹, —CH(CH₃)NHCOphenyl, —NHCO₂R¹², —(CH₂)ₙphenyl and 5-membered heteroaryl wherein the second 5-membered heteroaryl contains one or two heteroatoms independently selected from oxygen, nitrogen and sulphur and is optionally substituted by $C_{1-6}$alkyl;

R³ is hydrogen or fluoro;

R⁴ is hydrogen or methyl;

R⁵, R⁷ and R¹² are each independently hydrogen or $C_{1-6}$alkyl;

R⁶ is $C_{1-6}$alkyl;

R⁸ and R⁹ are each independently hydrogen or $C_{1-6}$alkyl, or R⁸ and R⁹, together with the nitrogen atom to which they are attached, are linked to form a 5- or 6-membered heterocyclyl optionally containing an oxygen atom;

R¹⁰ and R¹¹ are each independently hydrogen or $C_{1-6}$alkyl, or R¹⁰ and R¹¹, together with the nitrogen atom to which they are attached, are linked to form a 5- or 6-membered heterocyclyl optionally containing an oxygen atom; and m and n are each independently 0, 1 or 2;

and salts thereof.

In one embodiment, R¹ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo or —CN, or phenyl fused to a 5-membered heterocyclyl wherein the heterocyclyl contains one or two heteroatoms independently selected from oxygen and nitrogen and is substituted by oxo. In another embodiment, R¹ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo or —CN. In another embodiment, R¹ is 9-membered bicyclic heteroaryl wherein the 9-membered bicyclic heteroaryl contains one or two nitrogen atoms and is optionally substituted by $C_{1-6}$alkyl or halo. In another embodiment, R¹ is indolyl optionally substituted by fluoro. In another embodiment, R¹ is 9- or 10-membered bicyclic heteroaryl wherein the 9- or 10-membered bicyclic heteroaryl contains from one to three heteroatoms independently selected from oxygen and nitrogen and is optionally substituted by —NHSO$_2$R$^{14}$. In a further embodiment, R$^1$ is indolyl optionally substituted by —NHSO$_2$R$^{14}$.

In one embodiment, R$^2$ is 5-membered heteroaryl wherein the 5-membered heteroaryl contains from one to three heteroatoms independently selected from oxygen, nitrogen and sulphur and is optionally substituted by from one to three substituents independently selected from C$_{1-6}$alkyl and —(CH$_2$)$_m$NR$^{10}$R$^{11}$. In another embodiment, R$^2$ is 5-membered heteroaryl wherein the 5-membered heteroaryl contains two heteroatoms independently selected from nitrogen and sulphur and is optionally substituted by one or two substituents independently selected from C$_{1-6}$alkyl and —(CH$_2$)$_m$NR$^{10}$R$^{11}$. In a further embodiment, R$^2$ is thiazolyl optionally substituted by one or two substituents independently selected from C$_{1-6}$alkyl, for example C$_{1-4}$alkyl such as methyl or isopropyl, and —(CH$_2$)$_m$NR$^{10}$R$^{11}$.

In one embodiment, R$^3$ is hydrogen. In a further embodiment, R$^3$ is fluoro.

In one embodiment, R$^4$ is hydrogen. In a further embodiment, R$^4$ is methyl.

In one embodiment, R$^5$ is C$_{1-4}$alkyl such as methyl.
In one embodiment, R$^6$ is C$_{1-4}$alkyl such as methyl.
In one embodiment, R$^7$ is C$_{1-4}$alkyl such as t-butyl.
In one embodiment, R$^8$ and R$^9$, together with the nitrogen atom to which they are attached, are linked to form a 6-membered heterocyclyl optionally containing an oxygen atom. In a further embodiment, R$^8$ and R$^9$, together with the nitrogen atom to which they are attached, are linked to form morpholinyl.

In one embodiment, R$^{10}$ and R$^{11}$ are each independently hydrogen or C$_{1-6}$alkyl, or R$^{10}$ and R$^{11}$, together with the nitrogen atom to which they are attached, are linked to form a 5- or 6-membered heterocyclyl optionally containing an oxygen atom. In another embodiment, R$^{10}$ and R$^{11}$ are each independently hydrogen or C$_{1-6}$alkyl. In another embodiment, R$^{10}$ and R$^{11}$, together with the nitrogen atom to which they are attached, are linked to form a 5- or 6-membered heterocyclyl optionally containing an oxygen atom. In another embodiment, R$^{10}$ and R$^{11}$, together with the nitrogen atom to which they are attached, are linked to form pyrrolidinyl, piperidinyl or morpholinyl. In a further embodiment, R$^{10}$ and R$^{11}$, together with the nitrogen atom to which they are attached, are linked to form a 6-membered heterocyclyl wherein the 6-membered heterocyclyl optionally contains an oxygen atom or a further nitrogen atom and is optionally substituted by one or two substituents independently selected from C$_{1-6}$alkyl.

In one embodiment, R$^{12}$ is C$_{1-4}$alkyl such as t-butyl.
In one embodiment, R$^{13}$ is C$_{1-4}$alkyl such as methyl.
In one embodiment, R$^{14}$ is C$_{1-4}$alkyl such as methyl. In a further embodiment, R$^{14}$ is phenyl.

In one embodiment, R$^{15}$ is —(CH$_2$)$_q$phenyl;
In one embodiment, R$^{16}$ and R$^{17}$, together with the nitrogen atom to which they are attached, are linked to form a pyrrolidinyl. In one embodiment, R$^{16}$ and R$^{17}$, together with the nitrogen atom to which they are attached, are linked to form a morpholinyl.

In one embodiment, m is 0. In a further embodiment, m is 1.

In one embodiment, n is 0. In a further embodiment, n is 1.
In one embodiment, p is 0.
In one embodiment, q is 1. In a further embodiment, q is 2.
In one embodiment, r is 1.

It is to be understood that the present invention covers all combinations of substituent groups described hereinabove.

Compounds of the invention include the compounds of Examples 1 to 177 and salts thereof.

In one embodiment, the compound of the invention is:
N-[6-(1H-indol-4-yl)-1H-indazol-4-yl]-5-methyl-1H-pyrazole-3-carboxamide;
N-[6-(1H-indol-4-yl)-1H-indazol-4-yl]-1-methyl-1H-imidazole-2-carboxamide;
N-[6-(1H-indol-4-yl)-1H-indazol-4-yl]-1-methyl-1H-pyrrole-2-carboxamide;
N-[6-(1H-indol-4-yl)-1H-indazol-4-yl]-1-methyl-1H-imidazole-4-carboxamide;
N-[6-(1H-indol-4-yl)-1H-indazol-4-yl]-1-methyl-1H-pyrazole-5-carboxamide;
N-[6-(1H-indol-4-yl)-1H-indazol-4-yl]-1,5-dimethyl-1H-pyrazole-3-carboxamide;
N-[6-(1H-indol-4-yl)-1H-indazol-4-yl]-2-(phenylmethyl)-1,3-thiazole-4-carboxamide;
1-ethyl-N-[6-(1H-indol-4-yl)-1H-indazol-4-yl]-1H-pyrazole-3-carboxamide;
N-[6-(1H-indol-4-yl)-1H-indazol-4-yl]-2-methyl-3-furancarboxamide;
N-[6-(1H-indol-4-yl)-1H-indazol-4-yl]-5-methyl-2-furancarboxamide;
N-[6-(1H-indol-4-yl)-1H-indazol-4-yl]-1-methyl-1H-pyrazole-3-carboxamide;
N-[6-(1H-indol-4-yl)-1H-indazol-4-yl]-3-furancarboxamide;
N-[6-(1H-indol-4-yl)-1H-indazol-4-yl]-3-thiophenecarboxamide;
N-[6-(1H-indol-4-yl)-1H-indazol-4-yl]-5-(1-pyrrolidinylmethyl)-2-furancarboxamide;
N-[6-(1H-indol-4-yl)-1H-indazol-4-yl]-2-phenyl-1,3-thiazole-4-carboxamide;
2-chloro-N-[6-(1H-indol-4-yl)-1H-indazol-4-yl]-3-furancarboxamide;
1-ethenyl-N-[6-(1H-indol-4-yl)-1H-indazol-4-yl]-1H-pyrazole-5-carboxamide;
1-ethyl-N-[6-(1H-indol-4-yl)-1H-indazol-4-yl]-1H-pyrazole-5-carboxamide;
N-[6-(1H-indol-4-yl)-1H-indazol-4-yl]-2-(trifluoromethyl)-1,3-thiazole-4-carboxamide;
N-[6-(1H-indol-4-yl)-1H-indazol-4-yl]-2-{1-[(phenylcarbonyl)amino]ethyl}-1,3-thiazole-4-carboxamide;
N-[6-(1H-indol-4-yl)-1H-indazol-4-yl]-5-(trifluoromethyl)-2-furancarboxamide;
5-[(dimethylamino)methyl]-N-[6-(1H-indol-4-yl)-1H-indazol-4-yl]-2-furancarboxamide;
3-ethyl-N-[6-(1H-indol-4-yl)-1H-indazol-4-yl]-1H-pyrazole-5-carboxamide;
5-chloro-N-[6-(1H-indol-4-yl)-1H-indazol-4-yl]-2-furancarboxamide;
N-[6-(1H-indol-4-yl)-1H-indazol-4-yl]-4-methyl-2-thiophenecarboxamide;
N-[6-(1H-indol-4-yl)-1H-indazol-4-yl]-2-(4-morpholinylmethyl)-1,3-thiazole-4-carboxamide;
N-[6-(1H-indol-4-yl)-1H-indazol-4-yl]-1H-pyrazole-3-carboxamide;
N-[6-(1H-indol-4-yl)-1H-indazol-4-yl]-1,3-thiazole-5-carboxamide;
1-(1-methylethyl)-N-[6-(1H-pyrazolo[3,4-b]pyridin-4-yl)-1H-indazol-4-yl]-1H-pyrazole-5-carboxamide;
N-[6-(1H-Indol-4-yl)-1H-indazol-4-yl]-1H-imidazole-4-carboxamide;
N-[6-(1H-indol-4-yl)-1H-indazol-4-yl]-1,3-thiazole-4-carboxamide;
N-[6-(1H-Indol-4-yl)-1H-indazol-4-yl]-5-methyl-3-isoxazolecarboxamide;

N-[6-(1H-indol-4-yl)-1H-indazol-4-yl]-1,2,3-thiadiazole-4-carboxamide;
N-[6-(1H-indol-4-yl)-1H-indazol-4-yl]-2,5-dimethyl-1,3-oxazole-4-carboxamide;
N-[6-(1H-indol-4-yl)-1H-indazol-4-yl]-2-methyl-1,3-oxazole-4-carboxamide;
N-[6-(1H-indol-4-yl)-1H-indazol-4-yl]-3-isoxazolecarboxamide;
N-[6-(1H-indol-4-yl)-1H-indazol-4-yl]-2-methyl-5-(trifluoromethyl)-1,3-oxazole-4-carboxamide;
N-[6-(1H-indol-4-yl)-1H-indazol-4-yl]-5-(2-methyl-1,3-thiazol-4-yl)-3-isoxazolecarboxamide;
4-[(dimethylamino)methyl]-N-[6-(1H-indol-4-yl)-1H-indazol-4-yl]-5-methyl-3-isoxazolecarboxamide;
N-[6-(1H-indol-4-yl)-1H-indazol-4-yl]-5-(4-morpholinylmethyl)-3-isoxazolecarboxamide;
N-[6-(1H-indol-4-yl)-1H-indazol-4-yl]-5-methyl-4-(1-piperidinylmethyl)-3-isoxazolecarboxamide;
N-[6-(1H-indol-4-yl)-1H-indazol-4-yl]-5-methyl-4-(4-morpholinylmethyl)-3-isoxazolecarboxamide;
N-[6-(1H-indol-4-yl)-1H-indazol-4-yl]-5-methyl-4-(1-pyrrolidinylmethyl)-3-isoxazolecarboxamide;
N-[6-(1H-indol-4-yl)-1H-indazol-4-yl]-2-(1-piperidinylmethyl)-1,3-thiazole-4-carboxamide;
N-[6-(1H-indol-4-yl)-1H-indazol-4-yl]-1H-imidazole-2-carboxamide;
N-1H,1'H-5,6'-biindazol-4'-yl-2-methyl-1,3-thiazole-4-carboxamide;
4-chloro-N-[6-(1H-indol-4-yl)-1H-indazol-4-yl]-1-methyl-1H-pyrazole-5-carboxamide;
N-[6-(1H-indol-4-yl)-1H-indazol-4-yl]-1,4-dimethyl-1H-pyrazole-5-carboxamide;
N-[6-(1H-indol-4-yl)-1H-indazol-4-yl]-5-(1-methylethyl)-2-(4-morpholinylmethyl)-1,3-thiazole-4-carboxamide;
4-chloro-N-[6-(1H-indol-4-yl)-1H-indazol-4-yl]-1H-pyrazole-5-carboxamide;
4-chloro-N-[6-(1H-indol-4-yl)-1H-indazol-4-yl]-1-(1-methylethyl)-1H-pyrazole-3-carboxamide;
2-chloro-N-[6-(1H-indol-4-yl)-1H-indazol-4-yl]-5-(1-methylethyl)-1,3-thiazole-4-carboxamide;
N-[6-(1H-indol-4-yl)-1H-indazol-4-yl]-2,5-dimethyl-1,3-thiazole-4-carboxamide;
4-chloro-N-[6-(1H-indol-4-yl)-1H-indazol-4-yl]-1-(1-methylethyl)-1H-pyrazole-5-carboxamide;
N-[6-(1H-indol-4-yl)-1H-indazol-4-yl]-1-methyl-4-(trifluoromethyl)-1H-pyrazole-5-carboxamide;
N-[6-(1H-indol-4-yl)-1H-indazol-4-yl]-2-methyl-5-(1-methylethyl)-1,3-thiazole-4-carboxamide;
N-[6-(1H-indol-4-yl)-1H-indazol-4-yl]-1-(1-methylethyl)-3-(4-morpholinylmethyl)-1H-pyrazole-5-carboxamide;
N-[6-(1H-indol-4-yl)-1H-indazol-4-yl]-1-(1-methylethyl)-5-(4-morpholinylmethyl)-1H-pyrazole-3-carboxamide;
N-[6-(1H-indol-4-yl)-1H-indazol-4-yl]-1-methyl-1H-1,2,4-triazole-5-carboxamide;
N-[6-(1H-indol-4-yl)-1H-indazol-4-yl]-1-(1-methylethyl)-1H-1,2,4-triazole-5-carboxamide;
1-(1,1-dimethylethyl)-N-[6-(1H-indol-4-yl)-1H-indazol-4-yl]-3-methyl-1H-pyrazole-5-carboxamide;
N-[6-(1H-indol-4-yl)-1H-indazol-4-yl]-1-(2,2,2-trifluoroethyl)-1H-pyrazole-5-carboxamide;
1-(difluoromethyl)-N-[6-(1H-indol-4-yl)-1H-indazol-4-yl]-1H-pyrazole-5-carboxamide;
1,1-dimethylethyl[4-({[6-(1H-indol-4-yl)-1H-indazol-4-yl]amino}carbonyl)-1,3-thiazol-2-yl]carbamate;
1,1-dimethylethyl 3-cyclopropyl-4-({[6-(1H-indol-4-yl)-1H-indazol-4-yl]amino}carbonyl)-1H-pyrazole-1-carboxylate;
4-fluoro-N-[6-(1H-indol-4-yl)-1H-indazol-4-yl]-1-(1-methylethyl)-1H-pyrazole-5-carboxamide;
2-amino-N-[6-(1H-indol-4-yl)-1H-indazol-4-yl]-1,3-thiazole-4-carboxamide;
1-ethyl-4-fluoro-N-[6-(1H-indol-4-yl)-1H-indazol-4-yl]-1H-pyrazole-5-carboxamide;
2-amino-N-[6-(1H-indol-4-yl)-1H-indazol-4-yl]-4-(trifluoromethyl)-1,3-thiazole-5-carboxamide;
2-amino-N-[6-(1H-indol-4-yl)-1H-indazol-4-yl]-5-(1-methylethyl)-1,3-thiazole-4-carboxamide;
N-[6-(1H-indol-4-yl)-1H-indazol-4-yl]-2-(1-methylethyl)-2H-1,2,3-triazole-4-carboxamide;
4-bromo-N-[6-(1H-indol-4-yl)-1H-indazol-4-yl]-1,3-dimethyl-1H-pyrazole-5-carboxamide;
N-[6-(1H-indol-4-yl)-1H-indazol-4-yl]-5-(1-methylethyl)-1,3-thiazole-4-carboxamide;
1-(2-fluoroethyl)-N-[6-(1H-indol-4-yl)-1H-indazol-4-yl]-1H-pyrazole-5-carboxamide;
1-(2-fluoroethyl)-N-[6-(1H-indol-4-yl)-1H-indazol-4-yl]-1H-pyrazole-3-carboxamide;
5-acetyl-N-[6-(1H-indol-4-yl)-1H-indazol-4-yl]-2-methyl-1,3-thiazole-4-carboxamide;
N-[6-(1H-indol-4-yl)-1H-indazol-4-yl]-5-(1-methylethyl)-1,3-oxazole-4-carboxamide;
N-[6-(1H-indol-4-yl)-1H-indazol-4-yl]-1-(1-methylethyl)-1H-1,2,3-triazole-5-carboxamide;
N-[6-(1H-indol-4-yl)-1H-indazol-4-yl]-2-methyl-1,3-thiazole-4-carboxamide;
N-[6-(1H-indol-4-yl)-1H-indazol-4-yl]-1-methyl-1H-1,2,4-triazole-3-carboxamide;
N-[6-(1H-indol-5-yl)-1H-indazol-4-yl]-2-methyl-1,3-thiazole-4-carboxamide;
N-[6-(1H-benzimidazol-4-yl)-1H-indazol-4-yl]-2-methyl-1,3-thiazole-4-carboxamide;
2-methyl-N-[6-(2-methyl-1H-pyrrolo[2,3-b]pyridin-4-yl)-1H-indazol-4-yl]-1,3-thiazole-4-carboxamide;
N-[6-(2-cyclopropyl-1H-pyrrolo[2,3-b]pyridin-4-yl)-1H-indazol-4-yl]-2-methyl-1,3-thiazole-4-carboxamide;
N-1H,1'H-4,6'-biindazol-4'-yl-1-(1-methylethyl)-1H-pyrazole-5-carboxamide;
N-[3-fluoro-6-(1H-indol-4-yl)-1H-indazol-4-yl]-2-methyl-1,3-thiazole-4-carboxamide;
4-chloro-1-ethyl-N-[3-fluoro-6-(1H-indol-4-yl)-1H-indazol-4-yl]-1H-pyrazole-5-carboxamide;
N-[3-fluoro-6-(1H-indol-4-yl)-1H-indazol-4-yl]-1-(1-methylethyl)-1H-pyrazole-5-carboxamide;
N-[6-(6-fluoro-1H-indol-4-yl)-1H-indazol-4-yl]-2-methyl-1,3-thiazole-4-carboxamide;
N-[6-(1H-indol-4-yl)-1H-indazol-4-yl]-1-(1-methylethyl)-1H-imidazole-2-carboxamide;
4-fluoro-N-[6-(1H-indol-4-yl)-1H-indazol-4-yl]-1-methyl-1H-pyrazole-3-carboxamide;
ethyl-N-[6-(1H-indol-4-yl)-1H-indazol-4-yl]-3-methyl-1H-pyrazole-5-carboxamide;
N-[6-(1H-indol-4-yl)-1H-indazol-4-yl]-1,3-dimethyl-1H-pyrazole-5-carboxamide;
3-(1,1-dimethylethyl)-N-[6-(1H-indol-4-yl)-1H-indazol-4-yl]-1-methyl-1H-pyrazole-5-carboxamide;
4-chloro-1-ethyl-N-[6-(1H-indol-4-yl)-1H-indazol-4-yl]-1H-pyrazole-5-carboxamide;
N-[6-(1H-indol-4-yl)-1H-indazol-4-yl]-1-methyl-3-(trifluoromethyl)-1H-pyrazole-5-carboxamide;
N-[6-(1H-indol-4-yl)-1H-indazol-4-yl]-1-methyl-3-(1-methylethyl)-1H-pyrazole-5-carboxamide;
3-cyclopropyl-N-[6-(1H-indol-4-yl)-1H-indazol-4-yl]-1-methyl-1H-pyrazole-5-carboxamide;

1-ethyl-N-[6-(1H-indol-4-yl)-1H-indazol-4-yl]-3-(1-methylethyl)-1H-pyrazole-5-carboxamide;
N-[6-(1H-indol-4-yl)-1H-indazol-4-yl]-1-methyl-3-(2-methylpropyl)-1H-pyrazole-5-carboxamide;
N-[6-(1H-indol-4-yl)-1H-indazol-4-yl]-4-(methyloxy)-3-thiophenecarboxamide;
N-[6-(1H-indol-4-yl)-1H-indazol-4-yl]-1-methyl-3-(4-morpholinylcarbonyl)-1H-pyrazole-5-carboxamide;
N-[6-(1H-indol-4-yl)-1H-indazol-4-yl]-1,4-dimethyl-1H-pyrazole-3-carboxamide;
1-ethyl-N-[6-(1H-indol-4-yl)-1H-indazol-4-yl]-3-(2-methylpropyl)-1H-pyrazole-5-carboxamide;
N-[6-(1H-indol-4-yl)-1H-indazol-4-yl]-1-methyl-5-(4-morpholinylmethyl)-1H-pyrazole-3-carboxamide;
N-[6-(1H-indol-4-yl)-1H-indazol-4-yl]-1-methyl-3-(4-morpholinylmethyl)-1H-pyrazole-5-carboxamide;
2-acetyl-N-[6-(1H-indol-4-yl)-1H-indazol-4-yl]-1,3-thiazole-4-carboxamide;
N-[6-(5-isoquinolinyl)-1H-indazol-4-yl]-2-methyl-1,3-thiazole-4-carboxamide;
2-methyl-N-[6-(1-methyl-1H-indol-4-yl)-1H-indazol-4-yl]-1,3-thiazole-4-carboxamide;
N-[6-(4-isoquinolinyl)-1H-indazol-4-yl]-2-methyl-1,3-thiazole-4-carboxamide;
N-[6-(1H-indol-3-yl)-1H-indazol-4-yl]-2-methyl-1,3-thiazole-4-carboxamide;
N-[6-(1H-indol-6-yl)-1H-indazol-4-yl]-2-methyl-1,3-thiazole-4-carboxamide;
2-methyl-N-[6-(1-methyl-1H-indol-6-yl)-1H-indazol-4-yl]-1,3-thiazole-4-carboxamide;
N-[6-(1H-indol-4-yl)-1H-indazol-4-yl]-2-furancarboxamide;
N-[6-(1-benzofuran-2-yl)-1H-indazol-4-yl]-2-methyl-1,3-thiazole-4-carboxamide;
N-[6-(6-cyano-1H-indol-4-yl)-1H-indazol-4-yl]-1-(1-methylethyl)-1H-pyrazole-5-carboxamide;
1-(1-methylethyl)-N-[6-(6-methyl-1H-indol-4-yl)-1H-indazol-4-yl]-1H-pyrazole-5-carboxamide;
N-[6-(1-benzofuran-5-yl)-1H-indazol-4-yl]-1-(1-methylethyl)-1H-pyrazole-5-carboxamide;
5-bromo-N-[6-(1H-indol-4-yl)-1H-indazol-4-yl]-1,3-thiazole-4-carboxamide;
N-[6-(1H-indol-4-yl)-1H-indazol-4-yl]-5-(1-methylethyl)-4-isoxazolecarboxamide;
N-[6-(1-benzofuran-5-yl)-1H-indazol-4-yl]-2-methyl-1,3-thiazole-4-carboxamide;
N-{6-[2-(1,1-dimethylethyl)-1H-pyrrolo[2,3-b]pyridin-4-yl]-1H-indazol-4-yl}-2-methyl-1,3-thiazole-4-carboxamide;
1-(1-methylethyl)-N-[6-(2-methyl-1H-pyrrolo[2,3-b]pyridin-4-yl)-1H-indazol-4-yl]-1H-pyrazole-5-carboxamide;
1-(1-methylethyl)-N-[6-(1H-pyrrolo[2,3-b]pyridin-4-yl)-1H-indazol-4-yl]-1H-pyrazole-5-carboxamide;
1-(1-methylethyl)-N-[6-(1H-pyrrolo[2,3-c]pyridin-4-yl)-1H-indazol-4-yl]-1H-pyrazole-5-carboxamide;
1-(1-methylethyl)-N-[6-(2-oxo-2,3-dihydro-1H-indol-4-yl)-1H-indazol-4-yl]-1H-pyrazole-5-carboxamide;
1-(1-methylethyl)-N-[6-(2-oxo-2,3-dihydro-1,3-benzoxazol-7-yl)-1H-indazol-4-yl]-1H-pyrazole-5-carboxamide;
1-(1-methylethyl)-N-[6-(7H-pyrrolo[2,3-d]pyrimidin-4-yl)-1H-indazol-4-yl]-1H-pyrazole-5-carboxamide;
N-[6-(6-fluoro-1H-indol-4-yl)-1H-indazol-4-yl]-1-(1-methylethyl)-1H-pyrazole-5-carboxamide;
N-1H,1'H-4,6'-biindazol-4'-yl-2-methyl-1,3-thiazole-4-carboxamide;
2-methyl-N-[6-(1H-pyrrolo[2,3-b]pyridin-4-yl)-1H-indazol-4-yl]-1,3-thiazole-4-carboxamide;
2-methyl-N-[6-(1H-pyrrolo[2,3-c]pyridin-4-yl)-1H-indazol-4-yl]-1,3-thiazole-4-carboxamide;
1,4-dimethyl-N-[6-(2-methyl-1H-pyrrolo[2,3-b]pyridin-4-yl)-1H-indazol-4-yl]-1H-pyrazole-3-carboxamide;
1,4-dimethyl-N-[6-(1H-pyrrolo[2,3-c]pyridin-4-yl)-1H-indazol-4-yl]-1H-pyrazole-3-carboxamide;
1,4-dimethyl-N-[6-(1H-pyrrolo[2,3-b]pyridin-4-yl)-1H-indazol-4-yl]-1H-pyrazole-3-carboxamide;
N-1H,1'H-4,6'-biindazol-4'-yl-1,4-dimethyl-1H-pyrazole-3-carboxamide;
4-chloro-1-ethyl-N-[6-(2-methyl-1H-pyrrolo[2,3-b]pyridin-4-yl)-1H-indazol-4-yl]-1H-pyrazole-5-carboxamide;
4-chloro-1-ethyl-N-[6-(1H-pyrrolo[2,3-c]pyridin-4-yl)-1H-indazol-4-yl]-1H-pyrazole-5-carboxamide;
4-chloro-1-ethyl-N-[6-(1H-pyrrolo[2,3-b]pyridin-4-yl)-1H-indazol-4-yl]-1H-pyrazole-5-carboxamide;
N-1H,1'H-4,6'-biindazol-4'-yl-4-chloro-1-ethyl-1H-pyrazole-5-carboxamide;
4-chloro-1-ethyl-N-[6-(1H-pyrazolo[3,4-b]pyridin-4-yl)-1H-indazol-4-yl]-1H-pyrazole-5-carboxamide;
N-[3-fluoro-6-(6-fluoro-1H-indol-4-yl)-1H-indazol-4-yl]-2-methyl-1,3-thiazole-4-carboxamide;
2-[(4,4-dimethyl-1-piperidinyl)methyl]-N-[6-(1H-indol-4-yl)-1H-indazol-4-yl]-1,3-thiazole-4-carboxamide;
2-[(3,3-dimethyl-1-piperidinyl)methyl]-N-[6-(1H-indol-4-yl)-1H-indazol-4-yl]-1,3-thiazole-4-carboxamide;
N-[6-(1H-indol-4-yl)-1H-indazol-4-yl]-2-{[4-(2-methylpropyl)-1-piperazinyl]methyl}-1,3-thiazole-4-carboxamide;
N-[6-(1H-indol-4-yl)-1H-indazol-4-yl]-2-{[4-(1-methylethyl)-1-piperazinyl]methyl}-1,3-thiazole-4-carboxamide;
N-[6-(1H-indol-4-yl)-1H-indazol-4-yl]-2-({4-[2-(4-morpholinyl)ethyl]-1-piperazinyl}methyl)-1,3-thiazole-4-carboxamide;
N-[6-(1H-indol-4-yl)-1H-indazol-4-yl]-2-(octahydro-4H-1,4-benzoxazin-4-ylmethyl)-1,3-thiazole-4-carboxamide;
2-{[(2R,6S)-2,6-dimethyl-4-morpholinyl]methyl}-N-[6-(1H-indol-4-yl)-1H-indazol-4-yl]-1,3-thiazole-4-carboxamide;
2-{[4-(4-fluorophenyl)-1-piperazinyl]methyl}-N-[6-(1H-indol-4-yl)-1H-indazol-4-yl]-1,3-thiazole-4-carboxamide;
N-[6-(1H-indol-4-yl)-1H-indazol-4-yl]-2-(octahydro-2H-pyrido[1,2-a]pyrazin-2-ylmethyl)-1,3-thiazole-4-carboxamide;
N-[6-(1H-indol-4-yl)-1H-indazol-4-yl]-2-{[2-(1-pyrrolidinylmethyl)-4-morpholinyl]methyl}-1,3-thiazole-4-carboxamide;
N-[6-(1H-indol-4-yl)-1H-indazol-4-yl]-2-{[2-(2-methylpropyl)-4-morpholinyl]methyl}-1,3-thiazole-4-carboxamide;
N-[6-(1H-indol-4-yl)-1H-indazol-4-yl]-2-{[3-(3-pyridinyl)-1-pyrrolidinyl]methyl}-1,3-thiazole-4-carboxamide;
N-[6-(1H-indol-4-yl)-1H-indazol-4-yl]-2-{[3-methyl-4-(1-methylethyl)-1-piperazinyl]methyl}-1,3-thiazole-4-carboxamide;
N-[6-(1H-indol-4-yl)-1H-indazol-4-yl]-2-({3-[(phenylmethyl)oxy]-1-piperidinyl}methyl)-1,3-thiazole-4-carboxamide;
2-{[4-(1-ethylpropyl)-1-piperazinyl]methyl}-N-[6-(1H-indol-4-yl)-1H-indazol-4-yl]-1,3-thiazole-4-carboxamide;
2-[(4-cyclopentyl-1-piperazinyl)methyl]-N-[6-(1H-indol-4-yl)-1H-indazol-4-yl]-1,3-thiazole-4-carboxamide;
2-methyl-N-[6-(2-methyl-1H-indol-4-yl)-1H-indazol-4-yl]-1,3-thiazole-4-carboxamide;
N-[6-(6-chloro-1H-indol-4-yl)-1H-indazol-4-yl]-2-methyl-1,3-thiazole-4-carboxamide;
2-methyl-N-{6-[6-(methyloxy)-1H-indol-4-yl]-1H-indazol-4-yl}-1,3-thiazole-4-carboxamide;

N-[6-(6-cyano-1H-indol-4-yl)-1H-indazol-4-yl]-2-methyl-1,3-thiazole-4-carboxamide;
N-[6-(6-fluoro-1H-indol-4-yl)-1H-indazol-4-yl]-2-methyl-1,3-thiazole-4-carboxamide;
2-(1-piperidinylmethyl)-N-[6-(1H-pyrazolo[3,4-b]pyridin-5-yl)-1H-indazol-4-yl]-1,3-thiazole-4-carboxamide;
N-[6-(6-fluoro-1H-indol-4-yl)-1H-indazol-4-yl]-2-(1-piperidinylmethyl)-1,3-thiazole-4-carboxamide;
2-methyl-N-(6-{6-[(phenylsulfonyl)amino]-1H-indol-4-yl}-1H-indazol-4-yl)-1,3-thiazole-4-carboxamide;
2-methyl-N-(6-{6-[(methylsulfonyl)amino]-1H-indol-4-yl}-1H-indazol-4-yl)-1,3-thiazole-4-carboxamide;
2-methyl-N-[6-(7-methyl-1H-indol-4-yl)-1H-indazol-4-yl]-1,3-thiazole-4-carboxamide;
2-(4-morpholinylmethyl)-N-[6-(1H-pyrazolo[3,4-b]pyridin-5-yl)-1H-indazol-4-yl]-1,3-thiazole-4-carboxamide;
2-{[(2R,6S)-2,6-dimethyl-4-morpholinyl]methyl}-N-[6-(1H-pyrazolo[3,4-b]pyridin-5-yl)-1H-indazol-4-yl]-1,3-thiazole-4-carboxamide;
2-(4-morpholinylmethyl)-N-[6-(1H-pyrrolo[2,3-b]pyridin-4-yl)-1H-indazol-4-yl]-1,3-thiazole-4-carboxamide;
N-[6-(1H-indol-4-yl)-1H-indazol-4-yl]-2-[(2-methyl-4-morpholinyl)methyl]-1,3-thiazole-4-carboxamide;
N-[6-(1H-indol-4-yl)-1H-indazol-4-yl]-2-(6-oxa-9-azaspiro[4.5]dec-9-ylmethyl)-1,3-thiazole-4-carboxamide;
N-[6-(1H-indol-4-yl)-1H-indazol-4-yl]-2-(tetrahydro-1,4-oxazepin-4(5H)-ylmethyl)-1,3-thiazole-4-carboxamide;
2-[(1,1-dioxido-4-thiomorpholinyl)methyl]-N-[6-(1H-indol-4-yl)-1H-indazol-4-yl]-1,3-thiazole-4-carboxamide;
2-[(2,2-dimethyl-4-morpholinyl)methyl]-N-[6-(1H-indol-4-yl)-1H-indazol-4-yl]-1,3-thiazole-4-carboxamide;
2-{[(2R,6S)-2,6-dimethyl-4-morpholinyl]methyl}-N-[6-(1H-indol-4-yl)-1-methyl-1H-indazol-4-yl]-1,3-thiazole-4-carboxamide; or
a salt thereof.

In another embodiment, the compound of the invention is:
N-[6-(1H-indol-4-yl)-1H-indazol-4-yl]-5-methyl-1H-pyrazole-3-carboxamide;
N-[6-(1H-indol-4-yl)-1H-indazol-4-yl]-1-methyl-1H-imidazole-2-carboxamide;
N-[6-(1H-indol-4-yl)-1H-indazol-4-yl]-1-methyl-1H-pyrrole-2-carboxamide;
N-[6-(1H-indol-4-yl)-1H-indazol-4-yl]-1-methyl-1H-imidazole-4-carboxamide;
N-[6-(1H-indol-4-yl)-1H-indazol-4-yl]-1-methyl-1H-pyrazole-5-carboxamide;
N-[6-(1H-indol-4-yl)-1H-indazol-4-yl]-1,5-dimethyl-1H-pyrazole-3-carboxamide;
N-[6-(1H-indol-4-yl)-1H-indazol-4-yl]-2-(phenylmethyl)-1,3-thiazole-4-carboxamide;
1-ethyl-N-[6-(1H-indol-4-yl)-1H-indazol-4-yl]-1H-pyrazole-3-carboxamide;
N-[6-(1H-indol-4-yl)-1H-indazol-4-yl]-2-methyl-3-furancarboxamide;
N-[6-(1H-indol-4-yl)-1H-indazol-4-yl]-5-methyl-2-furancarboxamide;
N-[6-(1H-indol-4-yl)-1H-indazol-4-yl]-1-methyl-1H-pyrazole-3-carboxamide;
N-[6-(1H-indol-4-yl)-1H-indazol-4-yl]-3-furancarboxamide;
N-[6-(1H-indol-4-yl)-1H-indazol-4-yl]-3-thiophenecarboxamide;
N-[6-(1H-indol-4-yl)-1H-indazol-4-yl]-5-(1-pyrrolidinylmethyl)-2-furancarboxamide;
N-[6-(1H-indol-4-yl)-1H-indazol-4-yl]-2-phenyl-1,3-thiazole-4-carboxamide;
2-chloro-N-[6-(1H-indol-4-yl)-1H-indazol-4-yl]-3-furancarboxamide;
1-ethenyl-N-[6-(1H-indol-4-yl)-1H-indazol-4-yl]-1H-pyrazole-5-carboxamide;
1-ethyl-N-[6-(1H-indol-4-yl)-1H-indazol-4-yl]-1H-pyrazole-5-carboxamide;
N-[6-(1H-indol-4-yl)-1H-indazol-4-yl]-2-(trifluoromethyl)-1,3-thiazole-4-carboxamide;
N-[6-(1H-indol-4-yl)-1H-indazol-4-yl]-2-{1-[(phenylcarbonyl)amino]ethyl}-1,3-thiazole-4-carboxamide;
N-[6-(1H-indol-4-yl)-1H-indazol-4-yl]-5-(trifluoromethyl)-2-furancarboxamide;
5-[(dimethylamino)methyl]-N-[6-(1H-indol-4-yl)-1H-indazol-4-yl]-2-furancarboxamide;
3-ethyl-N-[6-(1H-indol-4-yl)-1H-indazol-4-yl]-1H-pyrazole-5-carboxamide;
5-chloro-N-[6-(1H-indol-4-yl)-1H-indazol-4-yl]-2-furancarboxamide;
N-[6-(1H-indol-4-yl)-1H-indazol-4-yl]-4-methyl-2-thiophenecarboxamide;
N-[6-(1H-indol-4-yl)-1H-indazol-4-yl]-2-(4-morpholinylmethyl)-1,3-thiazole-4-carboxamide;
N-[6-(1H-indol-4-yl)-1H-indazol-4-yl]-1H-pyrazole-3-carboxamide;
N-[6-(1H-indol-4-yl)-1H-indazol-4-yl]-1,3-thiazole-5-carboxamide;
1-(1-methylethyl)-N-[6-(1H-pyrazolo[3,4-b]pyridin-4-yl)-1H-indazol-4-yl]-1H-pyrazole-5-carboxamide;
N-[6-(1H-Indol-4-yl)-1H-indazol-4-yl]-1H-imidazole-4-carboxamide;
N-[6-(1H-indol-4-yl)-1H-indazol-4-yl]-1,3-thiazole-4-carboxamide;
N-[6-(1H-Indol-4-yl)-1H-indazol-4-yl]-5-methyl-3-isoxazolecarboxamide;
N-[6-(1H-indol-4-yl)-1H-indazol-4-yl]-1,2,3-thiadiazole-4-carboxamide;
N-[6-(1H-indol-4-yl)-1H-indazol-4-yl]-2,5-dimethyl-1,3-oxazole-4-carboxamide;
N-[6-(1H-indol-4-yl)-1H-indazol-4-yl]-2-methyl-1,3-oxazole-4-carboxamide;
N-[6-(1H-indol-4-yl)-1H-indazol-4-yl]-3-isoxazolecarboxamide;
N-[6-(1H-indol-4-yl)-1H-indazol-4-yl]-2-methyl-5-(trifluoromethyl)-1,3-oxazole-4-carboxamide;
N-[6-(1H-indol-4-yl)-1H-indazol-4-yl]-5-(2-methyl-1,3-thiazol-4-yl)-3-isoxazolecarboxamide;
4-[(dimethylamino)methyl]-N-[6-(1H-indol-4-yl)-1H-indazol-4-yl]-5-methyl-3-isoxazolecarboxamide;
N-[6-(1H-indol-4-yl)-1H-indazol-4-yl]-5-(4-morpholinylmethyl)-3-isoxazolecarboxamide;
N-[6-(1H-indol-4-yl)-1H-indazol-4-yl]-5-methyl-4-(1-piperidinylmethyl)-3-isoxazolecarboxamide;
N-[6-(1H-indol-4-yl)-1H-indazol-4-yl]-5-methyl-4-(4-morpholinylmethyl)-3-isoxazolecarboxamide;
N-[6-(1H-indol-4-yl)-1H-indazol-4-yl]-5-methyl-4-(1-pyrrolidinylmethyl)-3-isoxazolecarboxamide;
N-[6-(1H-indol-4-yl)-1H-indazol-4-yl]-2-(1-piperidinylmethyl)-1,3-thiazole-4-carboxamide;
N-[6-(1H-indol-4-yl)-1H-indazol-4-yl]-1H-imidazole-2-carboxamide;
N-1H,1'H-5,6'-biindazol-4'-yl-2-methyl-1,3-thiazole-4-carboxamide;
4-chloro-N-[6-(1H-indol-4-yl)-1H-indazol-4-yl]-1-methyl-1H-pyrazole-5-carboxamide;
N-[6-(1H-indol-4-yl)-1H-indazol-4-yl]-1,4-dimethyl-1H-pyrazole-5-carboxamide;

N-[6-(1H-indol-4-yl)-1H-indazol-4-yl]-5-(1-methylethyl)-2-(4-morpholinylmethyl)-1,3-thiazole-4-carboxamide;
4-chloro-N-[6-(1H-indol-4-yl)-1H-indazol-4-yl]-1H-pyrazole-5-carboxamide;
4-chloro-N-[6-(1H-indol-4-yl)-1H-indazol-4-yl]-1-(1-methylethyl)-1H-pyrazole-3-carboxamide;
2-chloro-N-[6-(1H-indol-4-yl)-1H-indazol-4-yl]-5-(1-methylethyl)-1,3-thiazole-4-carboxamide;
N-[6-(1H-indol-4-yl)-1H-indazol-4-yl]-2,5-dimethyl-1,3-thiazole-4-carboxamide;
4-chloro-N-[6-(1H-indol-4-yl)-1H-indazol-4-yl]-1-(1-methylethyl)-1H-pyrazole-5-carboxamide;
N-[6-(1H-indol-4-yl)-1H-indazol-4-yl]-1-methyl-4-(trifluoromethyl)-1H-pyrazole-5-carboxamide;
N-[6-(1H-indol-4-yl)-1H-indazol-4-yl]-2-methyl-5-(1-methylethyl)-1,3-thiazole-4-carboxamide;
N-[6-(1H-indol-4-yl)-1H-indazol-4-yl]-1-(1-methylethyl)-3-(4-morpholinylmethyl)-1H-pyrazole-5-carboxamide;
N-[6-(1H-indol-4-yl)-1H-indazol-4-yl]-1-(1-methylethyl)-5-(4-morpholinylmethyl)-1H-pyrazole-3-carboxamide;
N-[6-(1H-indol-4-yl)-1H-indazol-4-yl]-1-methyl-1H-1,2,4-triazole-5-carboxamide;
N-[6-(1H-indol-4-yl)-1H-indazol-4-yl]-1-(1-methylethyl)-1H-1,2,4-triazole-5-carboxamide;
1-(1,1-dimethylethyl)-N-[6-(1H-indol-4-yl)-1H-indazol-4-yl]-3-methyl-1H-pyrazole-5-carboxamide;
N-[6-(1H-indol-4-yl)-1H-indazol-4-yl]-1-(2,2,2-trifluoroethyl)-1H-pyrazole-5-carboxamide;
1-(difluoromethyl)-N-[6-(1H-indol-4-yl)-1H-indazol-4-yl]-1H-pyrazole-5-carboxamide;
1,1-dimethylethyl[4-({[6-(1H-indol-4-yl)-1H-indazol-4-yl]amino}carbonyl)-1,3-thiazol-2-yl]carbamate;
1,1-dimethylethyl 3-cyclopropyl-4-({[6-(1H-indol-4-yl)-1H-indazol-4-yl]amino}carbonyl)-1H-pyrazole-1-carboxylate;
4-fluoro-N-[6-(1H-indol-4-yl)-1H-indazol-4-yl]-1-(1-methylethyl)-1H-pyrazole-5-carboxamide;
2-amino-N-[6-(1H-indol-4-yl)-1H-indazol-4-yl]-1,3-thiazole-4-carboxamide;
1-ethyl-4-fluoro-N-[6-(1H-indol-4-yl)-1H-indazol-4-yl]-1H-pyrazole-5-carboxamide;
2-amino-N-[6-(1H-indol-4-yl)-1H-indazol-4-yl]-4-(trifluoromethyl)-1,3-thiazole-5-carboxamide;
2-amino-N-[6-(1H-indol-4-yl)-1H-indazol-4-yl]-5-(1-methylethyl)-1,3-thiazole-4-carboxamide;
N-[6-(1H-indol-4-yl)-1H-indazol-4-yl]-2-(1-methylethyl)-2H-1,2,3-triazole-4-carboxamide;
4-bromo-N-[6-(1H-indol-4-yl)-1H-indazol-4-yl]-1,3-dimethyl-1H-pyrazole-5-carboxamide;
N-[6-(1H-indol-4-yl)-1H-indazol-4-yl]-5-(1-methylethyl)-1,3-thiazole-4-carboxamide;
1-(2-fluoroethyl)-N-[6-(1H-indol-4-yl)-1H-indazol-4-yl]-1H-pyrazole-5-carboxamide;
1-(2-fluoroethyl)-N-[6-(1H-indol-4-yl)-1H-indazol-4-yl]-1H-pyrazole-3-carboxamide;
5-acetyl-N-[6-(1H-indol-4-yl)-1H-indazol-4-yl]-2-methyl-1,3-thiazole-4-carboxamide;
N-[6-(1H-indol-4-yl)-1H-indazol-4-yl]-5-(1-methylethyl)-1,3-oxazole-4-carboxamide;
N-[6-(1H-indol-4-yl)-1H-indazol-4-yl]-1-(1-methylethyl)-1H-1,2,3-triazole-5-carboxamide;
N-[6-(1H-indol-4-yl)-1H-indazol-4-yl]-2-methyl-1,3-thiazole-4-carboxamide;
N-[6-(1H-indol-4-yl)-1H-indazol-4-yl]-1-methyl-1H-1,2,4-triazole-3-carboxamide;
N-[6-(1H-indol-5-yl)-1H-indazol-4-yl]-2-methyl-1,3-thiazole-4-carboxamide;
N-[6-(1H-benzimidazol-4-yl)-1H-indazol-4-yl]-2-methyl-1,3-thiazole-4-carboxamide;
2-methyl-N-[6-(2-methyl-1H-pyrrolo[2,3-b]pyridin-4-yl)-1H-indazol-4-yl]-1,3-thiazole-4-carboxamide;
N-[6-(2-cyclopropyl-1H-pyrrolo[2,3-b]pyridin-4-yl)-1H-indazol-4-yl]-2-methyl-1,3-thiazole-4-carboxamide;
N-1H,1'H-4,6'-biindazol-4'-yl-1-(1-methylethyl)-1H-pyrazole-5-carboxamide;
N-[3-fluoro-6-(1H-indol-4-yl)-1H-indazol-4-yl]-2-methyl-1,3-thiazole-4-carboxamide;
4-chloro-1-ethyl-N-[3-fluoro-6-(1H-indol-4-yl)-1H-indazol-4-yl]-1H-pyrazole-5-carboxamide;
N-[3-fluoro-6-(1H-indol-4-yl)-1H-indazol-4-yl]-1-(1-methylethyl)-1H-pyrazole-5-carboxamide;
N-[6-(6-fluoro-1H-indol-4-yl)-1H-indazol-4-yl]-2-methyl-1,3-thiazole-4-carboxamide;
N-[6-(1H-indol-4-yl)-1H-indazol-4-yl]-1-(1-methylethyl)-1H-imidazole-2-carboxamide;
4-fluoro-N-[6-(1H-indol-4-yl)-1H-indazol-4-yl]-1-methyl-1H-pyrazole-3-carboxamide;
ethyl-N-[6-(1H-indol-4-yl)-1H-indazol-4-yl]-3-methyl-1H-pyrazole-5-carboxamide;
N-[6-(1H-indol-4-yl)-1H-indazol-4-yl]-1,3-dimethyl-1H-pyrazole-5-carboxamide;
3-(1,1-dimethylethyl)-N-[6-(1H-indol-4-yl)-1H-indazol-4-yl]-1-methyl-1H-pyrazole-5-carboxamide;
4-chloro-1-ethyl-N-[6-(1H-indol-4-yl)-1H-indazol-4-yl]-1H-pyrazole-5-carboxamide;
N-[6-(1H-indol-4-yl)-1H-indazol-4-yl]-1-methyl-3-(trifluoromethyl)-1H-pyrazole-5-carboxamide;
N-[6-(1H-indol-4-yl)-1H-indazol-4-yl]-1-methyl-3-(1-methylethyl)-1H-pyrazole-5-carboxamide;
3-cyclopropyl-N-[6-(1H-indol-4-yl)-1H-indazol-4-yl]-1-methyl-1H-pyrazole-5-carboxamide;
1-ethyl-N-[6-(1H-indol-4-yl)-1H-indazol-4-yl]-3-(1-methylethyl)-1H-pyrazole-5-carboxamide;
N-[6-(1H-indol-4-yl)-1H-indazol-4-yl]-1-methyl-3-(2-methylpropyl)-1H-pyrazole-5-carboxamide;
N-[6-(1H-indol-4-yl)-1H-indazol-4-yl]-4-(methyloxy)-3-thiophenecarboxamide;
N-[6-(1H-indol-4-yl)-1H-indazol-4-yl]-1-methyl-3-(4-morpholinylcarbonyl)-1H-pyrazole-5-carboxamide;
N-[6-(1H-indol-4-yl)-1H-indazol-4-yl]-1,4-dimethyl-1H-pyrazole-3-carboxamide;
1-ethyl-N-[6-(1H-indol-4-yl)-1H-indazol-4-yl]-3-(2-methylpropyl)-1H-pyrazole-5-carboxamide;
N-[6-(1H-indol-4-yl)-1H-indazol-4-yl]-1-methyl-5-(4-morpholinylmethyl)-1H-pyrazole-3-carboxamide;
N-[6-(1H-indol-4-yl)-1H-indazol-4-yl]-1-methyl-3-(4-morpholinylmethyl)-1H-pyrazole-5-carboxamide;
2-acetyl-N-[6-(1H-indol-4-yl)-1H-indazol-4-yl]-1,3-thiazole-4-carboxamide;
N-[6-(5-isoquinolinyl)-1H-indazol-4-yl]-2-methyl-1,3-thiazole-4-carboxamide;
2-methyl-N-[6-(1-methyl-1H-indol-4-yl)-1H-indazol-4-yl]-1,3-thiazole-4-carboxamide;
N-[6-(4-isoquinolinyl)-1H-indazol-4-yl]-2-methyl-1,3-thiazole-4-carboxamide;
N-[6-(1H-indol-3-yl)-1H-indazol-4-yl]-2-methyl-1,3-thiazole-4-carboxamide;
N-[6-(1H-indol-6-yl)-1H-indazol-4-yl]-2-methyl-1,3-thiazole-4-carboxamide;
2-methyl-N-[6-(1-methyl-1H-indol-6-yl)-1H-indazol-4-yl]-1,3-thiazole-4-carboxamide;
N-[6-(1H-indol-4-yl)-1H-indazol-4-yl]-2-furancarboxamide;

N-[6-(1-benzofuran-2-yl)-1H-indazol-4-yl]-2-methyl-1,3-thiazole-4-carboxamide;
N-[6-(6-cyano-1H-indol-4-yl)-1H-indazol-4-yl]-1-(1-methylethyl)-1H-pyrazole-5-carboxamide;
1-(1-methylethyl)-N-[6-(6-methyl-1H-indol-4-yl)-1H-indazol-4-yl]-1H-pyrazole-5-carboxamide;
N-[6-(1-benzofuran-5-yl)-1H-indazol-4-yl]-1-(1-methylethyl)-1H-pyrazole-5-carboxamide;
5-bromo-N-[6-(1H-indol-4-yl)-1H-indazol-4-yl]-1,3-thiazole-4-carboxamide;
N-[6-(1H-indol-4-yl)-1H-indazol-4-yl]-5-(1-methylethyl)-4-isoxazolecarboxamide;
N-[6-(1-benzofuran-5-yl)-1H-indazol-4-yl]-2-methyl-1,3-thiazole-4-carboxamide;
N-{6-[2-(1,1-dimethylethyl)-1H-pyrrolo[2,3-b]pyridin-4-yl]-1H-indazol-4-yl}-2-methyl-1,3-thiazole-4-carboxamide;
1-(1-methylethyl)-N-[6-(2-methyl-1H-pyrrolo[2,3-b]pyridin-4-yl)-1H-indazol-4-yl]-1H-pyrazole-5-carboxamide;
1-(1-methylethyl)-N-[6-(1H-pyrrolo[2,3-b]pyridin-4-yl)-1H-indazol-4-yl]-1H-pyrazole-5-carboxamide;
1-(1-methylethyl)-N-[6-(1H-pyrrolo[2,3-c]pyridin-4-yl)-1H-indazol-4-yl]-1H-pyrazole-5-carboxamide;
1-(1-methylethyl)-N-[6-(2-oxo-2,3-dihydro-1H-indol-4-yl)-1H-indazol-4-yl]-1H-pyrazole-5-carboxamide;
1-(1-methylethyl)-N-[6-(2-oxo-2,3-dihydro-1,3-benzoxazol-7-yl)-1H-indazol-4-yl]-1H-pyrazole-5-carboxamide;
1-(1-methylethyl)-N-[6-(7H-pyrrolo[2,3-d]pyrimidin-4-yl)-1H-indazol-4-yl]-1H-pyrazole-5-carboxamide;
N-[6-(6-fluoro-1H-indol-4-yl)-1H-indazol-4-yl]-1-(1-methylethyl)-1H-pyrazole-5-carboxamide;
N-1H,1'H-4,6'-biindazol-4'-yl-2-methyl-1,3-thiazole-4-carboxamide;
2-methyl-N-[6-(1H-pyrrolo[2,3-b]pyridin-4-yl)-1H-indazol-4-yl]-1,3-thiazole-4-carboxamide;
2-methyl-N-[6-(1H-pyrrolo[2,3-c]pyridin-4-yl)-1H-indazol-4-yl]-1,3-thiazole-4-carboxamide;
1,4-dimethyl-N-[6-(2-methyl-1H-pyrrolo[2,3-b]pyridin-4-yl)-1H-indazol-4-yl]-1H-pyrazole-3-carboxamide;
1,4-dimethyl-N-[6-(1H-pyrrolo[2,3-c]pyridin-4-yl)-1H-indazol-4-yl]-1H-pyrazole-3-carboxamide;
1,4-dimethyl-N-[6-(1H-pyrrolo[2,3-b]pyridin-4-yl)-1H-indazol-4-yl]-1H-pyrazole-3-carboxamide;
N-1H,1'H-4,6'-biindazol-4'-yl-1,4-dimethyl-1H-pyrazole-3-carboxamide;
4-chloro-1-ethyl-N-[6-(2-methyl-1H-pyrrolo[2,3-b]pyridin-4-yl)-1H-indazol-4-yl]-1H-pyrazole-5-carboxamide;
4-chloro-1-ethyl-N-[6-(1H-pyrrolo[2,3-c]pyridin-4-yl)-1H-indazol-4-yl]-1H-pyrazole-5-carboxamide;
4-chloro-1-ethyl-N-[6-(1H-pyrrolo[2,3-b]pyridin-4-yl)-1H-indazol-4-yl]-1H-pyrazole-5-carboxamide;
N-1H,1'H-4,6'-biindazol-4'-yl-4-chloro-1-ethyl-1H-pyrazole-5-carboxamide;
4-chloro-1-ethyl-N-[6-(1H-pyrazolo[3,4-b]pyridin-4-yl)-1H-indazol-4-yl]-1H-pyrazole-5-carboxamide; or
a salt thereof.

In another embodiment, the compound of the invention is:
N-[6-(1H-indol-4-yl)-1H-indazol-4-yl]-2-(4-morpholinylmethyl)-1,3-thiazole-4-carboxamide;
N-[6-(1H-indol-4-yl)-1H-indazol-4-yl]-2,5-dimethyl-1,3-oxazole-4-carboxamide;
N-[6-(1H-indol-4-yl)-1H-indazol-4-yl]-2-(1-piperidinylmethyl)-1,3-thiazole-4-carboxamide;
N-1H,1'H-5,6'-biindazol-4'-yl-2-methyl-1,3-thiazole-4-carboxamide;
N-[6-(1H-indol-4-yl)-1H-indazol-4-yl]-5-(1-methylethyl)-2-(4-morpholinylmethyl)-1,3-thiazole-4-carboxamide;
N-[6-(1H-indol-4-yl)-1H-indazol-4-yl]-2-methyl-1,3-thiazole-4-carboxamide;
2-methyl-N-[6-(2-methyl-1H-pyrrolo[2,3-b]pyridin-4-yl)-1H-indazol-4-yl]-1,3-thiazole-4-carboxamide;
N-[3-fluoro-6-(1H-indol-4-yl)-1H-indazol-4-yl]-2-methyl-1,3-thiazole-4-carboxamide;
N-[3-fluoro-6-(1H-indol-4-yl)-1H-indazol-4-yl]-1-(1-methylethyl)-1H-pyrazole-5-carboxamide;
N-[6-(6-fluoro-1H-indol-4-yl)-1H-indazol-4-yl]-2-methyl-1,3-thiazole-4-carboxamide;
N-[6-(1H-indol-4-yl)-1H-indazol-4-yl]-1,4-dimethyl-1H-pyrazole-3-carboxamide;
2-methyl-N-[6-(1H-pyrrolo[2,3-b]pyridin-4-yl)-1H-indazol-4-yl]-1,3-thiazole-4-carboxamide;
2-methyl-N-[6-(1H-pyrrolo[2,3-c]pyridin-4-yl)-1H-indazol-4-yl]-1,3-thiazole-4-carboxamide;
or
a salt thereof.

In a further embodiment, the compound of the invention is:
N-[3-fluoro-6-(6-fluoro-1H-indol-4-yl)-1H-indazol-4-yl]-2-methyl-1,3-thiazole-4-carboxamide;
N-[6-(1H-indol-4-yl)-1H-indazol-4-yl]-2-{[4-(1-methylethyl)-1-piperazinyl]methyl}-1,3-thiazole-4-carboxamide;
2-{[(2R,6S)-2,6-dimethyl-4-morpholinyl]methyl}-N-[6-(1H-indol-4-yl)-1H-indazol-4-yl]-1,3-thiazole-4-carboxamide;
2-methyl-N-(6-{6-[(methylsulfonyl)amino]-1H-indol-4-yl}-1H-indazol-4-yl)-1,3-thiazole-4-carboxamide;
2-{[(2R,6S)-2,6-dimethyl-4-morpholinyl]methyl}-N-[6-(1H-indol-4-yl)-1-methyl-1H-indazol-4-yl]-1,3-thiazole-4-carboxamide; or
a salt thereof.

Terms and Definitions

"Alkyl" refers to a saturated hydrocarbon chain having the specified number of member atoms. For example, $C_{1-6}$alkyl refers to an alkyl group having from 1 to 6 member atoms. Similarly, $C_{1-4}$alkyl refers to an alkyl group having from 1 to 4 member atoms. Alkyl groups may be optionally substituted with one or more substituents if so defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl. In one embodiment, alkyl is methyl, ethyl, isopropyl, isobutyl or t-butyl. In another embodiment, alkyl is methyl. In a further embodiment, alkyl is isopropyl.

"Alkenyl" refers to a hydrocarbon chain having the specified number of member atoms and at least one double bond. For example, $C_{2-6}$alkenyl refers to an alkenyl group having from 2 to 6 member atoms, for example 2 to 4 member atoms. Alkenyl groups may be straight or branched. Alkenyl includes ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl. In one embodiment, alkenyl is ethenyl.

"Cycloalkyl" refers to a saturated hydrocarbon ring having the specified number of member atoms. Cycloalkyl groups are monocyclic ring systems. For example, $C_{3-6}$cycloalkyl refers to a cycloalkyl group having from 3 to 6 member atoms. In one embodiment, the cycloalkyl groups have 3 or 4 member atoms. In a further embodiment, the cycloalkyl groups have 5 or 6 member atoms. Cycloalkyl includes cyclopropyl, cyclobutyl, cyclopentyl, and cyclohexyl. In one embodiment, cycloalkyl is cyclopropyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct species in vitro or in vivo.

"Halo" refers to the halogen radical fluoro, chloro, bromo, or iodo. In one embodiment, the halogen radical is fluoro, chloro or bromo.

"Heteroaryl", unless otherwise defined, refers to an aromatic ring containing from 1 to 3 heteroatoms as member atoms in the ring. Heteroaryl groups containing more than one heteroatom may contain different heteroatoms. Heteroaryl groups may be optionally substituted with one or more substituents if so defined herein. The heteroaryl groups herein are monocyclic ring systems or are fused bicyclic ring systems. Monocyclic heteroaryl rings have 5 member atoms. Bicyclic heteroaryl rings have 9 or 10 member atoms. Monocyclic heteroaryl includes pyrrolyl, furanyl, thienyl, pyrazolyl, imidazolyl, oxazolyl, isoxazolyl, thiazolyl, isothiazolyl, furazanyl, triazolyl and thiadiazolyl. In one embodiment, monocyclic heteroaryl is pyrrolyl, furanyl, thienyl, pyrazolyl, imidazolyl, oxazolyl, isoxazolyl, thiazolyl, triazolyl or thiadiazolyl. In a further embodiment, monocyclic heteroaryl is pyrazolyl, oxazolyl, or thiazolyl. Bicyclic heteroaryl includes indolyl, isoindolyl, indolizinyl, benzofuranyl, isobenzofuranyl, indazolyl, purinyl, benzimidazolyl, pyrrolopyridinyl, pyrazolopyridinyl, pyrrolopyrimidinyl, quinolyl, isoquinolinyl, quinoxalinyl, quinazolinyl, cinnolinyl, benzopyranyl, benzoxazolyl, furopyridinyl and naphthridinyl. In one embodiment, bicyclic heteroaryl is indolyl, benzofuranyl, indazolyl, benzimidazolyl, pyrrolopyridinyl, pyrazolopyridinyl, pyrrolopyrimidinyl, or isoquinolinyl. In a further embodiment, bicyclic heteroaryl is indolyl, indazolyl, or pyrrolopyridinyl.

"Heteroatom" refers to a nitrogen, sulphur, or oxygen atom.

"Heterocyclyl", unless otherwise defined, refers to a saturated or unsaturated ring containing 1 or 2 heteroatoms as member atoms in the ring. However, heterocyclyl rings are not aromatic. In certain embodiments, heterocyclyl is saturated. In other embodiments, heterocyclyl is unsaturated but not aromatic. Heterocyclyl groups containing more than one heteroatom may contain different heteroatoms. The heterocyclyl groups herein are monocyclic ring systems having 5, 6 or 7 member atoms. In one embodiment, the heterocyclyl groups herein are monocyclic ring systems having 5 or 6 member atoms. In another embodiment, the heterocyclyl groups herein are monocyclic ring systems having 7 member atoms. Heterocyclyl groups may be optionally substituted with one or more substituents if so defined herein. Monocyclic heterocyclyl includes pyrrolidinyl, pyrazolidinyl, imidazolidinyl, isoxazolidinyl, oxazolidinyl, isothiazolidinyl, thiazolidinyl, tetrahydrofuranyl, piperidinyl, piperazinyl, morpholinyl, thiamorpholinyl, hexahydro-1H-azepinyl and tetrahydro-1,4-oxazepin-4(5H)-yl. In one embodiment, monocyclic heterocyclyl includes pyrrolidinyl, tetrahydrofuranyl, dihydrofuranyl, pyrazolidinyl, oxazolidinyl, piperidinyl, piperazinyl and morpholinyl. In one embodiment, heterocyclyl is pyrrolidinyl. In another embodiment, heterocyclyl is piperidinyl. In a further embodiment, heterocyclyl is morpholinyl. In one embodiment, the heterocyclyl groups herein are bicyclic systems having 10 member atoms. Bicyclic heterocycyl groups include those rings wherein a monocyclic heterocyclyl and a monocyclic cycloalkyl or a further monocyclic heterocyclyl are attached forming a fused or spiro bicyclic ring system. Bicyclic heterocyclyl includes octahydro-4H-1,4-benzoxazinyl, octahydro-2H-pyrido[1,2-a]pyrazinyl and 6-oxa-9-azaspiro[4.5]dec-9-yl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as heteroaryl, may be unsubstituted or substituted with one or more substituents if so defined herein.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| DCM | dichloromethane |
| DIPEA | N,N-diisopropylethylamine |
| DME | dimethoxyethane |
| DMF | N,N-dimethylformamide |
| DMSO | dimethylsulfoxide |
| EtOAc | ethyl acetate |
| g | grams |
| h or hr | hour(s) |
| HATU | O-(7-Azabenzotriazol-1-yl)-N, N, N', N'-tetramethyluronium hexafluorophosphate |
| HPLC | high performance liquid chromatography |
| l | liters |
| LC/MS | liquid chromatography/mass spectroscopy |
| mg | milligrams |

-continued

| | |
|---|---|
| ml or mL | milliliters |
| Pl | microliters |
| M | molar |
| MDAP | Mass directed automated preparative HPLC |
| MeCN | acetonitrile |
| MeOH | methanol |
| mmol | millimoles |
| min | minutes |
| mp | melting point |
| Pd(dppf)Cl$_2$ | [1,1'-bis(diphenylphosphino)ferrocene]dichloropalladium(II) |
| Pd(PPh$_3$)$_4$ | tetrakis(triphenylphosphine)palladium(0) |
| Rt or R$_t$ | retention time |
| RT | room temperature |
| SPE | solid phase extraction |
| TFA | trifluoroacetic acid |
| THF | tetrahydrofuran |

All references to brine are to a saturated aqueous solution of NaCl.

Included within the scope of the "compounds of the invention" are all solvates (including hydrates), complexes, polymorphs, prodrugs, radiolabelled derivatives, stereoisomers and optical isomers of the compounds of formula (I) and salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs". The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making or recrystallising the compound. For example, changes in temperature, pressure, or solvent may result in polymorphs. In addition, one polymorph may spontaneously convert to another polymorph under certain conditions.

The invention also includes isotopically-labelled compounds, which are identical to the compounds of formula (I) and salts thereof, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as 3H, 11C, 14C and 18F.

The compounds according to formula (I) may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in formula (I), or in any chemical structure illustrated herein, is not specified the structure is intended to encompass any stereoisomer and all mixtures thereof. Thus, compounds according to formula (I) containing one or more chiral center may be used as racemic mixtures, enantiomerically enriched mixtures, or as enantiomerically pure individual stereoisomers.

Individual stereoisomers of a compound according to formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to formula (I) may also contain centers of geometric asymmetry. Where the stereochemistry of a center of geometric asymmetry present in formula (I), or in any chemical structure illustrated herein, is not specified, the structure is intended to encompass the trans geometric isomer, the cis geometric isomer, and all mixtures thereof. Likewise, all tautomeric forms are also included in formula (I) whether such tautomers exist in equilibrium or predominately in one form.

It is to be understood that the references herein to compounds of formula (I) and salts thereof covers the compounds of formula (I) as free acids or free bases, or as salts thereof, for example as pharmaceutically acceptable salts thereof. Thus, in one embodiment, the invention is directed to compounds of formula (I) as the free acid or free base. In another embodiment, the invention is directed to compounds of formula (I) and salts thereof. In a further embodiment, the invention is directed to compounds of formula (I) and pharmaceutically acceptable salts thereof.

The skilled artisan will appreciate that pharmaceutically acceptable salts of the compounds according to formula (I) may be prepared. Indeed, in certain embodiments of the invention, pharmaceutically acceptable salts of the compounds according to formula (I) may be preferred over the respective free base or free acid because such salts impart greater stability or solubility to the molecule thereby facilitating formulation into a dosage form. Accordingly, the invention is further directed to compounds of formula (I) and pharmaceutically acceptable salts thereof.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

Salts and solvates having non-pharmaceutically acceptable counter-ions or associated solvents are within the scope of the present invention, for example, for use as intermediates in the preparation of other compounds of formula (I) and their pharmaceutically acceptable salts. Thus one embodiment of the invention embraces compounds of formula (I) and salts thereof.

In certain embodiments, compounds according to formula (I) may contain an acidic functional group. Suitable pharmaceutically-acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

In certain embodiments, compounds according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the Examples section.

Process a

Compounds of formula (I) wherein $R^1$, $R^2$, $R^3$ and $R^4$ are as defined above, and salts thereof, may be prepared from compounds of formula (II)

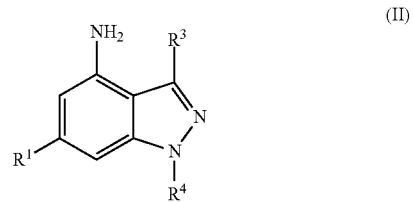

wherein $R^1$, $R^3$ and $R^4$ are as defined above, by a process comprising (i) treatment with an acid of formula $R^2COOH$, wherein $R^2$ is as defined above, or (ii) treatment with an acid chloride of formula $R^2COCl$, wherein $R^2$ is as defined above.

Suitable conditions for (i) include stirring in a suitable solvent such as N,N-dimethylformamide, at a suitable temperature such as room temperature, for example about 20° C., in the presence of a coupling reagent such as O-(7-azabenzotriazol-1-yl)-N,N,N'N'-tetramethyluronium hexafluorophosphate, and in the presence of a suitable base such as N,N-diisopropylethylamine. Alternatively, (ii) may be carried out by treatment with an acylating agent such as an acid chloride, in a suitable solvent such as dichloromethane, in the presence of a suitable base such as N,N-diisopropylethylamine, and at a suitable temperature such as room temperature, for example about 20° C.

Compounds of formula (II) wherein $R^1$ and $R^4$ are as defined above and $R^3$ is H, may be prepared from the compound of formula (III) (which is commercially available)

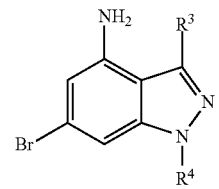

wherein $R^3$ is H and $R^4$ is as defined above, by treatment with a suitable boronic acid or boronate ester such as 4-(4,4,5,5-tetramethyl-1,3,2-dioxaborolan-2-yl)-1H-indole (commercially available), in the presence of a suitable palladium catalyst such as 1,1'-bis(diphenylphosphino)ferrocene palladium dichloride, in a suitable solvent such as a mixture of 1,4-dioxane and water, in the presence of a suitable base such as sodium carbonate, and at a suitable temperature such as 60-200° C., for example about 115° C. Alternatively, this process may be carried out under microwave irradiation, at a suitable temperature such as 60-200° C., for example about 150° C.

Alternatively, compounds of formula (II) wherein $R^1$, $R^3$ and $R^4$ are as defined above, may be prepared from compounds of formula (IV)

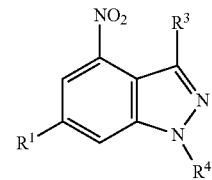

wherein $R^1$ and $R^4$ are as defined above, by (i) hydrogenation, in the presence of a suitable catalyst such as palladium on carbon, in a suitable solvent such as ethyl acetate, and at a suitable temperature such as room temperature, for example about 20° C., or (ii) by hydrogenation in a Thales H-Cube®, in the presence of a suitable catalyst such as palladium on carbon, in a suitable solvent such as ethyl acetate, at a suitable temperature such as 20-40° C., for example about 30° C., and at a suitable pressure such as 1-50 bar, for example about 30 bar.

Compounds of formula (IV), wherein $R^1$ and $R^4$ are as defined above and $R^3$ is H, may be prepared from the compound of formula (V) (which is commercially available)

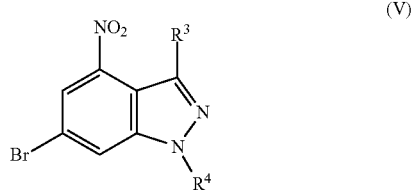

(V)

wherein $R^3$ is H and $R^4$ is as described above, by treatment with a suitable boronic acid or boronate ester such as 4-(4,4,5,5-tetramethyl-1,3,2-dioxaborolan-2-yl)-1H-indole (commercially available), in the presence of a suitable palladium catalyst such as 1,1'-bis(diphenylphosphino)ferrocene palladium dichloride, in a suitable solvent such as a mixture of 1,4-dioxane and water, in the presence of a suitable base such as sodium carbonate, and at a suitable temperature such as 60-200° C., for example about 115° C. Alternatively, this process may be carried out under microwave irradiation, at a suitable temperature such as 60-200° C., for example about 150° C.

Process b

Compounds of formula (I) wherein $R^1$, $R^2$, $R^3$ and $R^4$ are as defined above, and salts thereof, may be prepared from compounds of formula (VI)

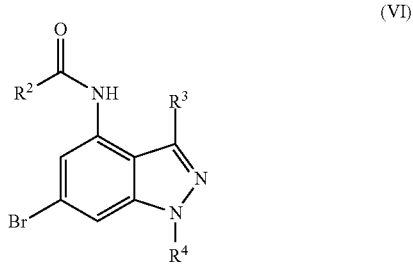

(VI)

wherein $R^2$, $R^3$ and $R^4$ are as defined above, by a process comprising treatment with a suitable boronic acid such as (2-methyl-1H-pyrrolo[2,3-b]pyridin-4-yl)boronic acid (commercially available), under microwave irradiation, in the presence of a suitable palladium catalyst such as chloro(di-2-norbornylphosphino)(2'-dimethylamino-1,1'-biphenyl-2-yl)palladium (II), in a suitable solvent such as a mixture of 1,4-dioxane and water, in the presence of a suitable base such as tri-potassium phosphate, and at a suitable temperature such as 60-200° C., for example about 120° C.

Alternatively, process b may be carried out by treatment of compounds of formula (VI) wherein $R^2$, $R^3$ and $R^4$ are as defined above, with a suitable boronic acid ester such as bis(pinacolato)diboron (commercially available), under microwave irradiation, in the presence of a suitable palladium catalyst such as 1,1'-bis(diphenylphosphino)ferrocene palladium dichloride, in a suitable solvent such as N,N-dimethylacetamide, in the presence of a suitable base such as potassium acetate, and at a suitable temperature such as 60-150° C., for example about 80° C., followed by treatment with a suitable halide such as 5-bromo-1H-pyrazo[3,4-b]pyridine (commercially available), under microwave irradiation, in the presence of a suitable palladium catalyst such as tetrakis(triphenylphosphine) palladium(0), in the presence of a suitable base such as sodium bicarbonate, and at a suitable temperature such as 60-200° C., for example about 150° C.

Compounds of formula (VI), wherein $R^2$, $R^3$ and $R^4$ are as defined above, may be prepared from the compound of formula (III) as described above, by treatment either with (i) a suitable acid of formula $R^2COOH$, wherein $R^2$ is as defined above, or (ii) by treatment with an acid chloride of formula $R^2COCl$, wherein $R^2$ is as defined above. Suitable conditions for (i) include stirring an acid such as, for example, 2-methyl-1,3-thiazole-4-carboxylic acid (commercially available), in a suitable solvent such as N,N-dimethylformamide, at a suitable temperature such as room temperature, for example about 20° C., in the presence of a coupling reagent such as O-(7-azabenzotriazol-1-yl)-N,N,N'N'-tetramethyluronium hexafluorophosphate, and in the presence of a suitable base such as N,N-diisopropylethylamine. Alternatively, (ii) may be carried out by acylation with a suitable acylating agent such as an acid chloride, in a suitable solvent such as dichloromethane, in the presence of a suitable base such as N,N-diisopropylamine, and at a suitable temperature such as room temperature, for example about 20° C.

Process c

Compounds of formula (I) wherein $R^1$, $R^2$ and $R^3$ are as defined above and $R^4$ is hydrogen, and salts thereof, may also be prepared by a process comprising deprotection of suitably protected derivatives of compounds of formula (Ia) wherein $R^1$, $R^2$ and $R^3$ are as defined above. Examples of suitable protecting groups and the means of their removal can be found in T. W. Greene and P. G. M. Wuts 'Protective Groups in Organic Synthesis' ($3^{rd}$ Ed., J. Wiley and Sons, 1999).

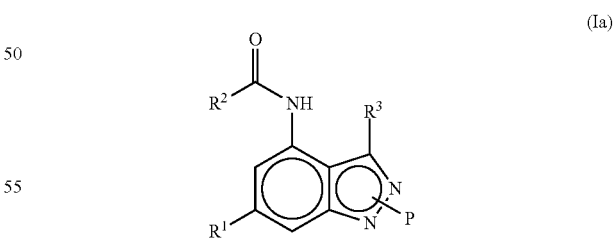

(Ia)

As an example of this, compounds of formula (I) may be prepared from compounds of formula (Ia) where the indazole ring nitrogen is protected, such as for example, with 2-tetrahydropyranyl, by deprotecting under appropriate conditions, such as treating with a strong acid, for example trifluoroacetic acid.

Compounds of formula (Ia), wherein $R^1$, $R^2$ and $R^3$ are as defined above and P is 2-tetrahydropyranyl, may be prepared from compounds of formula (VII)

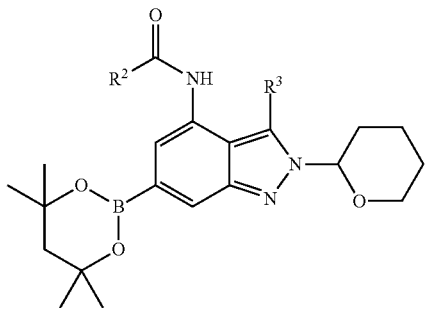

(VII)

wherein $R^2$ and $R^3$ are as defined above, by treatment with a suitable halide such as 4-bromo-1-H-pyrrolo[2,3-c]pyridine, under microwave irradiation, in the presence of a suitable palladium catalyst such as chloro[2'-(dimethylamino)-2-biphenylyl]palladium-(1R,4S)-bicyclo[2.2.1]hept-2-yl[(1S, 4R)-bicyclo[2.2.1]hept-2-yl]phosphane (1:1), in a suitable solvent such as 1,4-dioxane and water, in the presence of a suitable base such as tri-potassium phosphate, and at a suitable temperature, such as between 80-150° C., for example about 120° C.

Compounds of formula (VII) wherein $R^2$ and $R^3$ are as defined above may be prepared from compounds of formula (VIII)

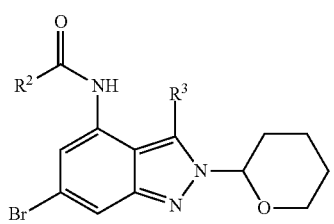

(VIII)

wherein $R^2$ and $R^3$ are as defined above, by treatment with a suitable boronate such as 4,4,4',4',6,6,6',6'-octamethyl-2,2'-bi-1,3,2-dioxaborinane (commercially available), under microwave irradiation, in the presence of a suitable palladium catalyst such as 1,1'-bis(diphenylphosphino)ferrocene palladium dichloride, in a suitable solvent such as 1,4-dioxane, in the presence of a base such as potassium acetate, and at a suitable temperature such as between 60-120° C., for example about 80° C.

Compounds of formula (VIII) wherein $R^2$ and $R^3$ are as defined above, may be prepared from compounds of formula (IX)

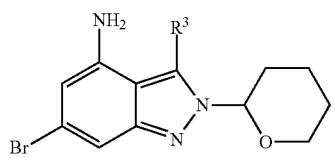

(IX)

wherein $R^3$ is as defined above, by treatment either with (i) a suitable acid of formula $R^2COOH$, wherein $R^2$ is as defined above, or (ii) by treatment with an acid chloride of formula $R^2COCl$, wherein $R^2$ is as defined above. Suitable conditions for (i) include stirring an acid such as, for example, 2-methyl-1,3-thiazole-4-carboxylic acid (commercially available), in a suitable solvent such as N,N-dimethylformamide, at a suitable temperature such as room temperature, for example about 20° C., in the presence of a coupling reagent such as O-(7-azabenzotriazol-1-yl)-N,N,N'N' tetramethyluronium hexafluorophosphate, and in the presence of a suitable base such as N,N-diisopropylethylamine. Alternatively, (ii) may be carried out by acylation with a suitable acylating agent such as an acid chloride, in a suitable solvent such as dichloromethane, in the presence of a suitable base such as N,N-diisopropylamine, and at a suitable temperature such as room temperature, for example about 20° C.

Compounds of formula (IX) wherein $R^3$ is as defined above, may be prepared from compounds of formula (X)

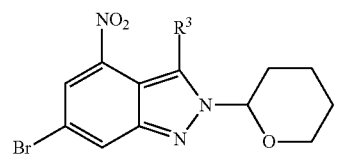

(X)

wherein $R^3$ is as described above, by reduction under suitable conditions, such as with iron filings and ammonium chloride, in a suitable solvent such as ethanol and water, and at a suitable temperature such as between 60-100° C., for example about 80° C.

Compounds of formula (X) wherein $R^3$ is as defined above, may be prepared from the compound of formula (V) as described above, by treatment with 3,4-dihydro-2H-pyran, with a suitable acid catalyst such as trifluoroacetic acid, and at a suitable temperature, such as reflux temperature.

Process d

Compounds of formula (I) wherein $R^1$, $R^2$ and $R^3$ are as defined above and $R^4$ is hydrogen, and salts thereof, may also be prepared by a process comprising deprotection of suitably protected derivatives of compounds of formula (Ia) as described above. Examples of suitable protection groups and the means of their removal can be found in T. W. Greene and P. G. M. Wuts 'Protective Groups in Organic Synthesis' (3rd Ed., J. Wiley and Sons, 1999).

As a further example of this, compounds of formula (I) may be prepared from compounds of formula (Ia) where the indazole ring nitrogen is protected (P), such as for example, with 1-phenylsulphonyl, by deprotection under appropriate conditions, such as treating with a base, for example aqueous sodium hydroxide.

Compounds of formula (Ia), wherein $R^1$, $R^2$ and $R^3$ are as defined above, may be prepared from compounds of formula (XI)

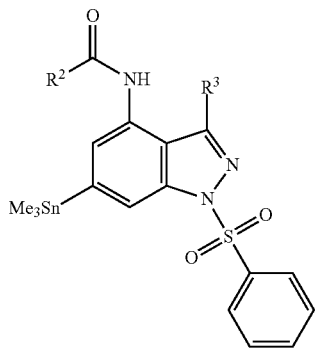
(XI)

wherein $R^2$ and $R^3$ are as defined above, by treatment with a suitable halide such as 4-bromo-1-(phenylsulphonyl)-1H-indole, in the presence of a suitable palladium catalyst such as tetrakis(triphenylphosphine) palladium (0), in a suitable solvent such as N,N-dimethylformamide, and at a suitable temperature such as 80-150° C., for example about 120° C.

Compounds of formula (XI) wherein $R^2$ and $R^3$ are as defined above, may be prepared from compounds of formula (XII)

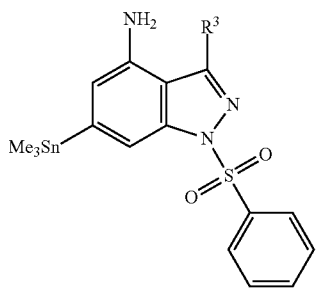
(XII)

wherein $R^3$ is defined as above, by (i) treatment with an acid of formula $R^2$COOH, wherein $R^2$ is as defined above, or (ii) by treatment with an acid chloride of formula $R^2$COCl, wherein $R^2$ is as defined above. Suitable conditions for (i) include stirring in a suitable solvent such as N,N-dimethylformamide, at a suitable temperature such as room temperature, for example about 20° C., in the presence of a coupling reagent such as O-(7-azabenzotriazol-1-yl)-N,N,N'N'-tetramethyluronium hexafluorophosphate, and in the presence of a suitable base such as N,N-diisopropylethylamine. Alternatively, (ii) may be carried out by treatment with an acylating agent such as an acid chloride, in a suitable solvent such as dichloromethane, in the presence of a suitable base such as N,N-diisopropylethylamine, and at a suitable temperature such as room temperature, for example about 20° C.

Compounds of formula (XII) wherein $R^3$ is as defined above, may be prepared from compounds of formula (XIII)

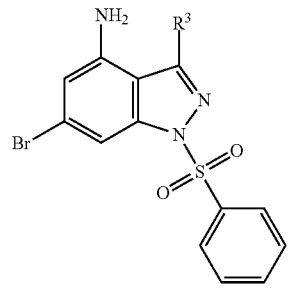
(XIII)

wherein $R^3$ is as defined above, by treatment with a suitable stannane such as hexamethyldistannane, under microwave irradiation, in the presence of a suitable palladium catalyst such as tetrakis(triphenylphosphine)palladium (0), in a suitable solvent such as toluene, in the presence of a suitable base such as triethylamine, and at a suitable temperature such as 80-150° C., for example about 120° C.

Process e

Compounds of formula (I) wherein $R^1$, $R^2$ and $R^3$ are as defined above and $R^4$ is methyl, and salts thereof, may be prepared from compounds of formula (XIV)

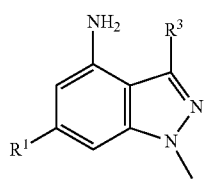
(XIV)

wherein $R^1$ and $R^3$ are as defined above, by a process comprising (i) treatment with an acid of formula $R^2$COOH, wherein $R^2$ is as defined above, or (ii) treatment with an acid chloride of formula $R^2$COCl, wherein $R^2$ is as defined above. Suitable conditions for (i) include stirring in a suitable solvent such as N,N-dimethylformamide, at a suitable temperature such as room temperature, for example about 20° C., in the presence of a coupling reagent such as O-(7-azabenzotriazol-1-yl)-N,N,N'N'-tetramethyluronium hexafluorophosphate, and in the presence of a suitable base such as N,N-diisopropylethylamine. Alternatively, (ii) may be carried out by treatment with an acylating agent such as an acid chloride, in a suitable solvent such as dichloromethane, in the presence of a suitable base such as N,N-diisopropylethylamine, and at a suitable temperature such as room temperature, for example about 20° C.

Compounds of formula (XIV) wherein $R^1$ and $R^3$ are as defined above, may be prepared from compounds of formula (XV)

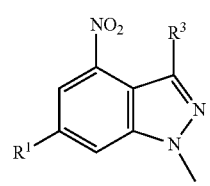
(XV)

wherein $R^1$ and $R^3$ are as defined above, by hydrogenation, in the presence of a suitable catalyst such as palladium on carbon, in a suitable solvent such as ethyl acetate, and at a suitable temperature such as room temperature, for example about 20° C.

Compounds of formula (XV), wherein $R^1$ and $R^3$ are as defined above, may be prepared from compounds of formula (XVI)

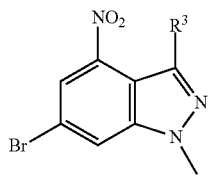
(XVI)

wherein $R^3$ is as defined above, by treatment with a suitable boronic acid or boronate ester such as 1H-indol-4-ylboronic acid (commercially available), under microwave irradiation, in the presence of a suitable palladium catalyst such as 1,1'-bis(diphenylphosphino)ferrocene palladium dichloride, in a suitable solvent such as propan-2-ol, in the presence of a suitable base such as sodium hydrogencarbonate, and at a suitable temperature such as 60-200° C., for example about 150° C.

Compounds of formula (XVI), wherein $R^3$ is as described above, may be prepared from the compound of formula (V) as described above, by treatment with a suitable alkylating agent such as iodomethane, in a suitable solvent such as tetrahydrofuran, in the presence of a suitable base such as sodium hydride, and at a suitable temperature such as between −10- 20° C., for example about 0° C.

Process f

Compounds of formula (I) wherein $R^1$, $R^2$ and $R^3$ are as defined above and $R^4$ is methyl, and salts thereof, may be prepared from compounds of formula (XVII)

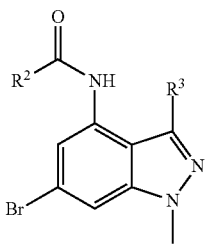
(XVII)

wherein $R^2$ and $R^3$ are as defined above, by a process comprising treatment with a suitable boronic acid or boronate ester such as 4-(4,4,5,5-tetramethyl-1,3,2-dioxaborolan-2-yl)-1H-indole (commercially available), under microwave irradiation, in the presence of a suitable palladium catalyst such as 1,1'-bis(diphenylphosphino)ferrocene palladium dichloride, in a suitable solvent such as a mixture of 1,4-dioxane and water, in the presence of a suitable base such as sodium carbonate, and at a suitable temperature such as 60-200° C., for example about 150° C.

Compounds of formula (XVII) wherein $R^2$ and $R^3$ are as defined above, may be prepared from compounds of formula (XVIII)

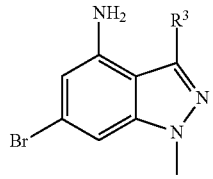
(XVIII)

wherein $R^3$ is as defined as above, by (i) treatment with an acid of formula $R^2$COOH, wherein $R^2$ is as defined above, or (ii) by treatment with an acid chloride of formula $R^2$COCl, wherein $R^2$ is as defined above. Suitable conditions for (i) include stirring in a suitable solvent such as N,N-dimethylformamide, at a suitable temperature such as room temperature, for example about 20° C., in the presence of a coupling reagent such as O-(7-azabenzotriazol-1-yl)-N,N,N'N' tetramethyluronium hexafluorophosphate, and in the presence of a suitable base such as N,N-diisopropylethylamine. Alternatively, (ii) may be carried out by treatment with an acylating agent such as an acid chloride, in a suitable solvent such as dichloromethane, in the presence of a suitable base such as N,N-diisopropylethylamine, and at a suitable temperature such as room temperature, for example about 20° C.

Compounds of formula (XVIII), wherein $R^3$ is as described above, may be prepared from the compound of formula (XIX) (which is commercially available)

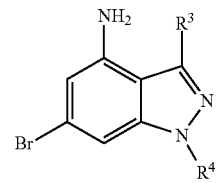
(XIX)

wherein $R^3$ and $R^4$ are H, by treatment with a suitable alkylating agent such as iodomethane, in a suitable solvent such as tetrahydrofuran, in the presence of a suitable base such as sodium hydride, and at a suitable temperature such as between −10-20° C., for example about 0° C.

Process q

Compounds of formula (I) wherein $R^1$, $R^2$ and $R^4$ are as defined above and $R^3$ is F, and salts thereof, may be prepared from compounds of formula (XX)

(XX)

wherein $R^1$ and $R^4$ are as defined above, by a process comprising (i) treatment with an acid of formula $R^2$COOH, wherein $R^2$ is as defined above, or (ii) treatment with an acid chloride of formula $R^2$COCl, wherein $R^2$ is as defined above. Suitable conditions for (i) include stirring in a suitable solvent such as N,N-dimethylformamide, at a suitable temperature such as room temperature, for example about 20° C., in the presence of a coupling reagent such as O-(7-azabenzotriazol- 1-yl)-N,N,N'N'-tetramethyluronium hexafluorophosphate, and in the presence of a suitable base such as N,N-diisopropylethylamine. Alternatively, (i) may be carried out by treatment with an acylating agent such as an acid chloride, in a suitable solvent such as dichloromethane, in the presence of a suitable base such as N,N-diisopropylethylamine, and at a suitable temperature such as room temperature, for example about 20° C.

Compounds of formula (XX) wherein $R^4$ is as defined above, may be prepared from compounds of formula (XXI)

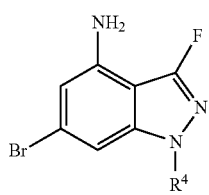

(XXI)

wherein $R^4$ is as defined above, by treatment with a suitable boronic acid or boronate ester such as 4-(4,4,5,5-tetramethyl-1,3,2-dioxaborolan-2-yl)-1H-indole (commercially available), under microwave irradiation, in the presence of a suitable palladium catalyst such as 1,1'-bis(diphenylphosphino)ferrocene palladium dichloride, in a suitable solvent such as a mixture of 1,4-dioxane and water, in the presence of a suitable base such as sodium carbonate, and at a suitable temperature such as 60-200° C., for example about 150° C.

Compounds of formula (XXI) wherein $R^4$ is as defined above, may be prepared from compounds of formula (XXII)

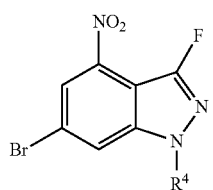

(XXII)

wherein $R^4$ is as described above, by treatment with a suitable reducing agent such as sodium dithionite, in a suitable solvent such as methanol, at a suitable temperature such as between 0-50° C., for example about 20° C.

Compounds of formula (XXII) wherein $R^4$ is H, may be prepared from the compound of formula (V) as described above (which is commercially available), by treatment with a suitable fluorinating agent such as 1-(chloromethyl)-4-fluoro-1,4-diazoniabicyclo[2.2.2]octane (commercially available), under microwave irradiation, in a suitable solvent such as acetonitrile and acetic acid, and at a suitable temperature such as between 80-180° C., for example 150° C.

Process h

Compounds of formula (I) wherein $R^1$, $R^3$ and $R^4$ are as defined above and $R^2$ is 5-membered heteroaryl wherein the 5-membered heteroaryl contains from one to three heteroatoms independently selected from oxygen, nitrogen and sulphur and is optionally substituted by —$(CH_2)_mNR^{10}R^{11}$, and salts thereof, may be prepared from compounds of formula (XXIIIA) or (XXIIIB)

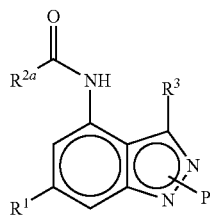

(XXIIIA)

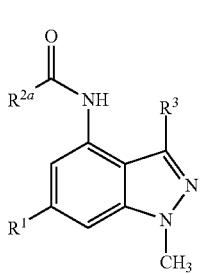

(XXIIIB)

wherein $R^1$ and $R^3$ are as defined above and $R^{2a}$ is 5-membered heteroaryl wherein the 5-membered heteroaryl contains from one to three heteroatoms independently selected from oxygen, nitrogen and sulphur and is optionally substituted by —$(CH_2)_mX$, wherein X is a leaving group, for example Cl, and wherein P is a protecting group, for example benzenesulphonyl, by a process comprising treatment with an amine of formula $NHR^{10}R^{11}$ in the presence of a suitable base such as DIPEA, a suitable activating agent such as sodium iodide and in a suitable solvent such as acetonitrile, heating to a suitable temperature such as 20° C.-120° C., for example about 70° C.

As the skilled person will appreciate, in the compound of formula (XXIIIA), the protecting group P may be on the 1 or 2 position of the indazole. Following reaction with the amine, the protecting group P may be removed by deprotection under appropriate conditions.

Compounds of formula (XXIIIA) and (XXIIIB) wherein $R^1$ and $R^3$ are as defined above and $R^{2a}$ is 5-membered heteroaryl wherein the 5-membered heteroaryl contains from one to three heteroatoms independently selected from oxygen, nitrogen and sulphur and is optionally substituted by —$(CH_2)_mX$, wherein X is a leaving group, for example Cl, and wherein P is a protecting group, for example benzenesulphonyl, may be prepared from compounds of formula (XXIVA) and (XXIVB)

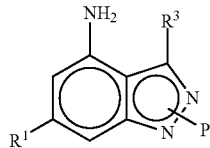

(XXIVA)

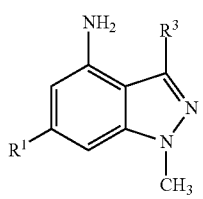

(XXIVB)

wherein $R^1$ and $R^3$ are as defined above, by a process comprising treatment with an acid chloride of formula $R^{2a}COCl$, wherein $R^{2a}$ is as defined above, in the presence of a suitable base such as pyridine, in a suitable solvent such as DCM, and at a suitable temperature such as room temperature.

Compounds of formula $R^{2a}COCl$ wherein $R^{2a}$ is as defined above, can be prepared from compounds of formula $R^{2a}CO_2H$ wherein $R^{2a}$ is as defined above, by treatment with thionyl chloride in a suitable solvent such as chloroform, in the presence of DMF (catalytic quantity) and heating to a suitable temperature such as reflux.

Thus, in one embodiment, the invention provides a process for preparing a compound of the invention comprising:
a) reacting a compound of formula (II)

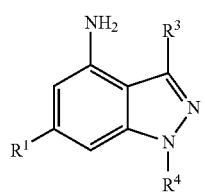

(II)

wherein $R^1$, $R^3$ and $R^4$ are as defined above, with (i) an acid of formula $R^2COOH$, wherein $R^2$ is as defined above, or (ii) an acid chloride of formula $R^2COCl$, wherein $R^2$ is as defined above;
b) reacting a compound of formula (VI)

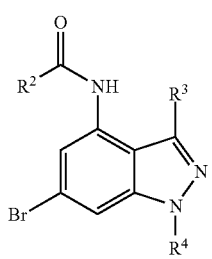

(VI)

wherein $R^2$, $R^3$ and $R^4$ are as defined above, with a suitable boronic acid;
c) deprotection of a suitably protected derivative of a compound of formula (Ia)

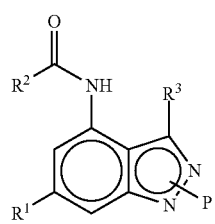

(Ia)

wherein $R^1$, $R^2$, $R^3$ and $R^4$ are as defined above;
d) for a compound of formula (I) wherein $R^1$, $R^2$ and $R^3$ are as defined above and $R^4$ is methyl, or a salt thereof, reacting a compound of formula (XIV)

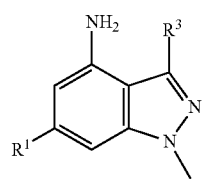

(XIV)

wherein $R^1$ and $R^3$ are as defined above, with (i) an acid of formula $R^2COOH$, wherein $R^2$ is as defined above, or (ii) an acid chloride of formula $R^2COCl$, wherein $R^2$ is as defined above;
e) reacting a compound of formula (XVII)

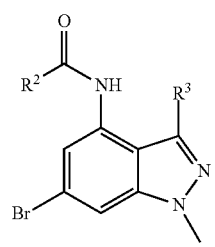

(XVII)

wherein $R^2$ and $R^3$ are as defined above, with a suitable boronic acid;
f) for a compound of formula (I) wherein $R^1$, $R^2$ and $R^4$ are as defined above and $R^3$ is F, or a salt thereof, reacting a compound of formula (XX)

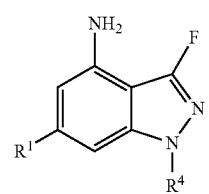

(XX)

wherein $R^1$ and $R^4$ are as defined above, with (i) an acid of formula $R^2COOH$, wherein $R^2$ is as defined above, or (ii) an acid chloride of formula $R^2COCl$, wherein $R^2$ is as defined above; or
g) for a compound of formula (I) wherein $R^1$, $R^3$ and $R^4$ are as defined above and $R^2$ is 5-membered heteroaryl wherein the 5-membered heteroaryl contains one or two heteroatoms independently selected from oxygen, nitrogen and sulphur and is optionally substituted by —(CH$_2$)$_m$NR$^{10}$R$^{11}$, and salts thereof, reacting a compound of formula (XXIIIA) or (XXIIIB)

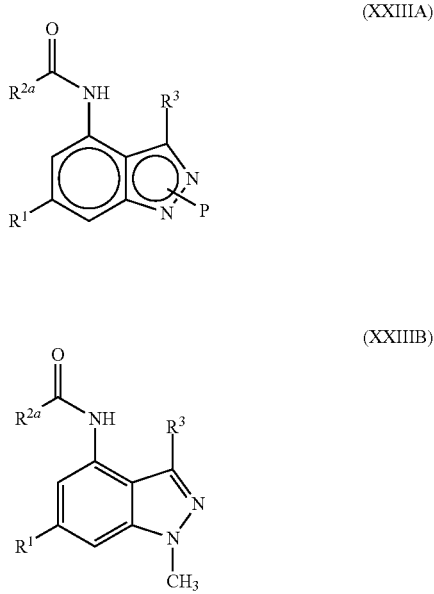

wherein R$^1$ and R$^3$ are as defined above and R$^{2a}$ is 5-membered heteroaryl wherein the 5-membered heteroaryl contains one or two heteroatoms independently selected from oxygen, nitrogen and sulphur and is optionally substituted by —(CH$_2$)$_{mq}$X, wherein X is a leaving group, and wherein P is a protecting group, with an amine of formula NHR$^{10}$R$^{11}$, followed where necessary by deprotection.

Methods of Use

The compounds of the invention are inhibitors of PI3-kinase activity. Compounds which are PI3-kinase inhibitors may be useful in the treatment of disorders wherein the underlying pathology is (at least in part) attributable to inappropriate PI3-kinase activity, such as asthma and chronic obstructive pulmonary disease (COPD). "Inappropriate PI3-kinase activity" refers to any PI3-kinase activity that deviates from the normal PI3-kinase activity expected in a particular patient. Inappropriate PI3-kinase may take the form of, for instance, an abnormal increase in activity, or an aberration in the timing and or control of PI3-kinase activity. Such inappropriate activity may result then, for example, from overexpression or mutation of the protein kinase leading to inappropriate or uncontrolled activation. Accordingly, in another aspect the invention is directed to methods of treating such disorders.

Such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

The methods of treatment of the invention comprise administering a safe and effective amount of a compound of formula (I) or a pharmaceutically acceptable salt thereof to a patient in need thereof. Individual embodiments of the invention include methods of treating any one of the above-mentioned disorders by administering a safe and effective amount of a compound of formula (I) or a pharmaceutically acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human (including adults and children) or other animal. In one embodiment, "patient" refers to a human.

The compounds of formula (I) or pharmaceutically acceptable salts thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formula (I) or pharmaceutically acceptable salts thereof may be administered orally. In another embodiment, the compounds of formula (I) or pharmaceutically acceptable salts thereof may be administered by inhalation. In a further embodiment, the compounds of formula (I) or pharmaceutically acceptable salts thereof may be administered intranasally. Preferably, the compounds of formula (I) or pharmaceutically acceptable salts thereof are administered by inhalation.

The compounds of formula (I) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formula (I) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formula (I) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight, for example from 1 mg to 10 mg per kg of total body weight. For example, daily dosages for oral administration may be from 0.5 mg to 2 g per patient, such as 10 mg to 1 g per patient.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

The invention thus provides a method of treating a disorder mediated by inappropriate PI3-kinase activity comprising administering a safe and effective amount of a compound of formula (I) or a pharmaceutically acceptable salt thereof to a patient in need thereof.

In one embodiment, the disorder mediated by inappropriate PI3-kinase activity is selected from the group consisting of respiratory diseases (including asthma and chronic obstructive pulmonary disease (COPD)); allergic diseases (including allergic rhinitis and atopic dermatitis); autoimmune diseases (including rheumatoid arthritis and multiple sclerosis); inflammatory disorders (including inflammatory bowel disease); cardiovascular diseases (including thrombosis and atherosclerosis); hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain (including pain associated with rheumatoid arthritis or osteoarthritis, back pain, general inflammatory pain, post hepatic neuralgia, diabetic neuropathy, inflammatory neuropathic pain (trama), trigeminal neuralgia and central pain).

In one embodiment, the disorder mediated by inappropriate PI3-kinase activity is a respiratory disease. In a further embodiment, the disorder mediated by inappropriate PI3-kinase activity is asthma. In a further embodiment, the disorder mediated by inappropriate PI3-kinase activity is chronic obstructive pulmonary disease (COPD).

In one embodiment, the disorder mediated by inappropriate PI3-kinase activity is pain.

In one embodiment, the invention provides a compound of formula (I) or a pharmaceutically acceptable salt thereof for use in medical therapy. In another embodiment, the invention provides a compound of formula (I) or a pharmaceutically acceptable salt thereof for use in the treatment of a disorder mediated by inappropriate PI3-kinase activity. In a further embodiment, the invention provides the use of a compound of formula (I) or a pharmaceutically acceptable salt thereof in the manufacture of a medicament for use in the treatment of a disorder mediated by inappropriate PI3-kinase activity.

Compositions

The compounds of formula (I) and pharmaceutically acceptable salts thereof will normally, but not necessarily, be formulated into pharmaceutical compositions prior to administration to a patient. Accordingly, in another aspect the invention is directed to pharmaceutical compositions comprising a compound of formula (I) or a pharmaceutically acceptable salt thereof and one or more pharmaceutically-acceptable excipients.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.5 mg to 1 g, or from 1 mg to 700 mg, or from 5 mg to 100 mg of a compound of formula (I) or a pharmaceutically acceptable salt thereof.

The pharmaceutical compositions of the invention typically contain one compound of formula (I) or a pharmaceutically acceptable salt thereof.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically-acceptable eg of sufficiently high purity.

The compound of formula (I) or a pharmaceutically acceptable salt thereof and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment, the compounds of formula (I) or pharmaceutically acceptable salts thereof will be formulated for oral administration. In another embodiment, the compounds of formula (I) or pharmaceutically acceptable salts thereof will be formulated for inhaled administration. In a further embodiment, the compounds of formula (I) or pharmaceutically acceptable salts thereof will be formulated for intranasal administration.

Preferably, the compounds of formula (I) or pharmaceutically acceptable salts thereof will be formulated for inhaled administration.

In one aspect, the invention is directed to a solid oral dosage form such as a tablet or capsule comprising a safe and effective amount of a compound of formula (I) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formula (I) or pharmaceutically acceptable salts thereof may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of formula (I) or pharmaceutically acceptable salts thereof may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a pharmaceutically acceptable salt thereof. Syrups can be prepared by dissolving the compound of formula (I) or a pharmaceutically acceptable salt thereof in a suitably flavored aqueous solution, while elixirs are prepared through the use of a non-toxic alcoholic vehicle. Suspensions can be formulated by dispersing the compound of formula (I) or a pharmaceutically acceptable salt thereof in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation, for example, as a dry powder, an aerosol, a suspension, or a solution composition. Preferably, the invention is directed to a dry powder composition adapted for inhalation comprising compound of formula (I) or a pharmaceutically acceptable salt thereof.

Dry powder compositions for delivery to the lung by inhalation typically comprise a compound of formula (I) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 μg-10 mg of the compound of formula (I) or a pharmaceutically acceptable salt thereof.

Aerosols may be formed by suspending or dissolving a compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 20 μg to 10 mg of the compound of formula (I) or pharmaceutically acceptable salt thereof. Alternatively, the compound of formula (I) or pharmaceutically acceptable salt thereof may be presented without excipients such as lactose.

The proportion of the active compound of formula (I) or pharmaceutically acceptable salt thereof in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 μg to 10 mg, preferably from 20 μg to 2000 μg, more preferably from about 20 μg to 500 μg of a compound of formula (I). Administration may be once daily or several times daily, for example 2, 3, 4 or 8 times, giving for example 1, 2 or 3 doses each time. The overall daily dose with an aerosol will be within the range from 100 μg to 10 mg, preferably from 200 μg to 2000 μg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channeling device. Suitable channeling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example of a bulk manufacturing method for preparing solution aerosol formulations, a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a compound of formula (I) or a pharmaceutically acceptable salt thereof may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formula (I) or pharmaceutically acceptable salt thereof may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of formula (I) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formula (I) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, such as antibiotics or antivirals, or antihistamines. The invention thus provides, in a further aspect, a combination comprising a compound of formula (I) or a pharmaceutically acceptable salt thereof together with one or more other therapeutically active agents, for example selected from an anti-inflammatory agent, such as a corticosteroid or an NSAID, an anticholinergic agent, a $\beta_2$-adrenoreceptor agonist, an antiinfective agent, such as an antibiotic or an antiviral, or an antihistamine. One embodiment of the invention encompasses combinations comprising a compound of formula (I) or a pharmaceutically acceptable salt thereof together with a $\beta_2$-adrenoreceptor agonist, and/or an anticholinergic, and/or a PDE-4 inhibitor, and/or an antihistamine.

Certain compounds of the invention may show selectivity for PI3Kδ over other PI3-kinases. The invention thus provides, in a further aspect, a combination comprising a compound of formula (I) or a pharmaceutically acceptable salt thereof which is selective for PI3Kδ together with a compound or pharmaceutically acceptable salt thereof which is selective for another PI3-kinase, for example PI3Kγ.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of formula (I) or a pharmaceutically acceptable salt thereof together with a β-adrenoreceptor agonist.

Examples of β$_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single diastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting β$_2$-adrenoreceptor agonists, for example, compounds which provide effective bronchodilation for about 12 hrs or longer, are preferred.

Other β$_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of β$_2$-adrenoreceptor agonists include:
3-(4-{[6-({(2R)-2-hydroxy-2-[4-hydroxy-3-(hydroxymethyl)phenyl]ethyl}amino)hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl)amino]-1-hydroxyethyl}-2-(hydroxymethyl)phenol;
4-{(1R)-2-[(6-{4-[3-(cyclopentylsulfonyl)phenyl]butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl]phenyl]formamide;
N-2{2-[4-(3-phenyl-4-methoxyphenyl)aminophenyl]ethyl}-2-hydroxy-2-(8-hydroxy-2(1H)-quinolinon-5-yl)ethylamine; and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The β$_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Suitable corticosteroids which may be used in combination with the compounds of formula (I) or pharmaceutically acceptable salts thereof are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium chromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

In one embodiment, the invention provides the use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a phthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:
(3-endo)-3-(2,2-di-2-thienylethenyl)-8,8-dimethyl-8-azoniabicyclo[3.2.1]octane iodide;
(3-endo)-3-(2-cyano-2,2-diphenylethyl)-8,8-dimethyl-8-azoniabicyclo[3.2.1]octane bromide;
4-[hydroxy(diphenyl)methyl]-1-{2-[(phenylmethyl)oxy]ethyl}-1-azoniabicyclo[2.2.2]octane bromide; and
(1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or (endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of formula (I) or a pharmaceutically acceptable salt thereof together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I) or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., J. Med. Chem. 46:3957-3960 (2003).

The invention thus provides, in a further aspect, a combination comprising a compound of formula (I) or a pharmaceutically acceptable salt thereof together with a PDE4 inhibitor.

The invention thus provides, in a further aspect, a combination comprising a compound of formula (I) or a pharmaceutically acceptable salt thereof together with a $\beta_2$-adrenoreceptor agonist.

The invention thus provides, in a further aspect, a combination comprising a compound of formula (I) or a pharmaceutically acceptable salt thereof together with a corticosteroid.

The invention thus provides, in a further aspect, a combination comprising a compound of formula (I) or a pharmaceutically acceptable salt thereof together with a non-steroidal GR agonist.

The invention thus provides, in a further aspect, a combination comprising a compound of formula (I) or a pharmaceutically acceptable salt thereof together with an anticholinergic.

The invention thus provides, in a further aspect, a combination comprising a compound of formula (I) or a pharmaceutically acceptable salt thereof together with an antihistamine.

The invention thus provides, in a further aspect, a combination comprising a compound of formula (I) or a pharmaceutically acceptable salt thereof together with a PDE4 inhibitor and a $\beta_2$-adrenoreceptor agonist.

The invention thus provides, in a further aspect, a combination comprising a compound of formula (I) or a pharmaceutically acceptable salt thereof together with an anticholinergic and a PDE-4 inhibitor.

In a preferred aspect, the invention provides a combination comprising a compound of formula (I) or a pharmaceutically acceptable salt thereof together with a corticosteroid.

In a further preferred aspect, the invention provides a combination comprising a compound of formula (I) or a pharmaceutically acceptable salt thereof together with a $\beta_2$-adrenoreceptor agonist.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of formula (I) or a pharmaceutically acceptable salt thereof together with another therapeutically active agent.

The invention thus provides, in a further aspect, a pharmaceutical composition comprising a combination of a compound of formula (I) or a pharmaceutically acceptable salt thereof together with a PDE4 inhibitor.

The invention thus provides, in a further aspect, a pharmaceutical composition comprising a combination of a compound of formula (I) or a pharmaceutically acceptable salt thereof together with a $\beta_2$-adrenoreceptor agonist.

The invention thus provides, in a further aspect, a pharmaceutical composition comprising a combination of a compound of formula (I) or a pharmaceutically acceptable salt thereof together with a corticosteroid.

The invention thus provides, in a further aspect, a pharmaceutical composition comprising a combination of a compound of formula (I) or a pharmaceutically acceptable salt thereof together with a non-steroidal GR agonist.

The invention thus provides, in a further aspect, a pharmaceutical composition comprising a combination of a compound of formula (I) or a pharmaceutically acceptable salt thereof together with an anticholinergic.

The invention thus provides, in a further aspect, a pharmaceutical composition comprising a combination of a compound of formula (I) or a pharmaceutically acceptable salt thereof together with an antihistamine.

The invention thus provides, in a further aspect, a pharmaceutical composition comprising a combination of a compound of formula (I) or a pharmaceutically acceptable salt thereof together with a PDE4 inhibitor and a $\beta_2$-adrenoreceptor agonist.

The invention thus provides, in a further aspect, a pharmaceutical composition comprising a combination of a compound of formula (I) or a pharmaceutically acceptable salt thereof together with an anticholinergic and a PDE4 inhibitor.

In a preferred aspect, the invention provides a pharmaceutical composition comprising a combination of a compound of formula (I) or a pharmaceutically acceptable salt thereof together with a corticosteroid.

In a further preferred aspect, the invention provides a pharmaceutical composition comprising a combination of a compound of formula (I) or a pharmaceutically acceptable salt thereof together with a $\beta_2$-adrenoreceptor agonist.

The invention will now be illustrated by way of the following non-limiting examples.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

General Methods
Florisil
References to Florisil generally refer to the magnesium silicate Florisil®, for example 60-100 mesh (available from Aldrich).

'Hydrophobic Frit'
This refers to a Whatman PTFE filter medium (frit), pore size 5.0 micrometres, housed in a polypropylene tube.

SPE
Solid phase extraction column. Unless otherwise specified the solid phase will be silica gel (eg. IST Isolute® silica columns). Aminopropyl ($NH_2$) SPE refers to a silica SPE column with aminopropyl residues immobilised on the solid phase (eg. IST Isolute® columns). C18 SPE refers to reverse phase SPE columns (eg Varian Bond Elut C18 columns).

SCX
Solid phase extraction (SPE) column with benzene sulfonic acid residues immobilised on the solid phase (eg. IST Isolute™ columns).

LC/MS (Liquid Chromatography/Mass Spectroscopy)
LC/MS analysis has been carried out using one of the methods listed below.

LC/MS Method A
Waters ZQ mass spectrometer operating in positive ion electrospray mode, mass range 100-1000 amu.
UV wavelength: 215-330 nm
Column: 3.3 cm×4.6 mm ID, 3 μm ABZ+PLUS
Flow Rate: 3 ml/min
Injection Volume: 5 μl
Solvent A: 95% acetonitrile+0.05% of a 1% v/v solution of formic acid in water
Solvent B: 0.1% v/v solution of formic acid in 10 mM aqueous ammonium acetate
Gradient: Mixtures of Solvent A and Solvent B are used according to the following gradient profiles (expressed as % Solvent A in the mixture): 0% A/0.7 min, 0-100% A/3.5 min, 100% A/0.4 min, 100-0% A/0.2 min LC/MS Method B
LC/MS instrumentation consists of the following:
Column: Acquity HPLC BEH $C_{18}$ 1.7 μm 2.1 mm×50 mm. Column oven set to 40 degrees centigrade
Solvent A: Water 0.1% Formic Acid+10 mM Ammonium Acetate
Solvent B: MeCN:Water 95:5+0.05% Formic Acid

| Injection volume: | 0.5 μl |
| --- | --- |
| Injection technique: | Partial loop overfill |
| UV detection: | 220 to 330 nm |
| UV sampling rate: | 40 points per second |
| MS scan range: | 100 to 1000 amu |
| MS scanning rate: | 0.2 second scan with a 0.1 second inter scan delay |
| MS scan function: | Electrospray with pos neg switching |
| Cycle time: | 2 min and 30 seconds |

Gradient:

| Time | Flow ml/min | % A | % B |
| --- | --- | --- | --- |
| 0 | 1 | 97 | 3 |
| 0.1 | 1 | 97 | 3 |
| 1.4 | 1 | 0 | 100 |
| 1.9 | 1 | 0 | 100 |
| 2 | 1 | 97 | 3 |

LC/MS Method C
The HPLC analysis was conducted on a Sunfire C18 column (30 mm×4.6 mm i.d. 3.5 μm packing diameter) at 30 degrees centigrade.
Solvent A=0.1% v/v solution of Formic Acid in Water.
Solvent B=0.1% v/v solution of Formic Acid in Acetonitrile.
The gradient employed was:

| Time (min) | Flow Rate (ml/min) | % A | % B |
| --- | --- | --- | --- |
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.

LC/MS Method D
The HPLC analysis was conducted on a Acquity HPLC BEH C18 column (50 mm×2.1 mm i.d. 1.7 μm packing diameter) at 40 degrees centigrade.
Solvent A=0.1% v/v solution of Formic Acid in Water.
Solvent B=0.1% v/v solution of Formic Acid in Acetonitrile.
The gradient employed was:

| Time (min) | Flow Rate (ml/min) | % A | % B |
| --- | --- | --- | --- |
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

Mass Directed Automated Preparative HPLC
The methods for the mass-directed automated preparative HPLC used for the purification of compounds are described below:

Mass Directed Automated Preparative HPLC Column, Conditions and Eluent
Method A
Columns
Small Scale Prep Column
Supelcosil ABZ+Plus column whose dimensions are 21.2 mm internal diameter by 100 mm in length. The stationary phase particle size is 5 μm.
Large Scale Prep Column
Supelcosil ABZ+Plus column whose dimensions are 30.0 mm internal diameter by 150 mm in length. The stationary phase particle size is 12 μm.
Solvents
A: Aqueous solvent=Water+0.1% Formic Acid
B: Organic solvent=MeCN:Water 95:5+0.05% Formic Acid
Make up solvent to ZQ=methanol:Water 80:20+50 mMol Ammonium Acetate
2767 Needle rinse solvent=methanol:Water:DMSO 80:10:10
Methods for Small Scale Prep for Up to 30 mg
There are ten methods available for use. The choice of method is dependant on the analytical retention time of the compound of interest.
Five methods have a 15-minute runtime, this comprises of a 10-minute gradient followed by a 5-minute column flush and re-equilibration step. The other five have a 25-minute runtime. Here the methods have the same starting and end points for the organic content of B but the gradients have been extended over a 20-minute period to provide greater chromatographic resolution.
compound retention time 1.5-2.2 mins=00-30% B
compound retention time 2.0-2.8 mins=10-40% B
compound retention time 2.5-3.0 mins=15-55% B
compound retention time 2.8-4.0 mins=30-80% B
compound retention time 3.8-5.5 mins=60-90% B
Flow rates for the above methods are 20 ml/min
Methods for Large Scale Prep for Up to 90 mgs
Due to the different column dimension and the phase particle size the percentage organic content varies slightly to the small scale methods. As for small scale there are ten methods available for use. The choice of method is dependant on the analytical retention time of the compound of interest.
Five methods have a 15-minute runtime, which comprises of a 10-minute gradient followed by a 5-minute column flush and re-equilibration step. The other five have a 25-minute runtime. Here the methods have the same starting and end points for the organic content of B but the gradients have been extended over a 20-minute period to provide greater chromatographic resolution.
compound retention time 1.5-2.2 mins=00-30% B
compound retention time 2.0-2.8 mins=10-40% B
compound retention time 2.5-3.0 mins=25-55% B
compound retention time 2.8-4.0 mins=40-75% B
compound retention time 3.8-5.5 mins=60-90% B
Flow rates for the above methods are 40 ml/min
It is thought that basic compounds isolated by this method are formate salts.
Mass Directed Automated Preparative HPLC Column, Conditions and Eluent
Method B
Column details: Zorbax EclipsexDB-C18 prep HT (dimensions 212×100 mm, 5 um packing)
Software/hardware: Agilent 1100 series LC/MSD hardware, chemstation 32 purification software
Solvents:
A=0.1% v/v solution of Trifluoroacetic Acid in Water.
B=0.1% v/v solution of Trifluoroacetic Acid in Acetonitrile.
20 ml/min solvent speed, gradient elution:
1 min 90% Water (0.1% TFA):10% MECN (0.1% TFA) increasing over 9 min to 5% Water (0.1% TFA):95% MECN (0.1% TFA) to elute compounds.
Or 1 min 70% Water (0.1% TFA):30% MECN (0.1% TFA) increasing over 9 min to 5% Water (0.1% TFA):95% MECN (0.1% TFA) to elute compounds.
Collects on uv and/or mass ion trigger
Mass Directed Automated Preparative HPLC column, Conditions and Eluent
Method C
Column Details:xBRIDGE C18 column (100 mm×19 mm id 5 uM packing diameter)
Solvents
A=10 mM ammonium bicarbonate in water adjusted to pH 10 with aq. ammonia solution
B=Acetonitrile
The UV detection was an averaged signal from wavelength of 210 nm to 350 nm and mass spectra were recorded on a mass spectrometer using an alternate-scan positive and negative mode electrospray ionization.
Mass Directed Automated Preparative HPLC Column, Conditions and Eluent
Method D
The HPLC analysis was conducted on a Sunfire C18 column (150 mm×30 mm i.d. 5 μm packing diameter) at ambient temperature.
The solvents employed were:
A=0.1% v/v solution of formic acid in water.
B=0.1% v/v solution of formic acid in acetonitrile.
The gradient employed was:

| Time (min) | Flow Rate (ml/min) | % A | % B |
| --- | --- | --- | --- |
| 0 | 40 | 70 | 30 |
| 1 | 40 | 70 | 30 |
| 20 | 40 | 15 | 85 |
| 20.5 | 40 | 1 | 99 |
| 25 | 40 | 1 | 99 |

The UV detection was an averaged signal from wavelength of 210 nm to 350 nm and mass spectra were recorded on a mass spectrometer using alternate-scan positive and negative mode electrospray ionisation.
Mass Directed Automated Preparative HPLC Column, Conditions and Eluent
Method E
The HPLC analysis was conducted on a Sunfire C18 column (150 mm×30 mm i.d. 5 μm packing diameter) at ambient temperature.
The solvents employed were:
A=0.1% v/v solution of formic acid in water.
B=0.1% v/v solution of formic acid in acetonitrile.
The gradient employed was:

| Time (min) | Flow Rate (ml/min) | % A | % B |
| --- | --- | --- | --- |
| 0 | 40 | 70 | 30 |
| 1 | 40 | 70 | 30 |
| 10 | 40 | 15 | 85 |
| 10.5 | 40 | 1 | 99 |
| 15 | 40 | 1 | 99 |

The UV detection was an averaged signal from wavelength of 210 nm to 350 nm and mass spectra were recorded on a mass spectrometer using alternate-scan positive and negative mode electrospray ionisation.

Mass Directed Automated Preparative HPLC Column, Conditions and Eluent

Method F

The HPLC analysis was conducted on a Sunfire C18 column (100 mm×19 mm i.d. 5 μm packing diameter) at ambient temperature.

The solvents employed were:
A=0.1% v/v solution of formic acid in water.
B=0.1% v/v solution of formic acid in acetonitrile.
The gradient employed was:

| Time (min) | Flow Rate (ml/min) | % A | % B |
|---|---|---|---|
| 0 | 20 | 70 | 30 |
| 1 | 20 | 70 | 30 |
| 10 | 20 | 15 | 85 |
| 10.5 | 20 | 1 | 99 |
| 15 | 20 | 1 | 99 |

The UV detection was an averaged signal from wavelength of 210 nm to 350 nm and mass spectra were recorded on a mass spectrometer using alternate-scan positive and negative mode electrospray ionisation.

Mass Directed Automated Preparative HPLC Column, Conditions and Eluent

Method G

The HPLC analysis was conducted on a Sunfire C18 column (150 mm×30 mm i.d. 5 μm packing diameter) at ambient temperature.

The solvents employed were:
A=0.1% v/v solution of formic acid in water.
B=0.1% v/v solution of formic acid in acetonitrile.
The gradient employed was:

| Time (min) | Flow Rate (ml/min) | % A | % B |
|---|---|---|---|
| 0 | 40 | 85 | 15 |
| 1 | 40 | 85 | 15 |
| 20 | 40 | 45 | 55 |
| 20.5 | 40 | 1 | 99 |
| 25 | 40 | 1 | 99 |

The UV detection was an averaged signal from wavelength of 210 nm to 350 nm and mass spectra were recorded on a mass spectrometer using alternate-scan positive and negative mode electrospray ionisation.

Mass Directed Automated Preparative HPLC Column, Conditions and Eluent

Method H

The HPLC analysis was conducted on a Sunfire C18 column (150 mm×30 mm i.d. 5 μm packing diameter) at ambient temperature.

The solvents employed were:
A=0.1% v/v solution of formic acid in water.
B=0.1% v/v solution of formic acid in acetonitrile.
The gradient employed was:

| Time (min) | Flow Rate (ml/min) | % A | % B |
|---|---|---|---|
| 0 | 40 | 50 | 50 |
| 1 | 40 | 50 | 50 |
| 20 | 40 | 1 | 99 |
| 20.5 | 40 | 1 | 99 |
| 25 | 40 | 1 | 99 |

The UV detection was an averaged signal from wavelength of 210 nm to 350 nm and mass spectra were recorded on a mass spectrometer using alternate-scan positive and negative mode electrospray ionisation.

Intermediates and Examples

When the name of a commercial supplier is given after the name of a compound or a reagent, for instance "compound X (Aldrich)" or "compound X/Aldrich", this means that compound X is obtainable from a commercial supplier, such as the commercial supplier named. If not referenced herein the compound or reagent can be purchased from a standard supplier such as Sigma Aldrich, Lancaster, Fluorochem, TCI etc.

Similarly, when a literature or a patent reference is given after the name of a compound, for instance compound Y (EP 0 123 456), this means that the preparation of the compound is described in the named reference.

The names of the Examples have been obtained using a compound naming programme which matches name to structure (e.g. ACD/Name Batch v 9.0).

Intermediate 1

6-(1H-Indol-4-yl)-2-(tetrahydro-2H-pyran-2-yl)-2H-indazol-4-amine

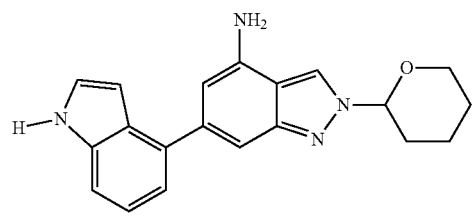 [SMILES: Nc1cc(-c2cccc3[nH]ccc23)cc2nn(C3CCCCO3)cc12]

6-(1H-Indol-4-yl)-4-nitro-2-(tetrahydro-2H-pyran-2-yl)-2H-indazole (2.54 g), ethyl acetate (100 ml) and 10% palladium on carbon (250 mg) were placed under an atmosphere of hydrogen and the mixture stirred overnight. The mixture was filtered through Celite and the solvent removed in vacuo to give the title compound as an off white solid (2.27 g).

LC/MS $R_t$ 0.96 min m/z 333 [MH$^+$]. Method B

Intermediate 2

Ethyl 2-[bis(ethyloxy)methyl]-5-(1-methylethyl)-1,3-thiazole-4-carboxylate

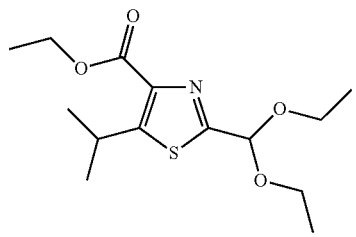 [SMILES: CCOC(=O)c1nc(C(OCC)OCC)sc1C(C)C]

To a solution of ethyl 3-bromo-4-methyl-2-oxopentanoatein (500 mg) in ethanol (20 ml) was added 2,2-bis(ethyloxy)ethanethioamide (344 mg) (available from Maybridge) in ethanol (0.5 ml). Molecular sieves (100 mg) were added and the mixture heated at 80° C. for 72 h. The mixture was filtered, washed with ethanol (5 ml) and the solvent removed in vacuo. The residue was triturated with DCM and the solid removed by filtration. The filtrate was concentrated to ~5 ml. Purification by chromatography on silica gel (10 g cartridge) eluting with 0-50% cyclohexane in ethyl acetate gave the title compound as a yellow oil (450 mg).

LC/MS $R_t$ 3.46 min m/z 302 [MH$^+$]. Method A

Intermediate 3

Ethyl 2-formyl-5-(1-methylethyl)-1,3-thiazole-4-carboxylate

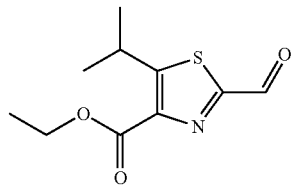

A solution of ethyl 2-[bis(ethyloxy)methyl]-5-(1-methylethyl)-1,3-thiazole-4-carboxylate (430 mg) in a mixture of 10% 1M hydrochloric acid solution in acetone (50 ml) was heated at reflux for 1 h. The mixture was concentrated in vacuo, taken up in DCM (20 ml), washed with saturated sodium bicarbonate solution (10 ml), separated by hydrophobic frit and evaporated to give the title compound as a yellow oil (324 mg).

LC/MS $R_t$ 3.04 min m/z 228 [MH$^+$]. Method A

Intermediate 4

Ethyl 5-(1-methylethyl)-2-(4-morpholinylmethyl)-1,3-thiazole-4-carboxylate

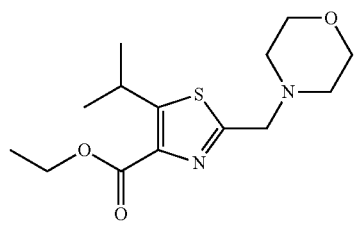 [SMILES: CCOC(=O)c1nc(CN2CCOCC2)sc1C(C)C]

Ethyl 2-formyl-5-(1-methylethyl)-1,3-thiazole-4-carboxylate (150 mg) was dissolved in anhydrous DCM (10 ml) and morpholine (0.064 ml) was added and the mixture stirred under nitrogen for 2 h at RT. Sodium triacetoxyborohydride (280 mg) was added and the mixture stirred at RT for 18 h. Sodium bicarbonate (20 ml) and DCM (20 ml) were added and separated by hydrophobic frit. The solvent was removed in vacuo and purified by column chromatography on silica gel (10 g silica), eluting with a gradient of 0-100% ethyl acetate in cyclohexane to give the title compound as a yellow oil (77 mg).

LC/MS $R_t$ 2.52 min m/z 299 [MH$^+$]. Method A

Intermediate 5

5-(1-Methylethyl)-2-(4-morpholinylmethyl)-1,3-thiazole-4-carboxylic acid

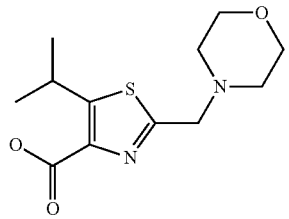 [SMILES: CC(C)c1sc(CN2CCOCC2)nc1C(=O)O]

A solution of ethyl 5-(1-methylethyl)-2-(4-morpholinylmethyl)-1,3-thiazole-4-carboxylate (77 mg) in methanol (5 ml) was treated with 2M sodium hydroxide solution (5 ml) and the mixture stirred at 20° C. for 18 h. The mixture was concentrated in vacuo and the residue taken up in water (3 ml). The pH was adjusted to pH 5-6 using 2M hydrochloric acid solution and extracted with DCM (10 ml), separated by hydrophobic frit and evaporated to give the title compound as a pale yellow gum (33 mg).

LC/MS $R_t$ 0.67 min m/z 271 [MH$^+$]. Method B

Intermediate 6

Methyl 4-methyl-1H-pyrazole-5-carboxylate

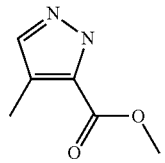

To a solution of diazomethane (nominally 0.68 g—generated from DIAZALD® (5 g) in diethyl ether (45 ml)) at −78° C. was added a solution of E/Z methyl-2-bromo-2-butenoate (3.58 g) (available from Fluka) in diethyl ether (15 ml), dropwise, over 15 min. The mixture was maintained at −78° C. for 1 h then allowed to warm to 20° C. with stirring overnight. Acetic acid (1 ml) was added to destroy excess diazomethane and the mixture evaporated under reduced pressure. The residue was co-evaporated with toluene. Purification of the residue by column chromatography on silica gel eluting with ethyl acetate:cyclohexane (1:1) gave the title compound (1.12 g) as an orange solid.

TLC $R_f$ 0.33 (ethyl acetate:cyclohexane 1:1)

Intermediate 7

Methyl 1,4-dimethyl-1H-pyrazole-5-carboxylate

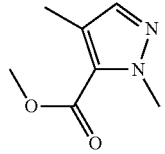

Methyl 4-methyl-1H-pyrazole-5-carboxylate (0.5 g) and cesium carbonate (1.16 g) were dissolved in acetonitrile (10 ml). Methyl iodide (0.25 ml) was added and the mixture stirred at RT for 16 h. The reaction mixture was diluted with water (20 ml) and DCM (20 ml) and separated using a hydrophobic frit. The aqueous layer was extracted with DCM (2×20 ml) using a hydrophobic frit. The solvent was removed in vacuo and the residue was purified by flash chromatography eluting with a gradient of 0-100% ethyl acetate in cyclohexane to give the title compound (0.172 g) as a colourless oil.

LC/MS R$_f$ 2.36 min m/z 155 [MH$^+$]. Method A

Intermediate 8

1,4-Dimethyl-1H-pyrazole-5-carboxylic acid

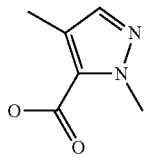

Methyl 1,4-dimethyl-1H-pyrazole-5-carboxylate (171 mg) was dissolved in 1,4-dioxane (2 ml). Hydrochloric acid (2 ml) was added and the mixture was heated at reflux for 70 h. One drop of concentrated hydrochloric acid was added and the mixture heated at reflux for 45 h. The solution was left to cool and then the solvent was removed in vacuo. To the residue toluene (15 ml) was added and the solvent was removed in vacuo. The solid was dried in a vacuum oven overnight to give the title compound (132 mg) as a white solid.

LC/MS R$_f$ 1.88 min m/z 141 [MH$^+$]. Method A

Intermediate 9

Methyl 1-(1-methylethyl)-1H-pyrazole-5-carboxylate and

Intermediate 10

Methyl 1-(1-methylethyl)-1H-pyrazole-3-carboxylate

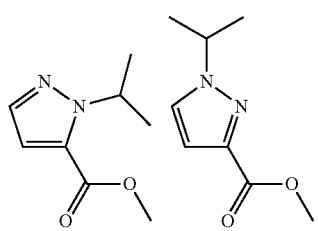

To a solution of methyl 1H-pyrazole-5-carboxylate (0.6 g) (available from Fluorochem), in acetonitrile (50 ml) was added cesium carbonate (1.55 g) followed by 2-iodopropane (0.476 ml) and the mixture stirred at 20° C. for 18 h. The solvent was removed in vacuo and the residue was partitioned between water (20 ml) and DCM (20 ml) and separated by hydrophobic frit. Purification by chromatography on silica gel (50 g silica), eluting with a gradient of 0-100% ethyl acetate in cyclohexane gave methyl 1-(1-methylethyl)-1H-pyrazole-5-carboxylate (0.24 g) as a colourless oil.

LC/MS R$_t$ 2.64 min m/z 169 [MH$^+$]. Method A and methyl 1-(1-methylethyl)-1H-pyrazole-3-carboxylate (0.27 g) as a yellow oil.

LC/MS R$_t$ 2.24 min m/z 169 [MH$^+$]. Method A

Intermediate 11

Methyl 4-chloro-1-(1-methylethyl)-1H-pyrazole-3-carboxylate

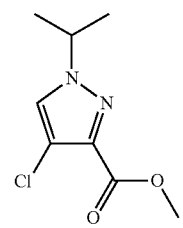

A solution of methyl 1-(1-methylethyl)-1H-pyrazole-3-carboxylate (0.13 g) in DMF (3 ml) was treated with N-chlorosuccinimide (0.103 g) and heated to 60° C. for 5 h under nitrogen. The cooled mixture was partitioned between diethyl ether (20 ml) and water (20 ml), separated, the organic extracts dried over sodium sulphate and evaporated to give the title compound as a pale yellow oil (0.105 g).

LC/MS R$_t$ 2.61 min m/z 203 [MH$^+$]. Method A

Intermediate 12

4-Chloro-1-(1-methylethyl)-1H-pyrazole-3-carboxylic acid

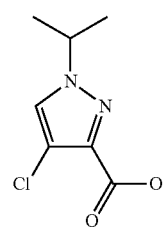

To a solution of methyl 4-chloro-1-(1-methylethyl)-1H-pyrazole-3-carboxylate (105 mg) in 1,4-dioxane (3 ml) was added 2M hydrochloric acid (3 ml) and the mixture heated at 105° C. for 18 h. The solvent was removed in vacuo to give the title compound as a yellow oil (98 mg).

LC/MS R$_t$ 2.19 min m/z 189 [MH$^+$]. Method A

Intermediate 13

Methyl 4-chloro-1-(1-methylethyl)-1H-pyrazole-5-carboxylate

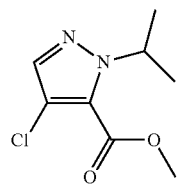

A solution of methyl 1-(1-methylethyl)-1H-pyrazole-5-carboxylate (120 mg) in DMF (3 ml) was treated with N-chlorosuccinimide (95 mg) and heated to 60° C. for 18 h under nitrogen. The cooled mixture was partitioned between diethyl ether (20 ml) and water (20 ml), separated and dried over sodium sulphate then evaporated to give the title compound as a pale yellow oil (135 mg).

LC/MS $R_t$ 3.09 min m/z 203 [MH$^+$]. Method A

Intermediate 14

4-Chloro-1-(1-methylethyl)-1H-pyrazole-5-carboxylic acid

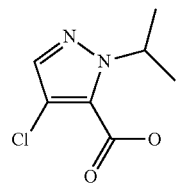

A solution of methyl 4-chloro-1-(1-methylethyl)-1H-pyrazole-5-carboxylate (130 mg) in 1,4-dioxane (3 ml) was treated with 2M hydrochloric acid (3 ml) and the mixture heated at 105° C. for 90 h. The mixture was evaporated in vacuo to give the title compound as a white solid (120 mg).

LC/MS $R_t$ 1.95 min m/z 189 [MH$^+$]. Method A

Intermediate 15

1-Methyl-4-(trifluoromethyl)-1H-pyrazole-5-carboxylic acid

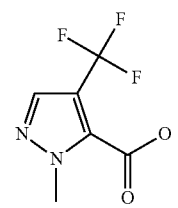

To a solution of diazomethane (0.781 g—generated from DIAZALD® (3.99 g) in diethyl ether (63 ml)), cooled by an ice/water bath, was added ethyl 4,4,4-trifluoro-2-butynoate (3.09 g) dropwise over 1 min. The cooling bath was removed and the mixture was stirred for 30 min when the solvent was removed under reduced pressure. The crude product was combined with the crude product from a similar experiment that was performed with 1,4 dioxane (5 ml) and n-pentane (15 ml) as the solvent and purified by column chromatography on silica gel to give a white solid. To a solution of a portion of this solid (100 mg) in 1,4-dioxane (2 ml) was added 2M hydrochloric acid (3 ml) and the mixture heated at reflux for 18 h, then concentrated hydrochloric acid (2 drops) was added and the mixture heated at reflux for a further 48 h. The mixture was concentrated in vacuo and the residue purified by mass directed preparative HPLC (Method A), to give the title compound, as a white solid (19 mg).

LC/MS $R_t$ 1.76 min m/z 195 [MH$^+$]. Method A

Intermediate 16

Ethyl 3-bromo-4-methyl-2-oxopentanoate

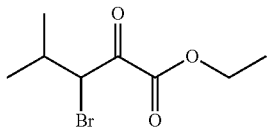

To a solution of 4-methyl-2-oxopentanoic acid (5 g) in acetic acid (40 ml) was added pyridine hydrobromide perbromide (12.3 g) and the mixture stirred at 20° C. for 18 hr, then the solvent was removed in vacuo. The residue was dissolved in DCM (100 ml) and washed with water (100 ml), separated by hydrophobic frit and evaporated. The residue was taken up in ethanol (100 ml) and treated with concentrated sulphuric acid (1 ml) and heated at reflux for 18 h, then concentrated in vacuo to approx 30 ml. The mixture was diluted with water (250 ml) and extracted with diethyl ether (100 ml), dried over sodium sulphate and evaporated to give the title compound as a pale yellow oil (5.3 g).

$^1$H NMR: (400 MHz, CDCl$_3$) δ: 4.86 (1H, d), 4.38 (2H, m), 2.37 (1H, m), 1.4 (3H, t), 1.15 (3H, d), 1.06 (3H, d).

Intermediate 17

Ethyl 2-methyl-5-(1-methylethyl)-1,3-thiazole-4-carboxylate

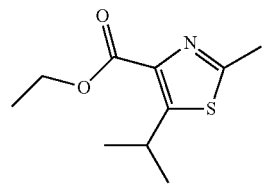

To a solution of thioacetamide (158 mg) in ethanol (20 ml) was added ethyl 3-bromo-4-methyl-2-oxopentanoate (500 mg) in ethanol (0.5 ml). Molecular sieves (100 mg) were added and the mixture was heated at 80° C. for 18 h. The mixture was filtered, washing with ethanol (5 ml) and the solvent removed in vacuo. The residue triturated with DCM and the solid removed by filtration. The filtrate was concentrated to ~5 ml and purified by column chromatography on silica gel (10 g silica), eluting with a gradient of 0-100% ethyl acetate in cyclohexane to give the title compound as a yellow oil (280 mg).

LC/MS $R_t$ 2.95 min m/z 214 [MH$^+$]. Method A

Intermediate 18

2-Methyl-5-(1-methylethyl)-1,3-thiazole-4-carboxylic acid

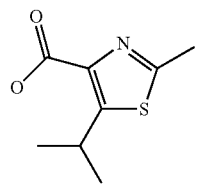

Ethyl 2-methyl-5-(1-methylethyl)-1,3-thiazole-4-carboxylate (200 mg) was dissolved in 1,4-dioxane (2 ml). Hydrochloric acid (2 ml) was added and the mixture was heated at reflux under nitrogen for 18 h. One drop of concentrated hydrochloric acid was added and the mixture was heated at reflux for 72 h. The mixture was cooled to RT, the solvent was removed in vacuo and toluene (15 ml) was added. The solvent was removed in vacuo to give a brown oil which solidified on standing. The product was dried in a vacuum oven overnight to give the title compound (171 mg) as a brown solid.

LC/MS $R_t$ 2.51 min m/z 186 [MH$^+$]. Method A

Intermediate 19

$N^2$-[Bis(methyloxy)methyl]glycinamide

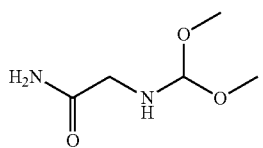

To a cooled solution of 2,2-dimethoxyethanamine (85 g) in water (300 ml) was added acetic acid (~44 ml) until the pH was 7-8 then potassium cyanate (131 g) in water (400 ml) was added and the mixture was heated at reflux for 1 h. During this time the pH was regularly checked and acetic acid was added to adjust the pH to 7-8. The reaction mixture was cooled to RT, evaporated under reduced pressure and extracted with DCM (4×250 ml). The combined organic extracts were dried over magnesium sulphate and concentrated in vacuo to give the title compound (100.5 g) as an oil that solidified under high vacuum.

TLC $R_f$ 0.10 (ethyl acetate).

Intermediate 20

Methyl 5-[bis(methyloxy)methyl]-1H-pyrazole-3-carboxylate

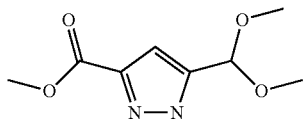

To a cooled suspension of $N^2$-[bis(methyloxy)methyl]glycinamide (14.8 g) and sodium acetate (18 g) in diethyl ether (200 ml) was added dropwise dinitrogen tetroxide (13.1 g) in diethyl ether (140 ml) at −10° C. and the resultant mixture was stirred at that temperature for 1.5 h. The reaction mixture was filtered and the filtrate was washed with saturated sodium bicarbonate solution (4×60 ml) and the combined aqueous layers were then extracted with diethyl ether (2×100 ml). The combined organic extracts were dried over magnesium sulphate and concentrated in vacuo. The residue was added portionwise at 0° C. to a stirred mixture of 1M sodium hydroxide solution (200 ml), diethyl ether (80 ml) and hexane (120 ml) and the resultant mixture was stirred for 15 min before the layers were separated. The organic layer was dried over potassium hydroxide then decanted and added dropwise at −15° C. to a solution of methyl propiolate (5.9 g) in diethyl ether (25 ml). The reaction mixture was left to warm to RT overnight before being evaporated under reduced pressure to give the title compound (9.5 g) as an oil.

TLC $R_f$ 0.45 (ethyl acetate).

Intermediate 21

1,1-Dimethylethyl 5-[bis(methyloxy)methyl]-1H-pyrazole-3-carboxylate

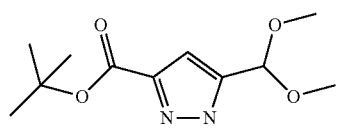 [SMILES: COC(OC)c1cc(C(=O)OC(C)(C)C)n[nH]1]

To a solution of methyl 5-[bis(methyloxy)methyl]-1H-pyrazole-3-carboxylate (20 g) in tert-butanol (250 ml) at 40° C. was added potassium tert-butoxide (28.1 g) and the mixture stirred at 50° C. for 45 h. The solution was evaporated under reduced pressure, diluted with water (150 ml) and extracted with ethyl acetate (4×100 ml). The combined organic extracts were dried over magnesium sulphate and evaporated under reduced pressure to give the title compound (18.6 g) as an oil.

TLC; $R_f$ 0.52 (2:1 ethyl acetate/hexane).

Intermediate 22

1,1-Dimethylethyl 5-formyl-1H-pyrazole-3-carboxylate

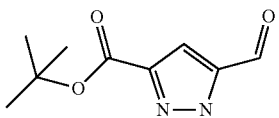

To a solution of 1,1-dimethylethyl 5-[bis(methyloxy)methyl]-1H-pyrazole-3-carboxylate (18.6 g) in acetone (100 ml) was added 1M potassium bisulphate solution (200 ml) and the resultant suspension stirred at RT overnight. The mixture was diluted with water (200 ml), stirred for 10 min, filtered and the resultant solid washed sequentially with water, isopropanol and hexane and dried under high vacuum to give the title compound (11.2 g) as a solid.

TLC; $R_f$ 0.58 (2:1 ethyl acetate:hexane).

Intermediate 23

1,1-Dimethylethyl 3-formyl-1-(1-methylethyl)-1H-pyrazole-5-carboxylate

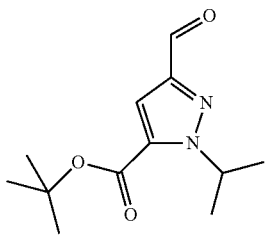 [SMILES: CC(C)n1nc(C=O)cc1C(=O)OC(C)(C)C]

1,1-Dimethylethyl 3-formyl-1H-pyrazole-5-carboxylate (600 mg) and cesium carbonate (996 mg) were dissolved in acetonitrile (60 ml). 2-Iodopropane (0.305 ml) was added and the mixture was stirred at RT for 20 h. A further portion of 2-iodopropane (0.03 ml) was added and the mixture was stirred at RT for 16 h. The solvent was removed in vacuo. The reaction mixture was diluted with water (80 ml) and DCM (80 ml) and separated using a hydrophobic frit. The aqueous layer was extracted with a further quantity of DCM (2×50 ml) using a hydrophobic frit. The solvent was removed in vacuo and the residue was purified by flash chromatography on silica gel (50 g silica), eluting with a gradient of 0-100% ethyl acetate in cyclohexane to give the title compound (377 mg), and a mixture (213 mg) of both isomers. The mixture was purified by flash chromatography on silica gel (20 g silica), eluting with a gradient of 0-50% ethyl acetate in cyclohexane to give another quantity (114 mg) of the title compound (114 mg) as a colourless oil.

LC/MS $R_t$ 3.40 min m/z 239 [MH$^+$]. Method A

Intermediate 24

1,1-Dimethylethyl 1-(1-methylethyl)-3-(4-morpholinylmethyl)-1H-pyrazole-5-carboxylate

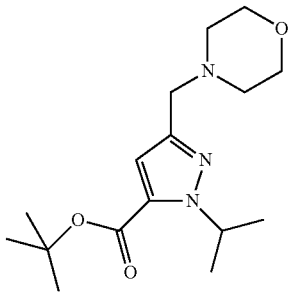 [SMILES: CC(C)n1nc(CN2CCOCC2)cc1C(=O)OC(C)(C)C]

1,1-Dimethylethyl 3-formyl-1-(1-methylethyl)-1H-pyrazole-5-carboxylate (491 mg) was dissolved in anhydrous DCM (20 ml), morpholine (0.198 ml) was added and the mixture was stirred under nitrogen for 2 h at RT. Sodium triacetoxyborohydride (873 mg) was added and the mixture was stirred at RT for 18 h. Sodium bicarbonate solution (50 ml) and DCM (50 ml) were added and separated and the aqueous layer was re-extracted with DCM (2×50 ml) and separated by hydrophobic frit. The solvent was removed in vacuo and the residue was purified by flash chromatography on silica gel (50 g silica), eluting with a gradient of 0-100% ethyl acetate in cyclohexane over 30 mins to give the title compound (628 mg) as a colourless oil.

LC/MS $R_t$ 2.53 min m/z 310 [MH$^+$]. Method A

Intermediate 25

1-(1-Methylethyl)-3-(4-morpholinylmethyl)-1H-pyrazole-5-carboxylic acid

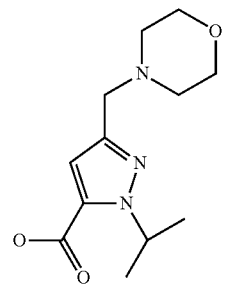 [SMILES: CC(C)n1nc(CN2CCOCC2)cc1C(=O)O]

1,1-Dimethylethyl 1-(1-methylethyl)-3-(4-morpholinylmethyl)-1H-pyrazole-5-carboxylate (628 mg) was dissolved in 1,4-dioxane (2 ml). 4M Hydrogen chloride in 1,4 dioxane (5 ml) was added and the mixture was stirred at RT under nitrogen. After 24 h further 4M hydrogen chloride in 1,4 dioxane (3 ml) was added and the mixture was stirred at RT for 72 h. One drop of water was added and the mixture was stirred at RT for 24 h. The solvent was removed in vacuo, toluene (20 ml) was added and removed in vacuo to give a white solid. The solid was dried in a vacuum oven over-night to give the title compound (513 mg) as a white solid.

LC/MS $R_t$ 1.01 min m/z 254 [MH$^+$]. Method B

Intermediate 26

1,1-Dimethylethyl 1-(1-methylethyl)-5-(4-morpholinylmethyl)-1H-pyrazole-3-carboxylate

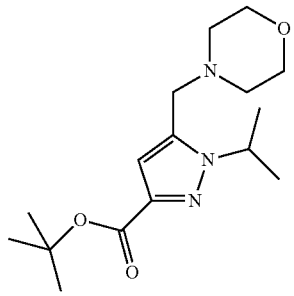 [SMILES: CC(C)n1nc(C(=O)OC(C)(C)C)cc1CN1CCOCC1]

1,1-Dimethylethyl 5-formyl-1-(1-methylethyl)-1H-pyrazole-3-carboxylate (118 mg) was dissolved in anhydrous DCM (10 ml), morpholine (0.048 ml) was added and the mixture was stirred under nitrogen for 2 h at RT. Sodium triacetoxyborohydride (210 mg) was added and the mixture was stirred at RT for 18 h. Sodium bicarbonate solution (20 ml) and DCM (20 ml) were added and separated then the aqueous layer was re-extracted with DCM (2×20 ml) and separated by hydrophobic frit. The combined organic layers were concentrated in vacuo and the residue was purified by flash chromatography on silica gel (20 g silica) eluting with a gradient of 0-100% ethyl acetate in cyclohexane over 20 mins to give the title compound (101 mg) as a white solid.

LC/MS $R_t$ 2.44 min m/z 310 [MH$^+$]. Method A Intermediate 27

1-(1-Methylethyl)-5-(4-morpholinylmethyl)-1H-pyrazole-3-carboxylic acid

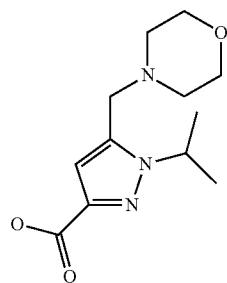 [SMILES: CC(C)n1nc(C(=O)O)cc1CN1CCOCC1]

1,1-Dimethylethyl 1-(1-methylethyl)-5-(4-morpholinylmethyl)-1H-pyrazole-3-carboxylate (101 mg) was dissolved in 1,4-Dioxane (2 ml). 4M hydrogen chloride in 1,4 dioxane (3 ml) was added and the mixture was stirred at RT under nitrogen for 6 h. The solvent was removed in vacuo, toluene (10 ml) was added and removed in vacuo to give a white solid. The solid was dried in a vacuum oven over-night to give the title compound (81 mg) as a white solid.

LC/MS $R_t$ 0.88 min m/z 254 [MH$^+$]. Method A

Intermediate 28

1-Methyl-1H-1,2,4-triazole

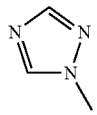

In a microwave vial sodium methoxide (2.34 g) was dissolved in methanol (10 ml), 1H-1,2,4-triazole (3 g) was added and the mixture was cooled to 5-10° C. Methyl iodide (3.26 ml) was added and the mixture was heated under microwave irradiation at 80° C. for 45 min. The solvent was removed in vacuo. The oil was allowed to stand for 2 h at RT until a solid was formed. To the solid, DCM was added, the DCM was decanted and the solvent was removed in vacuo. The residue was purified by flash chromatography on silica gel (100 g silica) eluting with a gradient of 0-25% methanol in DCM over 40 min to give the title compound (1.19 g) as a yellow oil.

$^1$H NMR: (400 MHz, DMSO) δ 8.45 (1H, s), 7.95 (1H, s), 3.85 (3H, s)

Intermediate 29

1-Methyl-1H-1,2,4-triazole-5-carboxylic acid

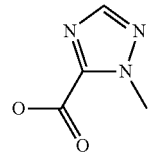

1-Methyl-1H-1,2,4-triazole (1.19 g) was dissolved in THF (15 ml) and cooled to −78° C. under nitrogen. A 1.6M solution of butyllithium in hexane (9.4 ml) was added dropwise. The solution was stirred for 1.5 h at −78° C., then the solution was treated with solid carbon dioxide (2 g). After 30 min at −78° C. the solution was allowed to warm to RT and stirred overnight. The reaction was quenched with water (1 ml) and the solvent was decanted off. To the residue was added ethyl acetate (20 ml) and water (20 ml). The solvent was removed in vacuo and the residue was dried in a vacuum oven for 1 day (50° C.) to give the title compound (1.61 g) as a white solid.

LC/MS $R_t$ 0.46 min m/z 126 [MH$^+$]. Method A

Intermediate 30

1-(1-Methylethyl)-1H-1,2,4-triazole

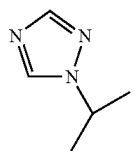

In two microwave vials sodium methoxide (2×1.36 g) was dissolved in anhydrous methanol (2×5 ml), 1H-1,2,4-triazole (2×1.73 g) was added and the mixtures were cooled to 5-10° C. 2-Iodopropane (2×3 ml) was and the two mixtures were heated under microwave irradiation at 80° C. for 45 min. The mixtures were combined and the solvent was removed in vacuo. The oil was allowed to stand for 2 h at RT until a solid formed. To the solid, DCM (5×15 ml) was added and the liquid phase was decanted. The solvent was removed in vacuo and the residue was purified by flash chromatography (100 g silica, gradient elution, 0-25% methanol/DCM) to give the title compound (2.34 g) as a yellow oil.

LC/MS $R_t$ 1.13 min m/z 112 [MH$^+$]. Method A

Intermediate 31

1-(1-Methylethyl)-1H-1,2,4-triazole-5-carboxylic acid

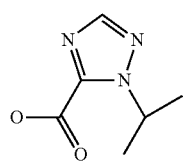

1-(1-Methylethyl)-1H-1,2,4-triazole (1 g) was dissolved in THF (15 ml) and cooled to −78° C. under nitrogen. A 1.6 M solution of butyllithium in hexane (5.9 ml) was added dropwise. The solution was stirred for 1.5 h at −78° C., then the solution was treated with solid carbon dioxide (2 g). After 30 min at −78° C. the solution was allowed to warm to RT and stirred overnight. The reaction was quenched with water (1 ml), concentrated in vacuo and dried in a vacuum oven for 1 day at 50° C. to give the title compound (1.29 g) as a white solid.

LC/MS $R_t$ 0.74 min m/z 156 [MH$^+$]. Method A

Intermediate 32

N-(6-Bromo-1H-indazol-4-yl)-2-methyl-1,3-thiazole-4-carboxamide

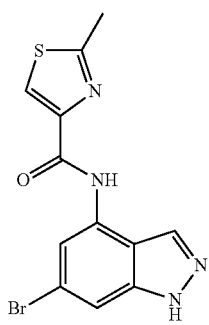 [SMILES: Cc1nc(C(=O)Nc2cc(Br)cc3[nH]ncc23)cs1]

2-Methyl-1,3-thiazole-4-carboxylic acid (4.59 g) (available from Maybridge), HATU (13.41 g) and DIPEA (16.80 ml) were stirred in DMF (140 ml) for 30 min at 20° C. 6-Bromo-1H-indazol-4-amine (3.4 g) (available from Sinova) was added and the reaction stirred at 20° C. for 2 days. The solvent was reduced to ~40 ml and the reaction mixture was applied across 5×70 g aminopropyl SPE cartridges and left to stand for 3 h. The cartridges were eluted with DCM:methanol (1:1) and the combined solvent was evaporated in vacuo. The residue was suspended in DCM:methanol, adsorbed onto Florisil® and purified by chromatography on silica gel (100 g cartridge) eluting with 0-15% gradient of methanol (containing 1% triethylamine) in DCM over 60 min to give title compound (1.02 g).

LC/MS $R_t$ 0.95 min m/z 337 [MH$^+$]. Method B

Intermediate 33

6-(1H-Indol-4-yl)-1H-indazol-4-amine

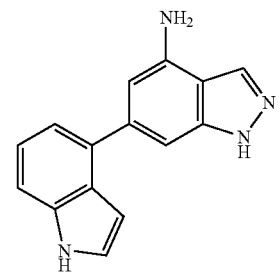 [SMILES: Nc1cc(-c2cccc3[nH]ccc23)cc2[nH]ncc12]

6-Bromo-1H-indazol-4-amine (10 g) (available from Sinova Inc.) and 4-(4,4,5,5-tetramethyl-1,3,2-dioxaborolan-2-yl)-1H-indole (16.05 g) (available from Frontier Scientific, Europe Ltd) were dissolved in 1,4-dioxane (60 ml) and water (60 ml). 2M sodium carbonate (70.7 ml) and Pd(dppf)Cl$_2$-DCM adduct (1.93 g) were added and the mixture was heated at 115° C. for 18 h. The reaction mixture was diluted with DCM (200 ml) and the organic and aqueous layers were separated using a hydrophobic frit. The aqueous layer was extracted with further quantities of DCM (2×200 ml), using a hydrophobic frit to separate the layers. The organic layers were combined and silica (80 g) was added. The solvent was removed in vacuo to give a crude material that was purified by chromatography on silica gel (750 g cartridge, Flashmaster II) eluting with 0-100% ethyl acetate in cyclohexane over 60 min. The oil was dried in vacuo on a drying rack overnight. The yellow foam was dissolved in DCM (3×400 ml), removing the solvent in vacuo after each dissolution. ethyl acetate (50 ml) was then added and the solvent was removed in vacuo. The solid obtained was dried in a vacuum oven to afford the title compound (12.8 g) as a yellow foam.

LC/MS $R_t$ 2.71 min m/z 249 [MH$^+$]. Method A

Intermediate 34

Methyl 1-methyl-1H-1,2,4-triazole-3-carboxylate

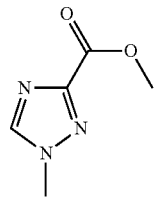

A mixture of methyl 1H-1,2,4-triazole-3-carboxylate (1 g) and sodium hydride (0.315 g) in anhydrous THF (30 ml) was heated at reflux for 7 h under nitrogen. The reaction was cooled to RT and methyl iodide (1.12 g) was added. The reaction was heated at reflux overnight. The solvent was evaporated and water (10 ml) was added. This was extracted with DCM, the organic layer collected and evaporated to dryness. The residue was dissolved in methanol:DMSO (6 ml, 1:1) and purified by mass directed preparative HPLC (Method A) to give title compound (0.290 g).

LC/MS $R_t$ 0.46 min m/z 142 [MH$^+$]. Method B

Intermediate 35

1-Methyl-1H-1,2,4-triazole-3-carboxylic acid

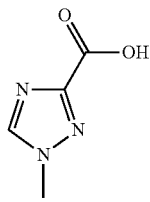

Methyl 1-methyl-1H-1,2,4-triazole-3-carboxylate (280 mg) and methanol (1 ml) were added to potassium hydroxide (145 mg) in water (1 ml). The reaction was stirred for 3 h at RT. The solvent was evaporated and the residue was loaded onto an aminopropyl SPE cartridge (5 g) in DMF. The cartridge was washed with 10% methanol in DCM (3×15 ml), followed by 30% acetic acid in methanol. The appropriate fractions were combined, the solvent was evaporated and the residue dried at 50° C. under vacuum to give title compound (180 mg).

LC/MS $R_t$ 0.2 min m/z 128 [MH$^+$]. Method B

Intermediate 36

4-Bromo-1-(phenylsulfonyl)-1H-pyrrolo[2,3-b]pyridine

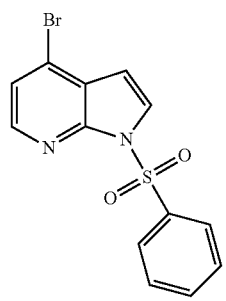 [SMILES: O=S(=O)(c1ccccc1)n1ccc2c(Br)ccnc21]

To a stirred suspension of sodium hydride (1.12 g; 60% dispersion in mineral oil) in THF (3 ml) kept below 15° C., a suspension of 4-bromo-1H-pyrrolo[2,3-b]pyridine (5 g) (prepared for example, according to the method described in Organic Letters, 2003, 5, 5023) in THF (27 ml) was added over 20 minutes. The reaction was left to stir for 10 minutes. Then a solution of benzenesulfonyl chloride (3.6 ml) in THF (6 ml) was added over 5 minutes. The reaction was left to stir at RT for 1 hour, then 0.5M hydrochloric acid solution (10 ml) was added. The layers were separated and the organic layer washed with brine, dried over magnesium sulphate and the solvent removed in vacuo and left on the vacuum line for 3 days. The solid was triturated using methanol (30 ml) then dried in the oven for 5 hours to give the title compound as a pale pink solid (7.42 g).

LC/MS $R_t$ 3.39 min m/z 337 [MH$^+$]. Method A

Intermediate 37

4-Bromo-2-methyl-1-(phenylsulfonyl)-1H-pyrrolo[2,3-b]pyridine

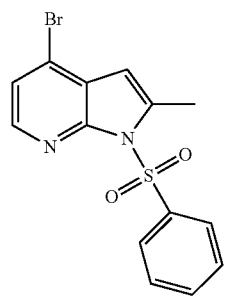 [SMILES: Cc1cc2c(Br)ccnc2n1S(=O)(=O)c1ccccc1]

1.8M Lithium diisopropylamide (270 ml) was added dropwise over 20 min to a solution of 4-bromo-1-(phenylsulfonyl)-1H-pyrrolo[2,3-b]pyridine (82 g) in dry THF (820 ml) and the reaction was stirred at −45° C. for 30 min. Methyl iodide (90 ml) was added drop wise to the solution and the mixture was stirred at −45° C. for 45 min, then allowed to warm to RT. The reaction was quenched with water. The organic layer was collected and the aqueous layer extracted with ethyl acetate. The combined organic layers were washed with brine, dried over magnesium sulphate and concentrated in vacuo. The residue was triturated with ethyl acetate:cyclohexane (3:1). The solid material was collected and washed with ethyl acetate:cyclohexane (3:1) and dried in vacuo at 35° C. This residue was dissolved in DCM, washed with water, dried over magnesium sulphate and the solvent removed in vacuo to give the title compound (37.6 g) as a cream solid.

LC/MS $R_t$ 1.32 min m/z 351 [MH$^+$]. Method B

Intermediate 38

4-Bromo-2-methyl-1H-pyrrolo[2,3-b]pyridine

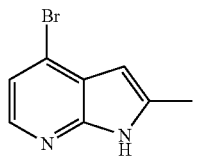

2M Sodium hydroxide solution (114 ml) was added to a solution of 4-bromo-2-methyl-1-(phenylsulfonyl)-1H-pyrrolo[2,3-b]pyridine (16 g) in 1,4-dioxane (320 ml) and the reaction heated at 60° C. overnight. After cooling, the aqueous layer was separated and washed with ethyl acetate. The combined organics were washed with brine, dried over magnesium sulphate, filtered, and then evaporated to give title compound (10.1 g) as a cream coloured solid.

LC/MS $R_t$ 1.04 min m/z 211 [MH$^+$]. Method B

Intermediate 39

(2-Methyl-1H-pyrrolo[2,3-b]pyridin-4-yl)boronic acid

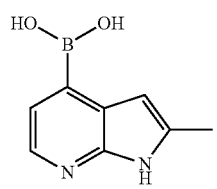

To a stirred suspension of 60% sodium hydride in mineral oil (1.18 g) in THF (25 ml) at 0° C. was added 4-bromo-2-methyl-1H-pyrrolo[2,3-b]pyridine (5 g) in THF (75 ml) dropwise. The reaction was cooled to −78° C. and 1.6M n-butyl lithium in hexane (30 ml) was added dropwise, keeping the temperature below −60° C. The reaction was stirred at −78° C. for 30 min before the dropwise addition of triisopropylborate (16.4 ml), keeping the temperature below −60° C. The reaction was stirred for 1 h at −78° C., warmed to RT and water (100 ml) was added. The layers were separated and the water washed with ethyl acetate (2×50 ml), before the combined organic layers were washed with 2M sodium hydroxide solution (50 ml). The combined aqueous layers were treated with 2M hydrochloric acid solution to pH 7.2 and the resultant precipitate collected by filtration and dried in vacuo at 40° C. overnight to give title compound (2.64 g).

LC/MS $R_t$ 0.51 min m/z 177 [MH$^+$]. Method B

Intermediate 40

2-Cyclopropyl-1H-pyrrolo[2,3-b]pyridine

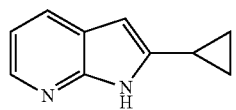 [SMILES: c1cnc2[nH]c(C3CC3)cc2c1]

To a stirred mixture of N-boc-2-aminopicoline (10.4 g) in dry THF (70 ml) in an ice/salt bath was added, under an atmosphere of nitrogen, n-butyl lithium (2M solution in cyclohexane, 50 ml), keeping the temperature below 0° C. The reaction was stirred below 0° C. for 1 h before the addition of a solution of N-methyl-N-(methyloxy)cyclopropanecarboxamide (7.5 g) (available from Pfaltz-Bauer) in dry THF (20 ml). The reaction mixture was stirred at 0° C. for 2 h then warmed to 10° C. and poured into 5M hydrochloric acid (130 ml). The mixture was heated at 60° C. for 2 h, cooled and the aqueous layer separated. The aqueous layer was basified by the addition of 10M sodium hydroxide, with ice/water cooling, until the pH was 10-12. The resulting mixture was extracted with DCM (2×100 ml) and the combined organic extracts were washed with water (50 ml), dried using a hydrophobic frit and evaporated to give the title compound (7.89 g).

LC/MS $R_t$ 0.78 min m/z 159 [MH$^+$]. Method B

Intermediate 41

2-Cyclopropyl-1H-pyrrolo[2,3-b]pyridine 7-oxide

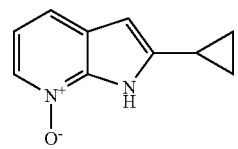 [SMILES: [O-][n+]1cccc2cc(C3CC3)[nH]c21]

To a stirred solution of 2-cyclopropyl-1H-pyrrolo[2,3-b]pyridine (7.6 g) in DME (100 ml) was added a solution of m-chloroperoxybenzoic acid (17.9 g) in DME (50 ml), under an atmosphere of nitrogen, keeping the temperature between 20 and 25° C. The resulting suspension was stirred at 20° C. for 45 min and then sodium metabisulphite solution (20 ml, 40%) was added. The mixture was concentrated in vacuo to ~80 ml. Water (100 ml) was added and the mixture basified by the addition of aqueous potassium carbonate solution. The suspension was stirred for 14 h and then the precipitate was collected by filtration, washed with water and dried to give the title compound (4.1 g).

LC/MS $R_t$ 0.70 min m/z 175 [MH$^+$]. Method B

Intermediate 42

4-Bromo-2-cyclopropyl-1H-pyrrolo[2,3-b]pyridine

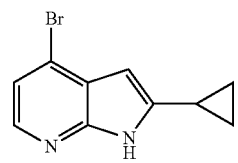 [SMILES: Brc1ccnc2[nH]c(C3CC3)cc12]

To a stirred solution of 2-cyclopropyl-1H-pyrrolo[2,3-b]pyridine 7-oxide (6.1 g) in DMF (150 ml) at 0° C. was added tetramethylammonium bromide (8.2 g), followed by methanesulphonic anhydride (12.2 g) portionwise over 10 min keeping the temperature below 10° C. The reaction was stirred at <10° C. for 1 h then warmed to RT over 18 h. Further tetramethylammonium bromide (2.1 g) and methanesulphonic anhydride (3 g) were added and the reaction was stirred at RT for 18 h. The reaction was poured into water (11) with stirring over 8 min. The suspension was basified to pH 11-12 with 2M sodium hydroxide, stirred for 1 h and filtered. The solid was washed with water and air dried to give title compound (6.88 g).

LC/MS $R_t$ 1.14 min m/z 237 [MH$^+$]. Method B

Intermediate 43

2-Cyclopropyl-1H-pyrrolo[2,3-b]pyridin-4-yl)boronic acid

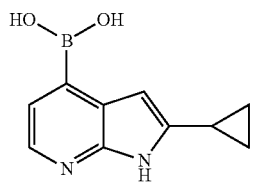 [SMILES: OB(O)c1ccnc2[nH]c(C3CC3)cc12]

To a stirred solution of 4-bromo-2-cyclopropyl-1H-pyrrolo[2,3-b]pyridine (7.35 g) in degassed THF at 5° C. was added 60% sodium hydride in mineral oil (1.88 g) portionwise over 10 min. The reaction was stirred at 10° C. for 1 h, degassed then cooled to −78° C. 2M n-Butyl lithium in cyclohexane (36 ml) was added dropwise and the reaction stirred at −78° C. for 30 min. Triisopropylborate (21.5 ml) was added dropwise, keeping the temperature below −70° C. and the reaction was stirred at −70° C. for 1 h then warmed to RT over 18 h. The reaction was quenched by addition of water (100 ml), acidified with 2M hydrochloric acid solution, then extracted with ethyl acetate (500 ml). The solid formed was filtered off and the organic layer was washed with brine then evaporated to dryness. The residue was loaded onto an aminopropyl SPE cartridge (50 g×5) that had been preconditioned with methanol. The cartridges were washed with methanol:DCM (1:1), then eluted with 2M ammonia in methanol. The product containing fractions were combined, evaporated to dryness to give title compound (1.1 g).

LC/MS $R_t$ 0.63 min m/z 203 [MH$^+$]. Method B

Intermediate 44

6-Bromo-3-fluoro-4-nitro-1H-indazole:6-bromo-4-nitro-1H-indazole (3:2)

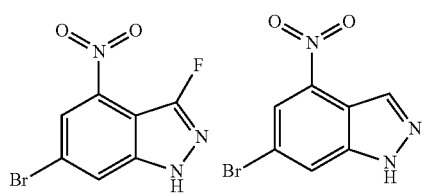

A microwave vial was charged with 6-bromo-4-nitro-1H-indazole (available from Sinova) (363 mg) and 1-(chloromethyl)-4-fluoro-1,4-diazoniabicyclo[2.2.2]octane ditetrafluoroborate (691 mg) followed by acetonitrile (5 ml) and acetic acid (1 ml). The reaction vessel was sealed and heated under microwave irradiation at 100° C. for two periods of 30 min then at 150° C. for two periods of 30 min. The solution was evaporated to dryness, dissolved in chloroform (~10 ml) and loaded onto a 20 g silica cartridge which was eluted on the Flashmaster 2 with a gradient of 0 to 100% ethyl acetate in cyclohexane over 60 min. The appropriate fractions were combined and blown to dryness to give the title compound (187 mg) as a yellow solid.

LC/MS $R_t$ 1.02 min m/z 258 [MH$^-$] and 0.98 min m/z 240. [MH$^-$]. Method B

Intermediate 45

6-Bromo-3-fluoro-1H-indazol-4-amine

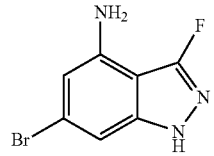 [SMILES: Nc1cc(Br)cc2[nH]nc(F)c12]

A mixture of 6-bromo-3-fluoro-4-nitro-1H-indazole and 6-bromo-4-nitro-1H-indazole (3:2) (187 mg) was dissolved in methanol (6 ml) and water (1.2 ml) and treated with sodium dithionate (519 mg). The solution was stirred for 2 h at 20° C. then left to stand for 3 days. This solution was then treated with sodium dithionite (438 mg) and stirred at 20° C. for 20 h. The solution was filtered through a filter tube, the residue washed with methanol (5 ml) then the combined filtrates were evaporated to dryness to give a yellow solid. This was treated with ethyl acetate (10 ml) and water (10 ml) and the solid dissolved. The organic phase was separated, dried with sodium sulphate, filtered then evaporated to give a pale yellow solid.

This solid was treated with DCM (5 ml), methanol (5 ml) and ethyl acetate (10 ml), but some white solid did not dissolve. The supernatant was pipetted off, then blown to dryness to give a yellow solid which was dissolved in 1:1 methanol:DMSO (1 ml) and purified by mass directed preparative HPLC (Method A). The residue was azeotroped with methanol (5 ml) to give the title compound (19 mg) as a white solid.

LC/MS $R_t$ 2.83 min m/z 228 [MH$^-$]. Method A

Intermediate 46

3-Fluoro-6-(1H-indol-4-yl)-1H-indazol-4-amine

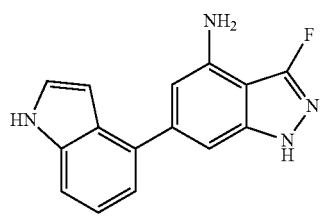 [SMILES: Nc1cc(-c2cccc3[nH]ccc23)cc2[nH]nc(F)c12]

To 4-(4,4,5,5-tetramethyl-1,3,2-dioxaborolan-2-yl)-1H-indole (24 mg) and 1,1'-bis(diphenylphosphino)ferrocene-dichloropalladium(II) (3 mg) at 20° C. in a microwave vial was added a solution of 6-bromo-3-fluoro-1H-indazol-4-amine (19 mg) in 1,4-dioxane (0.75 ml) followed by water (0.5 ml) and aqueous sodium carbonate (2M, 0.124 ml). The reaction vessel was sealed and heated under microwave irradiation at 150° C. for 15 min. After cooling, the black solution was loaded onto a 500 mg silica cartridge which was then eluted with methanol (4 column volumes). The eluant was blown to dryness, re-dissolved in methanol (3 ml), filtered and blown to dryness to give the title compound (67 mg) as a brown film.

LC/MS $R_t$ 2.99 min m/z 267 [MH$^+$]. Method A

Intermediate 47

A mixture of 4-Fluoro-1-methyl-1H-pyrazole-3-carboxylic acid and 4-fluoro-1-methyl-1H-pyrazole-5-carboxylic acid (45:55)

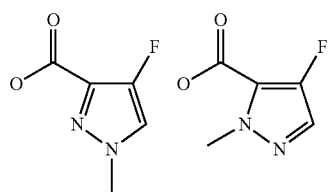

A solution of ethyl 4-fluoro-1H-pyrazole-3-carboxylate (0.545 g) (Ref: Nucleosides & Nucleotides (1999), 18(2), 203-216.) in dry DMF (4 ml) was added to a stirred suspension of 60% sodium hydride in mineral oil (0.159 g) in dry DMF (2 ml) at 0-5° C. under nitrogen. The resulting mixture was stirred at 0-5° C. for 45 min and the resulting solution was treated with iodomethane (0.237 ml). The resulting solution was stirred at RT for 3.5 h when ethanol (0.2 ml) was added followed by 2M sodium hydroxide solution (1.73 ml). The resulting mixture was stirred at RT for 2 h then adjusted to ca. pH 7 with 2M hydrochloric acid and evaporated to give a white solid. This solid was triturated with DCM (25 ml), then with DCM-methanol (4:1, 25 ml). The solid was then dissolved in methanol (15 ml) and applied to a 50 g aminopropyl SPE cartridge which was eluted successively with methanol (4 column volumes) and 10% triethylamine in methanol (5 column volumes). The appropriate fraction was evaporated to give the title compound (1.26 g) as a white solid.

LC/MS $R_t$ 0.39 and 0.41 min m/z 145 [MH$^+$]. Method B

Intermediate 48

2-Methyl-1,3-thiazole-4-carbonyl chloride

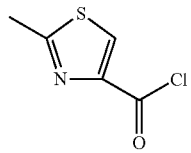

To 2-methyl-1,3-thiazole-4-carboxylic acid (1 g) was added thionyl chloride (5 ml). The mixture was heated at 80° C. for 8 h. Thionyl chloride (5 ml) was added and the mixture heated for 2 h at 80° C. Further thionyl chloride (5 ml) was added and the mixture heated for 2 h. The mixture was concentrated in vacuo and azeotroped with toluene to give the title compound (1.12 g) as a brown solid $^1$H NMR (DSMO) δ 8.34 (s, 1H), 2.80 (s, 3H)

Intermediate 49

Ethyl 2-(trifluoromethyl)-1,3-thiazole-4-carboxylate

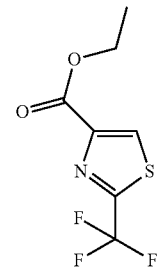

To a solution of 2,2,2-trifluoroacetamide (5 g) in THF (50 ml) was added Lawesson's reagent (9 g) and the mixture heated at reflux for 6 h. The mixture was cooled to RT overnight. The solvent was concentrated to a volume of 20 ml and this was diluted with DCM (60 ml). This solution was purified by chromatography on silica gel (3×50 g cartridges) eluting with DCM. The clean fractions were combined and the impure product containing fractions combined. The impure fractions were concentrated to a volume of 20 ml and purified by chromatography on silica gel (50 g cartridge) eluting with DCM. All the clean product containing fractions were combined and concentrated in vacuo to give 2,2,2-trifluoroethanethioamide as a dark yellow oil. A portion of this oil (1 g) was suspended in anhydrous ethanol (20 ml) and bromoethylpyruvate (0.97 ml) added. This mixture was heated at reflux for 18 h. The mixture was cooled and then poured into water (50 ml) and the pH adjusted to ~8 by the addition of solid sodium bicarbonate. The ethanol was removed in vacuo and the resultant aqueous solution extracted with ethyl acetate (3×50 ml). The combined organic extracts were dried over sodium sulphate and concentrated in vacuo. Purification by chromatography on silica gel (20 g cartridge) eluting with DCM gave the title compound (0.358 g) as an orange solid.

LC/MS $R_t$ 2.83 min m/z 226 [MH$^+$]. Method A

Intermediate 50

2-(Trifluoromethyl)-1,3-thiazole-4-carboxylic acid

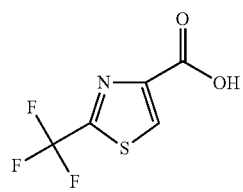

A mixture of ethyl 2-(trifluoromethyl)-1,3-thiazole-4-carboxylate (278 mg) in ethanol (3.5 ml) was added 2M sodium hydroxide solution (2.4 ml) and the mixture stirred at RT for 1 h. The mixture was acidified by the addition of 2M hydrochloric acid solution (2.5 ml) and the mixture blown to dryness. The residue was treated with water (2 ml) and extracted with ethyl acetate (3×5 ml). The combined organic extracts were dried over sodium sulphate and evaporated to give the title compound (168 mg) as a beige solid.

$^1$H NMR (DMSO) δ 8.84 (s, 1H)

Intermediate 51

Ethyl 3-ethyl-1H-pyrazole-5-carboxylate

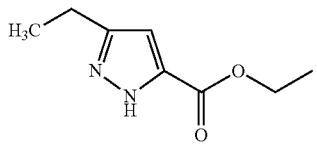

To a solution of diethyl ethanedioate (45.2 g) in absolute ethanol (140 ml) cooled in an ice/industrial methylated spirit bath was added ethanolic sodium ethoxide (100 ml; 21% w/w) dropwise, keeping the temperature below 3° C. and the mixture stirred for 15 min in an ice bath. 2-Butanone (22.1 g) was added and the mixture stirred in an ice bath for 15 min before being allowed to warm to RT overnight. The mixture was stirred at 40° C. for 6 h and then cooled to 0° C. Glacial acetic acid (17.5 ml) was added dropwise, maintaining the temperature below 3° C. The resultant precipitate was broken up and ethanol (100 ml) added to enable the mixture to stir. Hydrazine hydrate (14 ml) was added dropwise, maintaining the temperature below 7° C. The mixture was stirred in the cold bath for 10 min and then allowed to warm to RT overnight. The solvent was removed in vacuo and the residue partitioned between DCM (300 ml) and water (100 ml). The organic phase was washed with water (2×100 ml), dried over magnesium sulphate and the solvent removed to give the title compound (41.3 g) as a red oil.

LC/MS $R_t$ 2.60 min m/z 169 [MH$^+$]. Method D

Intermediate 52

3-Ethyl-1H-pyrazole-5-carboxylic acid

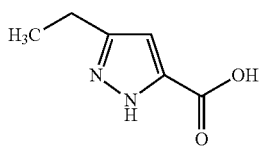

To a stirred solution of ethyl 3-ethyl-1H-pyrazole-5-carboxylate (41.3 g) in methanol (300 ml) was added dropwise 10M sodium hydroxide solution (63 ml) and the mixture heated at reflux for 4 h. The mixture was allowed to cool overnight and then concentrated. The residue was diluted with water (250 ml) and washed with toluene (3×100 ml). The aqueous phase was acidified to pH=4 by the addition of concentrated hydrochloric acid. The resultant precipitate was collected by filtration, washed with water and dried in a vacuum oven at 45° C. to give the title compound (18.4 g) as a buff solid.

$^1$H NMR (DMSO) δ 6.47 (s, 1H), 2.62 (q, 2H), 1.18 (t, 3H)

Intermediate 53

Ethyl 2-[bis(ethyloxy)methyl]-1,3-thiazole-4-carboxylate

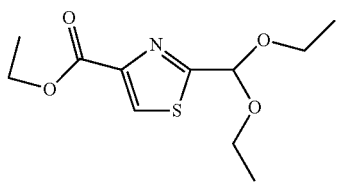 [SMILES: CCOC(=O)c1csc(C(OCC)OCC)n1]

To a solution of 2,2-bis(ethyloxy)ethanethioamide (648 mg) (available from Maybridge International) in ethanol (30 ml) was added ethyl bromopyruvate (0.598 ml) in ethanol (1 ml). Powdered molecular sieves (200 mg) were added and the mixture heated at 90° C. for 18 h. The mixture was filtered, washed with ethanol (10 ml) and the solvent removed in vacuo. The residue was triturated with DCM (15 ml) and the solid removed by filtration and washed with DCM (10 ml). The filtrate was concentrated in vacuo. Purification by chromatography on silica gel (70 g cartridge; FlashMaster II) eluting with 0-50% ethyl acetate in cyclohexane over 40 min gave the title compound (455 mg) as a yellow oil.

LC/MS $R_t$ 2.60 min m/z 260 [MH$^+$]. Method C

Intermediate 54

Ethyl 2-formyl-1,3-thiazole-4-carboxylate

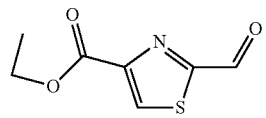

A solution of ethyl 2-[bis(ethyloxy)methyl]-1,3-thiazole-4-carboxylate (455 mg) in 10% 1M hydrochloric acid in acetone (50 ml) was heated at reflux for 1 h. The mixture was concentrated in vacuo, taken up in DCM (20 ml) and washed with saturated sodium bicarbonate solution (10 ml). The organic layer was separated using a hydrophobic frit and evaporated to give the title compound (317 mg) as a yellow solid.

LC/MS $R_t$ 1.54 min Method C

Intermediate 55

Ethyl 2-(4-morpholinylmethyl)-1,3-thiazole-4-carboxylate

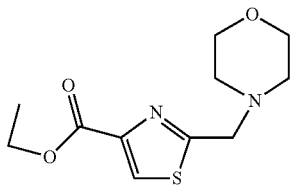 [SMILES: CCOC(=O)c1csc(CN2CCOCC2)n1]

To a solution of ethyl 2-formyl-1,3-thiazole-4-carboxylate (315 mg) in anhydrous DCM (25 ml) was added morpholine (0.164 ml) and the mixture stirred under nitrogen for 3 h at RT. Sodium triacetoxyborohydride (759 mg) was added and the mixture stirred at RT for 16 h. Sodium bicarbonate (50 ml) and DCM (50 ml) were added and the aqueous layer was extracted with DCM (2×25 ml) using a hydrophobic frit. The solvent was removed in vacuo, the residue was dissolved in DCM (5 ml) and purified by chromatography on silica gel eluting with a gradient of 0-100% ethyl acetate in cyclohexane over 30 min. The solvent was removed in vacuo to give a white solid. The solid was dissolved in methanol (15 ml) and loaded onto an SCX SPE cartridge (50 g), which was preconditioned with methanol and allowed to stand for 15 min. The column was washed with methanol (50 ml) and elution with 2M ammonia in ethanol gave the title compound.
LC/MS $R_t$ 0.99 min m/z 257 [MH$^+$]. Method C Intermediate 56

2-(4-Morpholinylmethyl)-1,3-thiazole-4-carboxylic acid ammoniate

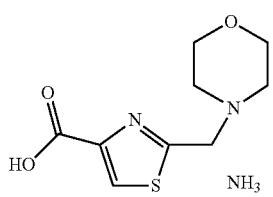

Ethyl 2-(4-morpholinylmethyl)-1,3-thiazole-4-carboxylate (260 mg) was dissolved in methanol (5 ml). Sodium hydroxide (5 ml) was added and the mixture was stirred at RT for 18 h. The solvent was removed in vacuo and water (10 ml) added. The pH was adjusted to pH 5-6 by the addition of 2M hydrochloric acid. The aqueous layer was washed with DCM (3×25 ml). The aqueous layer was loaded onto a SCX SPE cartridge (20 g) and allowed to stand for 15 min. Elution with ethanol (100 ml) followed by 2M ammonia in ethanol (100 ml) gave the title compound (121 mg) as a white solid.
LC/MS $R_t$ 0.27 min m/z 229 [MH$^+$]. Method C Intermediate 57

3-Cyclopropyl-1-{[(1,1-dimethylethyl)oxy]carbonyl}-1H-pyrazole-4-carboxylic acid

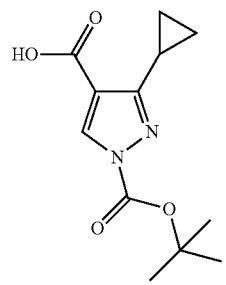 [SMILES: CC(C)(C)OC(=O)n1cc(C(=O)O)c(C2CC2)n1]

To a solution of 3-cyclopropyl-1H-pyrazole-4-carboxylic acid (150 mg) (for example, available from Aldrich) in DMF (2 ml) was added sodium hydride (87 mg; 60% dispersion in mineral oil) and the mixture stirred for 15 min at 20° C. bis(1,1-Dimethylethyl)dicarbonate (0.275 ml) was added and the mixture stirred under nitrogen at room temperature for 18 h. Saturated aqueous ammonium chloride solution (15 ml) was added and the mixture extracted with DCM (3×20 ml) and the organic layers collected using a hydrophobic frit. The solvent was removed in vacuo and the residue purified by chromatography on silica gel (20 g cartridge), eluting with 0-50% ethyl acetate in cyclohexane over 20 min to give the title compound (86 mg) as a colourless oil.
LC/MS $R_t$ 2.82 min m/z 235 [MH$^+$]. Method A Intermediate 58

Ethyl 1-(1-methylethyl)-1H-pyrazole-5-carboxylate

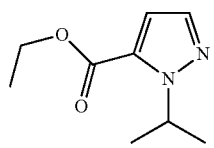

To a solution of ethyl 1H-pyrazole-5-carboxylate (1 g) (for example, available form Bio-Farma) in acetonitrile (80 ml) was added cesium carbonate (2.32 g). 20 min later 2-iodopropane (0.714 ml) was added and the mixture stirred under nitrogen at 20° C. for 18 h. 2-Iodopropane (0.714 ml) was added and the mixture stirred under nitrogen at 20° C. for 5 h. Then further 2-iodopropane (0.714 ml) was added and the mixture was stirred at 20° C. for 18 h. The solvent was removed in vacuo and the residue was partitioned between water (30 ml) and DCM (30 ml). The aqueous phase was extracted with DCM (2×20 ml) and separated by hydrophobic frit. The combined organic layers were concentrated in vacuo. Purification of the residue by chromatography on silica gel (70 g silica), eluting with a gradient of 0-100% ethyl acetate in cyclohexane over 30 min gave the title compound (513 mg) as a yellow oil.
LC/MS $R_t$ 2.91 min m/z 183 [MH$^+$]. Method A Intermediate 59

Ethyl 4-fluoro-1-(1-methylethyl)-1H-pyrazole-5-carboxylate

A microwave vial was charged with ethyl 1-(1-methylethyl)-1H-pyrazole-5-carboxylate (0.15 g) and Selectfluor™ (0.38 g) followed by acetonitrile (3 ml) and acetic acid (1 ml). The mixture was heated at 100° C. under microwave irradiation for 180 min. Selectfluor™ (0.076 g) was added and the mixture heated at 100° C. under microwave irradiation for 60 min. Further Selectfluor™ (0.15 g) was added and the mixture heated at 100° C. under microwave irradiation for 60 min.

Further Selectfluor (0.38 g) was added and the mixture heated at 100° C. under microwave irradiation for 60 min. The solvent was removed in vacuo and the residue was partitioned between DCM (15 ml) and water (15 ml) and separated using a hydrophobic frit. The aqueous layer was extracted with dichloromethane (2×5 ml) and the combined organic layers were concentrated in vacuo. Purification by chromatography on silica gel (20 g silica cartridge), eluting with a gradient of 0-50% DCM in cyclohexane over 20 minutes gave the title compound (100 mg) as a colourless oil.

LC/MS $R_t$ 3.13 min m/z 201 [MH$^+$]. Method A

Intermediate 60

4-Fluoro-1-(1-methylethyl)-1H-pyrazole-5-carboxylic acid

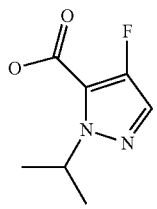

To a solution of ethyl 4-fluoro-1-(1-methylethyl)-1H-pyrazole-5-carboxylate (100 mg) in 1,4-dioxane (2 ml) was added 2M hydrochloric acid (2 ml) and the mixture heated at reflux under nitrogen for 58 h, allowed to stand at room temperature for 62 h, then heated at reflux under Nitrogen for 72 h. The mixture was cooled to room temperature and the solvent was removed in vacuo. Toluene (15 ml) was added and the solvent removed in vacuo to give a white solid that was dried in a vacuum oven overnight to give the title compound (20 mg) as a white solid.

LC/MS $R_t$ 1.91 min m/z 173 [MH$^+$]. Method A

Intermediate 61

2-Amino-1,3-thiazole-4-carboxylic acid

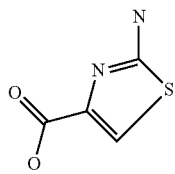

To a solution of ethyl 2-amino-1,3-thiazole-4-carboxylate (150 mg) (for example available, from Maybridge Chemical Company) in 1,4-dioxane (3 ml) was added 2M hydrochloric acid (2 ml) and the mixture heated at reflux under nitrogen for 70 h. The mixture was cooled to room temperature and the solvent removed in vacuo. Toluene (15 ml) was added and the solvent removed in vacuo to give a solid that was dried in an vacuum oven overnight to give the title compound (150 mg) as a brown solid.

$^1$H NMR (400 MHz, DMSO) δ 7.58 (s, 1H)

Intermediate 62

Ethyl 1-ethyl-1H-pyrazole-5-carboxylate

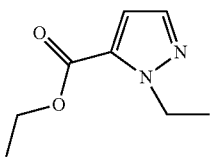

To a solution of 1-ethyl-1H-pyrazole-5-carboxylic acid (950 mg) (for example, available from Fluorochem) in ethanol (50 ml) was added sulphuric acid (0.5 ml) and the mixture stirred at reflux under nitrogen for 70 h. The solvent was removed in vacuo and the residue partitioned between DCM (25 ml) and saturated sodium bicarbonate solution (25 ml) and separated using a hydrophobic frit. The aqueous layer was washed with DCM (2×20 ml) and the organic phases were combined. The solvent was removed in vacuo to give the title compound (1.09 g) as a colourless oil.

LC/MS $R_t$ 2.65 min m/z 169 [MH$^+$]. Method A

Intermediate 63

Ethyl 1-ethyl-4-fluoro-1H-pyrazole-5-carboxylate

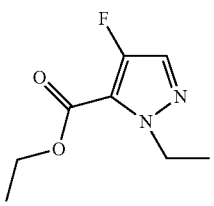

A microwave vial was charged with ethyl 1-ethyl-1H-pyrazole-5-carboxylate (0.2 g) and Selectfluor™ (0.548 g) followed by acetonitrile (3 ml) and acetic acid (0.5 ml). The mixture was heated at 100° C. under microwave irradiation for 120 min. Selectfluor™ (0.548 g) was added and the mixture was heated was heated at 100° C. under microwave irradiation for 60 min. The solvent was removed in vacuo and the residue was partitioned between DCM (15 ml) and water (15 ml) and separated by hydrophobic frit. The aqueous layer was washed with dichloromethane (2×5 ml) and the combined organic layers concentrated in vacuo. Purification by chromatography on silica gel (20 g silica cartridge) eluting with a gradient of 0-50% DCM in cyclohexane over 20 min gave the title compound (67 mg) as a colourless oil.

LC/MS $R_t$ 2.87 min m/z 187 [MH$^+$]. Method A

Intermediate 64

1-Ethyl-4-fluoro-1H-pyrazole-5-carboxylic acid

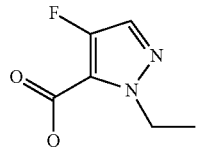

To a solution of ethyl 1-ethyl-4-fluoro-1H-pyrazole-5-carboxylate (67 mg) in 1,4-dioxane (3 ml) was added 2M hydrochloric acid (2 ml) was added and the mixture was heated at reflux under nitrogen for 120 h. The mixture was cooled to room temperature and the solvent was removed in vacuo. Toluene (15 ml) was added and the solvent was removed in vacuo to give a solid that was dried in a vacuum oven overnight to give the title compound (26 mg) as a brown solid.

LC/MS $R_t$ 1.46 min m/z 159 [MH$^+$]. Method A

Intermediate 65

2-Amino-5-(1-methylethyl)-1,3-thiazole-4-carboxylic acid

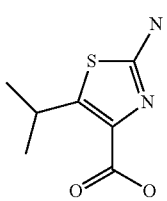

To a solution of methyl 2-amino-5-(1-methylethyl)-1,3-thiazole-4-carboxylate (220 mg) (for example, available from ABCR) in 1,4-dioxane (5 ml) was added 2M hydrochloric acid (5 ml) and the mixture heated at 110° C. for 72 h. The mixture was evaporated in vacuo to give the title compound (240 mg) as a pale yellow solid.

LC/MS $R_t$ 0.89 min m/z 187 [MH$^+$]. Method C

Intermediate 66

Ethyl 2H-1,2,3-triazole-4-carboxylate

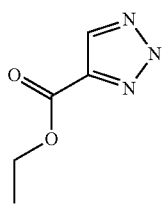

A mixture of ethyl 2-propynoate (4.13 ml) and trimethylsilyl azide (13.5 ml) was heated to 100° C. for 24 h. The cooled mixture was cautiously decomposed with methanol (50 ml) and evaporated in vacuo to give the title compound (5.7 g) as a white solid.

LC/MS $R_t$ 0.58 min m/z 241 [MH$^+$]. Method B

Intermediate 67

Ethyl 2-(1-methylethyl)-2H-1,2,3-triazole-4-carboxylate

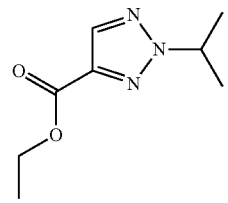

A mixture of ethyl 2H-1,2,3-triazole-4-carboxylate (1 g), potassium carbonate (1.76 g) and 2-iodopropane (1.27 ml) in dry acetonitrile (20 ml) was stirred at 50-60° C. under nitrogen for 2 h. Further 2-iodopropane (0.70 ml) was added and the mixture stirred at 50-60° C. under nitrogen for 16 h. After cooling to room temperature, the mixture was filtered through a 2 g SPE-Silica column with ethyl acetate and the filtrate concentrated in vacuo, Purification of the residue by chromatography on silica gel (70 g silica cartridge), eluting with a gradient of 0-25% ethyl acetate in cyclohexane over 40 min gave the title compound (670 mg) as a colourless oil.

LC/MS $R_t$ 2.25 min m/z 184 [MH$^+$]. Method C

Intermediate 68

2-(1-Methylethyl)-2H-1,2,3-triazole-4-carboxylic acid

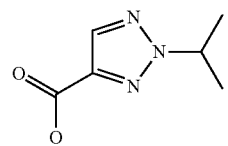

To a solution of ethyl 2-(1-methylethyl)-2H-1,2,3-triazole-4-carboxylate (670 mg) in methanol (6 ml) was added sodium hydroxide (4 ml) and the mixture was stirred at room temperature for 4 h. The methanol was removed in vacuo and water (10 ml) was added and the mixture neutralised (pH 5-6) by the addition of 2M hydrochloric acid. The aqueous layer was extracted with DCM, separated by hydrophobic frit and the organic layer evaporated in vacuo to give the title compound (455 mg) as a white solid.

LC/MS $R_t$ 1.41 min m/z 156 [MH$^+$]. Method C

Intermediate 69

4-Bromo-1,3-dimethyl-1H-pyrazole-5-carboxylic acid

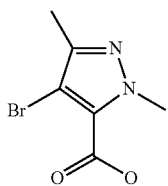

To a solution of ethyl 4-bromo-1,3-dimethyl-1H-pyrazole-5-carboxylate (200 mg) (for example, available from Sinova) in methanol (10 ml) was added 2M sodium hydroxide (5 ml) and the mixture stirred at 20° C. for 18 h. The mixture was concentrated in vacuo and the residue taken up in water (10 ml) and acidified to pH=5 using 2M hydrochloric acid. The mixture was extracted with ethyl acetate (20 ml) dried over sodium sulphate and evaporated to give the title compound (25 mg) as a white solid.

LC/MS $R_t$ 1.77 min m/z 219 [MH$^+$]. Method C

Intermediate 70

Methyl 5-(1-methylethyl)-1,3-thiazole-4-carboxylate

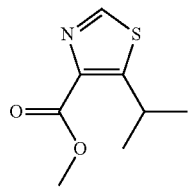

To a solution of methyl 2-amino-5-(1-methylethyl)-1,3-thiazole-4-carboxylate (2.15 g) (available from ABCR) in 30% hypophosphorus acid (53 ml) at −5° C. was added, slowly beneath the surface, maintaining the temperature between −5 and 0° C., sodium nitrite (1.6 g) and the mixture was stirred for a further 1 h at 0° C. The cooling bath was removed for 2 h, then replaced while a cool solution of sodium hydroxide (8.5 g) in water (100 ml) added slowly. The solution was neutralised by the addition of solid sodium hydrogencarbonate and extracted with diethyl ether (50 ml), then dried over sodium sulphate. The mixture was evaporated and purified by chromatography on silica gel eluting with a gradient of ethyl acetate in cyclohexane to give the title compound (1.9 g) as a yellow oil.

LC/MS $R_t$ 2.1 min m/z 186 [MH$^+$]. Method C

Intermediate 71

5-(1-Methylethyl)-1,3-thiazole-4-carboxylic acid

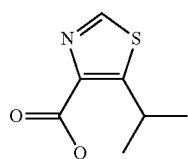

To a solution of methyl 5-(1-methylethyl)-1,3-thiazole-4-carboxylate (1.9 g) in methanol (20 ml) was added 2M sodium hydroxide (20 ml) and the mixture stirred at 20° C. for 18 h. The solvent was removed in vacuo and the residue taken up in water (20 ml) and acidified to pH=2 using 2M hydrochloric acid. The mixture was extracted with ethyl acetate (100 ml), dried over sodium sulphate and evaporated in vacuo to give the title compound (1.7 g) as a white solid.

LC/MS $R_t$ 1.71 min m/z 172 [MH$^+$]. Method C

Intermediates 72 and 73

Ethyl 1-(2-fluoroethyl)-1H-pyrazole-5-carboxylate and ethyl 1-(2-fluoroethyl)-1H-pyrazole-3-carboxylate

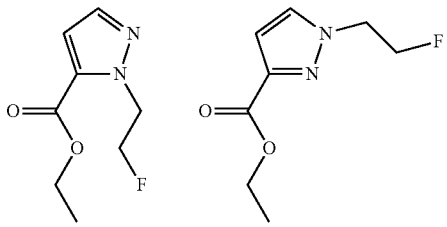

To a solution of ethyl 1H-pyrazole-3-carboxylate (0.77 g) (available from ABCR) in acetonitrile (30 ml) was added cesium carbonate (1.79 g) and the mixture stirred for 5 min when 1-fluoro-2-iodoethane (0.96 g) was added and the mixture stirred at 20° C. for 18 h. The mixture was evaporated and the residue taken up in water (30 ml) and DCM (30 ml) separated by hydrophobic frit and concentrated to ~5 ml, placed on an SPE cartridge (50 g silica) and eluted with a gradient of ethyl acetate in cyclohexane to give the Ethyl 1-(2-fluoroethyl)-1H-pyrazole-5-carboxylate (0.42 g) as a colourless oil.

LC/MS $R_t$ 2.09 min m/z 186 [MH$^+$]. Method C and ethyl 1-(2-fluoroethyl)-1H-pyrazole-3-carboxylate (g) as a colourless oil LC/MS $R_t$ 1.73 min m/z 186 [MH$^+$]. Method C

Intermediate 74

1-(2-Fluoroethyl)-1H-pyrazole-5-carboxylic acid

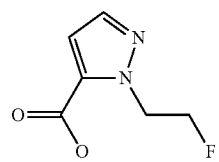 [SMILES: O=C(O)c1ccnn1CCF]

To a solution of ethyl 1-(2-fluoroethyl)-1H-pyrazole-5-carboxylate (0.2 g) in methanol (5 ml) was added 2M sodium hydroxide (5 ml) and the mixture stirred at 20° C. for 18 h. The solvent was removed in vacuo and the residue dissolved in water (20 ml) and acidified to pH-4 using 2M hydrochloric acid then extracted with ethyl acetate (20 ml), dried over sodium sulphate and evaporated to give the title compound (0.132 g) as a white solid.

LC/MS $R_t$ 1.13 min m/z 159 [MH$^+$]. Method C

Intermediate 75

1-(2-Fluoroethyl)-1H-pyrazole-3-carboxylic acid

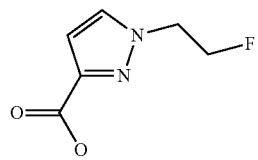 [SMILES: O=C(O)c1ccn(CCF)n1]

To a solution of ethyl 1-(2-fluoroethyl)-1H-pyrazole-3-carboxylate (0.1 g) in methanol (5 ml) was added 2M sodium hydroxide (5 ml) and the mixture stirred at 20° C. for 18 h. The solvent was removed in vacuo and the residue dissolved in water (20 ml) and acidified to pH=4 using 2M hydrochloric acid then extracted with ethyl acetate (20 ml), dried over sodium sulphate and evaporated to give the title compound (16 mg) as a white solid.

LC/MS $R_t$ 0.97 min m/z 159 [MH$^+$]. Method C

Intermediate 76

5-Acetyl-2-methyl-1,3-thiazole-4-carboxylic acid

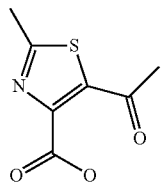

To a solution of ethyl 5-acetyl-2-methyl-1,3-thiazole-4-carboxylate (75 mg) (available from Butt Park Ltd.) in methanol (5 ml) was added 2M sodium hydroxide (5 ml) and the mixture stirred at 20° C. for 18 h. The solvent was removed in vacuo and the mixture taken up in water (5 ml) and acidified to pH=2 using 2M hydrochloric acid then extracted with ethyl acetate (20 ml), dried over sodium sulphate and the mixture evaporated to give the title compound (22 mg) as a yellow solid.

LC/MS $R_t$ 1.12 min m/z 186 [MH$^+$]. Method C

Intermediate 77

Methyl 5-(1-methylethyl)-1,3-oxazole-4-carboxylate

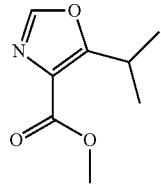

To a solution of sodium methoxide (1.86 g) in DMF (30 ml) was added methyl isocyanoacetate (2.38 ml) dropwise at −50° C. and the mixture stirred for 30 min at −50° C. 2-Methylpropanoyl chloride (3.36 ml) was added gradually to the mixture at −50° C. and the mixture stirred for 2 h at −50° C. The mixture was diluted with DCM (50 ml) and saturated sodium bicarbonate solution (50 ml) was added and the organic layer collected using a hydrophobic frit. The aqueous layer was washed with DCM (2×50 ml) and separated by hydrophobic frit. The combined organic phases were concentrated in vacuo. This was purified by chromatography on silica gel, eluting with a gradient of 0-100% ethyl acetate in cyclohexane, followed by 0-20% methanol. The residue was distilled using a Kugelrohr to give the title compound (553 mg) as yellow solid.

LC/MS $R_t$ 1.97 min m/z 170 [MH$^+$]. Method C

Intermediate 78

5-(1-Methylethyl)-1,3-oxazole-4-carboxylic acid

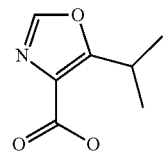

To a solution of methyl 5-(1-methylethyl)-1,3-oxazole-4-carboxylate (0.55 g) in methanol (10 ml) was added sodium hydroxide (10 ml) and the mixture stirred at 20° C. for 18 h. The solvent was removed in vacuo and the residue dissolved in water (10 ml) then acidified using 2M hydrochloric acid. The mixture was concentrated until precipitation commenced when the mixture was extracted with ethyl acetate, dried over sodium sulphate and evaporated to give the title compound (0.45 g) as a yellow solid.

LC/MS $R_t$ 1.6 min m/z 156 [MH$^+$]. Method C

Intermediate 79

Ethyl 1-(1-methylethyl)-1H-1,2,3-triazole-5-carboxylate

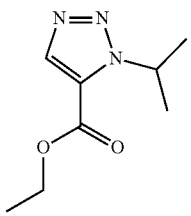

A mixture of ethyl 2H-1,2,3-triazole-4-carboxylate (1.5 g), potassium carbonate (2.64 g) and 2-iodopropane (1.91 ml) in dry acetonitrile (30 ml) was stirred at 50-60° C. under nitrogen for 2 h. Further 2-iodopropane (0.955 ml) was added and the mixture was stirred at 50-60° C. under nitrogen for 1.5 h. The mixture was cooled to room temperature and allowed to stand for 4 days. The mixture was filtered through a 2 g silica SPE column eluting with ethyl acetate. The solution was concentrated in vacuo, Purification by chromatography on silica gel (100 g cartridge), eluting with a gradient of 0-100% ethyl acetate in cyclohexane over 40 min gave the title compound (315 mg) as a colourless oil.

LC/MS $R_t$ 2.16 min m/z 184 [MH$^+$]. Method C

Intermediate 80

1-(1-Methylethyl)-1H-1,2,3-triazole-5-carboxylic acid

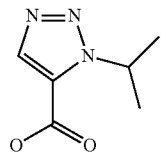

To a solution of ethyl 1-(1-methylethyl)-1H-1,2,3-triazole-5-carboxylate (0.315 g) in methanol (5 ml) was added sodium hydroxide (5 ml) and the mixture stirred at 20° C. for 18 h. The solvent was removed in vacuo and the residue taken up in water (5 ml) and acidified with 2M hydrochloric acid. The mixture was extracted with ethyl acetate and dried over sodium sulphate then filtered and evaporated to give the title compound (0.2 g) a white solid.

LC/MS $R_t$ 1.22 min m/z 154 [MH$^-$]. Method C

Intermediate 81

6-Bromo-4-nitro-2-(tetrahydro-2H-pyran-2-yl)-2H-indazole

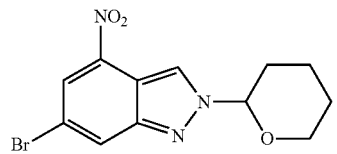 [SMILES: O=[N+]([O-])c1cc(Br)cc2nn(C3CCCCO3)cc12]

To 6-bromo-4-nitro-1H-indazole (10 g, available from Sinova Ltd) in dihydropyran (100 ml) was added TFA (0.068 ml) and the reaction was heated for 1.5 hours at reflux. After cooling, 180 ml DCM and 50 ml saturated sodium bicarbonate solution was added and stirred for 10 minutes. The DCM was separated from the aqueous which was re-washed with DCM (70 ml). The combined organic layers were passed through a hydrophobic frit and evaporated to dryness. The residual solid was triturated with ether then filtered. The solid material was dissolved in DCM and purified by chromatography on silica on the ISCO Companion, using an isocratic gradient of DCM. Purified fractions were combined and evaporated to dryness to afford the title compound (7.78 g).

LC/MS $R_t$ 3.51 min m/z 326 [MH$^-$]. Method A

Intermediate 82

6-Bromo-2-(tetrahydro-2H-pyran-2-yl)-2H-indazol-4-amine

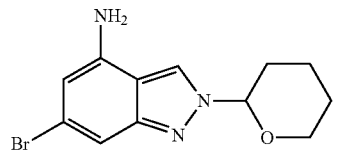 [SMILES: Nc1cc(Br)cc2nn(C3CCCCO3)cc12]

6-Bromo-4-nitro-2-(tetrahydro-2H-pyran-2-yl)-2H-indazole (6 g, 18.40 mmol), iron filings (3.29 g, 58.9 mmol) and ammonium chloride (0.492 g, 9.20 mmol) were weighed to a 250 ml flask and ethanol (60 ml) then water (18 ml) was added. The reaction was heated to 80° C. for 2.5 hr. The reaction mixture was cooled. 100 ml ethyl acetate and 50 ml water was added. There was no visible separation of layers so the reaction was evaporated to remove the ethyl acetate and ethanol. 250 ml ethyl acetate was then added and the organic layer was washed with a further 50 ml water, before passing through a hydrophobic frit. The organic layer was evaporated to dryness and purified by column chromatography on silica (120 g silica column, ISCO companion technology) eluting with a gradient of 1-2% methanol in DCM over 25 minutes. Fractions containing desired material were combined and evaporated to dryness to afford the title compound (3.95 g).

LC/MS $R_t$ 2.87 min m/z 298 [MH$^-$]. Method A

Intermediate 83

N-[6-Bromo-2-(tetrahydro-2H-pyran-2-yl)-2H-indazol-4-yl]-1-(1-methylethyl)-1H-pyrazole-5-carboxamide

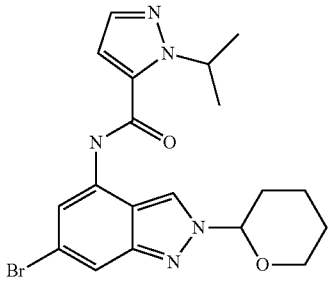 [SMILES: CC(C)n1nccc1C(=O)Nc1cc(Br)cc2nn(C3CCCCO3)cc12]

6-Bromo-2-(tetrahydro-2H-pyran-2-yl)-2H-indazol-4-amine (2.25 g, 7.59 mmol) was dissolved in DCM (40 ml) and DIPEA (2.85 ml, 16.34 mmol) was added. 1-(1-methylethyl)-1H-pyrazole-5-carbonyl chloride (1.41 g, 8.17 mmol) in DCM (10 ml) was added and the mixture left to stir at room temperature overnight. Water (50 ml) was added and the mixture vigorously stirred. The DCM layer was passed through a hydrophobic frit and evaporated to dryness. The material was combined with that obtained from a previous smaller scale reaction carried out in an identical manner but starting with 6-bromo-2-(tetrahydro-2H-pyran-2-yl)-2H-indazol-4-amine (0.2 g, 0.675 mmol). The combined crude materials were purified by chromatography on silica using a 50 g cartridge and eluting progressively with DCM, then 1-4% methanol in DCM. Product containing fractions were combined and evaporated to dryness to afford the title compound (2.8 g).

LC/MS $R_t$ 1.24 min m/z 434 [MH$^-$]. Method B

Similarly prepared was

| Intermediate Number | Compound Name | Structure | Acid chloride | LC/MS R$_t$ min | LC/MS MH⁺ |
|---|---|---|---|---|---|
| 84 | N-[6-Bromo-2-(tetrahydro-2H-pyran-2-yl)-2H-indazol-4-yl]-2-methyl-1,3-thiazole-4-carboxamide | 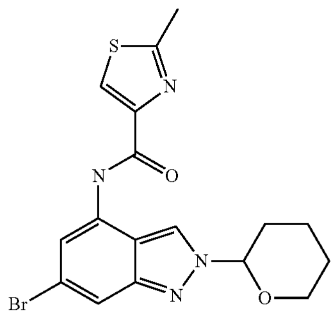 [SMILES: Cc1nc(C(=O)Nc2cc(Br)cc3nn(C4CCCCO4)cc23)cs1] | 2-methyl-1,3-thiazole-4-carbonyl chloride | 1.18 | 423 |

Intermediate 85

1-(1-Methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide

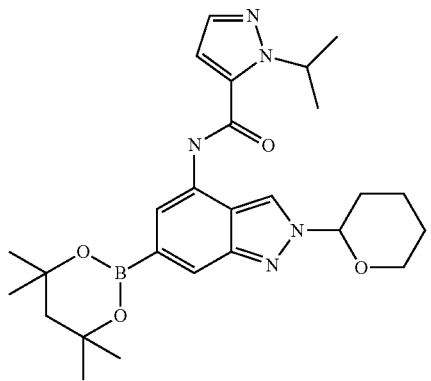 [SMILES: CC(C)n1nccc1C(=O)Nc1cc(B2OC(C)(C)CC(C)(C)O2)cc2nn(C3CCCCO3)cc12]

N-[6-Bromo-2-(tetrahydro-2H-pyran-2-yl)-2H-indazol-4-yl]-1-(1-methylethyl)-1H-pyrazole-5-carboxamide (500 mg, 1.16 mmol), Pd(dppf)Cl$_2$ DCM adduct (94 mg, 0.115 mmol), potassium acetate (341 mg, 3.47 mmol) and 4,4,4',4',6,6,6',6'-octamethyl-2,2'-bi-1,3,2-dioxaborinane (978 mg, 3.47 mmol) were combined in a microwave vial. 1,4-Dioxane (8 ml) was added and the mixture was heated at 80° C. for 30 min. Analysis by LCMS showed incomplete reaction so the mixture was heated again under microwave conditions for 30 min at 80° C. Further Pd(dppf)Cl$_2$ DCM adduct (38 mg) was then added and the reaction heated for another 30 min at 80° C.

The reaction mixture was applied to the top of a silica cartridge and washed through with methanol. After removal of solvent the residue was partitioned between DCM and water and the organics concentrated in vacuo. Purification was carried out by chromatography on silica (40 g) using a gradient of 40%-60% EtOAc in cyclohexane. Fractions containing desired product were combined, concentrated in vacuo and dried under vacuum to afford the title compound as a pale yellow solid.

LC/MS R$_t$ 1.33 min m/z 494 [MH⁻]. Method C

Similarly prepared was

| Intermediate Number | Compound Name | Structure | Aryl bromide | LC/MS R$_t$ min | LC/MS MH⁺ |
|---|---|---|---|---|---|
| 86 | 2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide | 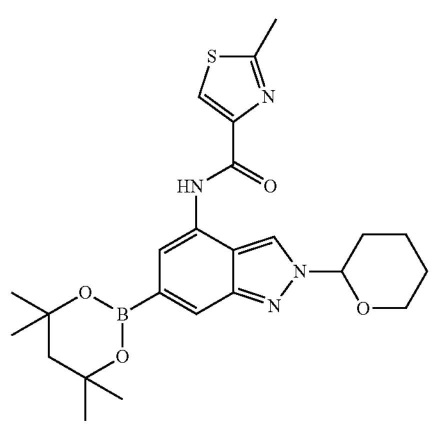 [SMILES: Cc1nc(C(=O)Nc2cc(B3OC(C)(C)CC(C)(C)O3)cc3nn(C4CCCCO4)cc23)cs1] | N-[6-bromo-2-(tetrahydro-2H-pyran-2-yl)-2H-indazol-4-yl]-2-methyl-1,3-thiazole-4-carboxamide | 1.36 | 483 |

Intermediate 87

2-(1,1-Dimethylethyl)-1H-pyrrolo[2,3-b]pyridine 7-oxide

2-(1,1-Dimethylethyl)-1H-pyrrolo[2,3-b]pyridine (10 g, 57 mmol) was dissolved in ethyl acetate:DCM (400 ml, 1:1, v/v), cooled to ~0° C. in an ice bath and treated by dropwise addition of m-chloroperbenzoic acid (15.85 g, 69.5 mmol). The reaction was warmed to room temperature over 3 hours then treated with 30% potassium carbonate (aq) (150 ml). The organic layer was separated and the aqueous washed with further DCM (2×100 ml). The combined organic layers were washed with a sodium metabisulphite solution, dried then evaporated to give title compound, 11.1 g.
LC/MS (method B) Rt=0.87 min m/z 191 [MH$^+$].

Intermediate 88

4-Bromo-2-(1,1-dimethylethyl)-1H-pyrrolo[2,3-b]pyridine

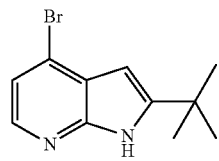

2-(1,1-Dimethylethyl)-1H-pyrrolo[2,3-b]pyridine 7-oxide (11 g, 58 mmol) and tetramethylammonium bromide (13.5 g, 87 mmol) were placed in DMF (78 ml). The mixture was cooled to 0° C. and treated with portion-wise addition of methanesulfonic acid (20.2 g, 116 mmol). The reaction was stirred at 5° C. for 1 hour then warmed to room temperature and stirred for a further hour. The solid was filtered to give title compound, 3.4 g.
LC/MS (method B) Rt=1.27 min m/z 255 [MH$^+$].

Intermediate 89

[2-(1,1-Dimethylethyl)-1H-pyrrolo[2,3-b]pyridin-4-yl]boronic acid

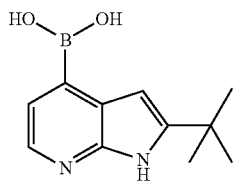 [SMILES: CC(C)(C)c1cc2c(B(O)O)ccnc2[nH]1]

4-Bromo-2-(1,1-dimethylethyl)-1H-pyrrolo[2,3-b]pyridine (430 mg, 1.7 mmol) was dissolved in anhydrous THF (12 ml) under nitrogen and degassed (nitrogen/vacuum 3 times). Sodium hydride (60% dispersion in mineral oil) (88 mg, 2.2 mmol) was added and the reaction stirred at room temperature for 50 mins. The reaction was then cooled to −78° C., further degassed as before and 1.5M ″butyl lithium in hexanes (1.6 ml, 2.4 mmol) was added dropwise over 5 mins. The reaction was stirred for 45 mins then tri-isopropyl borate (1.2 ml) was added. The reaction was stirred for a further hour before warming to room temperature. Saturated ammonium chloride (aq) (20 ml) was added and the reaction was extracted with DCM (2×25 ml). The combined organics were washed with water (50 ml), passed through a hydrophobic frit and concentrated. The residue was dissolved in DCM:MeOH (1:1, v/v) and loaded onto an aminopropyl cartridge (10 g). The cartridge was washed with DCM:MeOH (1:1, v/v) and eluted with 2M ammonia in MeOH, which was concentrated to give title compound, 164 mg.
$^1$H NMR (400 MHz, DMSO-d6): δ ppm 11.71 (br. s., 1H), 8.33 (br. s., 2H), 8.11 (d, J=4.8 Hz, 1H), 7.38 (d, J=5.0 Hz, 1H), 6.47 (d, J=2.0 Hz, 1H), 1.36 (s, 9H).

Intermediate 90

N-(5-Bromo-2-methyl-3-pyridinyl)methanesulfonamide

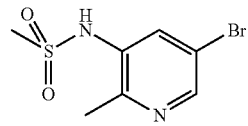

Methanesulfonyl chloride (97 μl) was added dropwise to 5-bromo-2-methyl-3-pyridinamine (Chempacific) (200 mg) in pyridine (5 ml). The reaction was stirred at room temperature for 20 min before addition of 2M HCl (aq) (5 ml) and extraction into DCM. The DCM was passed through a hydrophobic frit then dried under a stream of nitrogen. The residue was dissolved in DCM and washed through an aminopropyl cartridge (preconditioned with DCM) with DCM to give title compound, 77 mg.
LC/MS (Method B) Rt=0.77 min m/z 267 [MH$^+$].

Intermediate 91

6-Bromo-1-(phenylsulfonyl)-1H-indazol-4-amine

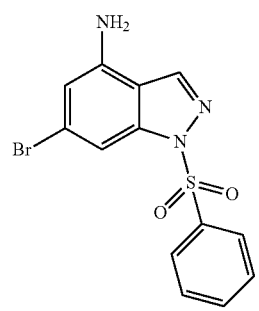 [SMILES: Nc1cc(Br)cc2c1cnn2S(=O)(=O)c1ccccc1]

6-Bromo-1H-indazol-4-amine (5 g) was dissolved in DMF (20 ml) and cooled in an ice bath. 60% Sodium hydride in mineral oil (0.94 g) was added portionwise and the reaction was left under an ice bath for 30 min. Benzenesulfonyl chloride (3 ml) in DMF (5 ml) was added slowly over 15 minutes and the reaction was left to warm up to room temperature overnight. Water (100 ml) was added and the reaction stirred for 20 minutes. Ethyl acetate (120 ml) was added and the water was separated, washed with ethyl acetate (50 ml×2) and the combined organics were washed with 7.5% lithium chlo-

Intermediate 92

1-(Phenylsulfonyl)-6-(trimethylstannanyl)-1H-indazol-4-amine

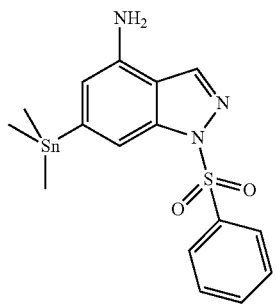 [SMILES: [CH3][Sn]([CH3])([CH3])[c]1cc(N)c2cnn(S(=O)(=O)c3ccccc3)c2c1]

A mixture of 6-bromo-1-(phenylsulfonyl)-1H-indazol-4-amine (1.3 g), hexamethylditin (2.4 g), triethylamine (1 ml) and Pd(PPh$_3$)$_4$ (0.2 g) in toluene (15 ml) was heated under microwave irradiation at 120° C. for 1 h. The reaction was applied to a silica cartridge using light petroleum 40-60° C. as eluent. This was changed to ether/light petroleum 40-60° C. The appropriate fractions were evaporated to give title compound, 1.2 g.

LC/MS R$_t$ 3.3 min m/z 438 [MH$^+$]. Method C.

Intermediate 93

2-Methyl-N-[1-(phenylsulfonyl)-6-(trimethylstannanyl)-1H-indazol-4-yl]-1,3-thiazole-4-carboxamide

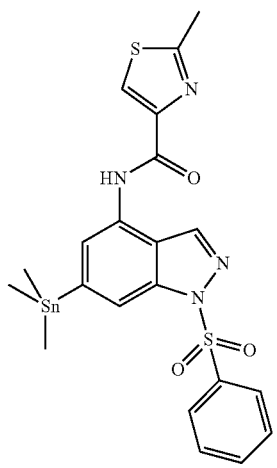 [SMILES: Cc1nc(C(=O)Nc2c[c]([Sn]([CH3])([CH3])[CH3])cc3c2cnn3S(=O)(=O)c2ccccc2)cs1]

2-Methyl-1,3-thiazole-4-carbonyl chloride (350 mg) in DCM (4 ml) was added dropwise to 1-(phenylsulfonyl)-6-(trimethylstannanyl)-1H-indazol-4-amine (300 mg) in DCM (15 ml) and pyridine (0.167 ml). The reaction was stirred at room temperature overnight. Saturated sodium bicarbonate (aq) (25 ml) was added and the reaction vigorously stirred for 15 min. The DCM was passed through a hydrophobic frit then evaporated to dryness. The residue was dissolved in DCM and purified on a silica cartridge, preconditioned with cyclohexane, washing with cyclohexane followed by elution with ether. The ether was evaporated to give title compound, 373 mg.

LC/MS R$_t$ 1.42 min m/z 563 [MH$^+$]. Method D.

Intermediate 94

1-(1-Methylethyl)-1H-pyrazole-5-carbonyl chloride

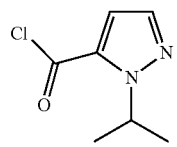

Thionyl chloride (5 ml) was added to 1-(1-methylethyl)-1H-pyrazole-5-carboxylic acid (1 g) and the reaction was heated at 80° C. for 5 h. The reaction was evaporated, then azeotroped with toluene to give title compound, 856 mg.

$^1$H NMR (CDCl$_3$) δ 7.6 (d, 1H), δ 7.1 (d, 1H), δ 5.2 (m, 1H), δ 1.5 (d, 6H).

Intermediate 95

1-(1-Methylethyl)-N-[1-(phenylsulfonyl)-6-(trimethylstannanyl)-1H-indazol-4-yl]-1H-pyrazole-5-carboxamide

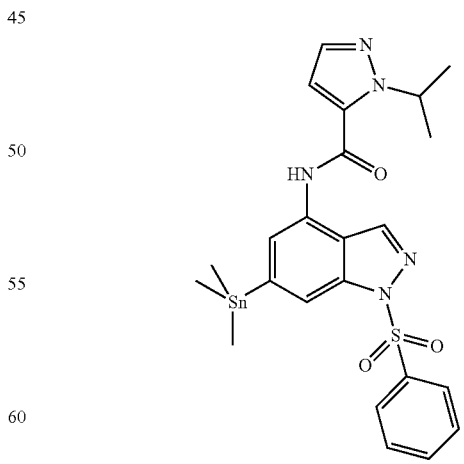

1-(1-Methylethyl)-1H-pyrazole-5-carbonyl chloride (152 mg) in DCM (10 ml) was added dropwise to 1-(phenylsulfonyl)-6-(trimethylstannanyl)-1H-indazol-4-amine (350 mg) in DCM (15 ml) and pyridine (0.07 ml). The reaction was stirred at room temperature for 10 min before addition of further 1-(1-methylethyl)-1H-pyrazole-5-carbonyl chloride (10 mg). The reaction was stirred for 30 min, saturated sodium bicarbonate (aq) (25 ml) was added and stirred vigorously for 10 min before the DCM was separated through a hydrophobic frit and evaporated to dryness. The residue was dissolved in DCM and loaded onto a silica cartridge preconditioned with cyclohexane. The cartridge was eluted with 0-100% ether in cyclohexane. The compound containing fraction was evaporated to dryness to give title compound, 360 mg.

LC/MS $R_t$ 3.66 min m/z 574 [MH$^+$]. Method C.

Intermediate 96

1,4-Dimethyl-1H-pyrazole-3-carboxylic acid

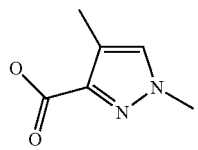

Lithium hydroxide (0.864 g), THF (30 ml) and water (30 ml) were added to methyl 1,4-dimethyl-1H-pyrazole-3-carboxylate (1.39 g) and the reaction was stirred at room temperature for 3 h. The reaction was acidified with 5M HCl (aq) to pH to 7 and then washed through a waters HLB OASIS cation exchange cartridge. The cartridge was preconditioned with methanol, then water. The reaction was loaded onto the cartridge and washed with water, then eluted with methanol. The methanol fraction was evaporated in vacuo to give title compound, 1.1 g.

LC/MS $R_t$ 0.49 min m/z 141 [MH$^+$]. Method D.

Intermediate 97

1,4-Dimethyl-1H-pyrazole-3-carbonyl chloride

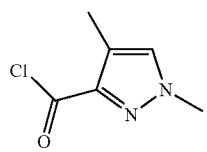

Thionyl chloride (4 ml) was added to 1,4-dimethyl-1H-pyrazole-3-carboxylic acid (0.5 g) and the reaction was heated at 80° C. for 2 h. Further thionyl chloride (2 ml) was added and the reaction was heated at 80° C. for 1 h. The reaction was evaporated, then azeotroped with toluene to give title compound, 511 mg.

$^1$H NMR (CDCl$_3$) δ 7.3 (s, 1H), δ 4 (s, 3H), δ 2.2 (s, 3H).

Intermediate 98

1,4-Dimethyl-N-[1-(phenylsulfonyl)-6-(trimethylstannanyl)-1H-indazol-4-yl]-1H-pyrazole-3-carboxamide

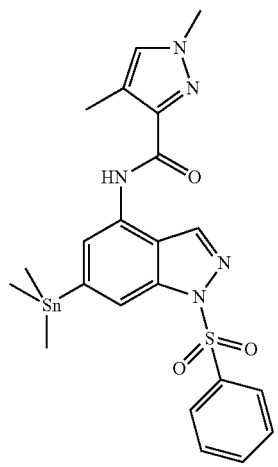 [SMILES: Cc1cn(C)nc1C(=O)Nc1c[c]([Sn]([CH3])([CH3])[CH3])cc2c1cnn2S(=O)(=O)c1ccccc1]

1,4-Dimethyl-1H-pyrazole-3-carbonyl chloride (46 mg) in DCM (2.5 ml) was added over 5 min to 1-(phenylsulfonyl)-6-(trimethylstannanyl)-1H-indazol-4-amine (100 mg) in DCM (2.5 ml) and pyridine (0.023 ml). The reaction was stirred at room temperature for 2 h. Separately, 1,4-dimethyl-1H-pyrazole-3-carbonyl chloride (273 mg) in DCM (5 ml) was added over 10 min to 1-(phenylsulfonyl)-6-(trimethylstannanyl)-1H-indazol-4-amine (600 mg) in DCM (25 ml) and pyridine (0.2 ml). The reaction was stirred at room temperature for 1 h. The reactions were combined and separated between saturated sodium bicarbonate (aq) and DCM. The DCM was passed through a hydrophobic frit then dried. The residue was dissolved in DCM and purified using a silica cartridge, preconditioned with cyclohexane. The cartridge was eluted with cyclohexane:diethyl ether (1:1, v/v) then diethyl ether, then 10% methanol in diethyl ether and finally with 50% methanol in diethyl ether. Pure fractions were combined and dried to give title compound, 753 mg.

LC/MS $R_t$ 1.41 min m/z 560 [MH$^+$]. Method D.

Intermediate 99

4-Chloro-1-ethyl-1H-pyrazole-5-carbonyl chloride

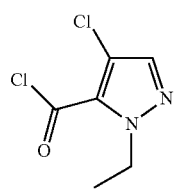

Thionyl chloride (5 ml) was added to 4-chloro-1-ethyl-1H-pyrazole-5-carboxylic acid (1 g) and the reaction was heated at 80° C. for 6 h then cooled to room temperature overnight. The reaction was evaporated, then azeotroped with toluene to give title compound, 970 mg.

$^1$H NMR (CDCl$_3$) δ 7.6 (s, 1H), δ 4.5 (q, 2H), δ 1.4 (t, 3H).

Intermediate 100

4-Chloro-1-ethyl-N-[1-(phenylsulfonyl)-6-(trimethylstannanyl)-1H-indazol-4-yl]-1H-pyrazole-5-carboxamide

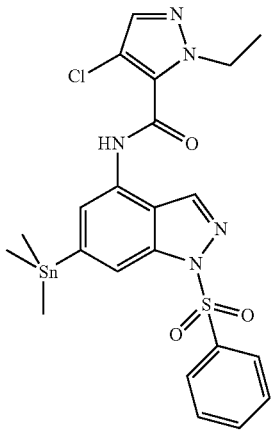 [SMILES: CCn1ncc(Cl)c1C(=O)Nc1c[c]([Sn]([CH3])([CH3])[CH3])cc2c1cnn2S(=O)(=O)c1ccccc1]

4-Chloro-1-ethyl-1H-pyrazole-5-carbonyl chloride (122 mg) in DCM (5 ml) was added over 5 min to 1-(phenylsulfonyl)-6-(trimethylstannanyl)-1H-indazol-4-amine (250 mg) in DCM (10 ml) and pyridine (0.05 ml). The reaction was stirred at room temperature for 1.5 h. Saturated sodium bicarbonate (aq) (20 ml) was added and the reaction stirred vigorously before the DCM was passed through a hydrophobic frit and evaporated to dryness. The residue was passed through a silica cartridge, preconditioned with cyclohexane. The silica cartridge was washed with cyclohexane:diethyl ether (1:1, v/v), then diethyl ether. The product containing ether fraction was evaporated to dryness to give title compound, 303 mg.

LC/MS $R_t$ 1.48 min m/z 594 [MH$^+$]. Method D.

Intermediate 101

4-Iodo-1H-pyrazolo[3,4-b]pyridine

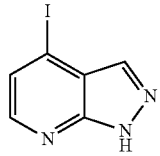

2-Fluoro-4-iodo-3-pyridinecarbaldehyde (from Asymchem) (0.97 g) was added portionwise over 5 min to hydrazine hydrate (5 ml). The resulting suspension was stirred at room temperature for 5 h. Water (10 ml) was added and the solid was filtered and washed with further water to give title compound, 664 mg.

LC/MS $R_t$ 0.84 min m/z 246 [MH$^+$]. Method B.

Intermediate 102

4-Iodo-1-(phenylsulfonyl)-1H-pyrazolo[3,4-b]pyridine

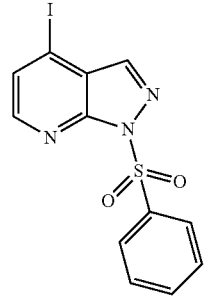 [SMILES: O=S(=O)(c1ccccc1)n1ncc2c(I)ccnc21]

To a stirring suspension of NaH (0.9 g) in anhydrous THF (25 ml) at −5° C. was added 4-iodo-1H-pyrazolo[3,4-b]pyridine (5 g) in anhydrous THF (75 ml) and DMF (25 ml). Triethylamine (3 ml) was added and the reaction was stirred for 30 min at 0° C. Benzenesulfonyl chloride (2.9 ml) in anhydrous THF (25 ml) was added dropwise over 10 min and the reaction was stirred for 1 h at 0° C. then quenched with water. The layers were separated and the aqueous was re-extracted with ethyl acetate. The combined organics were washed with brine, dried over magnesium sulfate, filtered and then evaporated to yield a solid residue that was triturated with methanol to give title compound, 4.1 g.

LC/MS $R_t$ 1.04 min m/z 386 [MH$^+$]. Method D.

Intermediate 103

4-Bromo-1-(phenylsulfonyl)-1H-indazole

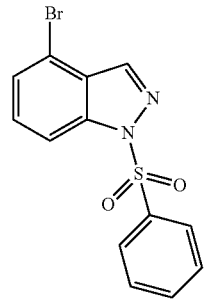 [SMILES: O=S(=O)(c1ccccc1)n1ncc2c(Br)cccc21]

To a stirring suspension of NaH (0.78 g) in anhydrous THF (17.5 ml) at −5° C. was added 4-bromo-1H-indazole (3.5 g) in anhydrous THF (35 ml). Benzenesulfonyl chloride (2.5 ml) in anhydrous THF (17.5 ml) was added dropwise over 10 mins. The reaction was stirred for 1 h at 0° C. then quenched with water. The layers were separated and the aqueous was re-extracted with ethyl acetate. The combined organics were washed with brine, dried over magnesium sulfate, filtered and then evaporated to yield a solid residue that was triturated with methanol to give title compound, 5.18 g.

LC/MS $R_t$ 1.24 min m/z 339 [MH$^+$]. Method D.

Intermediate 104

4-Bromo-1-(phenylsulfonyl)-1H-pyrrolo[2,3-c]pyridine

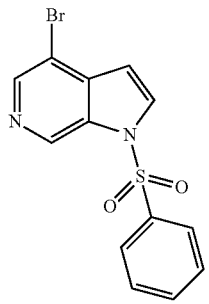

To a stirring suspension of NaH (1.3 g) in anhydrous THF (25 ml) at −5° C. was added 4-bromo-1H-pyrrolo[2,3-c]pyridine (prepared for example as described in patent US2005/0090529, 5 g) in anhydrous THF (75 ml) over 10 min. The reaction was stirred at −5° C. for 10 min then benzenesulfonyl chloride (3.6 ml) in anhydrous THF (25 ml) was added over 10 min. The reaction was stirred at 0° C. for 1 h then quenched with water. The layers were separated and the aqueous was re-extracted with ethyl acetate. The organics were combined, washed with brine, dried over magnesium sulfate, filtered and then evaporated to yield a residue that was triturated using methanol (25 ml). The resulting solid was collected by filtration, washed sparingly with methanol then dried in vacuo at 45° C. overnight to give title compound, 7.9 g.

LC/MS $R_t$ 1.11 min m/z 339 [MH+]. Method D.

Intermediate 105

6-(1H-Indol-4-yl)-1-(phenylsulfonyl)-1H-indazol-4-amine

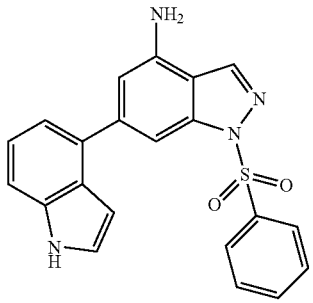 [SMILES: Nc1cc(-c2cccc3[nH]ccc23)cc2c1cnn2S(=O)(=O)c1ccccc1]

6-Bromo-1-(phenylsulfonyl)-1H-indazol-4-amine (3 g, 8.52 mmol), 4-(4,4,5,5-tetramethyl-1,3,2-dioxaborolan-2-yl)-1H-indole (2.278 g, 9.37 mmol), Pd(dppf)Cl$_2$ (0.623 g, 0.852 mmol) and sodium carbonate (2.71 g, 25.6 mmol) were divided between 2× microwave vials and dissolved in 1,4-dioxane (16 mL) and water (16 mL); 8 ml of each solvent in each vial. The vials were heated in the microwave at 100° C. for 10 min. The mixtures were combined and filtered through Celite, washing with EtOAc. The resulting mixture was partitioned between water (100 ml) and EtOAc (100 ml) and the layers separated. The aqueous layer was extracted with further EtOAc (2×50 ml) and the organic extracts were combined, passed through a hydrophobic frit and the solvent removed in vacuo to give a brown solid which was preadsorbed onto silica and added to the top of a 100 g silica SPE cartridge. This was eluted with 0-100% EtOAc/cyclohexane over 60 minutes on the FlashMaster II. The product-containing fractions were combined and the solvent was removed in vacuo to afford the title compound as orange crystals which were dried on a high vacuum line for 1 hour.

LCMS (Method D): $R_t$=1.11 mins, MH+=388.

Intermediate 106

2-(Chloromethyl)-N-[6-(1H-indol-4-yl)-1-(phenylsulfonyl)-1H-indazol-4-yl]-1,3-thiazole-4-carboxamide

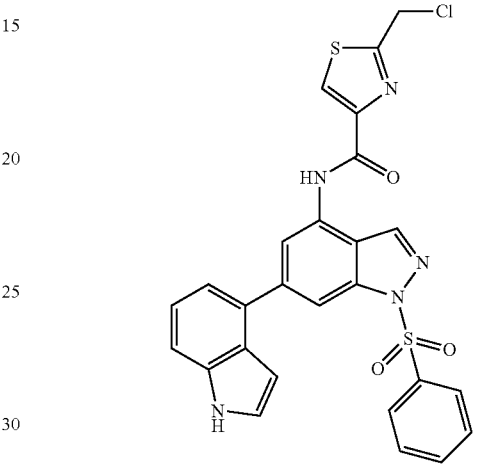

To solution of 6-(1H-indol-4-yl)-1-(phenylsulfonyl)-1H-indazol-4-amine (1.5 g, 3.86 mmol) in chloroform (20 ml) at 0° C. was added DIPEA (1.35 ml, 7.72 mmol). 2-(Chloromethyl)-1,3-thiazole-4-carbonyl chloride (1.8 g, 6.98 mmol) in chloroform (20 ml) was added dropwise and the mixture was stirred at 0° C. for 1 h 15 mins. The mixture was allowed to warm to room temperature and stirring continued for 18 h. A further portion of 2-(chloromethyl)-1,3-thiazole-4-carbonyl chloride (0.2 g, 1.02 mmol) was added to the mixture which was stirred at room temperature for 30 mins. Water (50 ml) was added to quench the reaction and the mixture was extracted with DCM (2×100 ml), separating the layers using a hydrophobic frit. The organics were collected and solvent removed in vacuo to give a brown solid which was triturated with ether (10 ml). The solid was filtered off and dried in a vacuum oven overnight to afford the title compound (1.6 g).

LCMS (Method C): $R_t$=1.26 mins, MH+=548.

Intermediate 107

6-Bromo-3-fluoro-4-nitro-1H-indazole

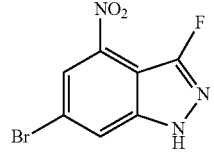

To a solution of 6-bromo-4-nitro-1H-indazole (10 g, 41.3 mmol, available from Sinova) in acetonitrile (100 ml) and acetic acid (20.00 ml) was added Selectfluor® (22.10 g, 83 mmol). The resultant mixture was heated to 100° C. and stirred overnight. The resultant orange solution was concentrated under vacuum then partitioned between ethyl acetate and water. The layers were separated and the aqueous extracted again with ethyl acetate. The combined organics were dried over MgSO₄, filtered and concentrated. The solid was then dissolved in 20 ml DCM, loaded onto a 330 g silica column and purified on a 0-100% EtOAc/Cyclohexane gradient. The relevant fractions were combined and concentrated to yield the title compound as an orange solid (6.9 g).

LCMS (Method D): $R_t$=0.98 mins, MH⁺=258/260.

Intermediate 108

6-Bromo-3-fluoro-4-nitro-1-(phenylsulfonyl)-1H-indazole

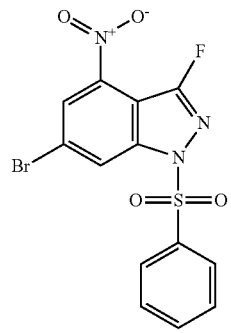 [SMILES: O=[N+]([O-])c1cc(Br)cc2c1c(F)nn2S(=O)(=O)c1ccccc1]

To a stirring suspension of sodium hydride (0.677 g, 16.92 mmol) in THF (25 ml) at 0° C. was added a solution of 6-bromo-3-fluoro-4-nitro-1H-indazole (4 g, 15.38 mmol) in THF (25 ml) dropwise. The reaction mixture was allowed to stir for 30 min then allowed to warm to room temperature before benzenesulfonyl chloride (2.170 ml, 16.92 mmol) was added. after approximately 2 h the reaction mixture was partitioned between ethyl acetate and water. The layers were separated and the aqueous was then extracted again with ethyl acetate. The combined organics were then washed with brine, dried over MgSO₄, filtered and concentrated. The solid was triturated with 50 ml methanol and filtered to yield the title compound as a yellow solid (5.96 g).

LCMS (Method D): $R_t$=1.27 mins (poor ionisation).

Intermediate 109

6-Bromo-3-fluoro-1-(phenylsulfonyl)-1H-indazol-4-amine

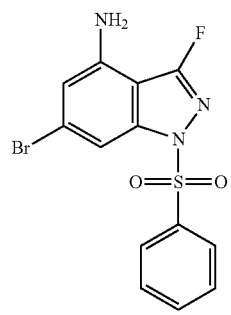

6-Bromo-3-fluoro-4-nitro-1-(phenylsulfonyl)-1H-indazole (5.9 g, 14.74 mmol) was suspended in acetic acid (60 ml) and to it added iron powder (4.12 g, 73.7 mmol). The suspension was heated to reflux for 2 h, then the reaction mixture was cooled, diluted with 100 ml EtOAc and filtered through celite. The filter cake was washed well with ethyl acetate then the filtrate basified till the colour moved from the aqueous layer to the organic (around pH 8-9). The biphasic system was then stirred for around 5 minutes and the aqueous layer turned cloudy. The layers were then separated, the aqueous washed with ethyl acetate and the combined organics washed with brine, dried (MgSO₄), filtered and concentrated in vacuo. The residue was dry loaded onto a 330 g silica cartridge, purified on a 0-100% EtOAc/Cyclohexane gradient and the relevant fractions combined and concentrated to yield the title compound as a yellow solid (2.4 g).

LCMS (Method D): $R_t$=1.17 mins, MH⁺=370/372.

Intermediate 110

3-Fluoro-1-(phenylsulfonyl)-6-(trimethylstannanyl)-1H-indazol-4-amine

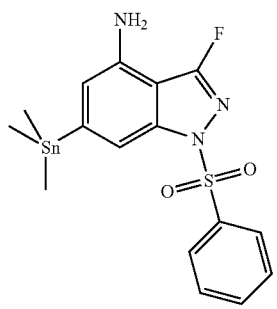 [SMILES: [CH3][Sn]([CH3])([CH3])[c]1cc(N)c2c(F)nn(S(=O)(=O)c3ccccc3)c2c1]

6-Bromo-3-fluoro-1-(phenylsulfonyl)-1H-indazol-4-amine (1.9 g, 5.13 mmol), hexamethylditin (2.66 ml, 12.8 mmol), triethylamine (1.431 ml, 10.26 mmol) and tetrakis(triphenylphosphine)palladium(0) (0.593 g, 0.513 mmol) were placed in toluene (30 ml). The mixture was split into 2 microwave vials and the mixtures heated at 110° C. for 1 hr in the microwave. The mixtures were combined and poured onto a 50 g silica cartridge which was eluted with cyclohexane followed by 1:1 cyclohexane:diethyl ether to give the title compound (2.25 g).

LCMS (Method C): $R_t$=3.46 mins, MH⁺=456.

Intermediate 111

4-Bromo-6-fluoro-1-[(4-nitrophenyl)sulfonyl]-1H-indole

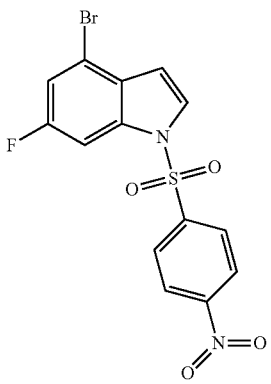 [SMILES: O=[N+]([O-])c1ccc(S(=O)(=O)n2ccc3c(Br)cc(F)cc32)cc1]

Sodium hydride (299 mg, 7.48 mmol) was added to a stirred solution of 4-bromo-6-fluoro-1H-indole (800 mg, 3.74 mmol) in DMF (20 ml) that had been cooled in an ice bath to 0° C. and placed under nitrogen. The mixture was stirred for 5 mins before 4-nitrobenzenesulfonyl chloride (911 mg, 4.11 mmol) was added. The mixture was stirred at 0° C. for 1 hour. The resultant orange/brown solution was poured into stirring water (40 ml). The mixture was rapidly stirred for 30 mins. The resulting brown suspension was collected by filtration, washed with water and dried in a vacuum oven at 50° C. overnight to give a pale brown solid, which was purified by Flashmaster II, on a silica cartridge (100 g) using a gradient of ethylacetate and cyclohexane to afford the title compound as a white solid.

LCMS (Method C): $R_t$=3.61 mins, MH$^+$=400.

Intermediate 112

3-Fluoro-6-{6-fluoro-1-[(4-nitrophenyl)sulfonyl]-1H-indol-4-yl}-1-(phenylsulfonyl)-1H-indazol-4-amine

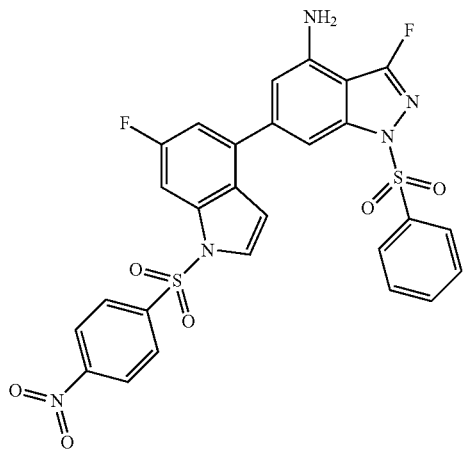 [SMILES: Nc1cc(-c2cc(F)cc3c2ccn3S(=O)(=O)c2ccc([N+](=O)[O-])cc2)cc2c1c(F)nn2S(=O)(=O)c1ccccc1]

A solution of 3-fluoro-1-(phenylsulfonyl)-6-(trimethyl-stannanyl)-1H-indazol-4-amine (0.65 g, 1.43 mmol), 4-bromo-6-fluoro-1-[(4-nitrophenyl)sulfonyl]-1H-indole (0.69 g, 1.71 mmol) and tetrakis(triphenylphosphine)palladium (0) (0.17 g, 0.14 mmol) in DMF (5 mL) was heated to 120° C. for 18 hr. The mixture was concentrated in vacuo and purified by silica cartridge (100 g) by Flashmaster II using a gradient of cyclohexane and ethyl acetate to give the title compound as an orange solid (0.48 g).

LCMS (Method D): $R_t$=1.39 mins, MH$^+$=610.

Intermediate 113

N-(4-Bromo-1H-indol-6-yl)methanesulfonamide

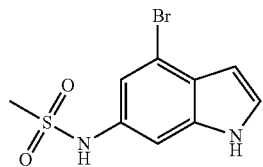

4-Bromo-6-amino indole (100 mg, 0.47 mmol) and triethylamine (0.1 ml, 0.71 mmol) were stirred together in pyridine at 0° C. Mesyl chloride (54 mg, 0.47 mmol) was then added and the mixture stirred for 1 hour, then allowed to warm to room temperature. The mixture was loaded directly onto an aminopropyl cartridge (10 g) and eluted with methanol. Solvent was evaporated and the residue was further purified by chromatography on silica (20 g cartridge) eluting with 0-25% methanol in DCM over 20 mins to afford the title compound as a orange/brown gum (110 mg).

LCMS (Method D): $R_t$=0.92 mins, MH$^+$=287/289.

Intermediate 114

N-(4-Bromo-1H-indol-6-yl)benzenesulfonamide

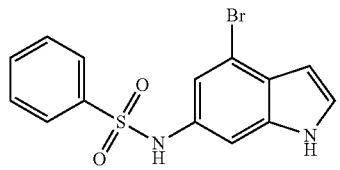 [SMILES: O=S(=O)(Nc1cc(Br)c2cc[nH]c2c1)c1ccccc1]

4-Bromo-6-amino indole (100 mg, 0.47 mmol) and triethylamine (0.1 ml, 0.71 mmol) were stirred together in pyridine at 0° C. Benzene sulphonyl chloride (84 mg, 0.47 mmol) was then added and the mixture stirred for 1 hour, then allowed to warm to room temperature. The mixture was loaded directly onto an aminopropyl cartridge (10 g) and eluted with methanol. Solvent was evaporated to afford the title compound as an orange/brown gum (90 mg).

LCMS (Method D): $R_t$=1.09 mins, MH$^+$=349/351.

Intermediate 115

2-(Chloromethyl)-N-{1-(phenylsulfonyl)-6-[1-(phenylsulfonyl)-1H-pyrrolo[2,3-b]pyridin-4-yl]-1H-indazol-4-yl}-1,3-thiazole-4-carboxamide

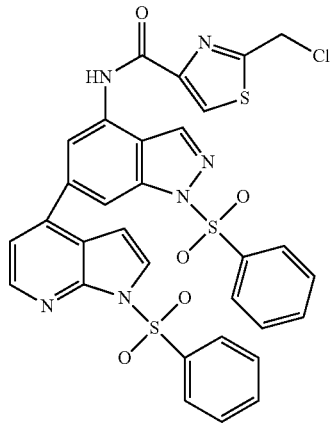 [SMILES: O=C(Nc1cc(-c2ccnc3c2ccn3S(O)(O)c2ccccc2)cc2c1cnn2S(O)(O)c1ccccc1)c1csc(CCl)n1]

1-(Phenylsulfonyl)-6-[1-(phenylsulfonyl)-1H-pyrrolo[2,3-b]pyridin-4-yl]-1H-indazol-4-amine (663 mg, 1.252 mmol) in chloroform (10 mL) was stirred at 0° C. DIPEA (0.437 mL, 2.504 mmol) was added into the reaction mixture, then 2-(chloromethyl)-1,3-thiazole-4-carbonyl chloride (300 mg, 1.530 mmol) in chloroform (10.00 mL) was added. The reaction mixture was stirred at 0° C. for 15 mins. A further portion of 2-(chloromethyl)-1,3-thiazole-4-carbonyl chloride (400 mg, 1.252 mmol) was added to the reaction mixture and stirring was continued. When no further product formation was observed, further 2-(chloromethyl)-1,3-thiazole-4-carbonyl chloride (1.6 g, 1.252 mmol) was added to the reaction mixture which was stirred under nitrogen for 18 h. The solution was treated with DCM (25 mL) and saturated aqueous sodium bicarbonate (25 mL), then stirred for 10 mins. The organic layer was separated, washed with diluted aqueous sodium chloride (25 mL) and then passed through a hydrophobic frit. A part of the solvent was removed then the solution was applied to a silica column (Flasmaster II, 100 g silica cartridge) and eluted with a gradient of 0-100% ethylacetate/cyclohexane over 60 min. Fractions containing desired product we combined and the solvent was removed to afford the title compound as a white solid (111 mg).

LCMS (Method C) Rt=1.34 min, MH+=690.

Intermediate 116

1-(Phenylsulfonyl)-6-[1-(phenylsulfonyl)-1H-pyrrolo[2,3-b]pyridin-4-yl]-1H-indazol-4-amine

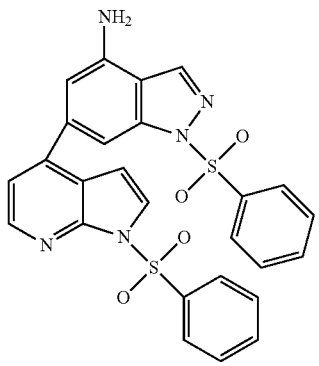 [SMILES: Nc1cc(-c2ccnc3c2ccn3S(O)(O)c2ccccc2)cc2c1cnn2S(O)(O)c1ccccc1]

4-Bromo-1-(phenylsulfonyl)-1H-pyrrolo[2,3-b]pyridine (1.546 g, 4.59 mmol), 1-(phenylsulfonyl)-6-(trimethylstannanyl)-1H-indazol-4-amine (2 g, 4.59 mmol) and Pd(Ph$_3$P)$_4$ (0.265 g, 0.229 mmol) were added to N,N-dimethylformamide (30 mL) under nitrogen. The mixture was heated at 100° C. for 2 days then cooled at room temperature and concentrated in vacuo. The mixture was purified by column chromatography on silica (70 g) eluting with ammonia and methanol in DCM, then again using the Companion and eluting with a gradient of 30 to 85% MeCN (+0.1% TFA)/H$_2$O (0.1% TFA). Fractions containing desired product were combined and the solvent was removed to afford the title compound as a brown solid (663 mg).

LCMS (Method C) Rt=1.17 min, MH$^+$=530.

Intermediate 117

1-(Phenylsulfonyl)-6-[1-(phenylsulfonyl)-1H-pyrazolo[3,4-b]pyridin-5-yl]-1H-indazol-4-amine

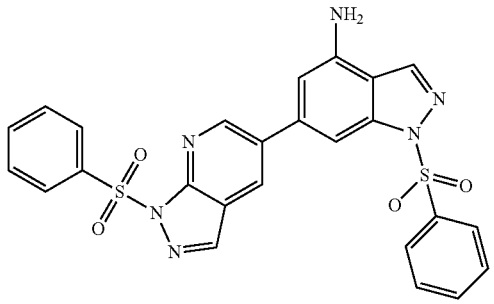

1-(Phenylsulfonyl)-6-(4,4,6,6-tetramethyl-1,3,2-dioxaborinan-2-yl)-1H-indazol-4-amine (1.5 g, 3.63 mmol), 5-bromo-1-(phenylsulfonyl)-1H-pyrazolo[3,4-b]pyridine (1.350 g, 3.99 mmol), Pd(dppf)Cl$_2$ (0.531 g, 0.726 mmol) and tripotassium phosphate (2.311 g, 10.89 mmol) were divided between 2 microwave vials and dissolved in 1,4-Dioxane (18 mL) and Water (6 mL); 9 ml dioxane and 3 ml water in each. Each vial was heated to 100° C. for 10 min in the microwave. Solvent was removed in vacuo and the residue was partitioned between DCM (100 ml) and water (100 ml). The organic layer was collected using a hydrophobic frit and the solvent was removed in vacuo. The residue was taken up in DCM (4 ml) and added to the top of 2×70 g silica SPE cartridges. These were subsequently eluted with 0-100% EtOAc/DCM over 40 mins. The product-containing fractions were combined to give the title compound as a pale yellow solid (581 mg).

LCMS (Method C) R$_f$=1.15 min, MH$^+$=531.

Intermediate 118

2-(Chloromethyl)-N-{1-(phenylsulfonyl)-6-[1-(phenylsulfonyl)-1H-pyrazolo[3,4-b]pyridin-5-yl]-1H-indazol-4-yl}-1,3-thiazole-4-carboxamide

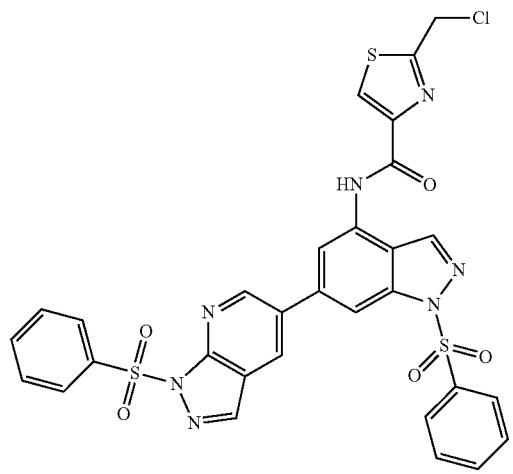 [SMILES: O=C(Nc1cc(-c2cnc3c(cnn3S(=O)(=O)c3ccccc3)c2)cc2c1cnn2S(=O)(=O)c1ccccc1)c1csc(CCl)n1]

1-(Phenylsulfonyl)-6-[1-(phenylsulfonyl)-1H-pyrazolo[3,4-b]pyridin-5-yl]-1H-indazol-4-amine (185 mg, 0.349 mmol) was dissolved in DCM (3 ml) and pyridine (0.034 mL, 0.418 mmol) was added. The mixture was cooled to 0° C. in an ice bath and 2-(chloromethyl)-1,3-thiazole-4-carbonyl chloride (77 mg, 0.349 mmol) in DCM (3 ml) was added dropwise over 5 mins. The mixture was stirred at 0° C. for 15 mins. A further portion of 2-(chloromethyl)-1,3-thiazole-4-carbonyl chloride (38.4 mg, 0.174 mmol) in DCM (1.5 ml) was added. The mixture was stirred for 2 hours, letting the ice melt over this time. A further portion of 2-(chloromethyl)-1,3-thiazole-4-carbonyl chloride (38.4 mg, 0.174 mmol) in DCM (1.5 ml) was added and stirring continued with monitoring by LCMS. The mixture was diluted with DCM (10 ml), saturated aqueous sodium bicarbonate (10 ml) was added and the mixture stirred vigorously for 10 mins. The organic layer was separated, washed with water (10 ml), passed through a hydrophobic frit and concentrated in vacuo. The residue was dissolved in DMSO and loaded onto a 43 g C18 Reverse Phase RediSep column that was then eluted with 30-85% acetonitrile (+0.1% TFA)/H$_2$O (+0.1% TFA) over 30 mins. The product-containing fractions were combined and concentrated in vacuo to give a cream solid which was then dried on the vacuum line for 1 hour to give the title compound (54 mg).

LCMS (Method D) $R_t$=1.26 min, MH$^+$ 689.

Intermediate 119

4-Bromo-1-(phenylsulfonyl)-1H-pyrrolo[2,3-b]pyridine

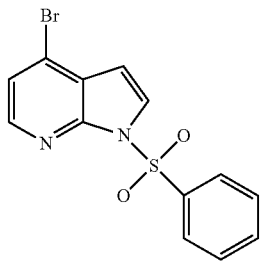 [SMILES: OS(O)(c1ccccc1)n1ccc2c(Br)ccnc21]

4-Bromo-1H-pyrrolo[2,3-b]pyridine (2 g, 10.15 mmol) and sodium hydride (0.406 g, 10.15 mmol) were added to N,N-Dimethylformamide (30 mL) with stirring and under nitrogen. After 15 minutes the reaction was cooled in an ice bath and benzenesulfonyl chloride (1.295 mL, 10.15 mmol) was added to the reaction mixture. The reaction was stirred in the ice bath for 30 min and then allowed to warm up to room temperature. Water (30 mL) was added to the reaction mixture and the precipitate was collected by filtration to afford the title compound as an orange solid: mass (4.8 g).

LCMS (Method D) $R_t$=1.19 min, MH$^+$=338.

Intermediate 120

5-Bromo-1-(phenylsulfonyl)-1H-pyrazolo[3,4-b]pyridine

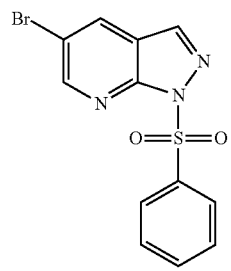 [SMILES: O=S(=O)(c1ccccc1)n1ncc2cc(Br)cnc21]

Sodium Hydride (0.667 g, 16.66 mmol) was added portionwise over 15 mins to a stirred solution of 5-bromo-1H-pyrazolo[3,4-b]pyridine (3 g, 15.15 mmol, available from ChemGenx LLC) in N,N-dimethylformamide (30 ml) that had been cooled in an ice bath to 0° C. and placed under nitrogen. The mixture was stirred for 20 mins, until hydrogen evolution ceased, and then benzenesulfonyl chloride (2.148 ml, 16.66 mmol) was added. The mixture was stirred for 18 hours, letting the ice melt over this time. The solution was poured into stirring water (10 ml) and rapidly stirred for 15 mins. The mixture was then poured onto water (70 ml) and filtered. The orange solid obtained was dried in the vacuum oven for 18 h to afford the title compound (3.86 g).

LCMS (Method D) $R_t$=1.01 min, MH$^+$=340.

Intermediate 121

2-{[(2R,6S)-2,6-Dimethyl-4-morpholinyl]methyl}-N-{1-(phenylsulfonyl)-6-[1-(phenylsulfonyl)-1H-pyrazolo[3,4-b]pyridin-5-yl]-1H-indazol-4-yl}-1,3-thiazole-4-carboxamide

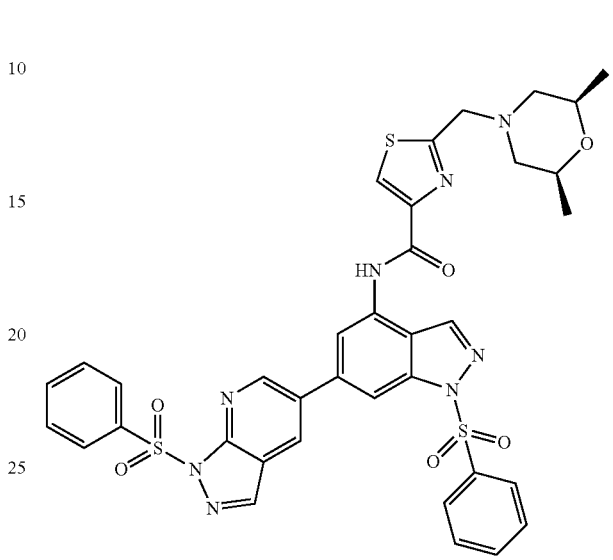

2-(Chloromethyl)-N-{1-(phenylsulfonyl)-6-[1-(phenylsulfonyl)-1H-pyrazolo[3,4-b]pyridin-5-yl]-1H-indazol-4-yl}-1,3-thiazole-4-carboxamide (53 mg, 0.077 mmol) and (2R,6S)-2,6-dimethylmorpholine (0.5 ml, 0.077 mmol) were placed in a microwave vial and heated in a microwave at 90° C. for 15 min, allowed to cool, then heated again in the microwave at 90° C. for 15 min. A further portion of (2R,6S)-2,6-dimethylmorpholine (0.3 ml) was added and the mixture was heated in the microwave at 90° C. for 30 mins. Volatiles were removed under a stream of nitrogen to give the title compound as a pale yellow solid (99 mg). The material was used without further purification.

LCMS (Method D) $R_t$=1.16 min, MH$^+$=769.

Intermediate 122

1-(Phenylsulfonyl)-6-(trimethylstannanyl)-1H-indazol-4-amine

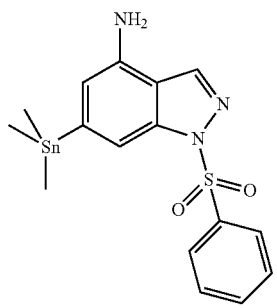 [SMILES: [CH3][Sn]([CH3])([CH3])[c]1cc(N)c2cnn(S(=O)(=O)c3ccccc3)c2c1]

A mixture of 6-bromo-1-(phenylsulfonyl)-1H-indazol-4-amine (1.3 g), hexamethylditin (2.4 g), triethylamine (1 ml)

and Pd(PPh$_3$)$_4$ (0.2 g) in toluene (15 ml) was heated under microwave irradiation at 120° C. for 1 h. The reaction was applied to a silica cartridge using light petroleum 40-60° C. as eluent. This was changed to ether/light petroleum 40-60° C. The appropriate fractions were evaporated to give title compound, 1.2 g.

LCMS (Method C) R$_t$=3.3 min, MH$^+$ 438.

Intermediate 123

2-{[Ethyl(propyl)amino]methyl}-1,3-thiazole-4-carboxylic acid

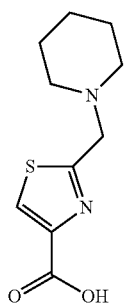 [SMILES: O=C(O)c1csc(CN2CCCCC2)n1]

To a solution of ethyl 2-(4-piperidinylmethyl)-1,3-thiazole-4-carboxylate (19 g, 74 mmol) was added a solution of sodium hydroxide (3.6 g, 88.8 mmol) in water (250 ml). The resulting mixture was stirred at room temperature for 18 h, then ethyl acetate was added and the layers were separated. The aqueous phase was acidified with conc. H$_2$SO$_4$ and concentrated to give a brown solid. The solid was recrystallised from methanol/ethyl acetate, then again from DCM/methanol to give the title compound as a light brown solid (16 g).

$^1$H NMR (400 MHz, DMSO-d6, δ ppm) 1.3-1.5 (6H, m), 2.5 (4H, m), 3.1 (2H, s), 3.7 (2H, s), 8.3 (1H, s).

Intermediate 124

2-(Chloromethyl)-N-{1-(phenylsulfonyl)-6-[1-(phenylsulfonyl)-1H-pyrrolo[2,3-b]pyridin-4-yl]-1H-indazol-4-yl}-1,3-thiazole-4-carboxamide

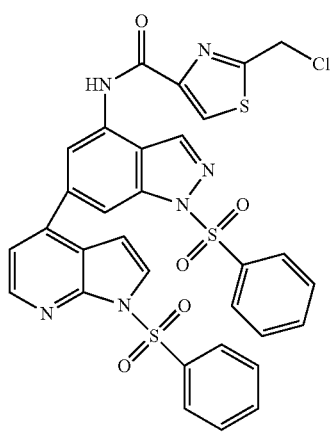 [SMILES: O=C(Nc1cc(-c2ccnc3c2ccn3S(=O)(=O)c2ccccc2)cc2c1cnn2S(=O)(=O)c1ccccc1)c1csc(CCl)n1]

1-(Phenylsulfonyl)-6-[1-(phenylsulfonyl)-1H-pyrrolo[2,3-b]pyridin-4-yl]-1H-indazol-4-amine (663 mg, 1.252 mmol) in chloroform (10 mL) was stirred at 0° C. DIPEA (0.437 mL, 2.504 mmol) was added into the reaction mixture, followed by 2-(chloromethyl)-1,3-thiazole-4-carbonyl chloride (300 mg, 1.530 mmol) in chloroform (10 mL). The reaction mixture was stirred at 0° C. for 15 mins. A further portion of 2-(chloromethyl)-1,3-thiazole-4-carbonyl chloride (400 mg, 1.252 mmol) was added and the reaction was monitored by LCMS. When no further conversion was apparent, a further portion of 2-(chloromethyl)-1,3-thiazole-4-carbonyl chloride (1.6 g, 1.252 mmol) was added and the reaction mixture was stirred for 18 h. The solution was treated with DCM (25 mL) and saturated aqueous sodium bicarbonate (25 mL) and stirred for 10 mins. The organic layer was separated, washed with aqueous sodium chloride (25 mL) and then passed through a hydrophobic frit. The residual solvent volume was reduced and the mixture was purified by silica column chromatography (Flashmaster II, 100 g cartridge) using a gradient of 0-100% ethylacetate/cyclohexane over 60 min to afford the title compound as a white solid (111 mg).

LCMS (Method D) R$_t$=1.34 min, MH$^+$=690.

Intermediate 125

2-(Chloromethyl)-1,3-thiazole-4-carbonyl chloride

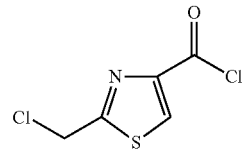

To a solution of 2-(hydroxymethyl)-1,3-thiazole-4-carboxylic acid (370 mg, 2.33 mmol) in Chloroform (5 mL) and N,N-Dimethylformamide (DMF) (0.1 mL) was added thionyl chloride (1 mL, 13.70 mmol). The mixture was heated to reflux for 1 hr. The mixture was cooled and the solvent removed in vacuo. The residue was azeotroped with chloroform (5 ml) and dried on a high vacuum line for 30 mins to afford the title compound. LCMS was run as a solution in MeOH (Method D) R$_t$ 0.77 min, MH$^+$ 191. The material was not suitable for long term storage at room temperature so was either used immediately or stored at −20° C. for up to 2 weeks.

Intermediate 126

2-(Hydroxymethyl)-1,3-thiazole-4-carboxylic acid

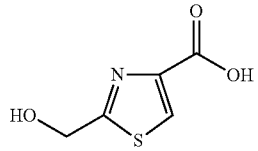

A solution of 2-{[(2,2-dimethylpropanoyl)oxy]methyl}-1,3-thiazole-4-carboxylic acid (3 g, 12.33 mmol, commercially available) and potassium carbonate (2.326 g, 16.83 mmol) in methanol (100 mL) and water (30 mL) was heated to reflux for 4 hr. The mixture was cooled and concentrated in vacuo to ~30 ml. It was then acidified with 2 M HCl (50 ml) and concentrated in vacuo. The resulting solid was treated with hot MeOH/EtOAc (2:1), washing well before filtering off the remaining solid. The filtrate was concentrated in vacuo to give a brown solid which was dissolved in MeOH and added to the top of 2×70 g aminopropyl cartridge that had been preconditioned with MeOH. The cartridges were both eluted with MeOH and then with 10% HCl in MeOH. The acidic fractions were combined and the solvent removed in vacuo to give the title compound as a brown oil (550 mg).

LCMS (Method D) R$_t$ 0.38 min, MH$^+$ 160.

Intermediate 127

6-Bromo-1-(phenylsulfonyl)-1H-indazol-4-amine

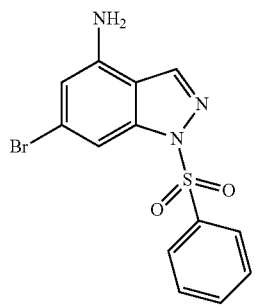 [SMILES: Nc1cc(Br)cc2c1cnn2S(=O)(=O)c1ccccc1]

To sodium hydride (1.886 g, 47.2 mmol) in DMF (10 ml) stirring at 0° C. was added a solution of 6-bromo-1H-indazol-4-amine (10 g, 47.2 mmol, available from Sinova) in DMF (30 ml) dropwise. NOTE—gas evolution. Upon complete addition the mixture was treated with benzene sulphonyl chloride (6.08 ml, 47.2 mmol) dropwise. The resulting mixture was stirred for 2 hrs at room temperature then the mixture was poured onto ice water (300 ml). The mixture was then extracted with ethyl acetate and the layers separated. The aqueous was re-extracted with ethyl acetate. The organics were then combined and washed with brine, dried over magnesium sulfate then filtered and evaporated to yield a brown gum that was triturated using DCM to yield the title compound as a peachy solid (8.72 g).

LCMS (Method D) Rt=1.14 mins, MH+=352/354.

Intermediate 128

4-(Chloromethyl)-1,3-thiazole-2-carbonyl chloride

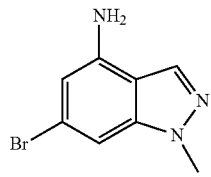

6-Bromo-1H-indazol-4-amine (5 g, 23.58 mmol) was added to tetrahydrofuran (THF) (100 mL) and the mixture stirred in an ice-water bath. Then sodium hydride (1.037 g, 25.9 mmol)–(60% dispersion in mineral oil) was added portionwise to the mixture. After 10 minutes, iodomethane (1.622 mL, 25.9 mmol) was added to the flask. The mixture was stirred at 0° C. for 2 hours. Water (100 ml) was added and the mixture stirred for 30 mins. Then ethyl acetate (100 ml) was added. The organic layer was collected and the aqueous layer extracted with ethyl acetate (2×100 ml). The combined organic layers were dried using a hydrophobic frit and the solvent removed in vacuo. The residue was purified by chromatography on silica (2×100 g cartridges) eluting with 0-100% ethyl acetate in cyclohexane over 60 mins to afford the title compound as a yellow solid (2.96 g).

LCMS (Method B) Rt 0.83 min, MH+ 226/228.

Intermediate 129

N-(6-Bromo-1-methyl-1H-indazol-4-yl)-2-(chloromethyl)-1,3-thiazole-4-carboxamide

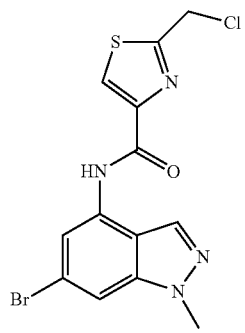 [SMILES: Cn1ncc2c(NC(=O)c3csc(CCl)n3)cc(Br)cc21]

6-Bromo-1-methyl-1H-indazol-4-amine (1 g, 4.42 mmol) was dissolved in dichloromethane (DCM) (10 mL) and pyridine (0.429 mL, 5.31 mmol) added. The mixture was cooled to 0° C. in an ice-water bath and 4-(chloromethyl)-1,3-thiazole-2-carbonyl chloride (0.867 g, 4.42 mmol) in DCM (10 ml) was added portionwise over 5 mins. The mixture was stirred for 2 hours and allowed to warm to room temperature. Saturated sodium bicarbonate solution (15 ml) was added and the mixture stirred vigorously for 10 mins. The mixture was diluted with water (50 ml) and DCM (50 ml), but a precipitate was still present. This was collected by filtration, washed with DCM and air dried to afford the title compound as a yellow/brown solid (860 mg).

LCMS (Method B) Rt 1.11 mins, MH+ 385/387.

The organic layer was collected and the aqueous layer extracted with further DCM (50 ml). the combined organic layers were dried using a hydrophobic frit and the solvent removed in vacuo. The residue was suspended in DCM 5 ml and the resultant precipitate collected by filtration and air dried to give a further portion of the title compound (259 mg). Analytical data identical to that obtained above.

125

Intermediate 130

N-(6-Bromo-1-methyl-1H-indazol-4-yl)-2-{[(2R,6S)-2,6-dimethyl-4-morpholinyl]methyl}-1,3-thiazole-4-carboxamide

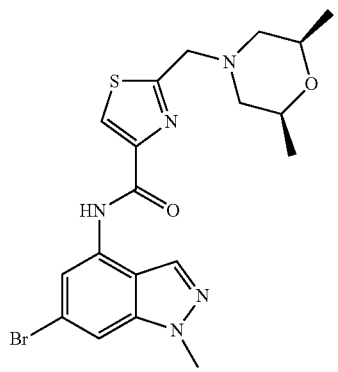 [SMILES: C[C@@H]1CN(Cc2nc(C(=O)Nc3cc(Br)cc4c3cnn4C)cs2)C[C@H](C)O1]

N-(6-Bromo-1-methyl-1H-indazol-4-yl)-2-(chloromethyl)-1,3-thiazole-4-carboxamide (860 mg, 2.230 mmol) was placed in dimethyl morpholine (3 mL, 2.230 mmol) and the mixture heated in a microwave at 90° C. for 15 mins. The solvent was blown off under a stream of nitrogen. The residue was partitioned between water (100 ml) and DCM (100 ml) and the organic layer collected, washed with water (2×75 ml), dried using a hydrophobic frit and the solvent removed in vacuo. NMR showed residual dimethyl morpholine. The material was dissolved in DCM (20 ml) and methanol (20 ml) and then put on the buchi with the water bath at 60° C. for 3 hours to afford the title compound as a yellow/brown solid.

LCMS (Method D) Rt 0.88 min, MH+ 464/466.

126

Example 1

N-[6-(1H-Indol-4-yl)-1H-indazol-4-yl]-5-methyl-1H-pyrazole-3-carboxamide

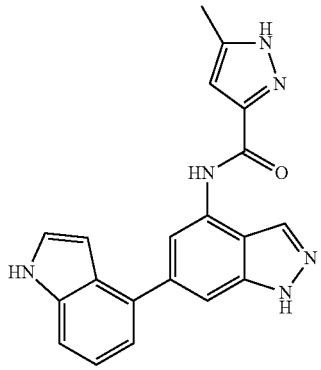 [SMILES: Cc1cc(C(=O)Nc2cc(-c3cccc4[nH]ccc34)cc3[nH]ncc23)n[nH]1]

5-Methyl-1H-pyrazole-3-carboxylic acid (10 mg) in DMF (0.2 ml) was treated with N-[(dimethylamino)(3H-[1,2,3]triazolo[4,5-b]pyridin-3-yloxy)methylidene]-N-methylmethanaminium hexafluorophosphate (27 mg) in DMF (0.2 ml) and DIPEA (0.03 ml). The reaction mixture was shaken for five min prior to treatment with 6-(1H-indol-4-yl)-2-(tetrahydro-2H-pyran-2-yl)-2H-indazol-4-amine (20 mg) in DMF (0.2 ml). The reaction mixture was shaken for five min and left to stand at 22° C. for 18 h. The solvent was removed in vacuo and the product re-dissolved in methanol (1 ml) prior to application on to an SCX SPE cartridge (1 g). The product was eluted after 1 h with 2M ammonia in methanol (2×3 ml), the fractions were combined and concentrated under a stream of nitrogen using blow down apparatus. Purification by mass directed preparative HPLC (Method C) afforded the title compound.

LC/MS $R_t$ 2.91 min m/z 357 [MH$^+$]. Method A

Similarly prepared from 6-(1H-indol-4-yl)-2-(tetrahydro-2H-pyran-2-yl)-2H-indazol-4-amine were the following:

| Example Number | Compound Name | Structure | Amine | LC/MS $R_t$ min | LC/MS MH$^+$ |
|---|---|---|---|---|---|
| 2 | N-[6-(1H-indol-4-yl)-1H-indazol-4-yl]-1-methyl-1H-imidazole-2-carboxamide | 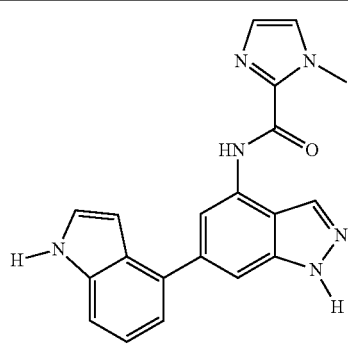 | 1-Methyl-1H-imidazole-2-carboxylic acid (Toronto Research Chemical) | 3.03 (a) | 357 (a) |

-continued

| Example Number | Compound Name | Structure | Amine | LC/MS R$_t$ min | LC/MS MH$^+$ |
|---|---|---|---|---|---|
| 3 | N-[6-(1H-indol-4-yl)-1H-indazol-4-yl]-1-methyl-1H-pyrrole-2-carboxamide | 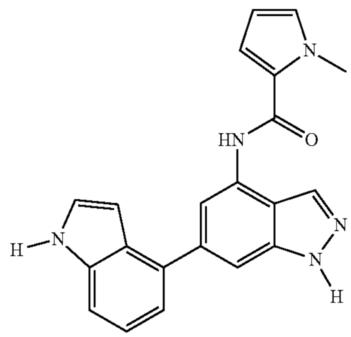 [SMILES: Cn1cccc1C(=O)Nc1cc(-c2cccc3[nH]ccc23)cc2[nH]ncc12] | 1-Methyl-1H-pyrrole-2-carboxylic acid | 3.14 (a) | 356 (a) |
| 4 | N-[6-(1H-indol-4-yl)-1H-indazol-4-yl]-1-methyl-1H-imidazole-4-carboxamide | 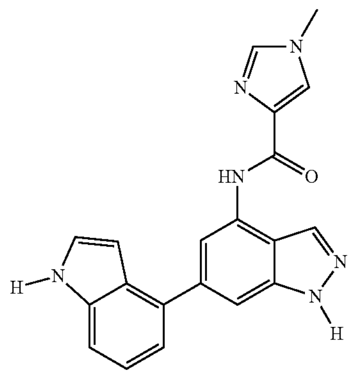 [SMILES: Cn1cnc(C(=O)Nc2cc(-c3cccc4[nH]ccc34)cc3[nH]ncc23)c1] | 1-Methyl-1H-imidazole-4-carboxylic acid | 2.76 (a) | 357 (a) |
| 5 | N-[6-(1H-indol-4-yl)-1H-indazol-4-yl]-1-methyl-1H-pyrazole-5-carboxamide | 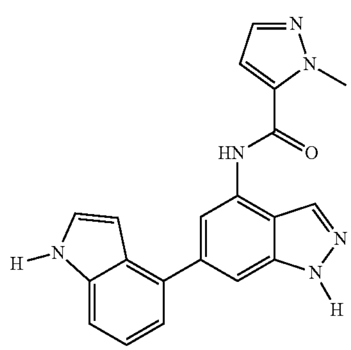 [SMILES: Cn1nccc1C(=O)Nc1cc(-c2cccc3[nH]ccc23)cc2[nH]ncc12] | 1-Methyl-1H-pyrazole-5-carboxylic acid | 2.90 (a) | 357 (a) |
| 6 | N-[6-(1H-indol-4-yl)-1H-indazol-4-yl]-1,5-dimethyl-1H-pyrazole-3-carboxamide | 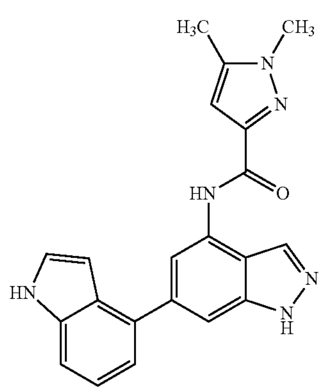 [SMILES: Cc1cc(C(=O)Nc2cc(-c3cccc4[nH]ccc34)cc3[nH]ncc23)nn1C] | 1,5-Dimethyl-1H-pyrazole-3-carboxylic acid | 0.91 (b) | 371 (b) |

-continued

| Example Number | Compound Name | Structure | Amine | LC/MS R$_t$ min | LC/MS MH$^+$ |
|---|---|---|---|---|---|
| 7 | N-[6-(1H-indol-4-yl)-1H-indazol-4-yl]-2-(phenylmethyl)-1,3-thiazole-4-carboxamide | 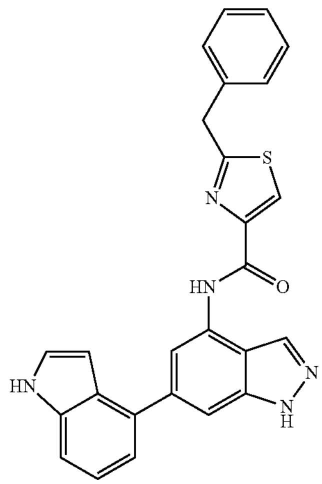 [SMILES: O=C(Nc1cc(-c2cccc3[nH]ccc23)cc2[nH]ncc12)c1csc(Cc2ccccc2)n1] | 2-(Phenylmethyl)-1,3-thiazole-4-carboxylic acid | 1.17 (b) | 450 (b) |
| 8 | 1-ethyl-N-[6-(1H-indol-4-yl)-1H-indazol-4-yl]-1H-pyrazole-3-carboxamide | 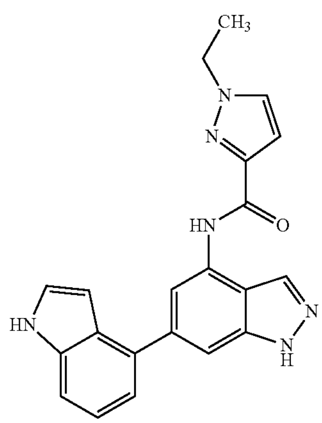 [SMILES: CCn1ccc(C(=O)Nc2cc(-c3cccc4[nH]ccc34)cc3[nH]ncc23)n1] | 1-Ethyl-1H-pyrazole-3-carboxylic acid | 0.94 (b) | 371 (b) |
| 9 | N-[6-(1H-indol-4-yl)-1H-indazol-4-yl]-2-methyl-3-furancarboxamide | 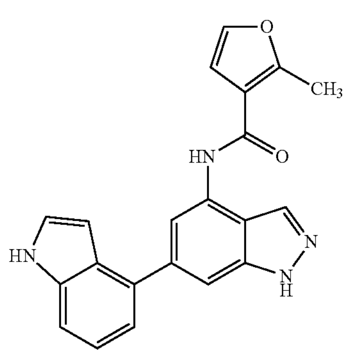 [SMILES: Cc1occc1C(=O)Nc1cc(-c2cccc3[nH]ccc23)cc2[nH]ncc12] | 2-Methyl-3-furancarboxylic acid | 0.98 (b) | 357 (b) |

-continued

| Example Number | Compound Name | Structure | Amine | LC/MS R$_t$ min | LC/MS MH$^+$ |
|---|---|---|---|---|---|
| 10 | N-[6-(1H-indol-4-yl)-1H-indazol-4-yl]-5-methyl-2-furancarboxamide | 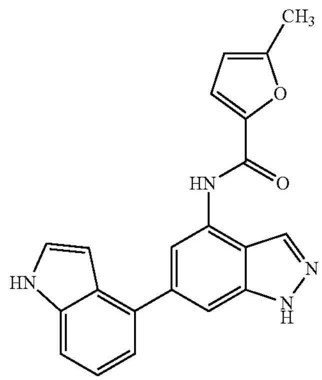 [SMILES: Cc1ccc(C(=O)Nc2cc(-c3cccc4[nH]ccc34)cc3[nH]ncc23)o1] | 5-Methyl-2-furancarboxylic acid | 0.97 (b) | 357 (b) |
| 11 | N-[6-(1H-indol-4-yl)-1H-indazol-4-yl]-1-methyl-1H-pyrazole-3-carboxamide | 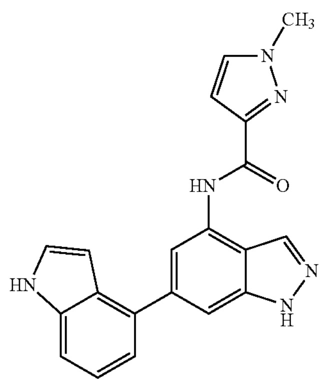 [SMILES: Cn1ccc(C(=O)Nc2cc(-c3cccc4[nH]ccc34)cc3[nH]ncc23)n1] | 1H-Pyrazole-3-carboxylic acid | 0.88 (b) | 357 (b) |
| 12 | N-[6-(1H-indol-4-yl)-1H-indazol-4-yl]-3-furancarboxamide | 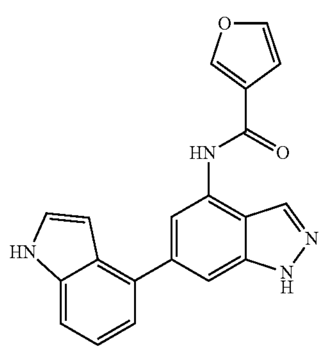 [SMILES: O=C(Nc1cc(-c2cccc3[nH]ccc23)cc2[nH]ncc12)c1ccoc1] | 3-Furancarboxylic acid | 0.91 (b) | 343 (b) |
| 13 | N-[6-(1H-indol-4-yl)-1H-indazol-4-yl]-3-thiophene-carboxamide | 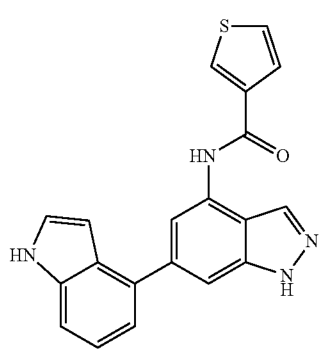 [SMILES: O=C(Nc1cc(-c2cccc3[nH]ccc23)cc2[nH]ncc12)c1ccsc1] | 3-Thiophene-carboxylic acid | 0.96 (b) | 359 (b) |

| Example Number | Compound Name | Structure | Amine | LC/MS R$_t$, min | LC/MS MH$^+$ |
|---|---|---|---|---|---|
| 14 | N-[6-(1H-indol-4-yl)-1H-indazol-4-yl]-5-(1-pyrrolidinyl-methyl)-2-furancarboxamide | 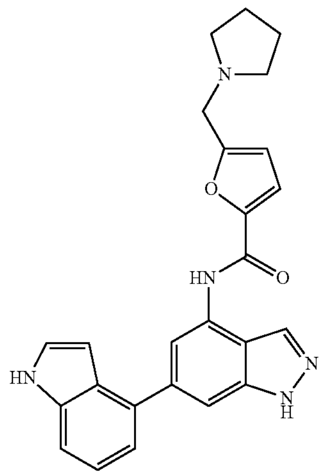 [SMILES: O=C(Nc1cc(-c2cccc3[nH]ccc23)cc2[nH]ncc12)c1ccc(CN2CCCC2)o1] | 5-(1-Pyrrolidinyl-methyl)-2-furancarboxylic acid | 0.75 (b) | 426 (b) |
| 15 | N-[6-(1H-indol-4-yl)-1H-indazol-4-yl]-2-phenyl-1,3-thiazole-4-carboxamide | 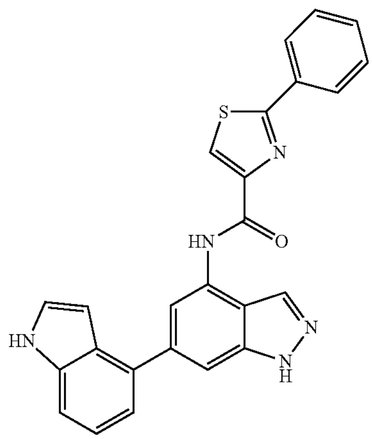 [SMILES: O=C(Nc1cc(-c2cccc3[nH]ccc23)cc2[nH]ncc12)c1csc(-c2ccccc2)n1] | 2-Phenyl-1,3-thiazole-4-carboxylic acid | 1.19 (b) | 436 (b) |
| 16 | 2-chloro-N-[6-(1H-indol-4-yl)-1H-indazol-4-yl]-3-furancarboxamide | 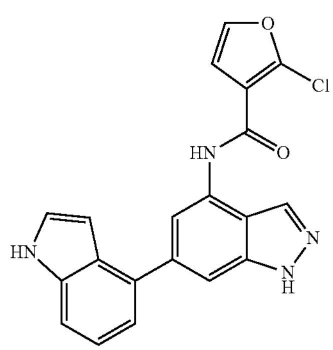 [SMILES: O=C(Nc1cc(-c2cccc3[nH]ccc23)cc2[nH]ncc12)c1ccoc1Cl] | 2-Chloro-3-furancarboxylic acid | 1.01 (b) | 377 (b) |
| 17 | 1-ethenyl-N-[6-(1H-indol-4-yl)-1H-indazol-4-yl]-1H-pyrazole-5-carboxamide | 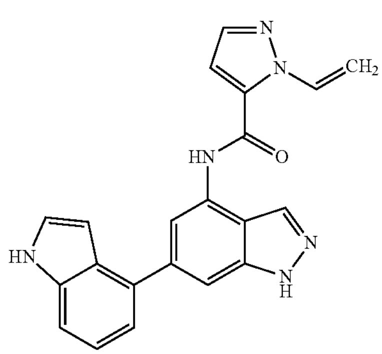 [SMILES: C=Cn1nccc1C(=O)Nc1cc(-c2cccc3[nH]ccc23)cc2[nH]ncc12] | 1-Ethenyl-1H-pyrazole-5-carboxylic acid | 0.96 (b) | 369 (b) |

| Example Number | Compound Name | Structure | Amine | LC/MS R$_t$, min | LC/MS MH$^+$ |
|---|---|---|---|---|---|
| 18 | 1-ethyl-N-[6-(1H-indol-4-yl)-1H-indazol-4-yl]-1H-pyrazole-5-carboxamide | 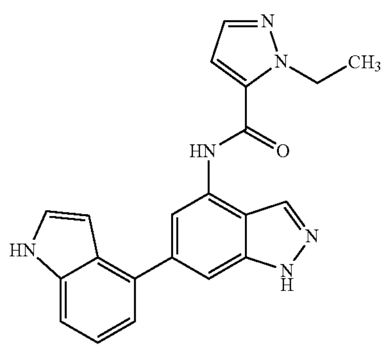 [SMILES: CCn1nccc1C(=O)Nc1cc(-c2cccc3[nH]ccc23)cc2[nH]ncc12] | 1-Ethyl-1H-pyrazole-5-carboxylic acid | 0.95 (b) | 371 (b) |
| 19 | N-[6-(1H-indol-4-yl)-1H-indazol-4-yl]-2-(trifluoromethyl)-1,3-thiazole-4-carboxamide | 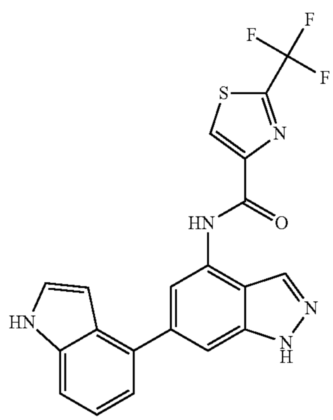 [SMILES: O=C(Nc1cc(-c2cccc3[nH]ccc23)cc2[nH]ncc12)c1csc(C(F)(F)F)n1] | 2-(Trifluoromethyl)-1,3-thiazole-4-carboxylic acid | 1.09 (b) | 428 (b) |
| 20 | N-[6-(1H-indol-4-yl)-1H-indazol-4-yl]-2-{1-[(phenylcarbonyl)-amino]ethyl}-1,3-thiazole-4-carboxamide | 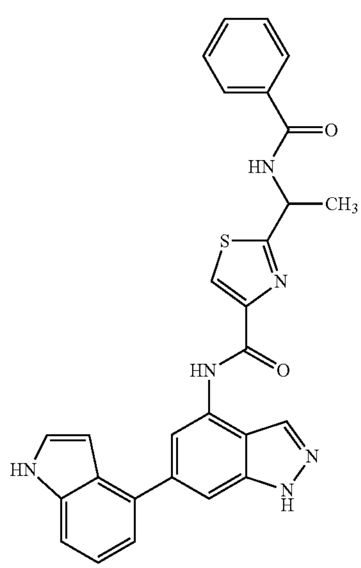 [SMILES: CC(NC(=O)c1ccccc1)c1nc(C(=O)Nc2cc(-c3cccc4[nH]ccc34)cc3[nH]ncc23)cs1] | 2-{1-[(Phenylcarbonyl)-amino]ethyl}-1,3-thiazole-4-carboxylic acid (for example prepared as described in Journal of the Chemical Society (1963), 2143-50) | 1.04 (b) | 507 (b) |

-continued

| Example Number | Compound Name | Structure | Amine | LC/MS R$_t$ min | LC/MS MH$^+$ |
|---|---|---|---|---|---|
| 21 | N-[6-(1H-indol-4-yl)-1H-indazol-4-yl]-5-(trifluoromethyl)-2-furancarboxamide | 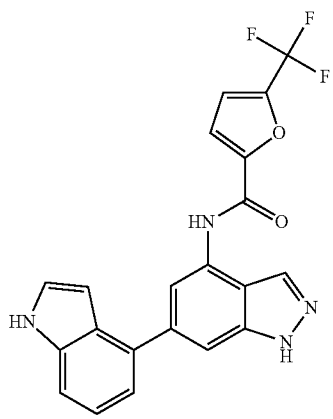 [SMILES: O=C(Nc1cc(-c2cccc3[nH]ccc23)cc2[nH]ncc12)c1ccc(C(F)(F)F)o1] | 5-(Trifluoromethyl)-2-furancarboxylic acid | 1.07 (b) | 411 (b) |
| 22 | 5-[(dimethylamino)methyl]-N-[6-(1H-indol-4-yl)-1H-indazol-4-yl]-2-furancarboxamide | 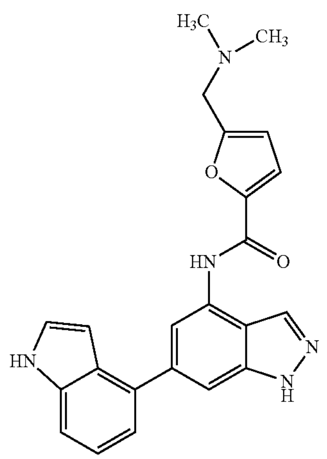 [SMILES: CN(C)Cc1ccc(C(=O)Nc2cc(-c3cccc4[nH]ccc34)cc3[nH]ncc23)o1] | 5-[(Dimethylamino)methyl]-2-furancarboxylic acid | 0.7 (b) | 400 (b) |
| 23 | 3-ethyl-N-[6-(1H-indol-4-yl)-1H-indazol-4-yl]-1H-pyrazole-5-carboxamide | 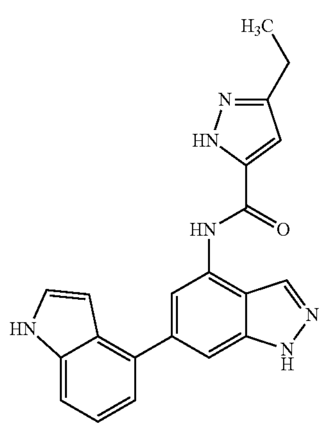 [SMILES: CCc1cc(C(=O)Nc2cc(-c3cccc4[nH]ccc34)cc3[nH]ncc23)[nH]n1] | 3-Ethyl-1H-pyrazole-5-carboxylic acid | 0.92 (b) | 371 (b) |

| Example Number | Compound Name | Structure | Amine | LC/MS R$_t$ min | LC/MS MH$^+$ |
|---|---|---|---|---|---|
| 24 | 5-chloro-N-[6-(1H-indol-4-yl)-1H-indazol-4-yl]-2-furancarboxamide | 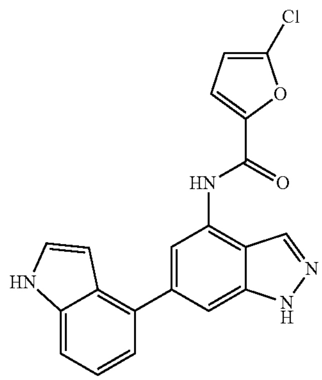 [SMILES: O=C(Nc1cc(-c2cccc3[nH]ccc23)cc2[nH]ncc12)c1ccc(Cl)o1] | 5-Chloro-2-furancarboxylic acid | 1.01 (b) | 377 (b) |
| 25 | N-[6-(1H-indol-4-yl)-1H-indazol-4-yl]-4-methyl-2-thiophene-carboxamide | 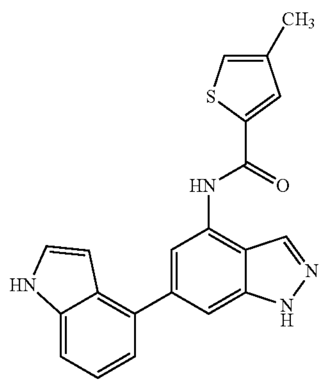 [SMILES: Cc1csc(C(=O)Nc2cc(-c3cccc4[nH]ccc34)cc3[nH]ncc23)c1] | 4-Methyl-2-thiophene-carboxylic acid | 1.03 (b) | 373 (b) |
| 26 | N-[6-(1H-indol-4-yl)-1H-indazol-4-yl]-2-(4-morpholinylmethyl)-1,3-thiazole-4-carboxamide | 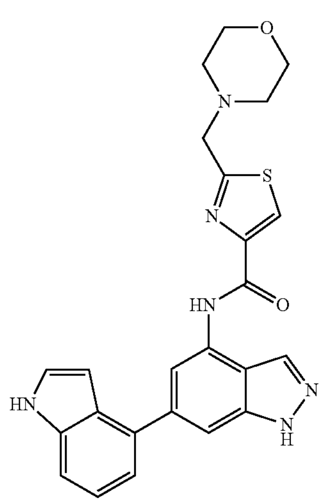 [SMILES: O=C(Nc1cc(-c2cccc3[nH]ccc23)cc2[nH]ncc12)c1csc(CN2CCOCC2)n1] | 2-(4-Morpholinyl-methyl)-1,3-thiazole-4-carboxylic acid ammoniate | 0.85 (b) | 459 (b) |

-continued

| Example Number | Compound Name | Structure | Amine | LC/MS R$_t$ min | LC/MS MH$^+$ |
|---|---|---|---|---|---|
| 27 | N-[6-(1H-indol-4-yl)-1H-indazol-4-yl]-1H-pyrazole-3-carboxamide | 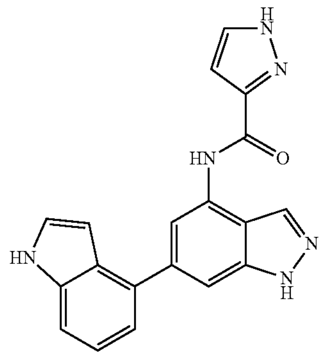 [SMILES: O=C(Nc1cc(-c2cccc3[nH]ccc23)cc2[nH]ncc12)c1cc[nH]n1] | 1-Methyl-1H-pyrazole-3-carboxylic acid | 2.88 (a) | 343 (a) |
| 28 | N-[6-(1H-indol-4-yl)-1H-indazol-4-yl]-1,3-thiazole-5-carboxamide | 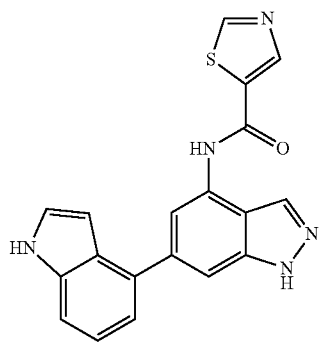 [SMILES: O=C(Nc1cc(-c2cccc3[nH]ccc23)cc2[nH]ncc12)c1cncs1] | 1,3-Thiazole-5-carboxylic acid | 2.95 (a) | 360 (a) |

(a) LC/MS Method A
(b) LC/MS Method B

Example 29

1-(1-Methylethyl)-N-[6-(1H-pyrazolo[3,4-b]pyridin-4-yl)-1H-indazol-4-yl]-1H-pyrazole-5-carboxamide

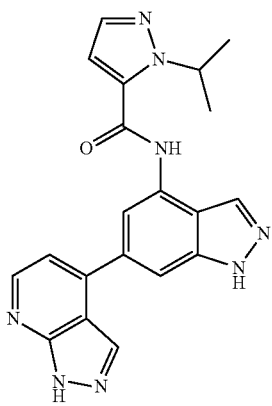 [SMILES: CC(C)n1nccc1C(=O)Nc1cc(-c2ccnc3[nH]ncc23)cc2[nH]ncc12]

4-Iodo-1-(phenylsulfonyl)-1H-pyrazolo[3,4-b]pyridine (69 mg) in DMF (0.4 ml) was added to 1,4-dimethyl-N-[1-(phenylsulfonyl)-6-(trimethylstannanyl)-1H-indazol-4-yl]-1H-pyrazole-3-carboxamide (100 mg) in DMF (0.4 ml). Solvias catalyst (4 mg) was added and the sealed vessel was heated in the Anton Paar microwave at 135° C. for 20 min. PS-thiophenol resin was added and the reaction was stirred overnight before being filtered onto a C$_{18}$SPE cartridge, pre-washed with 0.1% TFA, with acetonitrile. The cartridge was washed with 0.1% TFA in acetonitrile and the collected solvent was removed under a stream of nitrogen. The residue was dissolved in DMSO (1 ml) and purified by MDAP (method C). The solvent was evaporated in vacuo. The residue was dissolved in isopropanol (0.3 ml), 2M sodium hydroxide (aq) (0.3 ml) was added and the reaction was left at room temperature overnight. The solvent was removed under a stream of nitrogen and the residue was dissolved in DMSO (0.5 ml) and purified by MDAP (method C). The solvent was evaporated in vacuo to give title compound, 9 mg.

LC/MS R$_t$ 0.76 min m/z 387 [MH$^+$]. Method D.

Example 30

N-[6-(1H-Indol-4-yl)-1H-indazol-4-yl]-1H-imidazole-4-carboxamide

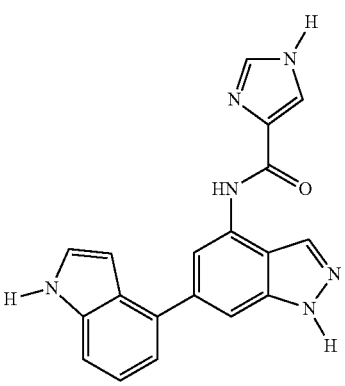 [SMILES: O=C(Nc1cc(-c2cccc3[nH]ccc23)cc2[nH]ncc12)c1c[nH]cn1]

1H-Imidazole-4-carboxylic acid (7 mg) in DMF (0.2 ml) was treated with N-[(dimethylamino)(3H-[1,2,3]triazolo[4,5-b]pyridin-3-yloxy)methylidene]-N-methylmethanaminium hexafluorophosphate (27 mg) in DMF (0.2 ml) and DIPEA (0.03 ml). The reaction mixture was shaken for five min prior to treatment with 6-(1H-indol-4-yl)-2-(tetrahydro-2H-pyran-2-yl)-2H-indazol-4-amine (20 mg) in DMF (0.2 ml). The reaction mixture was shaken for five min and left to stand at 22° C. for 18 h. Solvent was removed in vacuo and the product re-dissolved in methanol (0.5 ml) prior to application on to an SCX SPE cartridge (1 g). The product was eluted after 1 h with 2M ammonia in methanol (2×3 ml), the fractions were combined and concentrated under a stream of nitrogen using blow down apparatus. Purification by mass directed preparative HPLC (Method C) gave the title compound.

LC/MS $R_t$ 0.71 min m/z 343 [MH$^+$]. Method B

Similarly prepared from 6-(1H-indol-4-yl)-2-(tetrahydro-2H-pyran-2-yl)-2H-indazol-4-amine was the following:

Example 32

N-[6-(1H-Indol-4-yl)-1H-indazol-4-yl]-5-methyl-3-isoxazolecarboxamide

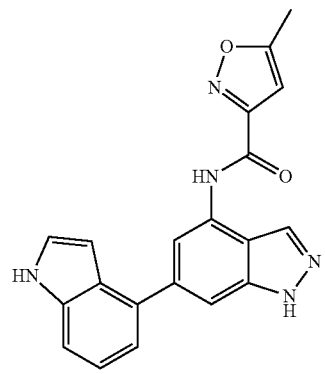

5-Methyl-3-isoxazolecarboxylic acid (21 mg) was treated with anhydrous THF (2 ml) and then 1-chloro-N,N,2-trimethylpropenylamine (0.026 ml). The reaction was stirred at RT under nitrogen for 2 h. The reaction was then treated with anhydrous DIPEA (0.131 ml) and 2 ml of solution of 6-(1H-indol-4-yl)-2-(tetrahydro-2H-pyran-2-yl)-2H-indazol-4-amine (750 mg) in THF (30 ml). The reaction was then stirred at RT under nitrogen for 69 h. The solvent was blown off under a stream of nitrogen, dissolved in methanol (3 ml) and then the solvent removed under reduced pressure. The crude reaction mixture was dissolved in methanol (5 ml), treated with macroporous tosic acid resin (102 mg; 4.45 mmol/g) stirred at RT for 17 h and then treated with 0.88 ammonia (0.5 ml), stirred for 30 min and then filtered. The solvent was removed under reduced pressure and then purified by mass directed preparative HPLC (Method A) to give the title compound.

LC/MS $R_t$ 0.99 min m/z 358 [MH$^+$]. Method B

Similarly prepared from 6-(1H-indol-4-yl)-2-(tetrahydro-2H-pyran-2-yl)-2H-indazol-4-amine were the following:

| Example number | Compound Name | Structure | Carboxylic acid | LC/MS $R_t$ min | LC/MS MH$^+$ |
|---|---|---|---|---|---|
| 31 | N-[6-(1H-indol-4-yl)-1H-indazol-4-yl]-1,3-thiazole-4-carboxamide | 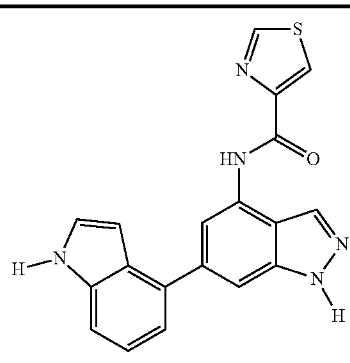 | 1,3-Thiazole-4-carboxylic acid | 0.92 (a) | 360 (a) |

(a) LC/MS Method B

| Example number | Compound Name | Structure | Carboxylic acid | LC/MS R$_t$ min | LC/MS MH$^+$ |
|---|---|---|---|---|---|
| 33 | N-[6-(1H-indol-4-yl)-1H-indazol-4-yl]-1,2,3-thiadiazole-4-carboxamide | 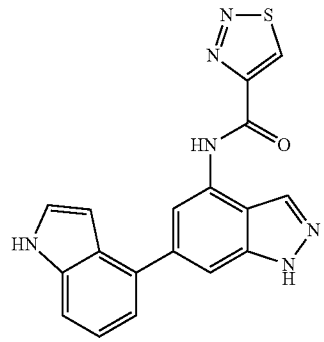 [SMILES: O=C(Nc1cc(-c2cccc3[nH]ccc23)cc2[nH]ncc12)c1csnn1] | 1,2,3-Thiadiazole-4-carboxylic acid | 0.94 (a) | 361 (a) |
| 34 | N-[6-(1H-indol-4-yl)-1H-indazol-4-yl]-2,5-dimethyl-1,3-oxazole-4-carboxamide | 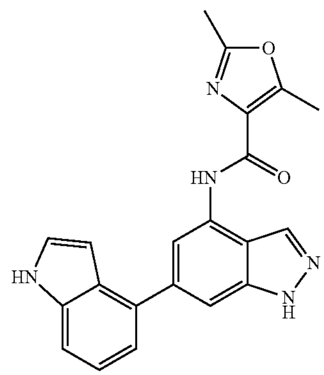 [SMILES: Cc1nc(C(=O)Nc2cc(-c3cccc4[nH]ccc34)cc3[nH]ncc23)c(C)o1] | 2,5-Dimethyl-1,3-oxazole-4-carboxylic acid | 1.01 (a) | 372 (a) |
| 35 | N-[6-(1H-indol-4-yl)-1H-indazol-4-yl]-2-methyl-1,3-oxazole-4-carboxamide | 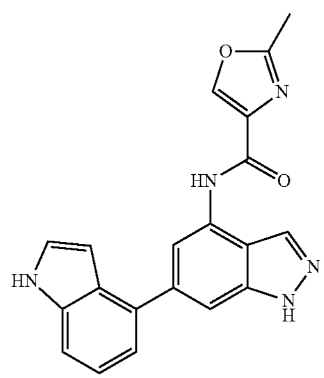 [SMILES: Cc1nc(C(=O)Nc2cc(-c3cccc4[nH]ccc34)cc3[nH]ncc23)co1] | 2-Methyl-1,3-oxazole-4-carboxylic acid | 0.94 (a) | 358 (a) |
| 36 | N-[6-(1H-indol-4-yl)-1H-indazol-4-yl]-3-isoxazole-carboxamide | 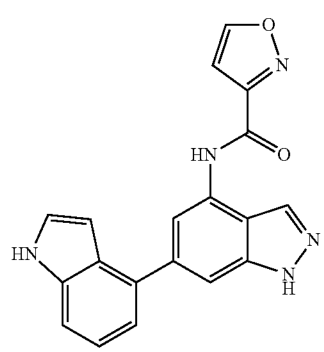 [SMILES: O=C(Nc1cc(-c2cccc3[nH]ccc23)cc2[nH]ncc12)c1ccon1] | 3-Isoxazole-carboxylic acid | 0.93 (a) | 344 (a) |

-continued

| Example number | Compound Name | Structure | Carboxylic acid | LC/MS R$_t$ min | LC/MS MH$^+$ |
|---|---|---|---|---|---|
| 37 | N-[6-(1H-indol-4-yl)-1H-indazol-4-yl]-2-methyl-5-(trifluoromethyl)-1,3-oxazole-4-carboxamide | 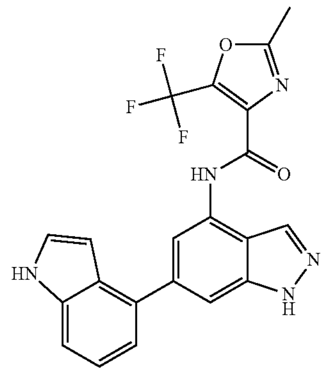 [SMILES: Cc1nc(C(=O)Nc2cc(-c3cccc4[nH]ccc34)cc3[nH]ncc23)c(C(F)(F)F)o1] | 2-Methyl-5-(trifluoromethyl)-1,3-oxazole-4-carboxylic acid | 1.10 (a) | 426 (a) |
| 38 | N-[6-(1H-indol-4-yl)-1H-indazol-4-yl]-5-(2-methyl-1,3-thiazol-4-yl)-3-isoxazole-carboxamide | 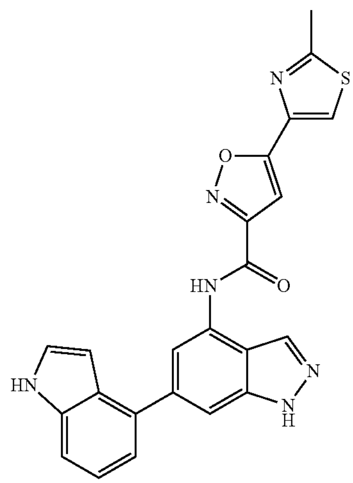 [SMILES: Cc1nc(-c2cc(C(=O)Nc3cc(-c4cccc5[nH]ccc45)cc4[nH]ncc34)no2)cs1] | 5-(2-Methyl-1,3-thiazol-4-yl)-3-isoxazole-carboxylic acid | 1.06 (a) | 441 (a) |

(a) LC/MS Method B

Example 39

4-[(Dimethylamino)methyl]-N-[6-(1H-indol-4-yl)-1H-indazol-4-yl]-5-methyl-3-isoxazolecarboxamide

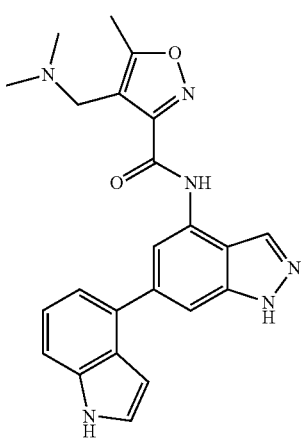 [SMILES: Cc1onc(C(=O)Nc2cc(-c3cccc4[nH]ccc34)cc3[nH]ncc23)c1CN(C)C]

4-[(Dimethylamino)methyl]-5-methyl-3-isoxazolecarboxylic acid (28 mg) (available from Chem Div, 6605 Nancy Ridge Drive San Diego, Calif. 92121 USA) was treated with anhydrous DCM (5 ml). The mixture was then treated with oxalyl chloride (0.13 ml) and anhydrous DMF (~0.01 ml). The mixture was heated at 60° C. under nitrogen for 3 h. The reaction was left to cool and then the solvent was removed under reduced pressure azeotroping with anhydrous toluene twice. The residue, assumed to be 4-[(dimethylamino)methyl]-5-methyl-3-isoxazolecarbonyl chloride hydrochloride, was treated with anhydrous THF (2 ml), anhydrous DIPEA (0.13 ml) and 2 ml of a solution of 6-(1H-indol-4-yl)-2-(tetrahydro-2H-pyran-2-yl)-2H-indazol-4-amine (300 mg) in THF (12 ml). The mixture was stirred at RT for 19 h and then heated to 50° C. for 17 h. The reaction was treated with a further aliquot of 4-[(dimethylamino)methyl]-5-methyl-3-isoxazolecarbonyl chloride hydrochloride (36 mg), prepared as above and the mixture was heated at 50° C. for 4 h. The mixture was treated with methanol (3 ml) and then solvent removed. The residue was then dissolved in methanol (5 ml) and treated with macroporous-tosic acid resin (135 mg; 4.45 mmol/g) then stirred at RT overnight. The mixture was treated with 0.88 ammonia solution (0.50 ml) and then DMF (3 ml). The reactions were then filtered and solvent was blown-off under a stream of nitrogen. The crude material was then purified by mass directed preparative HPLC (Method A) to give the title compound.

LC/MS $R_t$ 0.79 min m/z 415 [MH$^+$]. Method B

Similarly prepared from 6-(1H-indol-4-yl)-2-(tetrahydro-2H-pyran-2-yl)-2H-indazol-4-amine were the following:

| Example number | Compound Name | Structure | Monomer Name | LC/MS $R_t$ min | LC/MS MH$^+$ |
|---|---|---|---|---|---|
| 40 | N-[6-(1H-indol-4-yl)-1H-indazol-4-yl]-5-(4-morpholinyl-methyl)-3-isoxazole-carboxamide | 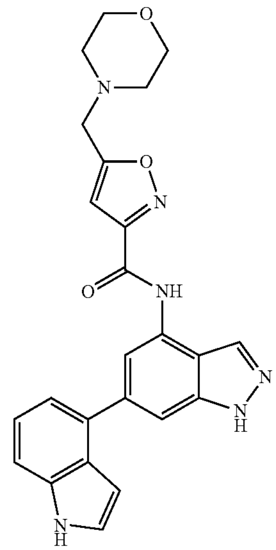 [SMILES: O=C(Nc1cc(-c2cccc3[nH]ccc23)cc2[nH]ncc12)c1cc(CN2CCOCC2)on1] | 5-(4-Morpholinyl-methyl)-3-isoxazole-carboxylic acid (available from Chem Div) | 0.84 (a) | 443 (a) |
| 41 | N-[6-(1H-indol-4-yl)-1H-indazol-4-yl]-5-methyl-4-(1-piperidinyl-methyl)-3-isoxazole-carboxamide | 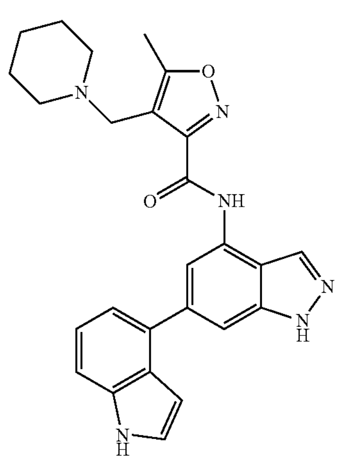 [SMILES: Cc1onc(C(=O)Nc2cc(-c3cccc4[nH]ccc34)cc3[nH]ncc23)c1CN1CCCCC1] | 5-Methyl-4-(1-piperidinyl-methyl)-3-isoxazole-carboxylic acid (available from Chem Div) | 0.85 (a) | 455 (a) |

-continued

| Example number | Compound Name | Structure | Monomer Name | LC/MS R, min | LC/MS MH+ |
|---|---|---|---|---|---|
| 42 | N-[6-(1H-indol-4-yl)-1H-indazol-4-yl]-5-methyl-4-(4-morpholinyl-methyl)-3-isoxazole-carboxamide | 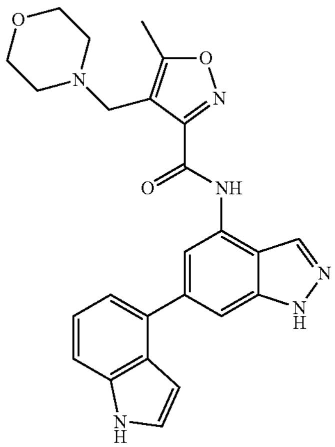 [SMILES: Cc1onc(C(=O)Nc2cc(-c3cccc4[nH]ccc34)cc3[nH]ncc23)c1CN1CCOCC1] | 5-Methyl-4-(4-morpholinyl-methyl)-3-isoxazole-carboxylic acid (available from Chem Div) | 0.81 (a) | 457 (a) |
| 43 | N-[6-(1H-indol-4-yl)-1H-indazol-4-yl]-5-methyl-4-(1-pyrrolidinyl-methyl)-3-isoxazole-carboxamide | 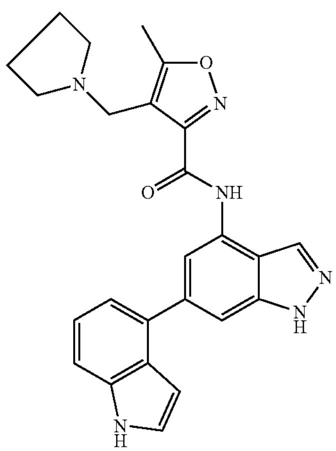 [SMILES: Cc1onc(C(=O)Nc2cc(-c3cccc4[nH]ccc34)cc3[nH]ncc23)c1CN1CCCC1] | 5-Methyl-4-(1-pyrrolidinyl-methyl)-3-isoxazole-carboxylic acid | 0.83 (a) | 441 (a) |
| 44 | N-[6-(1H-indol-4-yl)-1H-indazol-4-yl]-2-(1-piperidinyl-methyl)-1,3-thiazole-4-carboxamide | 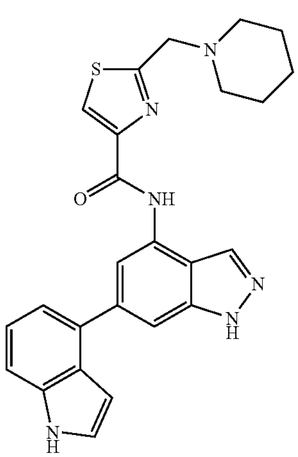 [SMILES: O=C(Nc1cc(-c2cccc3[nH]ccc23)cc2[nH]ncc12)c1csc(CN2CCCCC2)n1] | 2-(1-Piperidinyl-methyl)-1,3-thiazole-4-carboxylic acid (available from ZereneX Molecular Building Blocks) | 0.82 (a) | 457 (a) |

(a) LC/MS Method B

Example 45

N-[6-(1H-Indol-4-yl)-1H-indazol-4-yl]-1H-imidazole-2-carboxamide

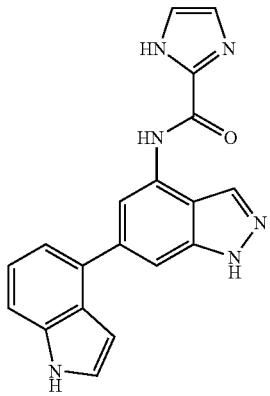 [SMILES: O=C(Nc1cc(-c2cccc3[nH]ccc23)cc2[nH]ncc12)c1ncc[nH]1]

1H-Imidazole-2-carboxylic acid (17 mg) (available from Maybridge), HATU (63 mg) and 6-(1H-indol-4-yl)-2-(tetrahydro-2H-pyran-2-yl)-2H-indazol-4-amine (50 mg) were dissolved in anhydrous DMF (3 ml) and then treated with DIPEA (0.052 ml) and stirred at RT for 15 h. The mixture was treated with methanol (3 ml) and then macroporous-tosic acid resin (170 mg; 4.4 mmol/g) then stirred for 15 h. The mixture was then treated with 0.88 ammonia solution (0.600 ml), stirred for 10 min, then filtered and solvent blown off under a stream of nitrogen. The crude residue was purified by mass directed preparative HPLC (Method A) to give the title compound.

LC/MS $R_t$ 0.87 min m/z 343 [MH$^+$]. Method B

Example 46

N-1H,1'H-5,6'-Biindazol-4'-yl-2-methyl-1,3-thiazole-4-carboxamide

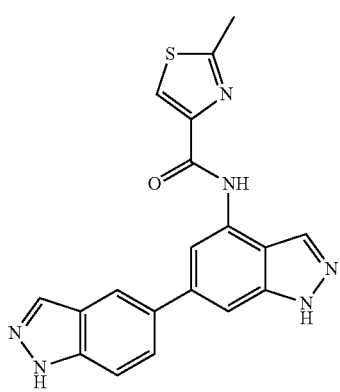 [SMILES: Cc1nc(C(=O)Nc2cc(-c3ccc4[nH]ncc4c3)cc3[nH]ncc23)cs1]

N-(6-Bromo-1H-indazol-4-yl)-2-methyl-1,3-thiazole-4-carboxamide (200 mg), 4,4,4',4',5,5,5',5'-octamethyl-2,2'-bi-1,3,2-dioxaborolane (166 mg), Pd(dppf)Cl$_2$ (48.mg) and potassium acetate (175 mg) were combined in a microwave vial and N,N-dimethylacetamide (10 ml) was added. The solution was degassed with nitrogen and vacuum and then heated under microwave irradiation at 80° C. for 20 min. More Pd(dppf)Cl$_2$ (48.mg) was added, the solution was degassed and heated under microwave irradiation at 80° C. for 20 min. 5-Bromo-1H-pyrazo[3,4-b]pyridine (available from Chemgenex) (235 mg), tetrakis(triphenylphosphine) palladium(0) (34.3 mg) (available from Alfa Aesar) and sodium bicarbonate (0.890 ml) were added to the mixture, which was heated under microwave irradiation at 150° C. for 30 min. Saturated sodium bicarbonate (100 ml) was added to the mixture. The resulting suspension was washed with ethyl acetate (3×100 ml). A spatula of sodium chloride was added to improve layer separation. The combined organic layers were dried and filtered with a hydrophobic frit and dried under vacuum. The sample was pre-absorbed on silica and purified by column chromatography on silica gel (100 g silica) eluting with a gradient of 0-15% methanol in DCM over 60 min. The Appropriate fractions were combined and dried under vacuum, the crude product was dissolved in DMSO (1 ml) and purified by mass directed preparative HPLC (Method A) to give the title compound (8.7 mg).

LC/MS $R_t$ 0.81 min m/z 376 [MH$^+$]. Method B

Example 47

4-Chloro-N-[6-(1H-indol-4-yl)-1H-indazol-4-yl]-1-methyl-1H-pyrazole-5-carboxamide

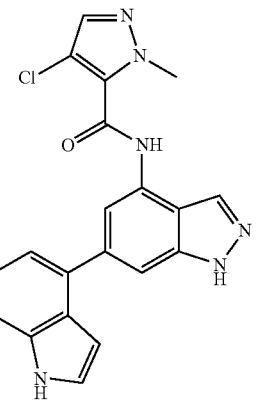

A solution of 4-chloro-1-methyl-1H-pyrazole-5-carboxylic acid (available from Fluorochem) (50 mg) in dry DCM (10 ml) was treated with 1-chloro-N,N,2-trimethyl-1-propen-1-amine (0.041 ml) (available from Acros) and allowed to stir at 20° C. for 10 min when a solution of 6-(1H-indol-4-yl)-1H-indazol-4-amine (77 mg) and triethylamine (0.043 ml) in DCM (5 ml) was added and the mixture stirred at 20° C. for 18 h. The mixture was poured onto an aminopropyl SPE cartridge (1 g) and allowed to stand for 2 h, then the mixture was eluted with methanol (5 ml) and blown to dryness under a stream of nitrogen. The crude product was purified by mass directed preparative HPLC (Method A) to give the title compound as a white solid (15 mg).

LC/MS $R_t$ 3.25 min m/z 391 [MH$^+$]. Method A

Example 48

N-[6-(1H-Indol-4-yl)-1H-indazol-4-yl]-1,4-dimethyl-1H-pyrazole-5-carboxamide

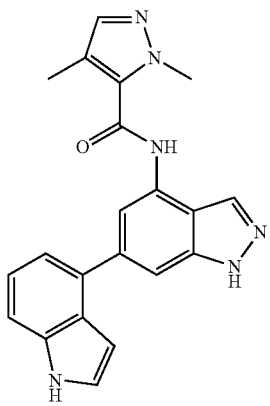 [SMILES: Cc1cnn(C)c1C(=O)Nc1cc(-c2cccc3[nH]ccc23)cc2[nH]ncc12]

A solution of 1,4-dimethyl-1H-pyrazole-5-carboxylic acid (21 mg) in dry DCM (10 ml) was treated with 1-chloro-N,N,2-trimethyl-1-propen-1-amine (0.02 ml) and allowed to stir at 20° C. for 10 min when a solution of 6-(1H-indol-4-yl)-1H-indazol-4-amine (25 mg) and triethylamine (0.028 ml) in DCM (5 ml) was added and the mixture stirred at 20° C. for 18 h. The mixture was poured onto an aminopropyl SPE cartridge (1 g) and allowed to stand for 2 h, then the mixture was eluted with methanol (5 ml) and blown to dryness under a stream of nitrogen and purified by mass directed preparative HPLC (Method A) to give the title compound (6 mg) as a white solid.

LC/MS $R_t$ 3.01 min m/z 371 [MH$^+$]. Method A

Example 49

N-[6-(1H-Indol-4-yl)-1H-indazol-4-yl]-5-(1-methylethyl)-2-(4-morpholinylmethyl)-1,3-thiazole-4-carboxamide

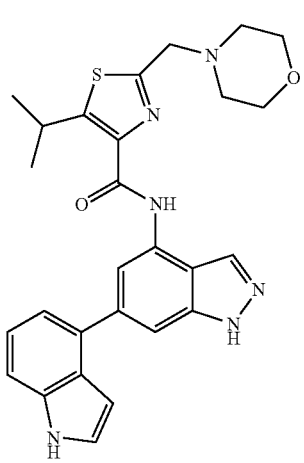 [SMILES: CC(C)c1sc(CN2CCOCC2)nc1C(=O)Nc1cc(-c2cccc3[nH]ccc23)cc2[nH]ncc12]

To a solution of 5-(1-methylethyl)-2-(4-morpholinylmethyl)-1,3-thiazole-4-carboxylic acid (31 mg) in DMF (3 ml) was added HATU (44 mg) and the mixture stirred at 20° C. for 10 min, then 6-(1H-indol-4-yl)-1H-indazol-4-amine (13 mg) and DIPEA (0.037 ml) were added and the mixture allowed to stand for 18 h. The mixture was blown to dryness under a stream of nitrogen and the residue purified by mass directed preparative HPLC (Method A) to give the title compound (8 mg) as a pale brown solid.

LC/MS $R_t$ 3.46 min m/z 501 [MH$^+$]. Method A

Similarly prepared from 6-(1H-indol-4-yl)-1H-indazol-4-amine were the following:

| Example number | Compound Name | Structure | Monomers | LC/MS $R_t$ min | LC/MS MH$^+$ | Purification Comment |
|---|---|---|---|---|---|---|
| 50 | 4-chloro-N-[6-(1H-indol-4-yl)-1H-indazol-4-yl]-1H-pyrazole-5-carboxamide | 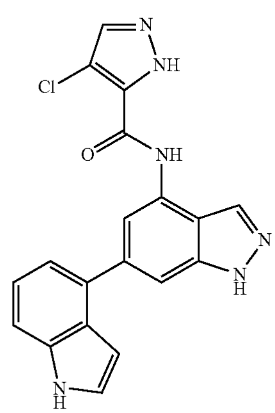 [SMILES: O=C(Nc1cc(-c2cccc3[nH]ccc23)cc2[nH]ncc12)c1[nH]ncc1Cl] | 4-Chloro-1H-pyrazole-5-carboxylic acid (available from Fluorochem) | 3.16 (a) | 377 (a) | |

-continued

| Example number | Compound Name | Structure | Monomers | LC/MS R, min | LC/MS MH+ | Purification Comment |
|---|---|---|---|---|---|---|
| 51 | 4-chloro-N-[6-(1H-indol-4-yl)-1H-indazol-4-yl]-1-(1-methylethyl)-1H-pyrazole-3-carboxamide | 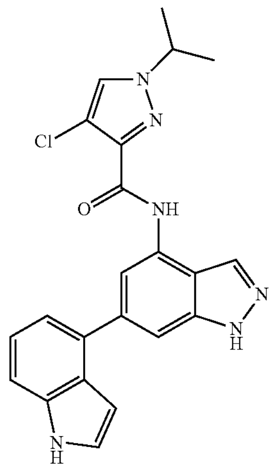 [SMILES: CC(C)n1cc(Cl)c(C(=O)Nc2cc(-c3cccc4[nH]ccc34)cc3[nH]ncc23)n1] | 4-Chloro-1-(1-methylethyl)-1H-pyrazole-3-carboxylic acid | 3.46 (a) | 419 (a) | |
| 52 | 2-chloro-N-[6-(1H-indol-4-yl)-1H-indazol-4-yl]-5-(1-methylethyl)-1,3-thiazole-4-carboxamide | 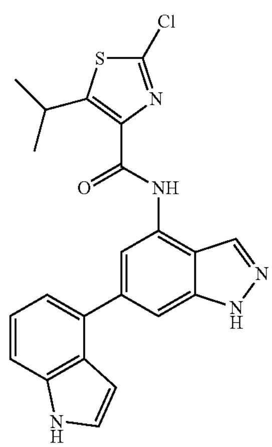 [SMILES: CC(C)c1sc(Cl)nc1C(=O)Nc1cc(-c2cccc3[nH]ccc23)cc2[nH]ncc12] | 2-Chloro-5-(1-methylethyl)-1,3-thiazole-4-carboxylic acid (available from Bionet-Int.) | 4.01 (a) | 436 (a) | |
| 53 | N-[6-(1H-indol-4-yl)-1H-indazol-4-yl]-2,5-dimethyl-1,3-thiazole-4-carboxamide | 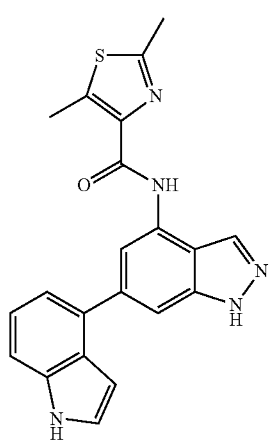 [SMILES: Cc1nc(C(=O)Nc2cc(-c3cccc4[nH]ccc34)cc3[nH]ncc23)c(C)s1] | 2,5-Dimethyl-1,3-thiazole-4-carboxylic acid (available from Aldrich) | 0.92 (b) | 388 (b) | |

-continued

| Example number | Compound Name | Structure | Monomers | LC/MS R$_t$ min | LC/MS MH$^+$ | Purification Comment |
|---|---|---|---|---|---|---|
| 54 | 4-chloro-N-[6-(1H-indol-4-yl)-1H-indazol-4-yl]-1-(1-methylethyl)-1H-pyrazole-5-carboxamide | 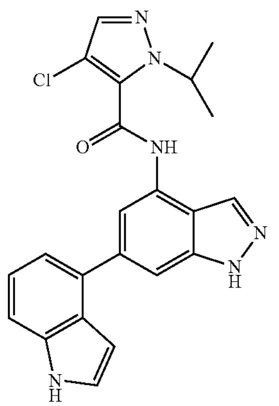 [SMILES: CC(C)n1ncc(Cl)c1C(=O)Nc1cc(-c2cccc3[nH]ccc23)cc2[nH]ncc12] | 4-Chloro-1-(1-methylethyl)-1H-pyrazole-5-carboxylic acid | 3.49 | 419 | |
| 55 | N-[6-(1H-indol-4-yl)-1H-indazol-4-yl]-1-methyl-4-(trifluoromethyl)-1H-pyrazole-5-carboxamide | 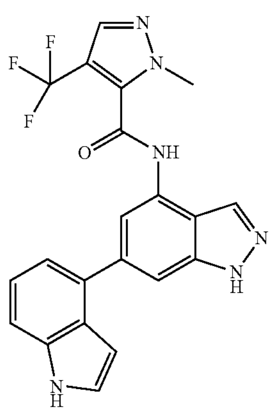 [SMILES: Cn1ncc(C(F)(F)F)c1C(=O)Nc1cc(-c2cccc3[nH]ccc23)cc2[nH]ncc12] | 1-Methyl-4-(trifluoromethyl)-1H-pyrazole-5-carboxylic acid | 3.31 (a) | 425 (a) | |
| 56 | N-[6-(1H-indol-4-yl)-1H-indazol-4-yl]-2-methyl-5-(1-methylethyl)-1,3-thiazole-4-carboxamide | 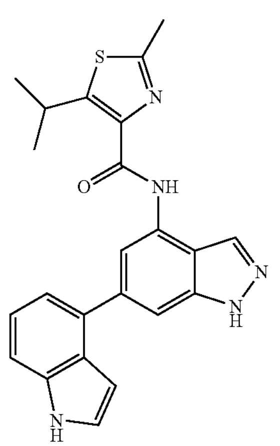 [SMILES: Cc1nc(C(=O)Nc2cc(-c3cccc4[nH]ccc34)cc3[nH]ncc23)c(C(C)C)s1] | 2-Methyl-5-(1-methylethyl)-1,3-thiazole-4-carboxylic acid | 3.88 (a) | 416 (a) | |

| Example number | Compound Name | Structure | Monomers | LC/MS R$_t$ min | LC/MS MH$^+$ | Purification Comment |
|---|---|---|---|---|---|---|
| 57 | N-[6-(1H-indol-4-yl)-1H-indazol-4-yl]-1-(1-methylethyl)-3-(4-morpholinyl-methyl)-1H-pyrazole-5-carboxamide | 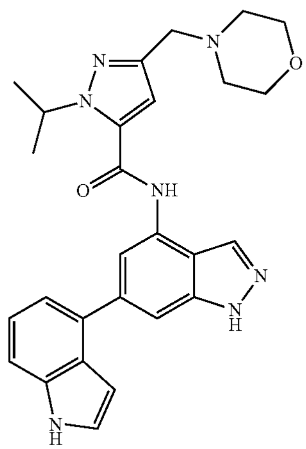 [SMILES: CC(C)n1nc(CN2CCOCC2)cc1C(=O)Nc1cc(-c2cccc3[nH]ccc23)cc2[nH]ncc12] | 1-(1-Methyl-ethyl)-3-(4-morpholinyl-methyl)-1H-pyrazole-5-carboxylic acid | 2.79 (a) | 484 (a) | |
| 58 | N-[6-(1H-indol-4-yl)-1H-indazol-4-yl]-1-(1-methylethyl)-5-(4-morpholinyl-methyl)-1H-pyrazole-3-carboxamide | 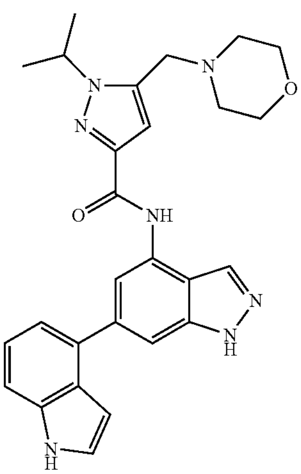 [SMILES: CC(C)n1nc(C(=O)Nc2cc(-c3cccc4[nH]ccc34)cc3[nH]ncc23)cc1CN1CCOCC1] | 1-(1-Methyl-ethyl)-5-(4-morpholinyl-methyl)-1H-pyrazole-3-carboxylic acid | 2.93 (a) | 484 (a) | |
| 59 | N-[6-(1H-indol-4-yl)-1H-indazol-4-yl]-1-methyl-1H-1,2,4-triazole-5-carboxamide | 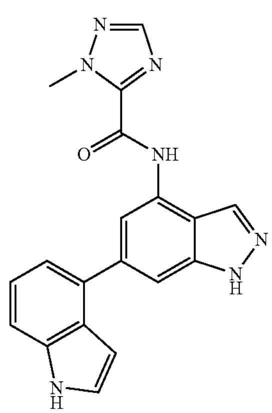 [SMILES: Cn1ncnc1C(=O)Nc1cc(-c2cccc3[nH]ccc23)cc2[nH]ncc12] | 1-Methyl-1H-1,2,4-triazole-5-carboxylic acid | 2.99 (a) | 358 (a) | |

-continued

| Example number | Compound Name | Structure | Monomers | LC/MS R$_t$ min | LC/MS MH$^+$ | Purification Comment |
|---|---|---|---|---|---|---|
| 60 | N-[6-(1H-indol-4-yl)-1H-indazol-4-yl]-1-(1-methylethyl)-1H-1,2,4-triazole-5-carboxamide | 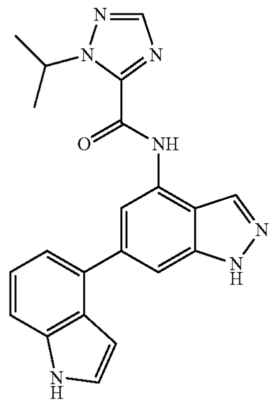 [SMILES: CC(C)n1ncnc1C(=O)Nc1cc(-c2cccc3[nH]ccc23)cc2[nH]ncc12] | 1-(1-Methylethyl)-1H-1,2,4-triazole-5-carboxylic acid | 3.31 (a) | 386 (a) | |
| 61 | 1-(1,1-dimethylethyl)-N-[6-(1H-indol-4-yl)-1H-indazol-4-yl]-3-methyl-1H-pyrazole-5-carboxamide | 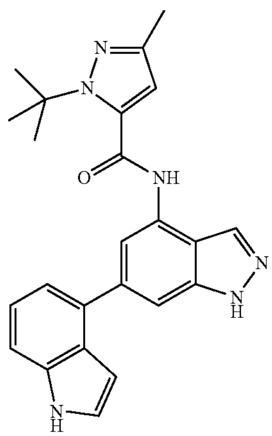 [SMILES: Cc1cc(C(=O)Nc2cc(-c3cccc4[nH]ccc34)cc3[nH]ncc23)n(C(C)(C)C)n1] | 1-(1,1-Dimethylethyl)-3-methyl-1H-pyrazole-5-carboxylic acid (available from Butt Park) | 3.33 (a) | 413 (a) | |
| 62 | N-[6-(1H-indol-4-yl)-1H-indazol-4-yl]-1-(2,2,2-trifluoroethyl)-1H-pyrazole-5-carboxamide | 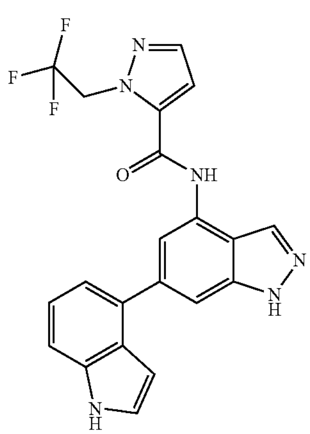 [SMILES: O=C(Nc1cc(-c2cccc3[nH]ccc23)cc2[nH]ncc12)c1ccnn1CC(F)(F)F] | 1-(2,2,2-Trifluoroethyl)-1H-pyrazole-5-carboxylic acid (available from N D Zelinsky Institute Building Blocks) | 3.26 (a) | 425 (a) | |

| Example number | Compound Name | Structure | Monomers | LC/MS R, min | LC/MS MH+ | Purification Comment |
|---|---|---|---|---|---|---|
| 63 | 1-(difluoromethyl)-N-[6-(1H-indol-4-yl)-1H-indazol-4-yl]-1H-pyrazole-5-carboxamide | 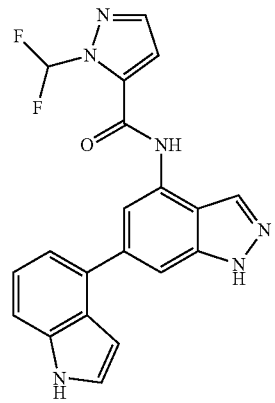 [SMILES: O=C(Nc1cc(-c2cccc3[nH]ccc23)cc2[nH]ncc12)c1ccnn1C(F)F] | 1-(Difluoromethyl)-1H-pyrazole-5-carboxylic acid (available from Fluorochem) | 3.19 (a) | 393 (a) | |
| 64 | 1,1-dimethylethyl [4-({[6-(1H-indol-4-yl)-1H-indazol-4-yl]amino}carbonyl)-1,3-thiazol-2-yl]carbamate | 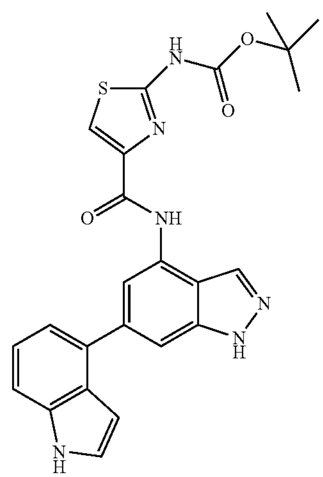 [SMILES: CC(C)(C)OC(=O)Nc1nc(C(=O)Nc2cc(-c3cccc4[nH]ccc34)cc3[nH]ncc23)cs1] | 2-({[(1,1-Dimethylethyl)oxy]carbonyl}amino)-1,3-thiazole-4-carboxylic acid (available from Fluorochem) | 3.61 (a) | 475 (a) | |
| 65 | 1,1-dimethylethyl 3-cyclopropyl-4-({[6-(1H-indol-4-yl)-1H-indazol-4-yl]amino}carbonyl)-1H-pyrazole-1-carboxylate | 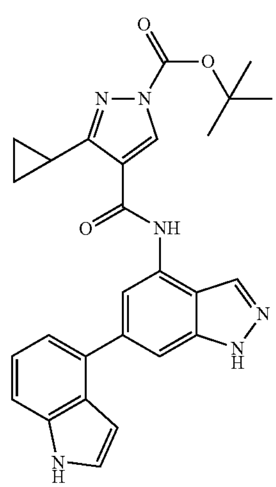 [SMILES: CC(C)(C)OC(=O)n1cc(C(=O)Nc2cc(-c3cccc4[nH]ccc34)cc3[nH]ncc23)c(C2CC2)n1] | 3-Cyclopropyl-1-{[(1,1-dimethylethyl)oxy]carbonyl}-1H-pyrazole-4-carboxylic acid | 3.53 (a) | 483 (a) | |

-continued

| Example number | Compound Name | Structure | Monomers | LC/MS R, min | LC/MS MH+ | Purification Comment |
|---|---|---|---|---|---|---|
| 66 | 4-fluoro-N-[6-(1H-indol-4-yl)-1H-indazol-4-yl]-1-(1-methylethyl)-1H-pyrazole-5-carboxamide | 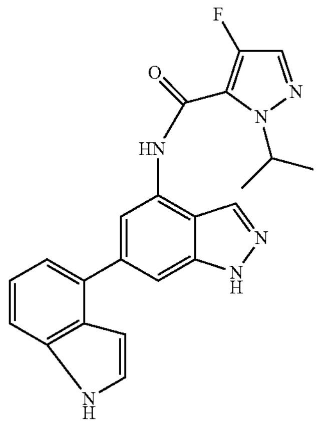 [SMILES: CC(C)n1ncc(F)c1C(=O)Nc1cc(-c2cccc3[nH]ccc23)cc2[nH]ncc12] | 4-Fluoro-1-(1-methylethyl)-1H-pyrazole-5-carboxylic acid | 3.42 (a) | 403 (a) | |
| 67 | 2-amino-N-[6-(1H-indol-4-yl)-1H-indazol-4-yl]-1,3-thiazole-4-carboxamide | 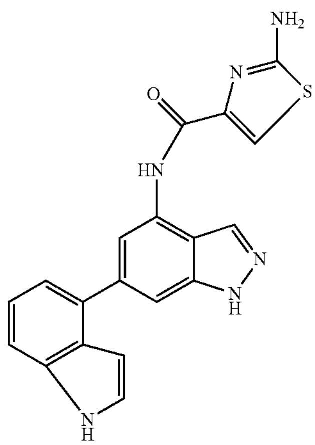 [SMILES: Nc1nc(C(=O)Nc2cc(-c3cccc4[nH]ccc34)cc3[nH]ncc23)cs1] | 2-Amino-1,3-thiazole-4-carboxylic acid | 3.05 (a) | 375 (a) | |
| 68 | 1-ethyl-4-fluoro-N-[6-(1H-indol-4-yl)-1H-indazol-4-yl]-1H-pyrazole-5-carboxamide | 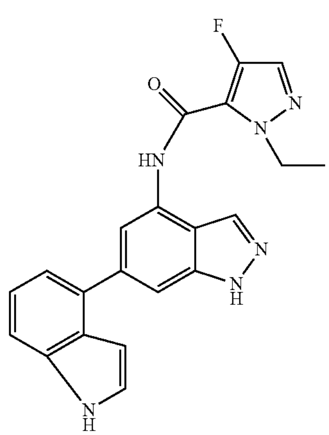 [SMILES: CCn1ncc(F)c1C(=O)Nc1cc(-c2cccc3[nH]ccc23)cc2[nH]ncc12] | 1-Ethyl-4-fluoro-1H-pyrazole-5-carboxylic acid | 1.03 (b) | 389 (b) | |

| Example number | Compound Name | Structure | Monomers | LC/MS R$_t$ min | LC/MS MH$^+$ | Purification Comment |
|---|---|---|---|---|---|---|
| 69 | 2-amino-N-[6-(1H-indol-4-yl)-1H-indazol-4-yl]-4-(trifluoromethyl)-1,3-thiazole-5-carboxamide | 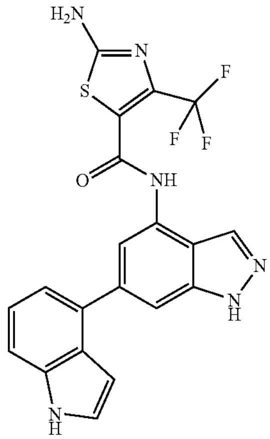 [SMILES: Nc1nc(C(F)(F)F)c(C(=O)Nc2cc(-c3cccc4[nH]ccc34)cc3[nH]ncc23)s1] | 2-Amino-4-(trifluoromethyl)-1,3-thiazole-5-carboxylic acid (for example, available from Apollo) | 2.27 (c) | 443 (c) | (e) |
| 70 | formic acid-2-amino-N-[6-(1H-indol-4-yl)-1H-indazol-4-yl]-5-(1-methylethyl)-1,3-thiazole-4-carboxamide (1:1) | 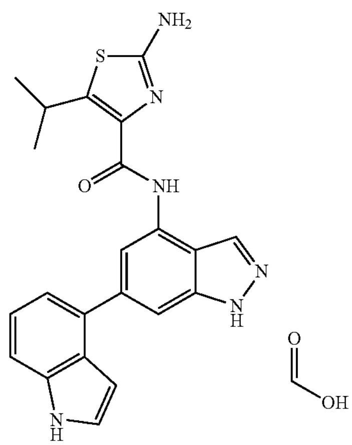 [SMILES: CC(C)c1sc(N)nc1C(=O)Nc1cc(-c2cccc3[nH]ccc23)cc2[nH]ncc12 ; O=CO] | 2-Amino-5-(1-methylethyl)-1,3-thiazole-4-carboxylic acid | 2.71 (c) | 417 (c) | (d) |
| 71 | N-[6-(1H-indol-4-yl)-1H-indazol-4-yl]-2-(1-methylethyl)-2H-1,2,3-triazole-4-carboxamide | 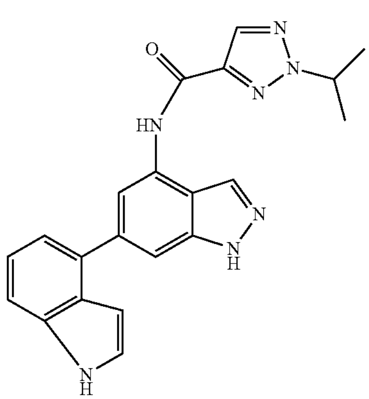 [SMILES: CC(C)n1ncc(C(=O)Nc2cc(-c3cccc4[nH]ccc34)cc3[nH]ncc23)n1] | 2-(1-Methylethyl)-2H-1,2,3-triazole-4-carboxylic acid | 2.52 (c) | 386 (c) | (d) |

-continued

| Example number | Compound Name | Structure | Monomers | LC/MS R, min | LC/MS MH+ | Purification Comment |
|---|---|---|---|---|---|---|
| 72 | 4-bromo-N-[6-(1H-indol-4-yl)-1H-indazol-4-yl]-1,3-dimethyl-1H-pyrazole-5-carboxamide | 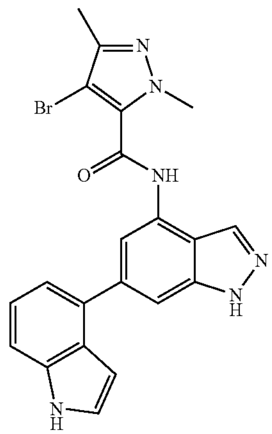 [SMILES: Cc1nn(C)c(C(=O)Nc2cc(-c3cccc4[nH]ccc34)cc3[nH]ncc23)c1Br] | 4-Bromo-1,3-dimethyl-1H-pyrazole-5-carboxylic acid | 2.60 (c) | 449 (c) | (d) |
| 73 | N-[6-(1H-indol-4-yl)-1H-indazol-4-yl]-5-(1-methylethyl)-1,3-thiazole-4-carboxamide | 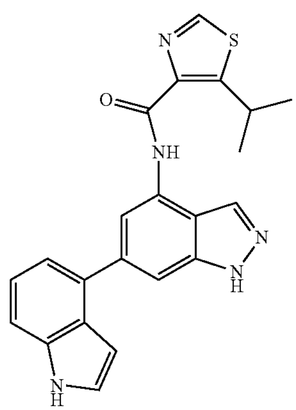 [SMILES: CC(C)c1scnc1C(=O)Nc1cc(-c2cccc3[nH]ccc23)cc2[nH]ncc12] | 5-(1-Methylethyl)-1,3-thiazole-4-carboxylic acid | 2.97 (c) | 402 (c) | (f) |
| 74 | 1-(2-fluoroethyl)-N-[6-(1H-indol-4-yl)-1H-indazol-4-yl]-1H-pyrazole-5-carboxamide | 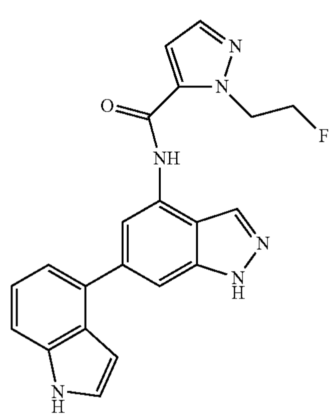 [SMILES: O=C(Nc1cc(-c2cccc3[nH]ccc23)cc2[nH]ncc12)c1ccnn1CCF] | 1-(2-Fluoroethyl)-1H-pyrazole-5-carboxylic acid | 2.26 (c) | 389 (c) | (f) |

-continued

| Example number | Compound Name | Structure | Monomers | LC/MS R$_t$ min | LC/MS MH$^+$ | Purification Comment |
|---|---|---|---|---|---|---|
| 75 | 1-(2-fluoroethyl)-N-[6-(1H-indol-4-yl)-1H-indazol-4-yl]-1H-pyrazole-3-carboxamide | 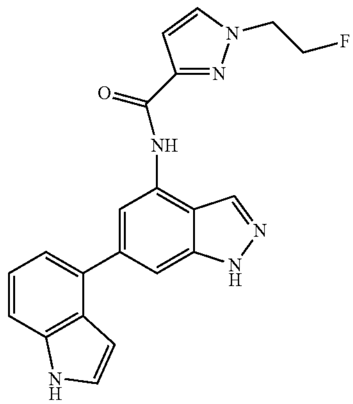 [SMILES: O=C(Nc1cc(-c2cccc3[nH]ccc23)cc2[nH]ncc12)c1ccn(CCF)n1] | 1-(2-Fluoro-ethyl)-1H-pyrazole-3-carboxylic acid | 2.26 (c) | 389 (c) | (g) |
| 76 | 5-acetyl-N-[6-(1H-indol-4-yl)-1H-indazol-4-yl]-2-methyl-1,3-thiazole-4-carboxamide | 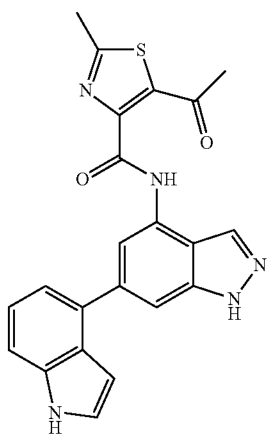 [SMILES: CC(=O)c1sc(C)nc1C(=O)Nc1cc(-c2cccc3[nH]ccc23)cc2[nH]ncc12] | 5-Acetyl-2-methyl-1,3-thiazole-4-carboxylic acid | 2.4 (c) | 416 (c) | (f) |
| 77 | N-[6-(1H-indol-4-yl)-1H-indazol-4-yl]-5-(1-methylethyl)-1,3-oxazole-4-carboxamide | 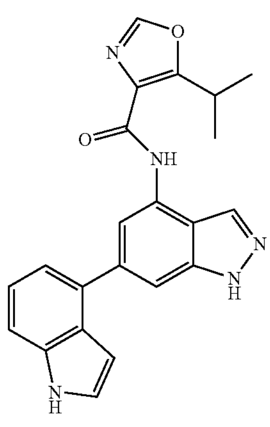 [SMILES: CC(C)c1ocnc1C(=O)Nc1cc(-c2cccc3[nH]ccc23)cc2[nH]ncc12] | 5-(1-Methyl-ethyl)-1,3-oxazole-4-carboxylic acid | 2.77 (c) | 386 (c) | |

| Example number | Compound Name | Structure | Monomers | LC/MS R$_t$ min | LC/MS MH$^+$ | Purification Comment |
|---|---|---|---|---|---|---|
| 78 | N-[6-(1H-indol-4-yl)-1H-indazol-4-yl]-1-(1-methylethyl)-1H-1,2,3-triazole-5-carboxamide | 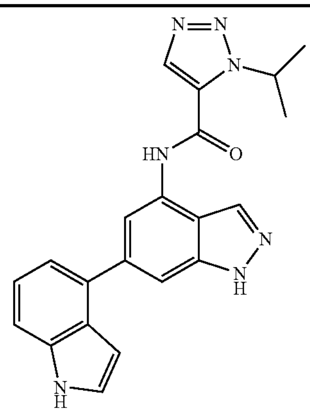 | 1-(1-Methyl-ethyl)-1H-1,2,3-triazole-5-carboxylic acid | 2.36 (c) | 386 (c) | (f) |

(a) LC/MS Method A
(b) LC/MS Method B
(c) LC/MS Method C
(d) Purified by MDAP Method D
(e) Post MDAP, the sample was dissolved in methanol (1 ml and loaded onto an aminopropyl cartridge (0.5 g) and eluted with methanol. The solvent was removed under a stream of nitrogen to give the title compound.
(f) Purified by MDAP Method E
(g) Purified by MDAP Method F

Example 79

N-[6-(1H-Indol-4-yl)-1H-indazol-4-yl]-2-methyl-1,3-thiazole-4-carboxamide

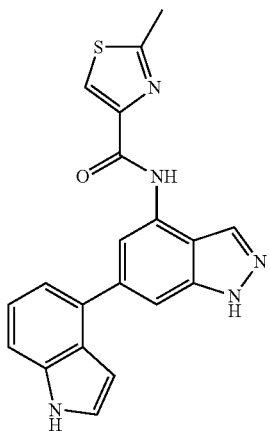 [SMILES: Cc1nc(C(=O)Nc2cc(-c3cccc4[nH]ccc34)cc3[nH]ncc23)cs1]

2M Sodium carbonate solution (0.059 ml), Pd(dppf)Cl$_2$ (5 mg), and water (1 ml) were added to solution of N-(6-bromo-1H-indazol-4-yl)-2-methyl-1,3-thiazole-4-carboxamide (40 mg) and 4-(4,4,5,5-tetramethyl-1,3,2-dioxaborolan-2-yl)-1H-indole (35 mg) (Frontier Scientific) in 1,4-dioxane (1 ml). The reaction vessel was sealed and heated under microwave irradiation at 150° C. for 15 min. After cooling, water (4 ml) was added, and then the mixture was extracted into DCM (3×10 ml). The organic layers were combined and the solvent evaporated. The residue was dissolved in methanol:DMSO (0.5 ml, 1:1) and purified by mass directed preparative HPLC (Method A) to give title compound (16 mg).

LC/MS R$_t$ 1.00 min m/z 374 [MH$^+$]. Method B

Example 80

N-[6-(1H-Indol-4-yl)-1H-indazol-4-yl]-1-methyl-1H-1,2,4-triazole-3-carboxamide

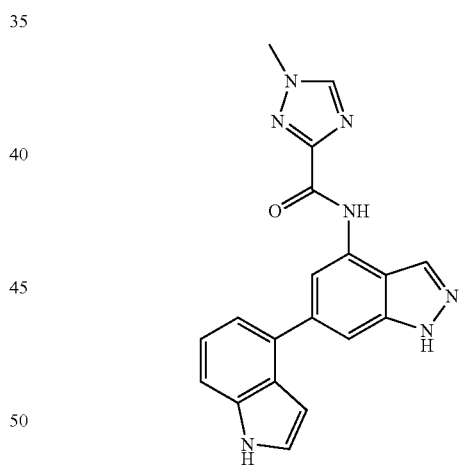

HATU (248 mg) and DIPEA (0.211 ml) were added to a flask containing 1-methyl-1H-1,2,4-triazole-3-carboxylic acid (51 mg) in DMF (1 ml). The reaction was stirred for 30 min under nitrogen. 6-(1H-Indol-4-yl)-1H-indazol-4-amine (50 mg) was added and the mixture was stirred for 3 h at RT under nitrogen. The reaction mixture was applied to an aminopropyl SPE cartridge (5 g) and left for 3 h. The column was washed with 10% methanol in DCM. The appropriate fractions were combined and the solvent was evaporated. The residue was dissolved in methanol:DMSO (1 ml, 1:1) and purified by mass directed preparative HPLC (Method A) to give title compound (37 mg).

LC/MS R$_t$ 0.79 min m/z 358 [MH$^+$]. Method B

Example 81

N-[6-(1H-Indol-5-yl)-1H-indazol-4-yl]-2-methyl-1,3-thiazole-4-carboxamide

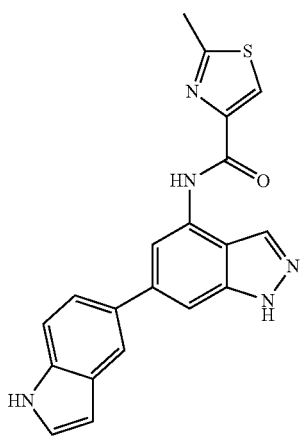 [SMILES: Cc1nc(C(=O)Nc2cc(-c3ccc4[nH]ccc4c3)cc3[nH]ncc23)cs1]

N-(6-Bromo-1H-indazol-4-yl)-2-methyl-1,3-thiazole-4-carboxamide (50 mg), Pd(dppf)Cl$_2$ (12 mg), 2M sodium carbonate (0.222 ml), 1,4-dioxane (1 ml) and water (1 ml) were added to 1H-indol-5-ylboronic acid (29 mg) in a microwave vial. The vial was sealed and heated under microwave irradiation at 150° C. for 15 min. The reaction mixture was extracted with DCM (2×20 ml) and then separated, combined organic layers were evaporated to dryness. The residue was dissolved in methanol:DMSO (1 ml, 1:1) and purified by mass directed preparative HPLC (Method A) to give title compound (3.7 mg).

LC/MS R$_t$ 0.99 min m/z 374 [MH$^+$]. Method B

Example 82

N-[6-(1H-Benzimidazol-4-yl)-1H-indazol-4-yl]-2-methyl-1,3-thiazole-4-carboxamide

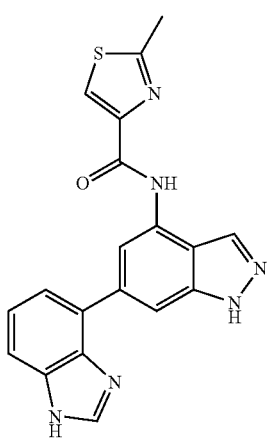 [SMILES: Cc1nc(C(=O)Nc2cc(-c3cccc4[nH]cnc34)cc3[nH]ncc23)cs1]

N-(6-Bromo-1H-indazol-4-yl)-2-methyl-1,3-thiazole-4-carboxamide (200 mg), 3-(4,4,5,5-tetramethyl-1,3,2-dioxaborolan-2-yl)-1,2-benzenediamine (167 mg) (WO2006/005915, page 90-91), Pd(dppf)Cl$_2$ (43 mg) and 2M sodium carbonate (0.890 ml) were charged in 1,4-dioxane (2 ml) and water (2 ml). The reaction vial was sealed and heated under microwave irradiation at 150° C. for 15 min. The reaction was extracted with DCM (3×30 ml). The combined organic layers were evaporated. To a solution of the residue in DMF (3 ml) was added triethylorthoformate (10 ml) and the mixture heated at reflux for 2 h. The solvent was evaporated and the residue dissolved in methanol:DMSO (3 ml, 1:1) and purified by mass directed preparative HPLC (Method A) to give title compound (26 mg).

LC/MS R$_t$ 0.78 min m/z 375 [MH$^+$]. Method B

Example 83

2-Methyl-N-[6-(2-methyl-1H-pyrrolo[2,3-b]pyridin-4-yl)-1H-indazol-4-yl]-1,3-thiazole-4-carboxamide 2-Methyl-1H-pyrrolo[2,3-b]pyridin-4-yl)boronic acid (150 mg), tripotassium phosphate (378 mg), N-(6-bromo-1H-indazol-4-yl)-2-methyl-1,3-thiazole-4-carboxamide (86 mg) and chloro(di-2-norbornylphosphino)(2'-dimethylamino-1,1'-biphenyl-2-yl)palladium (II) (25 mg) were placed in a microwave vial and 1,4-dioxane (4 ml) and water (0.8 ml) added. The reaction was heated under microwave irradiation at 120° C. for a total of 2 h. Chloro(di-2-norbornylphosphino)(2'-dimethylamino-1,1'-biphenyl-2-yl)palladium (II) (10 mg) was added and the reaction heated under microwave irradiation for 10 min at 120° C. 2-Methyl-1H-pyrrolo[2,3-b]pyridin-4-yl)boronic acid (24 mg) was added and the reaction was heated under microwave irradiation at 120° C. for 30 min. The reaction was applied to a silica cartridge (1 g), preconditioned with methanol and eluted with methanol. The solvent was evaporated and DCM (20 ml) and water (20 ml) were added to the residue. A precipitate formed which was filtered, dissolved in 1% methanol in DCM and passed through a silica cartridge, eluting with 0-5% methanol in DCM to give the title compound (45 mg).

LC/MS R$_t$ 0.76 min m/z 389 [MH$^+$]. Method B

Example 84

N-[6-(2-Cyclopropyl-1H-pyrrolo[2,3-b]pyridin-4-yl)-1H-indazol-4-yl]-2-methyl-1,3-thiazole-4-carboxamide

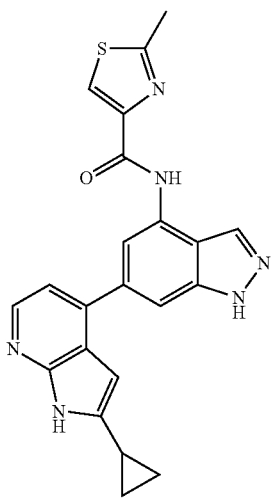 [SMILES: Cc1nc(C(=O)Nc2cc(-c3ccnc4[nH]c(C5CC5)cc34)cc3[nH]ncc23)cs1]

N-(6-Bromo-1H-indazol-4-yl)-2-methyl-1,3-thiazole-4-carboxamide (50 mg), Pd(dppf)Cl$_2$-DCM adduct (12 mg), 2M sodium carbonate (0.222 ml), 1,4-dioxane (0.5 ml) and water (0.278 ml) were added to 2-cyclopropyl-1H-pyrrolo[2,3-b]pyridin-4-yl)boronic acid (36 mg) in a Biotage microwave vial. The vial was sealed and heated under microwave irradiation at 150° C. for a total of 25 min. The reaction was passed through a silica cartridge (1 g), preconditioned with methanol, eluting with a gradient of DCM:methanol. The solvent was evaporated and the residue dissolved in DMSO and purified by HPLC using the following system:

Column: 5 µm Supelco ABZ+Plus 100×21.2 mm ID
Solvent A: 0.1% Formic acid in water
Solvent B: 0.05% Formic acid in acetonitrile
Flow rate: 20 ml/min
Gradient: 0-99% B over 25 min.

Appropriate fractions were dried under a stream of nitrogen, redissolved in MeCN, combined and dried to give the title compound (4.4 mg).

LC/MS R$_t$ 0.97 min m/z 415 [MH$^+$]. Method B

Example 85

N-1H,1'H-4,6'-Biindazol-4'-yl-1-(1-methylethyl)-1H-pyrazole-5-carboxamide

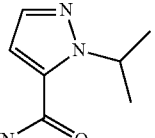
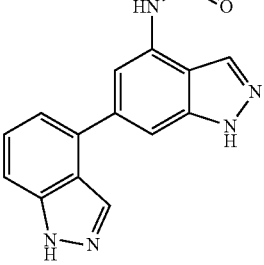

4-Bromo-1-(phenylsulfonyl)-1H-indazole (61 mg) in DMF (0.4 ml) was added to 1-(1-Methylethyl)-N-[1-(phenylsulfonyl)-6-(trimethylstannanyl)-1H-indazol-4-yl]-1H-pyrazole-5-carboxamide (100 mg) in DMF (0.4 ml). Solvias catalyst (4 mg) was added and the sealed vessel was heated in the Anton Paar microwave at 135° C. for 20 min. PS-thiophenol resin was added and the reaction was stirred overnight before being filtered onto a C$_{18}$SPE cartridge, pre-washed with 0.1% TFA, with acetonitrile. The cartridge was washed with 0.1% TFA in acetonitrile and the collected solvent was removed under a stream of nitrogen. The residue was dissolved in DMSO (1 ml) and purified by MDAP (method C). The solvent was evaporated in vacuo. The residue was dissolved in isopropanol (0.3 ml), 2M sodium hydroxide (aq) (0.3 ml) was added and the reaction was left at room temperature overnight, then heated to 60° C. for 2 h. The solvent was removed under a stream of nitrogen and the residue was dissolved in DMSO (0.5 ml) and purified by MDAP (method C). The solvent was evaporated in vacuo to give title compound, 15 mg.

LC/MS R$_t$ 0.86 min m/z 386 [MH$^+$]. Method D.

Example 86

N-[3-Fluoro-6-(1H-indol-4-yl)-1H-indazol-4-yl]-2-methyl-1,3-thiazole-4-carboxamide

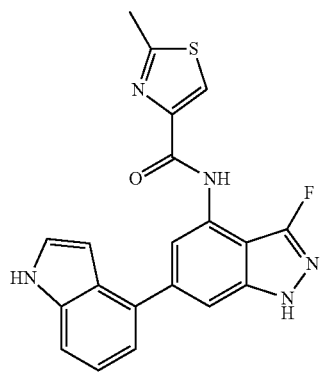 [SMILES: Cc1nc(C(=O)Nc2cc(-c3cccc4[nH]ccc34)cc3[nH]nc(F)c23)cs1]

To 2-methyl-1,3-thiazole-4-carboxylic acid (24 mg) in DMF (0.375 ml) was added HATU (69 mg) followed by DIPEA (0.043 ml), and the solution stirred for 10 min at 20° C. To this was then added a solution of 3-fluoro-6-(1H-indol-4-yl)-1H-indazol-4-amine (67 mg) in DMF (0.375 ml) and the top was placed on the vial which had been pierced with a needle. The solution was stirred at 20° C. for 73 h, heated at 50° C. for 3 h, then left to stand for 3.5 days. A further portion of 2-methyl-1,3-thiazole-4-carboxylic acid (0.024 g) in DMF (0.375 ml) was treated with HATU (0.069 g) followed by DIPEA (0.043 ml). This solution was stirred for 15 min at 20° C. then added to the original reaction mixture. This was then stirred at 20° C. for a further 72 h then loaded onto a dried aminopropyl SPE cartridge (1 g) which had been preconditioned with chloroform. The material was left on the cartridge for 2 h, then the cartridge was eluted with methanol (3 column volumes) and the solvent blown off. This was purified directly by mass directed preparative HPLC (Method A). The residue was azeotroped with methanol (5 ml) to give the title compound (7 mg) as a beige solid.

LC/MS $R_t$ 3.68 min m/z 392 [MH$^+$]. Method A

Similarly prepared from 3-fluoro-6-(1H-indol-4-yl)-1H-indazol-4-amine were the following:

| Example number | Compound Name | Structure | Carboxylic acid | LC/MS $R_t$ min (Method C) | LC/MS MH$^+$ (Method C) |
|---|---|---|---|---|---|
| 87 | 4-Chloro-1-ethyl-N-[3-fluoro-6-(1H-indol-4-yl)-1H-indazol-4-yl]-1H-pyrazole-5-carboxamide | 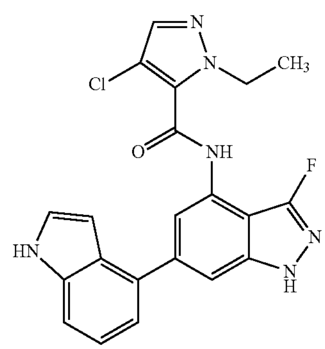 [SMILES: CCn1ncc(Cl)c1C(=O)Nc1cc(-c2cccc3[nH]ccc23)cc2[nH]nc(F)c12] | 4-Chloro-1-ethyl-1H-pyrazole-5-carboxylic acid | 2.99 | 423 |
| 88 | N-[3-Fluoro-6-(1H-indol-4-yl)-1H-indazol-4-yl]-1-(1-methylethyl)-1H-pyrazole-5-carboxamide | 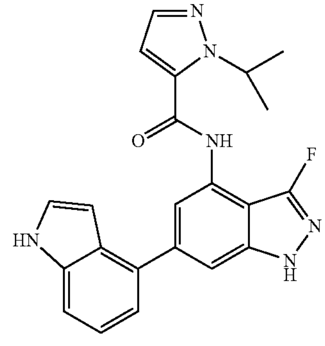 [SMILES: CC(C)n1nccc1C(=O)Nc1cc(-c2cccc3[nH]ccc23)cc2[nH]nc(F)c12] | 1-(1-Methylethyl)-1H-pyrazole-5-carboxylic acid | 2.71 | 403 |

Example 89

N-[6-(6-Fluoro-1H-indol-4-yl)-1H-indazol-4-yl]-2-methyl-1,3-thiazole-4-carboxamide

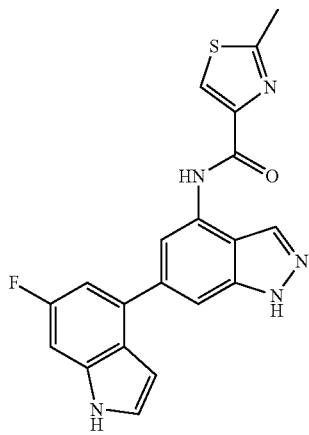 [SMILES: Cc1nc(C(=O)Nc2cc(-c3cc(F)cc4[nH]ccc34)cc3[nH]ncc23)cs1]

A microwave vial was charged with Solvias catalyst (15 mg), tripotassium phosphate (116 mg), 4-bromo-6-fluoro-1H-indole (available from Sinova, 32 mg), 1-(1-methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide (66 mg), 1,4-dioxane (0.5 ml) and water (0.1 ml). The reaction mixture was heated under microwave irradiation for a total of 25 min at 120° C. The mixture was passed through a silica cartridge pre-conditioned with methanol, washing with methanol, then dried. The residue was separated between DCM and water and the organic layer was passed through a hydrophobic frit and dried. The residue was dissolved in DMSO:methanol (1 ml, 1:1, v/v) and purified by MDAP (Method H). Appropriate fractions were dried, redissolved in methanol and a few drops of 2M HCl (aq) were added. The reaction was left to stir for 30 min. The reaction was passed through an aminopropyl cartridge, preconditioned with methanol, washing with methanol, then dried under a stream of nitrogen to give title compound, 11 mg.

LC/MS (Method D) 1.00 min m/z 392 [MH$^+$].

Example 90

N-[6-(1H-Indol-4-yl)-1H-indazol-4-yl]-1-(1-methylethyl)-1H-imidazole-2-carboxamide

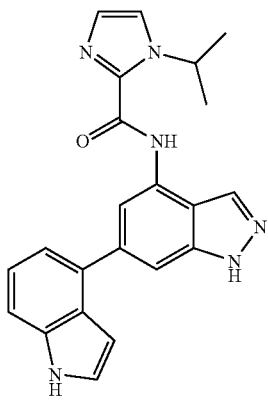 [SMILES: CC(C)n1ccnc1C(=O)Nc1cc(-c2cccc3[nH]ccc23)cc2[nH]ncc12]

A mixture of 1-(1-methylethyl)-1H-imidazole-2-carboxylic acid (467 mg, contained 50% ethyl 1H-imidazole-2-carboxylate plus inorganic impurities) (now available pure from AKos), HATU (576 mg), and DIPEA (0.793 ml) in DMF (2 ml) was stirred at RT for 10 min. 6-(1H-Indol-4-yl)-1H-indazol-4-amine (188 mg) in DMF (3 ml) was then added and the mixture was stirred at RT. After 3 h at RT, a further quantity of premixed [1-(1-methylethyl)-1H-imidazole-2-carboxylic acid (467 mg), HATU (576 mg), and DIPEA (0.793 ml) in DMF (2 ml)] was added to the reaction mixture and stirring was continued for 2 h at RT. Water (0.5 ml) was added to the reaction mixture, and it was then evaporated to dryness. The residue was partitioned between ethyl acetate (25 ml) and water (10 ml). The phases were separated and the aqueous phase was extracted with further ethyl acetate (2×25 ml). The combined organic extracts were dried over anhydrous sodium sulphate and evaporated to give a brown oily residue which was dissolved in DCM (15 ml) and applied to a 100 g silica SPE cartridge. The cartridge was eluted on a Flashmaster (II) using a gradient of 0-100% ethyl acetate in cyclohexane over 60 min to give a pale brown oil which was dissolved in DCM (5 ml) and applied to a 20 g silica SPE cartridge. The cartridge was eluted with a gradient of 0-100% ethyl acetate in cyclohexane over 40 min followed by 0-20% methanol in ethyl acetate over 15 min to give the title compound (53 mg) as a buff-coloured solid.

LC/MS R$_t$ 1.04 min m/z 385 [MH$^+$]. Method B

Example 91

4-Fluoro-N-[6-(1H-indol-4-yl)-1H-indazol-4-yl]-1-methyl-1H-pyrazole-3-carboxamide

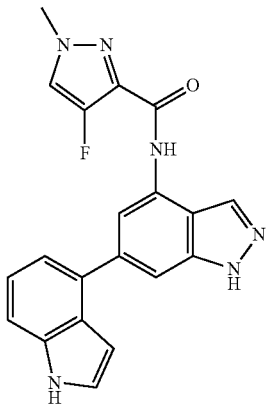 [SMILES: Cn1cc(F)c(C(=O)Nc2cc(-c3cccc4[nH]ccc34)cc3[nH]ncc23)n1]

A mixture 4-fluoro-1-methyl-1H-pyrazole-3-carboxylic acid and 4-fluoro-1-methyl-1H-pyrazole-5-carboxylic acid (45:55) (580 mg, 20% $^w/_w$), HATU (306 mg), and DIPEA (0.422 ml) in DMF (3 ml) was stirred at RT for 10 min. 6-(1H-Indol-4-yl)-1H-indazol-4-amine (100 mg) in DMF (3 ml) was then added and the mixture was stirred at RT overnight. The reaction mixture was added to a 20 g aminopropyl SPE cartridge which had been preconditioned with methanol. The reaction mixture was allowed to remain on the cartridge for 3 h before being eluted with methanol (4 column volumes) and then 10%-triethylamine in methanol (6 column volumes). The appropriate fractions were evaporated to give a brown oil which was partitioned between ethyl acetate (25 ml) and water (5 ml). The phases were separated and the organic phase was dried over anhydrous sodium sulphate and evaporated to a brown oil. This was dissolved in ethyl acetate (10 ml) and pre-adsorbed on silica (1.2 g) which was then added to the top of a 20 g silica SPE cartridge. The cartridge was eluted with a gradient of 0-100% ethyl acetate in cyclohexane over 60 min to give the title compound (65 mg) as a buff-coloured solid.

LC/MS R$_t$ 0.89 min m/z 375 [MH$^+$]. Method B

Example 92

1-Ethyl-N-[6-(1H-indol-4-yl)-1H-indazol-4-yl]-3-methyl-1H-pyrazole-5-carboxamide

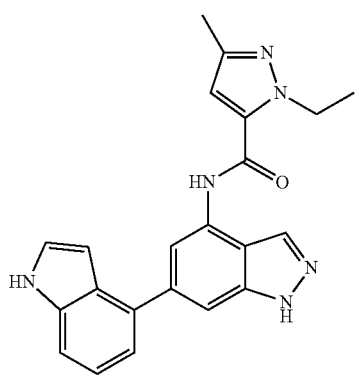 [SMILES: CCn1nc(C)cc1C(=O)Nc1cc(-c2cccc3[nH]ccc23)cc2[nH]ncc12]

1-Ethyl-3-methyl-1H-pyrazole-5-carboxylic acid (67.8 mg) was treated with N-[(dimethylamino)(3H-[1,2,3]triazolo[4,5-b]pyridin-3-yloxy)methylidene]-N-methylmethanaminium hexafluorophosphate (168 mg) in DMF (750 μl) and DIPEA (150 μl). Reaction mixture was shaken for five min prior to treatment with 6-(1H-indol-4-yl)-1H-indazol-4-amine (50 mg) in DMF (350 μl). Reaction mixture was left to stand at 22° C. for 16 hrs. Solvent was removed in vacuo and the product re-dissolved in chloroform (0.3 ml) prior to application on to a preconditioned (methanol then chloroform) aminopropyl SPE cartridge (1 g). Product was eluted after 2 h with ethyl acetate:methanol (1:1, 3.2 ml), and concentrated under a stream of nitrogen using blow down apparatus. Purification by mass directed preparative HPLC (Method B) gave the title compound.

LC/MS $R_t$ 3.08 min m/z 385 [MH$^+$]. Method A

Similarly prepared from 6-(1H-indol-4-yl)-1H-indazol-4-amine were the following:

| Example number | Compound Name | Structure | Carboxylic acid | LC/MS $R_t$ min | LC/MS MH$^+$ |
|---|---|---|---|---|---|
| 93 | N-[6-(1H-indol-4-yl)-1H-indazol-4-yl]-1,3-dimethyl-1H-pyrazole-5-carboxamide | 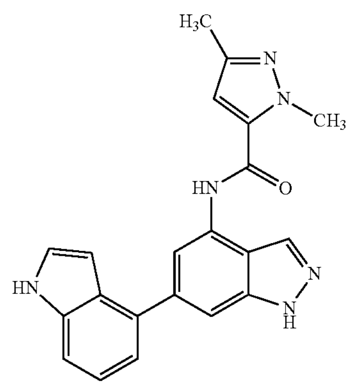 [SMILES: Cc1cc(C(=O)Nc2cc(-c3cccc4[nH]ccc34)cc3[nH]ncc23)n(C)n1] | 1,3-Dimethyl-1H-pyrazole-5-carboxylic acid | 2.96 (a) | 371 (a) |
| 94 | 3-(1,1-dimethylethyl)-N-[6-(1H-indol-4-yl)-1H-indazol-4-yl]-1-methyl-1H-pyrazole-5-carboxamide | 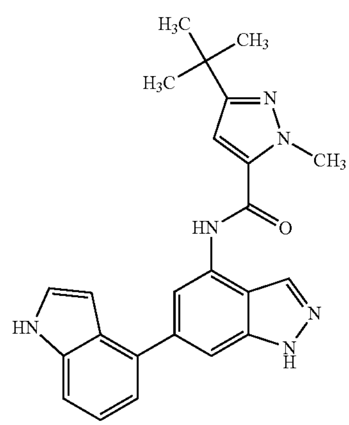 [SMILES: Cn1nc(C(C)(C)C)cc1C(=O)Nc1cc(-c2cccc3[nH]ccc23)cc2[nH]ncc12] | 3-(1,1-Dimethylethyl)-1-methyl-1H-pyrazole-5-carboxylic acid | 3.36 (a) | 413 (a) |

-continued

| Example number | Compound Name | Structure | Carboxylic acid | LC/MS R<sub>t</sub> min | LC/MS MH<sup>+</sup> |
|---|---|---|---|---|---|
| 95 | 4-chloro-1-ethyl-N-[6-(1H-indol-4-yl)-1H-indazol-4-yl]-1H-pyrazole-5-carboxamide | 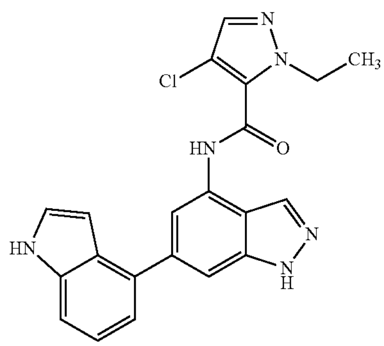 [SMILES: CCn1ncc(Cl)c1C(=O)Nc1cc(-c2cccc3[nH]ccc23)cc2[nH]ncc12] | 4-Chloro-1-ethyl-1H-pyrazole-5-carboxylic acid | 3.28 (a) | 405 (a) |
| 96 | N-[6-(1H-indol-4-yl)-1H-indazol-4-yl]-1-methyl-3-(trifluoromethyl)-1H-pyrazole-5-carboxamide | 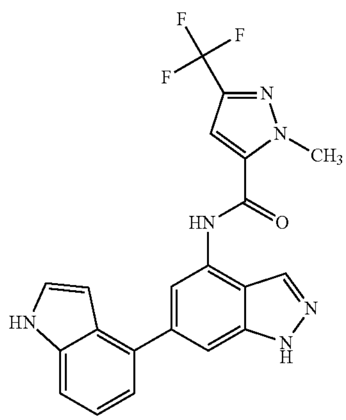 [SMILES: Cn1nc(C(F)(F)F)cc1C(=O)Nc1cc(-c2cccc3[nH]ccc23)cc2[nH]ncc12] | 1-Methyl-3-(trifluoromethyl)-1H-pyrazole-5-carboxylic acid | 3.36 (a) | 425 (a) |
| 97 | N-[6-(1H-indol-4-yl)-1H-indazol-4-yl]-1-methyl-3-(1-methylethyl)-1H-pyrazole-5-carboxamide | 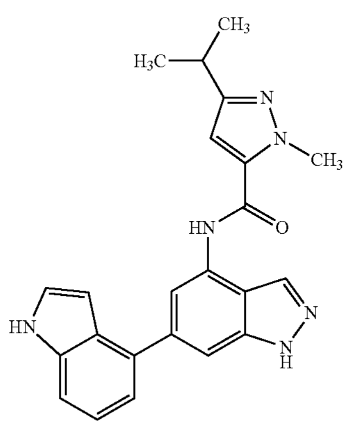 [SMILES: CC(C)c1cc(C(=O)Nc2cc(-c3cccc4[nH]ccc34)cc3[nH]ncc23)n(C)n1] | 1-Methyl-3-(1-methylethyl)-1H-pyrazole-5-carboxylic acid | 3.26 (a) | 399 (a) |

-continued

| Example number | Compound Name | Structure | Carboxylic acid | LC/MS R_t min | LC/MS MH+ |
|---|---|---|---|---|---|
| 98 | 3-cyclopropyl-N-[6-(1H-indol-4-yl)-1H-indazol-4-yl]-1-methyl-1H-pyrazole-5-carboxamide | 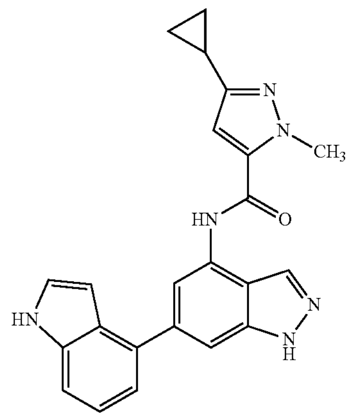 [SMILES: Cn1nc(C2CC2)cc1C(=O)Nc1cc(-c2cccc3[nH]ccc23)cc2[nH]ncc12] | 3-Cyclopropyl-1-methyl-1H-pyrazole-5-carboxylic acid | 3.15 (a) | 397 (a) |
| 99 | 1-ethyl-N-[6-(1H-indol-4-yl)-1H-indazol-4-yl]-3-(1-methylethyl)-1H-pyrazole-5-carboxamide | 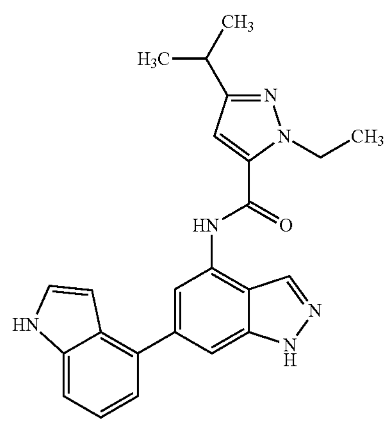 [SMILES: CCn1nc(C(C)C)cc1C(=O)Nc1cc(-c2cccc3[nH]ccc23)cc2[nH]ncc12] | 1-Ethyl-3-(1-methylethyl)-1H-pyrazole-5-carboxylic acid | 3.34 (a) | 413 (a) |
| 100 | N-[6-(1H-indol-4-yl)-1H-indazol-4-yl]-1-methyl-3-(2-methylpropyl)-1H-pyrazole-5-carboxamide | 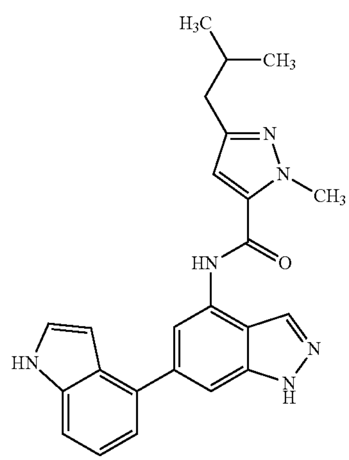 [SMILES: CC(C)Cc1cc(C(=O)Nc2cc(-c3cccc4[nH]ccc34)cc3[nH]ncc23)n(C)n1] | 1-Methyl-3-(2-methylpropyl)-1H-pyrazole-5-carboxylic acid | 3.34 (a) | 413 (a) |

(a) LC/MS Method A

Example 101

N-[6-(1H-Indol-4-yl)-1H-indazol-4-yl]-4-(methyloxy)-3-thiophenecarboxamide

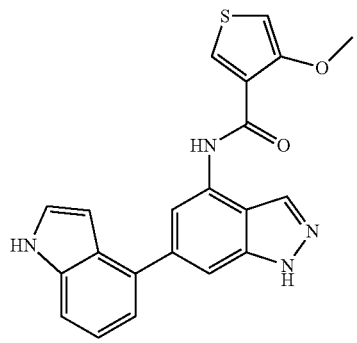 [SMILES: COc1cscc1C(=O)Nc1cc(-c2cccc3[nH]ccc23)cc2[nH]ncc12]

4-(Methyloxy)-3-thiophenecarboxylic acid (35 mg) was treated with N-[(dimethylamino)(3H-[1,2,3]triazolo[4,5-b]pyridin-3-yloxy)methylidene]-N-methylmethanaminium hexafluorophosphate (84 mg) in DMF (250 µl) and DIPEA (69 µl). The reaction mixture was shaken for five min prior to treatment with 6-(1H-indol-4-yl)-1H-indazol-4-amine (25 mg) in DMF (250 µl). The reaction mixture was left to stand at 22° C. for 18 h. The solvent was removed in vacuo and the product re-dissolved in chloroform (0.3 ml) prior to application on to an aminopropyl SPE cartridge (0.5 g) that had been preconditioned with methanol and then chloroform. The product was eluted after 2 hr with ethyl acetate/methanol (1:1, 3 ml), and concentrated under a stream of nitrogen using blow down apparatus. Purification by mass directed preparative HPLC (Method C) gave the title compound.

LC/MS $R_t$ 1.08 min m/z 389 [MH$^+$]. Method B

Similarly prepared from 6-(1H-indol-4-yl)-1H-indazol-4-amine were the following:

| Example Number | Compound Name | Structure | Carboxylic acid | LC/MS $R_t$ min | LC/MS MH$^+$ |
|---|---|---|---|---|---|
| 102 | N-[6-(1H-indol-4-yl)-1H-indazol-4-yl]-1-methyl-3-(4-morpholinylcarbonyl)-1H-pyrazole-5-carboxamide | 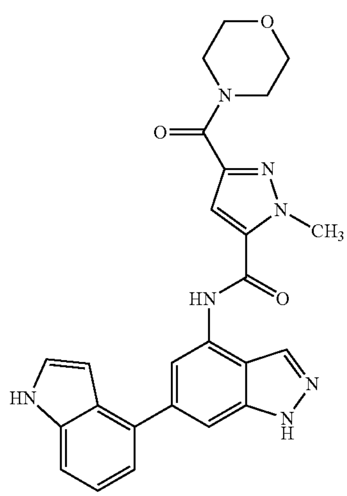 [SMILES: Cn1nc(C(=O)N2CCOCC2)cc1C(=O)Nc1cc(-c2cccc3[nH]ccc23)cc2[nH]ncc12] | 1-Methyl-3-(4-morpholinylcarbonyl)-1H-pyrazole-5-carboxylic acid | 0.87 (a) | 470 (a) |
| 103 | N-[6-(1H-indol-4-yl)-1H-indazol-4-yl]-1,4-dimethyl-1H-pyrazole-3-carboxamide | 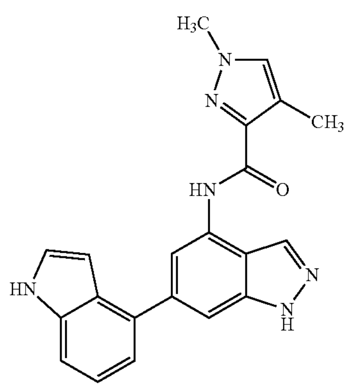 [SMILES: Cc1cn(C)nc1C(=O)Nc1cc(-c2cccc3[nH]ccc23)cc2[nH]ncc12] | 1,4-Dimethyl-1H-pyrazole-3-carboxylic acid | 0.99 (a) | 371 (a) |

| Example Number | Compound Name | Structure | Carboxylic acid | LC/MS R$_t$ min | LC/MS MH$^+$ |
|---|---|---|---|---|---|
| 104 | 1-ethyl-N-[6-(1H-indol-4-yl)-1H-indazol-4-yl]-3-(2-methylpropyl)-1H-pyrazole-5-carboxamide | 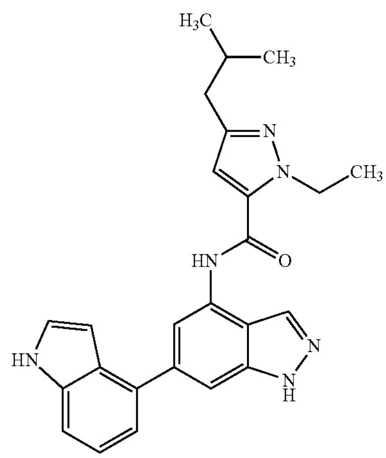 [SMILES: CCn1nc(CC(C)C)cc1C(=O)Nc1cc(-c2cccc3[nH]ccc23)cc2[nH]ncc12] | 1-Ethyl-3-(2-methylpropyl)-1H-pyrazole-5-carboxylic acid | 1.19 (a) | 427 (a) |
| 105 | N-[6-(1H-indol-4-yl)-1H-indazol-4-yl]-1-methyl-5-(4-morpholinylmethyl)-1H-pyrazole-3-carboxamide | 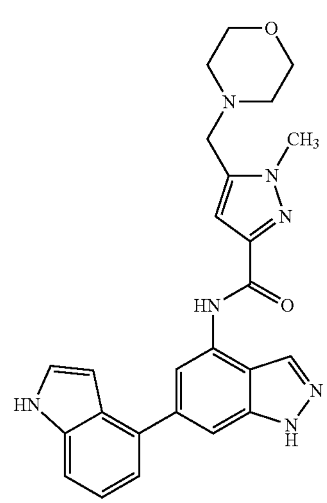 [SMILES: Cn1nc(C(=O)Nc2cc(-c3cccc4[nH]ccc34)cc3[nH]ncc23)cc1CN1CCOCC1] | 1-Methyl-5-(4-morpholinylmethyl)-1H-pyrazole-3-carboxylic acid | 0.68 | 456 (a) |

-continued
| Example Number | Compound Name | Structure | Carboxylic acid | LC/MS R, min | LC/MS MH+ |
|---|---|---|---|---|---|
| 106 | N-[6-(1H-indol-4-yl)-1H-indazol-4-yl]-1-methyl-3-(4-morpholinylmethyl)-1H-pyrazole-5-carboxamide | 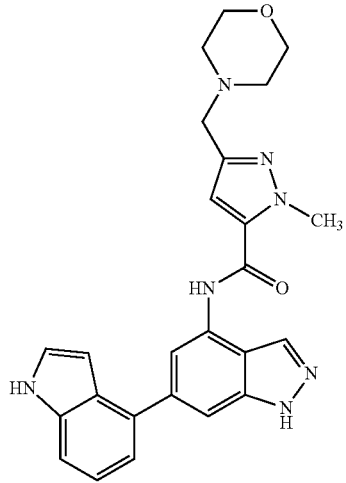 [SMILES: Cn1nc(CN2CCOCC2)cc1C(=O)Nc1cc(-c2cccc3[nH]ccc23)cc2[nH]ncc12] | 1-Methyl-3-(4-morpholinylmethyl)-1H-pyrazole-5-carboxylic acid | 0.68 (a) | 456 (a) |
| 107 | 2-acetyl-N-[6-(1H-indol-4-yl)-1H-indazol-4-yl]-1,3-thiazole-4-carboxamide | 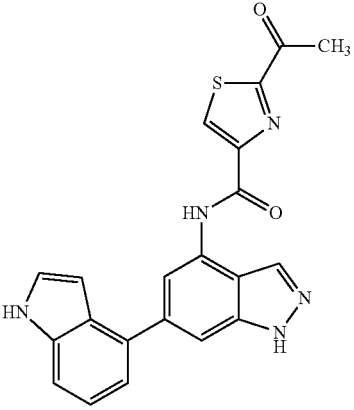 [SMILES: CC(=O)c1nc(C(=O)Nc2cc(-c3cccc4[nH]ccc34)cc3[nH]ncc23)cs1] | 2-Acetyl-1,3-thiazole-4-carboxylic acid | 1.02 (a) | 402 (a) |
(a) LC/MS Method B

Example 108

N-[6-(5-Isoquinolinyl)-1H-indazol-4-yl]-2-methyl-1,3-thiazole-4-carboxamide

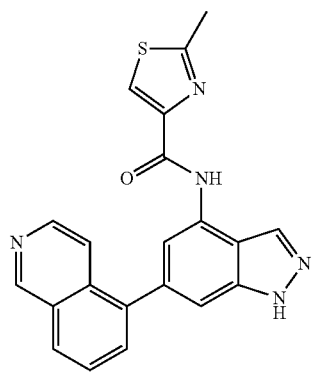 [SMILES: Cc1nc(C(=O)Nc2cc(-c3cccc4cnccc34)cc3[nH]ncc23)cs1]

5-Isoquinolinylboronic acid (21 mg), 0.6M potassium carbonate solution (200 μl) and Pd(dppf)Cl$_2$ (10 mg) in 1,4-dioxane (1 ml) were treated with a solution of N-(6-bromo-1H-indazol-4-yl)-2-methyl-1,3-thiazole-4-carboxamide (40 mg) in 1,4-dioxane (1 ml). The reaction vessel was sealed and heated under microwave irradiation at 150° C. for 30 min. After cooling the solvent was removed in vacuo. The sample was redissolved in methanol and loaded onto C18 reverse phase SPE (0.5 g). Product was eluted with acetonitrile/TFA (0.1%) (3×3 ml), and concentrated under a stream of nitrogen using blow down apparatus. Purification by mass directed preparative HPLC (Method C) gave the title compound.

LC/MS R$_t$ 0.67 min m/z 386 [MH$^+$]. Method B

Similarly prepared from N-(6-bromo-1H-indazol-4-yl)-2-methyl-1,3-thiazole-4-carboxamide were the following:

| Example Number | Compound Name | Structure | Boronic acid/ester | LC/MS R$_t$ min | LC/MS MH$^+$ |
|---|---|---|---|---|---|
| 109 | 2-methyl-N-[6-(1-methyl-1H-indol-4-yl)-1H-indazol-4-yl]-1,3-thiazole-4-carboxamide | 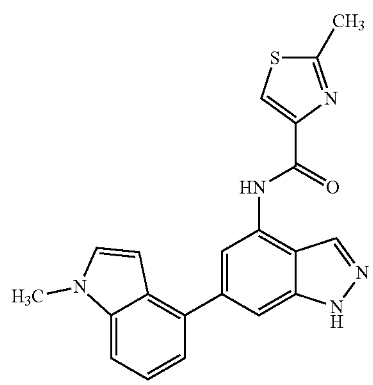 [SMILES: Cc1nc(C(=O)Nc2cc(-c3cccc4c3ccn4C)cc3[nH]ncc23)cs1] | 1-methyl-4-(4,4,5,5-tetramethyl-1,3,2-dioxaborolan-2-yl)-1H-indole | 1.03 (a) | 388 (a) |
| 110 | N-[6-(4-isoquinolinyl)-1H-indazol-4-yl]-2-methyl-1,3-thiazole-4-carboxamide | 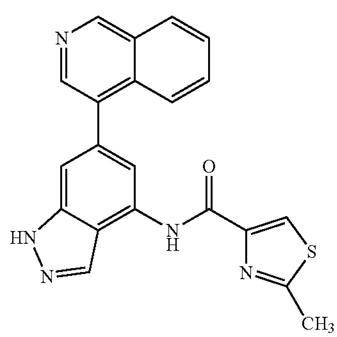 [SMILES: Cc1nc(C(=O)Nc2cc(-c3cncc4ccccc34)cc3[nH]ncc23)cs1] | 4-Isoquinolinylboronic acid | 0.7 (a) | 386 (a) |

-continued

| Example Number | Compound Name | Structure | Boronic acid/ester | LC/MS R$_t$ min | LC/MS MH$^+$ |
|---|---|---|---|---|---|
| 111 | N-[6-(1H-indol-3-yl)-1H-indazol-4-yl]-2-methyl-1,3-thiazole-4-carboxamide | 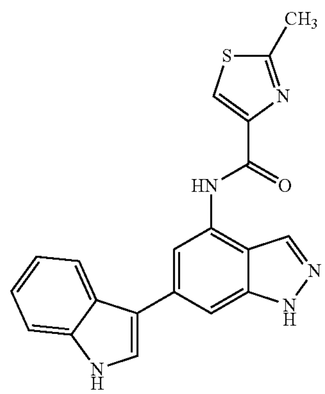 [SMILES: Cc1nc(C(=O)Nc2cc(-c3c[nH]c4ccccc34)cc3[nH]ncc23)cs1] | (1-{[(1,1-Dimethylethyl)-oxy]carbonyl}-1H-indol-3-yl)boronic acid | 0.96 (a) | 374 (a) |
| 112 | N-[6-(1H-indol-6-yl)-1H-indazol-4-yl]-2-methyl-1,3-thiazole-4-carboxamide | 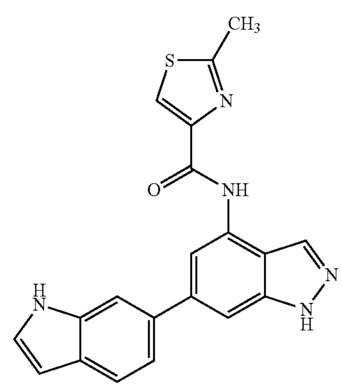 [SMILES: Cc1nc(C(=O)Nc2cc(-c3ccc4cc[nH]c4c3)cc3[nH]ncc23)cs1] | 1H-Indol-6-ylboronic acid | 0.99 (a) | 374 (a) |
| 113 | 2-methyl-N-[6-(1-methyl-1H-indol-6-yl)-1H-indazol-4-yl]-1,3-thiazole-4-carboxamide | 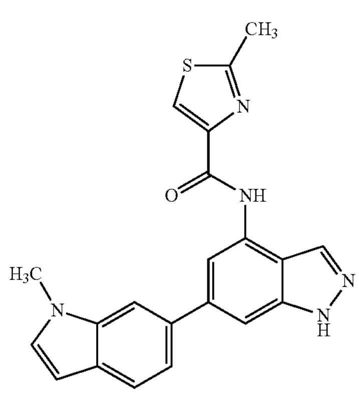 [SMILES: Cc1nc(C(=O)Nc2cc(-c3ccc4ccn(C)c4c3)cc3[nH]ncc23)cs1] | 1-Methyl-6-(4,4,5,5-tetramethyl-1,3,2-dioxaborolan-2-yl)-1H-indole | 1.07 (a) | 388 (a) |

(a) LC/MS Method B

Example 114

N-[6-(1H-Indol-4-yl)-1H-indazol-4-yl]-2-furancarboxamide

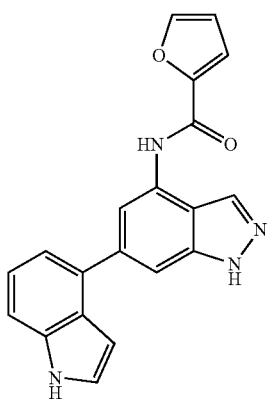 [SMILES: O=C(Nc1cc(-c2cccc3[nH]ccc23)cc2[nH]ncc12)c1ccco1]

To a solution of 6-(1H-indol-4-yl)-2-(tetrahydro-2H-pyran-2-yl)-2H-indazol-4-amine (50 mg) in DCM (1 ml) was added DIPEA (131 µl) followed by 2-furancarbonyl chloride (39 mg) (available from ABCR) and the mixture stirred at RT for 1 h, then the solvent was removed. To a mixture of the residue in methanol (2 ml) was added 4M hydrochloric acid in 1,4-dioxane (2 ml) and the mixture stirred at RT for 2 h. Purification of the residue by mass directed preparative HPLC (Method A), followed by freeze drying gave the title compound as an off white solid (13 mg).

LC/MS $R_t$ 2.92 min m/z 343 [MH$^+$]. Method A

Example 115

N-[6-(1-Benzofuran-2-yl)-1H-indazol-4-yl]-2-methyl-1,3-thiazole-4-carboxamide

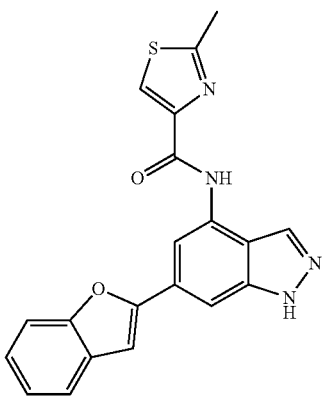 [SMILES: Cc1nc(C(=O)Nc2cc(-c3cc4ccccc4o3)cc3[nH]ncc23)cs1]

To a solution of 1-benzofuran-2-ylboronic acid (24 mg, available from Lancaster Synthesis) in 1,4-dioxane (1 ml) was added a solution of .N-(6-bromo-1H-indazol-4-yl)-2-methyl-1,3-thiazole-4-carboxamide (34 mg) in 1,4-dioxane (1 ml). A solution of potassium carbonate (17 mg) in water (0.2 ml) was then added, followed by Pd(dppf)Cl$_2$ (10 mg). The reaction vessel was sealed and heated under microwave irradiation in CEM Discover at 150° C. for 30 min. The mixture was cooled and the solvent was evaporated in vacuo using the Genevac to give the crude products. The sample was loaded in methanol and applied to a reverse phase (C18) cartridge (500 mg) and eluted using MeCN/TFA 0.1% (3×3 ml). The appropriate fractions were combined and dried under a stream of nitrogen then the residue was dissolved in (3:1, DMSO:MeOH, 0.5 ml) and purified by mass directed preparative HPLC (Method C) to afford the title compound (1.2 mg).

LC/MS $R_t$ 1.11 min m/z 375 [MH$^+$]. Method B

Example 116

N-[6-(6-Cyano-1H-indol-4-yl)-1H-indazol-4-yl]-1-(1-methylethyl)-1H-pyrazole-5-carboxamide

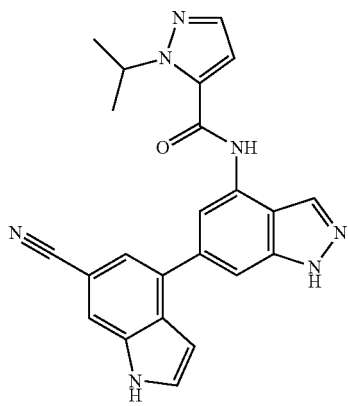 [SMILES: CC(C)n1nccc1C(=O)Nc1cc(-c2cc(C#N)cc3[nH]ccc23)cc2[nH]ncc12]

1-(1-Methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide (49 mg, 0.1 mmol) was dissolved in 1,4-Dioxane (0.4 mL) and added to 4-bromo-1H-indole-6-carbonitrile (22 mg, 0.1 mmol, available from Sinova) in a microwave vessel. 1,4-Dioxane (0.4 ml) was added followed by chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1) (Solvias catalyst, 2 mg, 0.004 mmol, (heaped microspatula) available from ABCR) and a solution of potassium triphosphate (0.2 g, 0.1 mmol) in water (0.2 ml). The vessel was sealed and heated in CEM Discover using initial 150 W to 110° C. for 20 min. After cooling the solution was loaded onto a C18 SPE cartridge (pre-conditioned with MeCN/0.1% TFA) and flushed through with a further 3 ml MeCN/0.1% TFA. Solvent was removed by blowdown under a stream of nitrogen. The residue was dissolved in MeOH (0.5 ml) and loaded onto a SCX-2 SPE cartridge (1 g) pre-conditioned with MeOH. The material was left on the column for 1 hr then eluted with 2M ammonia/MeOH and evaporated to dryness. The sample was purified by Mass Directed AutoPrep (Method C) to afford the title compound (6.4 mg).

LC/MS $R_t$ 0.95 min m/z 410 [MH$^+$]. Method C

Similarly prepared were:

| Example Number | Compound Name | Structure | Aryl bromide Monomer | LC/MS R$_t$ min | LC/MS MH$^+$ |
|---|---|---|---|---|---|
| 117 | 1-(1-methylethyl)-N-[6-(6-methyl-1H-indol-4-yl)-1H-indazol-4-yl]-1H-pyrazole-5-carboxamide | 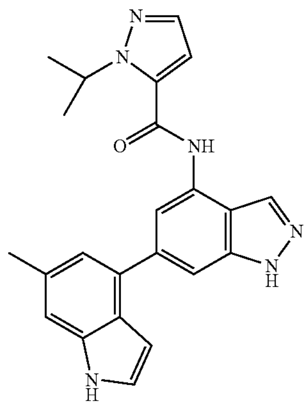 [SMILES: Cc1cc(-c2cc(NC(=O)c3ccnn3C(C)C)c3cn[nH]c3c2)c2cc[nH]c2c1] | (available from Sinova) | 1.00 | 399 |
| 118 | N-[6-(1-benzofuran-5-yl)-1H-indazol-4-yl]-1-(1-methylethyl)-1H-pyrazole-5-carboxamide | 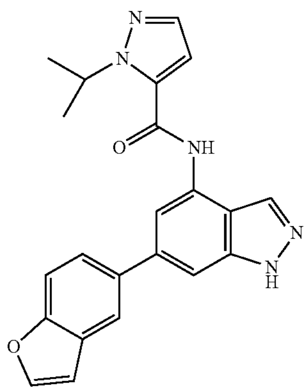 [SMILES: CC(C)n1nccc1C(=O)Nc1cc(-c2ccc3occc3c2)cc2[nH]ncc12] | (available from ABCR) | 1.11 | 386 |

Example 119

5-Bromo-N-[6-(1H-indol-4-yl)-1H-indazol-4-yl]-1,3-thiazole-4-carboxamide

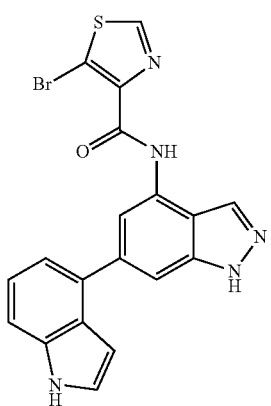 [SMILES: O=C(Nc1cc(-c2cccc3[nH]ccc23)cc2[nH]ncc12)c1ncsc1Br]

To a solution of 5-bromo-1,3-thiazole-4-carboxylic acid (46 mg) (for example, available from Synchem Inc.) in DMF (1 ml) was added DIPEA (0.065 ml) and the mixture stirred for 10 min when 5-bromo-1,3-thiazole-4-carboxylic acid (46 mg) and HATU (85 mg) were added and the mixture allowed to stand for 18 h at 20° C. The solvent was removed under a stream of nitrogen and the residue purified by mass directed preparative HPLC (Method A), to give the title compound (11 mg) as a brown solid.

LC/MS R$_t$ 2.56 min m/z 440 [MH$^+$]. Method A

Example 120

N-[6-(1H-Indol-4-yl)-1H-indazol-4-yl]-5-(1-methylethyl)-4-isoxazolecarboxamide

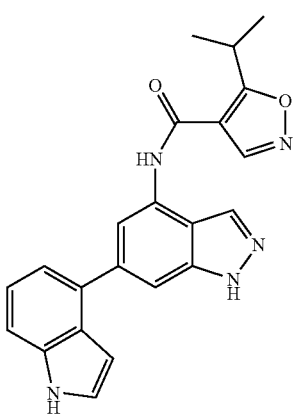 [SMILES: CC(C)c1oncc1C(=O)Nc1cc(-c2cccc3[nH]ccc23)cc2[nH]ncc12]

To a solution of 5-(1-methylethyl)-4-isoxazolecarboxylic acid (19 mg) (for example, available from Aldrich) in DCM (5 ml) was added oxalyl chloride (10.5 µl) followed by DMF (1 drop) and the mixture stirred for 30 min, then the solvent was removed in vacuo and the residue taken up in pyridine (1 ml). 6-(1H-indol-4-yl)-1H-indazol-4-amine (30 mg) was added and the mixture allowed to stand for 18 h at 20° C. then evaporated and purified by mass directed preparative HPLC (Method E) to give the title compound (5 mg) a white solid.

LC/MS $R_t$ 2.65 min m/z 386 [MH$^+$]. Method C

Example 121

N-[6-(1-Benzofuran-5-yl)-1H-indazol-4-yl]-2-methyl-1,3-thiazole-4-carboxamide

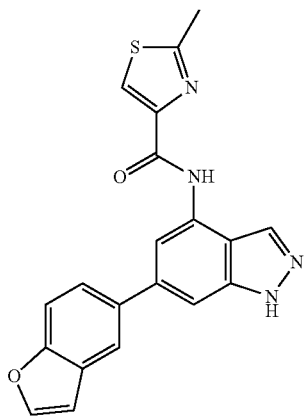 [SMILES: Cc1nc(C(=O)Nc2cc(-c3ccc4occc4c3)cc3[nH]ncc23)cs1]

2-methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (53 mg, 0.11 mmol) was dissolved in 1,4-Dioxane (0.4 mL) and added to 5-bromo-1-benzofuran (20 mg, 0.1 mmol, available from ABCR) in a microwave vessel. 1,4-Dioxane (0.4 ml) was added followed by chloro[2'-(dimethylamino)-2-biphenylyl]palladium-(1R,4S)-bicyclo[2.2.1]hept-2-yl[(1S,4R)-bicyclo[2.2.1]hept-2-yl]phosphane (1:1) (Solvias catalyst, 2 mg, 0.004 mmol, (heaped microspatula) available from ABCR) and a solution of potassium triphosphate (0.2 g, 0.1 mmol) in water (0.2 ml). The vessel was sealed and heated in CEM Discover using initial 150 W to 110° C. for 20 min. After cooling the solution was loaded onto a C18 SPE cartridge (pre-conditioned with MeCN/0.1% TFA) and flushed through with a further 3 ml MeCN/0.1% TFA. Solvent was removed by blowdown under a stream of nitrogen. The residue was dissolved in MeOH (0.51) and loaded onto a SCX-2 SPE cartridge (1 g) preconditioned with MeOH. The material was left on the column for 1 hr then eluted with 2M ammonia/MeOH and evaporated to dryness. The sample was purified by Mass Directed AutoPrep (Method C) to afford the title compound (4 mg).

LC/MS $R_t$ 1.07 min m/z 375 [MH$^+$]. Method D

Example 122

N-{6-[2-(1,1-Dimethylethyl)-1H-pyrrolo[2,3-b]pyridin-4-yl]-1H-indazol-4-yl}-2-methyl-1,3-thiazole-4-carboxamide

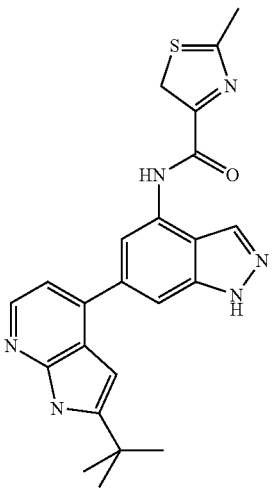

N-(6-Bromo-1H-indazol-4-yl)-2-methyl-1,3-thiazole-4-carboxamide (50 mg), Pd(dppf)Cl$_2$-DCM adduct (12 mg), 2 M sodium carbonate (aq) (0.22 ml), 1,4-dioxane (0.5 ml) and water (0.278 ml) were added to [2-(1,1-dimethylethyl)-1H-pyrrolo[2,3-b]pyridin-4-yl]boronic acid (39 mg). The reaction was heated under microwave irradiation at 150° C. for a total of 25 min. The reaction was passed through a silica cartridge, preconditioned with MeOH, washing with MeOH. The solvent was evaporated and the residue purified using the following system:

Column: 5 µm Waters Atlantis dC18 100×19 mm i.d.
Solvent A: 0.1% Formic acid (aq)
Solvent B: 0.05% Formic acid in acetonitrile
Flow rate: 20 ml/min.
Gradient: 0-99% B over 25 mins.

Pure fractions were dried, redissolved in acetonitrile, combined and dried down to give title compound, 5 mg.

LC/MS (method B) 1.07 min m/z 431 [MH$^+$].

Example 123

1-(1-Methylethyl)-N-[6-(2-methyl-1H-pyrrolo[2,3-b]pyridin-4-yl)-1H-indazol-4-yl]-1H-pyrazole-5-carboxamide

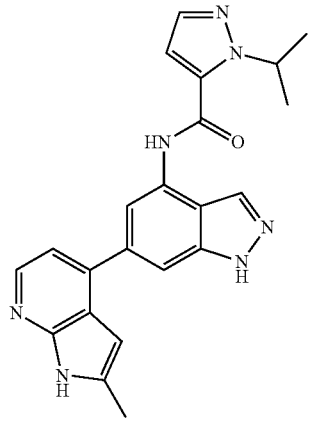 [SMILES: Cc1cc2c(-c3cc(NC(=O)c4ccnn4C(C)C)c4cn[nH]c4c3)ccnc2[nH]1]

A microwave vial was charged with N-[6-bromo-2-(tetrahydro-2H-pyran-2-yl)-2H-indazol-4-yl]-1-(1-methylethyl)-1H-pyrazole-5-carboxamide (70 mg), (2-methyl-1H-pyrrolo[2,3-b]pyridin-4-yl)boronic acid (29 mg), tripotassium phosphate (103 mg) and Solvias catalyst (9 mg), 1,4-dioxane (1.2 ml) and water (0.24 ml). The reaction was heated under microwave irradiation at 100° C. for 30 min, twice. Further (2-methyl-1H-pyrrolo[2,3-b]pyridin-4-yl)boronic acid (10 mg) and Solvias catalyst (9 mg) were added and the reaction heated under microwave irradiation at 100° C. for 30 min. Again further (2-methyl-1H-pyrrolo[2,3-b]pyridin-4-yl)boronic acid (11 mg), tripotassium phosphate (30 mg) and Solvias catalyst (9 mg) were added and the reaction heated under microwave irradiation at 100° C. for 30 min. The reaction was passed through a silica cartridge, preconditioned with methanol, washing with methanol. The solvent was evaporated and the residue was dissolved in DMSO:methanol (1:1, v/v) and purified by MDAP (Method A). Appropriate fractions were evaporated to dryness, dissolved in methanol (2 ml) and 2 M HCl (aq) (0.5 ml) and left at room temperature for 30 min. The solvent was evaporated, the residue was dissolved in DMSO:methanol (1:10, v/v) and passed through an aminopropyl cartridge preconditioned with methanol, washing with methanol. The solvent was evaporated and the residue was purified by MDAP (method A). Purified fractions were evaporated to dryness, dissolved in methanol, passed through an aminopropyl cartridge preconditioned with methanol, washing with methanol, then evaporated to dryness to give title compound, 19 mg.

LC/MS (method B) 0.99 min m/z 400 [MH$^+$].

Example 124

1-(1-Methylethyl)-N-[6-(1H-pyrrolo[2,3-b]pyridin-4-yl)-1H-indazol-4-yl]-1H-pyrazole-5-carboxamide

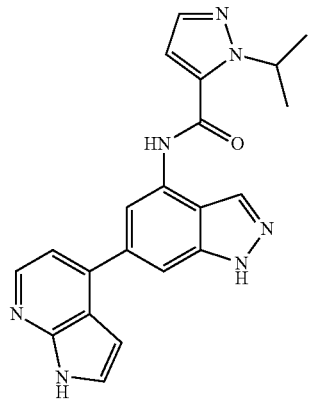 [SMILES: CC(C)n1nccc1C(=O)Nc1cc(-c2ccnc3[nH]ccc23)cc2[nH]ncc12]

A microwave vial was charged with Solvias catalyst (7 mg), tripotassium phosphate (84 mg) and 4-bromo-1H-pyrrolo[2,3-b]pyridine (commercial from Sinova, 29 mg). 1-(1-Methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide (65 mg) in 1,4-dioxane (0.5 ml) was added, followed by water (0.1 ml) and the reaction was heated under microwave irradiation for 10 min at 120° C. The reaction was washed through a silica cartridge, preconditioned with methanol, with methanol. The solvent was removed under a stream of nitrogen, then washed with DCM and water. The resultant solution was evaporated under a stream of nitrogen. The residue was dissolved in DMSO:methanol (1 ml, 1:1, v/v) and purified by MDAP (method A). Appropriate fractions were dried under a stream of nitrogen. The residue was dissolved in methanol, 2 M HCl (aq) (3 drops) was added and the solution was left to stand for 30 min. The solvent was removed under a stream of nitrogen and the residue was dissolved in methanol, washed with methanol through an aminopropyl cartridge preconditioned with methanol and dried under a stream of nitrogen to give title compound, 20 mg.

LC/MS (method B) 0.88 min m/z 386 [MH$^+$].

Example 125

1-(1-Methylethyl)-N-[6-(1H-pyrrolo[2,3-c]pyridin-4-yl)-1H-indazol-4-yl]-1H-pyrazole-5-carboxamide

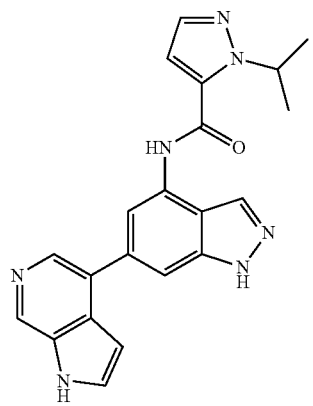 [SMILES: CC(C)n1nccc1C(=O)Nc1cc(-c2cncc3[nH]ccc23)cc2[nH]ncc12]

A microwave vial was charged with Solvias catalyst (7 mg), tripotassium phosphate (84 mg) and 4-bromo-1H-pyrrolo[2,3-c]pyridine (from prep such as in US2005/0090529, 29 mg). 1-(1-methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide (65 mg) in 1,4-dioxane (0.5 ml) was added, followed by water (0.1 ml) and the reaction was heated under microwave irradiation for a total of 30 min at 120° C. The reaction was washed through a silica cartridge preconditioned with methanol, with methanol. The solvent was removed under a stream of nitrogen, then washed with DCM and water. The resultant solution was evaporated under a stream of nitrogen. The residue was dissolved in DMSO:methanol (1 ml, 1:1, v/v) and purified by MDAP (method A). Appropriate fractions were dried under a stream of nitrogen. The residue was dissolved in methanol, 2M HCl (aq) (3 drops) was added and the solution was left to stand for 60 min. The solvent was removed under a stream of nitrogen and the residue was dissolved in methanol, washed with methanol through an aminopropyl cartridge preconditioned with methanol and dried under a stream of nitrogen to give title compound, 5 mg.

LC/MS (method B) 0.77 min m/z 386 [MH$^+$].

Example 126

1-(1-Methylethyl)-N-[6-(2-oxo-2,3-dihydro-1H-indol-4-yl)-1H-indazol-4-yl]-1H-pyrazole-5-carboxamide

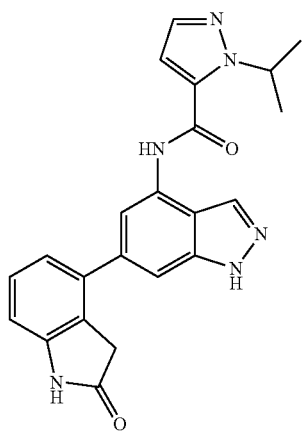 [SMILES: CC(C)n1nccc1C(=O)Nc1cc(-c2cccc3c2CC(=O)N3)cc2[nH]ncc12]

A microwave vial was charged with 1-(1-methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide (70 mg), Solvias catalyst (8 mg), tripotassium phosphate (90 mg) and 4-bromo-1,3-dihydro-2H-indol-2-one (available from Apollo, 33 mg), 1,4-dioxane (0.5 ml) and water (0.1 ml). The reaction was heated under microwave irradiation for a total of 30 min at 120° C.). Further tripotassium phosphate (60 mg) and Solvias catalyst (8 mg) were added and the reaction was heated under microwave irradiation for 10 min at 120° C. The reaction was passed through a silica cartridge, dried, then extracted with DCM and water before drying the DCM under a stream of nitrogen. The residue was purified as follows:

Column: Supelco ABZ+Plus, 5 μm, 100×21.2 mm i.d.

Solvent A: 0.1% formic acid in water

Solvent B: 1% formic acid in water:acetonitrile (5:95, v/v)

Flow rate: 20 ml/min.

Gradient: 30-65% B over 12 min.

Appropriate fractions were dried. The residue was dissolved in methanol and a few drops of 2M HCl (aq) were added. The solution was dried, dissolved in methanol and passed through an aminopropyl cartridge preconditioned with methanol, washing with methanol. The solvent was dried to give title compound, 10 mg.

LC/MS (method B) 0.77 min m/z 386 [MH+].

Example 127

1-(1-Methylethyl)-N-[6-(2-oxo-2,3-dihydro-1,3-benzoxazol-7-yl)-1H-indazol-4-yl]-1H-pyrazole-5-carboxamide

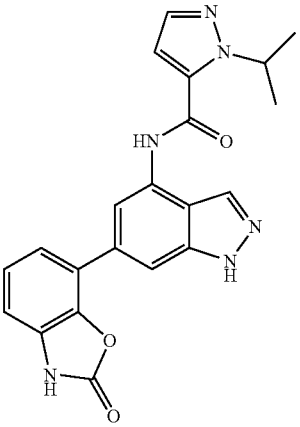 [SMILES: CC(C)n1nccc1C(=O)Nc1cc(-c2cccc3[nH]c(=O)oc23)cc2[nH]ncc12]

A microwave vial was charged with Solvias catalyst (8 mg), tripotassium phosphate (90 mg) and 7-bromo-1,3-benzoxazol-2(3H)-one (from prep. such as US2006/0122189A1, 33 mg). 1-(1-Methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide (70 mg) in 1,4-dioxane (0.5 ml) was added followed by water (0.1 ml). The reaction was heated under microwave irradiation at 120° C. for 10 min. The reaction was passed through a silica cartridge preconditioned with methanol, washing with methanol, then dried under a stream of nitrogen. The residue was subjected to a DCM/water wash and then dried under a stream of nitrogen. The residue was dissolved in DMSO:methanol (1 ml, 1:1, v/v) and purified by MDAP (method A). Appropriate fractions were evaporated under a stream of nitrogen. The residues were dissolved in a minimum amount of methanol and combined. A few drops of 2M HCl (aq) were added and the reaction was left to stand at room temperature. The reaction was then evaporated under a stream of nitrogen, passed through an aminopropyl cartridge and dried to give title compound, 10 mg.

LC/MS (method B) 0.92 min m/z 403 [MH+].

Example 128

1-(1-Methylethyl)-N-[6-(7H-pyrrolo[2,3-d]pyrimidin-4-yl)-1H-indazol-4-yl]-1H-pyrazole-5-carboxamide

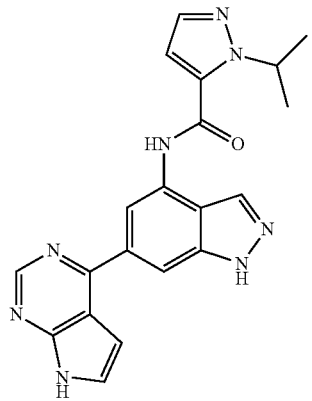 [SMILES: CC(C)n1nccc1C(=O)Nc1cc(-c2ncnc3[nH]ccc23)cc2[nH]ncc12]

A microwave vial was charged with Solvias catalyst (8 mg), tripotassium phosphate (90 mg) and 4-chloro-1H-pyrrolo[2,3-d]pyrimidine (available from ABCR, 24 mg). 1-(1-Methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide (70 mg) in 1,4-dioxane (0.5 ml) was added followed by water (0.1 ml). The reaction was heated under microwave irradiation at 120° C. for 10 min. Solvias catalyst (8 mg) was added and the reaction heated under microwave irradiation at 120° C. for 10 min. Further Solvias catalyst (8 mg) and tripotassium phosphate (30 mg) were added and the reaction was heated under microwave irradiation at 120° C. for 30 min. Again further Solvias catalyst (8 mg) and tripotassium phosphate (90 mg) were added and the reaction was heated under microwave irradiation at 120° C. for 30 min. 4-Chloro-1H-pyrrolo[2,3-d]pyrimidine (12 mg) was added and the reaction was heated under microwave irradiation at 120° C. for 30 min. Addition of catalyst and base was repeated and the reaction was heated under microwave irradiation at 120° C. for 30 min. The reaction was passed through a silica cartridge preconditioned with methanol, washing with methanol, then dried under a stream of nitrogen. The residue was subjected to a DCM/water wash and then dried under a stream of nitrogen. The residue was dissolved in DMSO:methanol (1 ml, 1:1, v/v) and purified by MDAP (method A). The appropriate fraction was evaporated under a stream of nitrogen. The residue was dissolved in methanol, a few drops of 2M HCl (aq) were added and the mixture was left to stand briefly at room temperature, then evaporated under a stream of nitrogen. Sequential purification was carried out using the following system and the two gradients shown:
Column: Supelco ABZ+Plus, 5 μm, 100×21.2 mm i.d.
Solvent A: 0.1% formic acid in water
Solvent B: 1% formic acid in water:acetonitrile (5:95, v/v)
Flow rate: 20 ml/min.
Gradient 1: 25-45% B over 12 min.
Gradient 2: 25-35% B over 12 min.

Appropriate fractions were evaporated under a stream of nitrogen to give title compound, 5 mg.
LC/MS (method B) 0.92 min m/z 403 [MH⁺].

Example 129

N-[6-(6-Fluoro-1H-indol-4-yl)-1H-indazol-4-yl]-1-(1-methylethyl)-1H-pyrazole-5-carboxamide

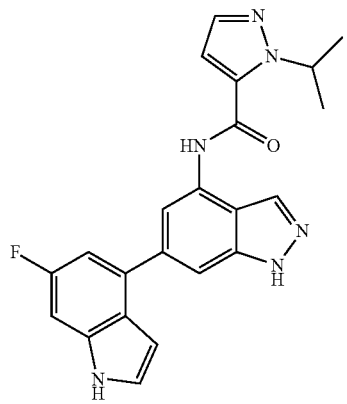 [SMILES: CC(C)n1nccc1C(=O)Nc1cc(-c2cc(F)cc3[nH]ccc23)cc2[nH]ncc12]

A microwave vial was charged with Solvias catalyst (8 mg), tripotassium phosphate (90 mg) and 4-bromo-6-fluoro-1H-indole (available from Sinova, 33 mg). 1-(1-Methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide (70 mg) in 1,4-dioxane (0.5 ml) was added followed by water (0.1 ml). The mixture was heated under microwave irradiation at 120° C. for 10 min. The mixture was passed through a silica cartridge which had been preconditioned with methanol, washed through with methanol, then dried under a stream of nitrogen. The residue was subjected to a DCM/water wash and then dried under a stream of nitrogen. The residue was dissolved in DMSO:methanol (1 ml, 1:1, v/v) and purified by MDAP (method A). Appropriate fractions were evaporated under a stream of nitrogen. The residues were dissolved in a minimum amount of methanol, a few drops of 2M HCl (aq) were added and the reactions were left to stand briefly at room temperature. The reactions were combined then passed through an aminopropyl cartridge preconditioned with methanol and dried. Purification was carried out using the following system:
Column: Supelco ABZ+Plus, 5 μm, 100×21.2 mm i.d.
Solvent A: 0.1% formic acid in water
Solvent B: 1% formic acid in water:acetonitrile (5:95, v/v)
Flow rate: 20 ml/min.
Gradient: 35-70% B over 12 min.

The appropriate fraction was dried under a stream of nitrogen to give title compound, 7 mg.
LC/MS (method B) 1.00 min m/z 404 [MH⁺].

Example 130

N-1H,1'H-4,6'-Biindazol-4'-yl-2-methyl-1,3-thiazole-4-carboxamide

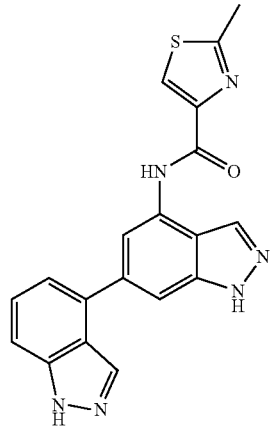 [SMILES: Cc1nc(C(=O)Nc2cc(-c3cccc4[nH]ncc34)cc3[nH]ncc23)cs1]

A microwave vial was charged with N-[6-bromo-2-(tetrahydro-2H-pyran-2-yl)-2H-indazol-4-yl]-2-methyl-1,3-thiazole-4-carboxamide (50 mg), Solvias catalyst (7 mg), tripotassium phosphate (101 mg), 4-(4,4,5,5-tetramethyl-1,3,2-dioxaborolan-2-yl)-1H-indazole (available from J&W Pharmlab, 29 mg), 1,4-dioxane (0.5 ml) and water (0.1 ml). The reaction was heated under microwave irradiation for a total of 60 min at 80° C., then 30 min at 120° C. The reaction was passed through a silica cartridge preconditioned with methanol, washing with methanol, then dried in vacuo. The residue was subjected to a DCM/water wash, dried through a hydrophobic frit and dried in vacuo. The residue was dissolved in DMSO:methanol (1 ml, 1:1, v/v) and purified by MDAP (Method D). Appropriate fractions were evaporated under a stream of nitrogen. The residue was dissolved in methanol and a few drops of 2M HCl (aq) were added and the reaction was stirred for 30 min. The reaction was diluted with methanol and passed through an aminopropyl cartridge, preconditioned with methanol, washing with methanol, then dried to give title compound, 11 mg.
LC/MS (method D) 0.87 min m/z 375 [MH⁺].

Example 131

2-Methyl-N-[6-(1H-pyrrolo[2,3-b]pyridin-4-yl)-1H-indazol-4-yl]-1,3-thiazole-4-carboxamide

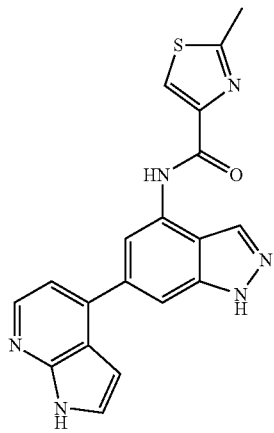 [SMILES: Cc1nc(C(=O)Nc2cc(-c3ccnc4[nH]ccc34)cc3[nH]ncc23)cs1]

A microwave vial was charged with Solvias catalyst (15 mg), tripotassium phosphate (116 mg), 4-bromo-1H-pyrrolo[2,3-b]pyridine (available from Sinova, 30 mg), 1-(1-methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide (66 mg), 1,4-dioxane (0.5 ml) and water (0.1 ml). The reaction mixture was heated under microwave irradiation for 15 min at 120° C. The mixture was passed through a silica cartridge preconditioned with methanol, washing with methanol, then dried. The residue was separated between DCM and water and the organic layer was dried. The residue was dissolved in DMSO:methanol (1 ml, 1:1, v/v) and purified by MDAP (Method D). A few drops of 2M HCl (aq) were added to the appropriate fractions which were dried under a stream of nitrogen. The residue was dissolved in methanol and passed through an aminopropyl cartridge, preconditioned with methanol, washing with methanol, then dried under a stream of nitrogen to give title compound, 16 mg.

LC/MS (Method D) 0.76 min m/z 375 [MH+].

Example 132

2-Methyl-N-[6-(1H-pyrrolo[2,3-c]pyridin-4-yl)-1H-indazol-4-yl]-1,3-thiazole-4-carboxamide

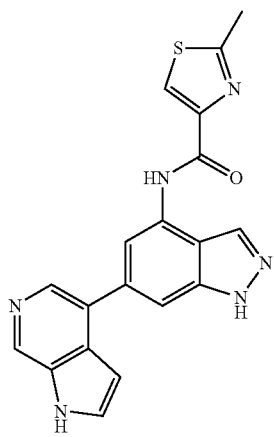 [SMILES: Cc1nc(C(=O)Nc2cc(-c3cncc4[nH]ccc34)cc3[nH]ncc23)cs1]

A microwave vial was charged with Solvias catalyst (15 mg), tripotassium phosphate (116 mg), 4-bromo-1H-pyrrolo[2,3-c]pyridine (prepared for example as described in patent US2005/0090529, 30 mg), 1-(1-methylethyl)-N-[2-(tetrahydro-2H-pyran-2-yl)-6-(4,4,6,6-tetramethyl-1,3,2-dioxaborinan-2-yl)-2H-indazol-4-yl]-1H-pyrazole-5-carboxamide (66 mg), 1,4-dioxane (0.5 ml) and water (0.1 ml). The reaction mixture was heated under microwave irradiation for a total of 35 min at 120° C. The mixture was passed through a silica cartridge preconditioned with methanol, washing with methanol, then dried. The residue was separated between DCM and water and the organic layer was passed through a hydrophobic frit and dried. The residue was dissolved in DMSO:methanol (1 ml, 1:1, v/v) and purified by MDAP (Method G). A few drops of 2M HCl (aq) were added to the appropriate fractions which were dried under a stream of nitrogen. The residue was dissolved in methanol and passed through an aminopropyl cartridge, preconditioned with methanol, washing with methanol, then dried under a stream of nitrogen to give title compound, 10 mg.

LC/MS (Method D) 0.68 min m/z 375 [MH+].

Example 133

1,4-Dimethyl-N-[6-(2-methyl-1H-pyrrolo[2,3-b]pyridin-4-yl)-1H-indazol-4-yl]-1H-pyrazole-3-carboxamide

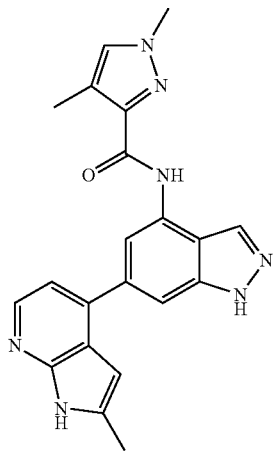 [SMILES: Cc1cc2c(-c3cc(NC(=O)c4nn(C)cc4C)c4cn[nH]c4c3)ccnc2[nH]1]

4-Bromo-2-methyl-1-(phenylsulfonyl)-1H-pyrrolo[2,3-b]pyridine (63 mg) in DMF (0.4 ml) was added to 1,4-dimethyl-N-[1-(phenylsulfonyl)-6-(trimethylstannanyl)-1H-indazol-4-yl]-1H-pyrazole-3-carboxamide (100 mg) in DMF (0.4 ml). Solvias catalyst (4 mg) was added and the sealed vessel was heated in the Anton Paar microwave at 135° C. for 20 min. PS-thiophenol resin was added and the reaction was stirred overnight before being filtered onto a $C_{18}$ SPE cartridge, pre-washed with 0.1% TFA, with acetonitrile. The cartridge was washed with 0.1% TFA in acetonitrile and the collected solvent was removed under a stream of nitrogen. The residue was dissolved in DMSO (1 ml) and purified by MDAP (method C). The solvent was evaporated in vacuo. The residue was dissolved in isopropanol (0.3 ml), 2M sodium hydroxide (aq) (0.3 ml) was added and the reaction was left at room temperature overnight, then heated to 60° C. for 2 h. The solvent was removed under a stream of nitrogen and the residue was dissolved in DMSO (0.5 ml) and purified by MDAP (method C). The solvent was evaporated in vacuo to give title compound, 8 mg.

LC/MS $R_t$ 0.67 min m/z 386 [MH+]. Method D.

Similarly prepared from 1,4-dimethyl-N-[1-(phenylsulfonyl)-6-(trimethylstannanyl)-1H-indazol-4-yl]-1H-pyrazole-3-carboxamide were the following:

| Example Number | Compound Name | Structure | Halide | LC/MS R$_t$ min | LC/MS MH$^+$ |
|---|---|---|---|---|---|
| 134[a] | 1,4-dimethyl-N-[6-(1H-pyrrolo[2,3-c]pyridin-4-yl)-1H-indazol-4-yl]-1H-pyrazole-3-carboxamide | 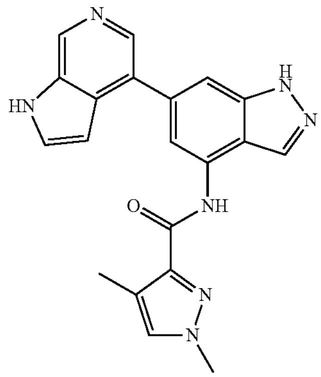 [SMILES: Cc1cn(C)nc1C(=O)Nc1cc(-c2cncc3[nH]ccc23)cc2[nH]ncc12] | 4-Bromo-1-(phenylsulfonyl)-1H-pyrrolo[2,3-c]pyridine | 0.59 | 372 |
| 135[b] | 1,4-dimethyl-N-[6-(1H-pyrrolo[2,3-b]pyridin-4-yl)-1H-indazol-4-yl]-1H-pyrazole-3-carboxamide | 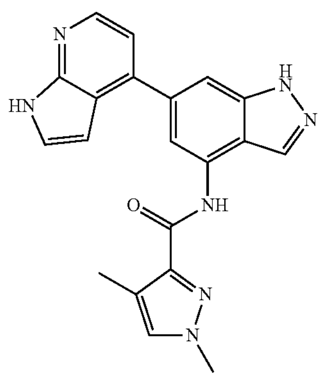 [SMILES: Cc1cn(C)nc1C(=O)Nc1cc(-c2ccnc3[nH]ccc23)cc2[nH]ncc12] | 4-Bromo-1-(phenylsulfonyl)-1H-pyrrolo[2,3-b]pyridine | 0.67 | 372 |
| 136[c] | N-1H,1'H-4,6'-biindazol-4'-yl-1,4-dimethyl-1H-pyrazole-3-carboxamide | 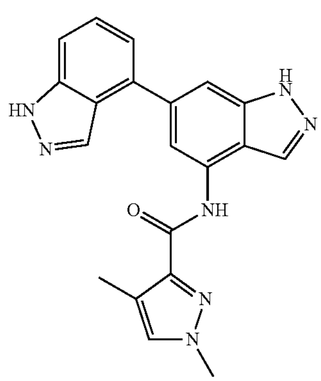 [SMILES: Cc1cn(C)nc1C(=O)Nc1cc(-c2cccc3[nH]ncc23)cc2[nH]ncc12] | 4-Bromo-1-(phenylsulfonyl)-1H-indazole | 2.09[d] | 372 |

[a] Reaction only required 1 h heating in isopropanol/2M sodium hydroxide
[b] Reaction required no heating in isopropanol/2M sodium hydroxide
[c] Required re-purification using MDAP
[d] LCMS method C.

Example 137

4-Chloro-1-ethyl-N-[6-(2-methyl-1H-pyrrolo[2,3-b]pyridin-4-yl)-1H-indazol-4-yl]-1H-pyrazole-5-carboxamide

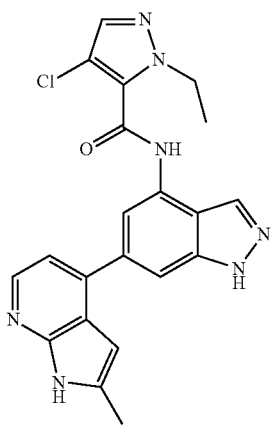 [SMILES: CCn1ncc(Cl)c1C(=O)Nc1cc(-c2ccnc3[nH]c(C)cc23)cc2[nH]ncc12]

4-Bromo-2-methyl-1-(phenylsulfonyl)-1H-pyrrolo[2,3-b]pyridine (63 mg) in DMF (0.4 ml) was added to 4-chloro-1-ethyl-N-[1-(phenylsulfonyl)-6-(trimethylstannanyl)-1H-indazol-4-yl]-1H-pyrazole-5-carboxamide (100 mg) in DMF (0.4 ml). Solvias catalyst (4 mg) was added and the sealed vessel was heated in the Anton Paar microwave at 135° C. for 20 min. PS-thiophenol resin was added and the reaction was stirred overnight before being filtered onto a $C_{18}$SPE cartridge, pre-washed with 0.1% TFA, with acetonitrile. The cartridge was washed with 0.1% TFA in acetonitrile and the collected solvent was removed under a stream of nitrogen. The residue was dissolved in DMSO (1 ml) and purified by MDAP (method C). The solvent was evaporated in vacuo. The residue was dissolved in isopropanol (0.3 ml), 2M sodium hydroxide (aq) (0.3 ml) was added and the reaction was left at room temperature overnight, then heated to 60° C. for 1 h. The solvent was removed under a stream of nitrogen and the residue was dissolved in DMSO (0.5 ml) and purified by MDAP (method C). The solvent was evaporated in vacuo to give title compound, 6 mg.

LC/MS $R_t$ 0.76 min m/z 420 [MH$^+$]. Method D.

Similarly prepared from 4-chloro-1-ethyl-N-[1-(phenylsulfonyl)-6-(trimethylstannanyl)-1H-indazol-4-yl]-1H-pyrazole-5-carboxamide but without heating in isopropanol/2M sodium hydroxide were the following:

| Example Number | Compound Name | Structure | Halide | LC/MS $R_t$ min | LC/MS MH$^+$ |
|---|---|---|---|---|---|
| 138 | 4-chloro-1-ethyl-N-[6-(1H-pyrrolo[2,3-c]pyridin-4-yl)-1H-indazol-4-yl]-1H-pyrazole-5-carboxamide | 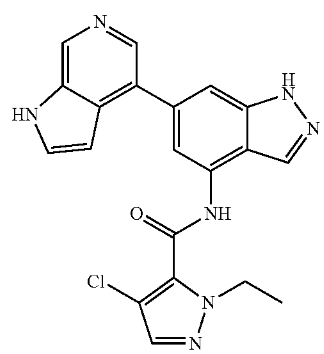 [SMILES: CCn1ncc(Cl)c1C(=O)Nc1cc(-c2cncc3[nH]ccc23)cc2[nH]ncc12] | 4-Bromo-1-(phenylsulfonyl)-1H-pyrrolo[2,3-c]pyridine | 0.65 | 406 |
| 139 | 4-chloro-1-ethyl-N-[6-(1H-pyrrolo[2,3-b]pyridin-4-yl)-1H-indazol-4-yl]-1H-pyrazole-5-carboxamide | 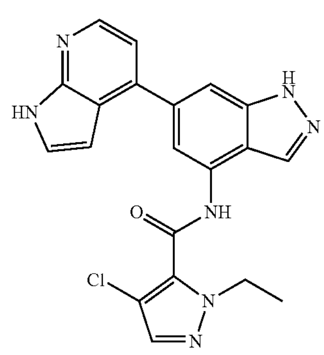 [SMILES: CCn1ncc(Cl)c1C(=O)Nc1cc(-c2ccnc3[nH]ccc23)cc2[nH]ncc12] | 4-Bromo-1-(phenylsulfonyl)-1H-pyrrolo[2,3-b]pyridine | 0.76 | 406 |

-continued

| Example Number | Compound Name | Structure | Halide | LC/MS $R_t$ min | LC/MS MH+ |
|---|---|---|---|---|---|
| 140 | N-1H,1'H-4,6'-biindazol-4'-yl-4-chloro-1-ethyl-1H-pyrazole-5-carboxamide | 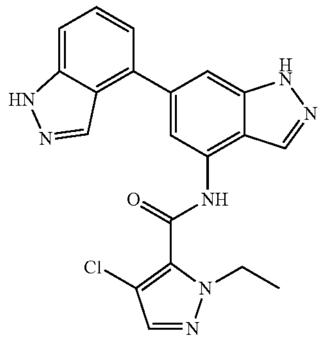 | 4-Bromo-1-(phenylsulfonyl)-1H-indazole | 0.91 | 406 |
| 141 | 4-chloro-1-ethyl-N-[6-(1H-pyrazolo[3,4-b]pyridin-4-yl)-1H-indazol-4-yl]-1H-pyrazole-5-carboxamide | 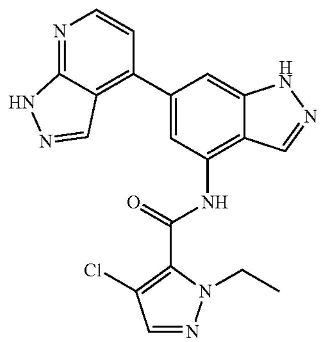 [SMILES: CCn1ncc(Cl)c1C(=O)Nc1cc(-c2ccnc3[nH]ncc23)cc2[nH]ncc12] | 4-Iodo-1-(phenylsulfonyl)-1H-pyrazolo[3,4-b]pyridine | 0.82 | 407 |

Example 142

N-[3-Fluoro-6-(6-fluoro-1H-indol-4-yl)-1H-indazol-4-yl]-2-methyl-1,3-thiazole-4-carboxamide

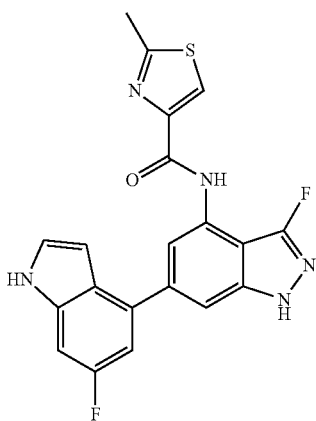 [SMILES: Cc1nc(C(=O)Nc2cc(-c3cc(F)cc4[nH]ccc34)cc3[nH]nc(F)c23)cs1]

2-Methyl-1,3-thiazole-4-carboxylic acid was dissolved in THF (0.2 ml) and (1-chloro-2-methyl-1-propen-1-yl)dimethylamine (0.013 ml, 0.1 mmol) was added. The mixture was shaken, then left to stand for 30 mins. 3-fluoro-6-{6-fluoro-1-[(4-nitrophenyl)sulfonyl]-1H-indol-4-yl}-1-(phenylsulfonyl)-1H-indazol-4-amine (0.1 mmol) was dissolved in THF (0.4 ml) and added to the reaction mixture, followed by pyridine (0.016 ml, 0.2 mmol). The reaction mixture was shaken and then left to stand for 1 hour. A further portion of 2-methyl-1,3-thiazole-4-carboxylic acid was dissolved in THF (0.2 ml) and (1-chloro-2-methyl-1-propen-1-yl)dimethylamine (0.013 ml, 0.1 mmol) was added. The mixture was shaken, then left to stand for 20 mins before being added to the ongoing reaction mixture above, along with further pyridine (0.097 ml, 1.2 mmol). The mixture was shaken and left to stand for 30 mins. A further portion of 2-methyl-1,3-thiazole-4-carboxylic acid was dissolved in THF (0.2 ml) and (1-chloro-2-methyl-1-propen-1-yl)dimethylamine (0.013 ml, 0.1 mmol) was added. The mixture was shaken, then left to stand for 20 mins before being added to the ongoing reaction mixture above, along with further pyridine (0.097 ml, 1.2 mmol). The mixture was shaken and left to stand for 30 mins, then evaporated by blow down under a stream of nitrogen. The crude reaction mixture was dissolved in isopropanol (0.3 ml) and NaOH (2M aqueous, 0.3 ml) was added. The mixture was stood for 60 h at room temperature. Further NaOH (2M aqueous, 0.3 ml) was added and the mixture was heated to 80° C. for 1 hour. The reaction mixture was neutralised with HCl (2 M, aq.) and blown down under a stream of nitrogen. The crude material was dissolved in DMSO (0.5 ml), filtered and purified by Mass Directed Auto Prep on an Xbridge column using Acetonitrile/Water with a formic acid modifier (Method F). The solvent was evaporated in vacuo using the Genevac. The residue was dissolved in DMSO (0.5 ml) and further purified by formic acid MDAP (as above), over an extended run time. The product-containing fractions were blown down under a stream of nitrogen to give the title compound (11 mg). LCMS (Method D) $R_t$=1.16 min, MH+=410.

Example 143

Formic acid-2-[(4,4-dimethyl-1-piperidinyl)methyl]-N-[6-(1H-indol-4-yl)-1H-indazol-4-yl]-1,3-thiazole-4-carboxamide (1:1)

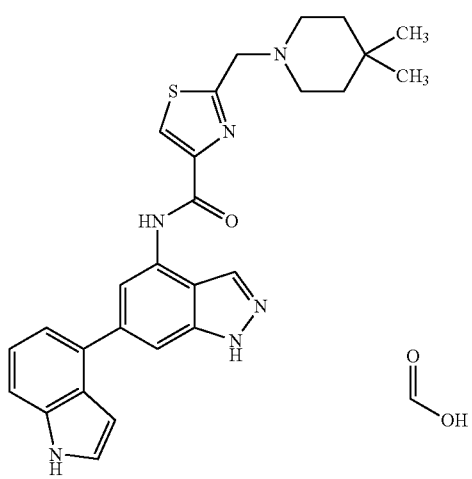 [SMILES: CC1(C)CCN(Cc2nc(C(=O)Nc3cc(-c4cccc5[nH]ccc45)cc4[nH]ncc34)cs2)CC1 ; O=CO]

A solution of 2-(chloromethyl)-N-[6-(1H-indol-4-yl)-1-(phenylsulfonyl)-1H-indazol-4-yl]-1,3-thiazole-4-carboxamide (55 mg, 0.1 mmol) in acetonitrile (0.5 ml) was added to 4,4-dimethylpiperidine hydrochloride (0.11 mmol, available from Microchemistry Ltd). DIPEA was then added (0.026 ml, 0.15 mmol), followed by sodium iodide (13 mg). The vial was capped and the stirred solution heated to 70° C. for 18 h. Potassium trimethylsilanolate (26 mg) was dissolved in THF (0.3 ml) and added to the vessel, which was then stirred at room temperature for 21 h, then heated at 50° C. for 3 h. A further equivalent of potassium trimethylsilanolate was added as a solution in THF (150 ul) and the mixture was heated at 50° C. for a further 18 h. The solution was quenched with aqueous acetonitrile (500 ul, 50:50) and neutralised. Solvent was removed by blowdown. The residue was dissolved in DMSO 0.5 mL and purified by Mass Directed AutoPrep HPLC (Method F). The solvent was removed by vacuum centrifugation to give the title compound (7 mg). LCMS (Method C) $R_t$=1.69 min, $MH^+$=485.

Similarly prepared were the following:

| Example Number | Structure | Name | Precursor Amine | MH+ | LCMS Rt (min) |
|---|---|---|---|---|---|
| 144 | 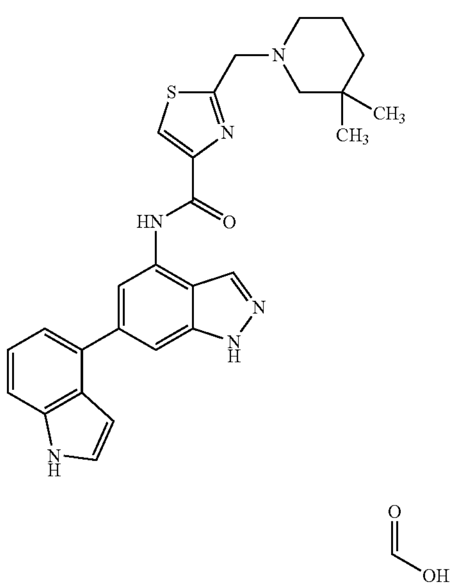 [SMILES: CC1(C)CCCN(Cc2nc(C(=O)Nc3cc(-c4cccc5[nH]ccc45)cc4[nH]ncc34)cs2)C1 ; O=CO] | formic acid-2-[(3,3-dimethyl-1-piperidinyl)methyl]-N-[6-(1H-indol-4-yl)-1H-indazol-4-yl]-1,3-thiazole-4-carboxamide (1:1) | 3,3-dimethyl-piperidine hydrochloride (available from Manchester Organics) | 485 | 1.78 |

US 8,658,635 B2

223                                                                                             224

-continued

| Example Number | Structure | Name | Precursor Amine | MH+ | LCMS Rt (min) |
|---|---|---|---|---|---|
| 145 | 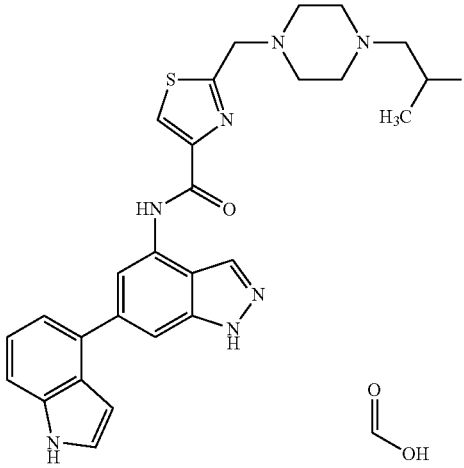 | formic acid-N-[6-(1H-indol-4-yl)-1H-indazol-4-yl]-2-{[4-(2-methylpropyl)-1-piperazinyl]-methyl}-1,3-thiazole-4-carboxamide (1:1) | 1-(2-methylpropyl)-piperazine (available from Fluorochem) | 514 | 1.64 |
| 146 | 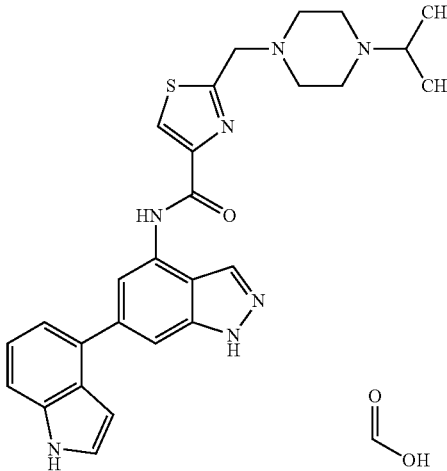 | formic acid-N-[6-(1H-indol-4-yl)-1H-indazol-4-yl]-2-{[4-(1-methylethyl)-1-piperazinyl]-methyl}-1,3-thiazole-4-carboxamide (1:1) | 4-(1-methylethyl)-piperazine (available from Aldrich) | 500 | 1.58 |
| 147 | 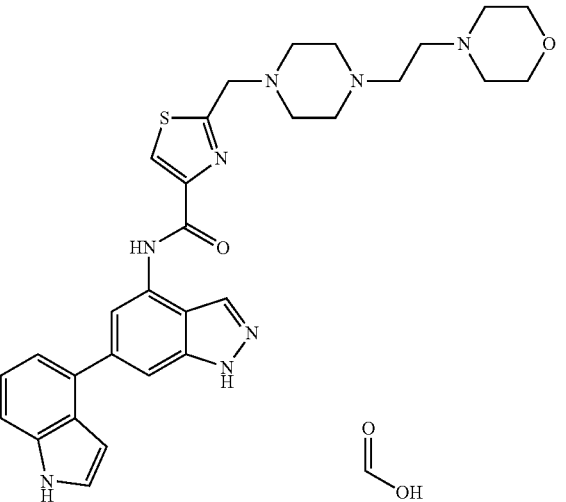 [SMILES: O=C(Nc1cc(-c2cccc3[nH]ccc23)cc2[nH]ncc12)c1csc(CN2CCN(CCN3CCOCC3)CC2)n1 ; O=CO] | formic acid-N-[6-(1H-indol-4-yl)-1H-indazol-4-yl]-2-({4-[2-(4-morpholinyl)-ethyl]-1-piperazinyl}-methyl)-1,3-thiazole-4-carboxamide (1:1) | 4-[2-(1-piperazinyl)-ethyl]-morpholine (available from Emka-Chemie) | 571 | 1.28 |

| Example Number | Structure | Name | Precursor Amine | MH+ | LCMS Rt (min) |
|---|---|---|---|---|---|
| 148 | 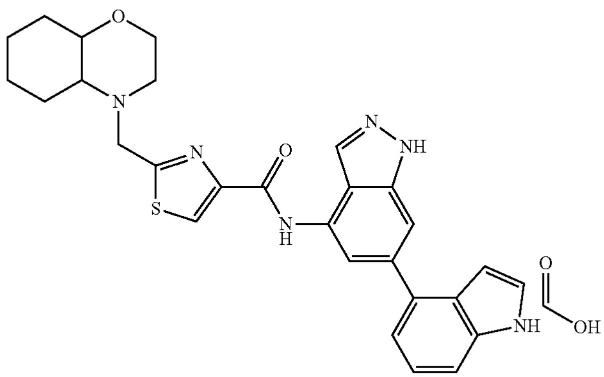 | formic acid-N-[6-(1H-indol-4-yl)-1H-indazol-4-yl]-2-(octahydro-4H-1,4-benzoxazin-4-ylmethyl)-1,3-thiazole-4-carboxamide (1:1) | octahydro-2H-1,4-benzoxazine (available from Chemical Block Ltd) | 513 | 2 |
| 149 | 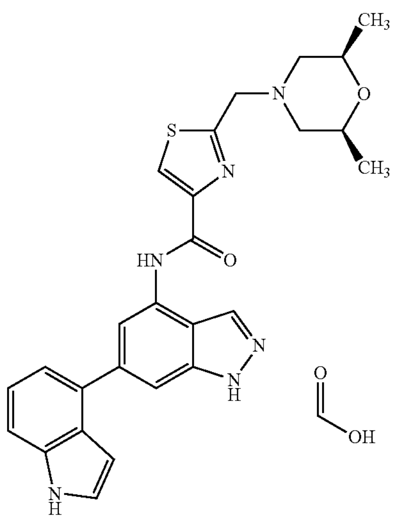 [SMILES: C[C@@H]1CN(Cc2nc(C(=O)Nc3cc(-c4cccc5[nH]ccc45)cc4[nH]ncc34)cs2)C[C@H](C)O1 ; O=CO] | formic acid-2-{[(2R,6S)-2,6-dimethyl-4-morpholinyl]-methyl}-N-[6-(1H-indol-4-yl)-1H-indazol-4-yl]-1,3-thiazole-4-carboxamide (1:1) | (2R,6S)-2,6-dimethyl-morpholine (available from Lancaster Synthesis) | 487 | 1.86 |
| 150 | 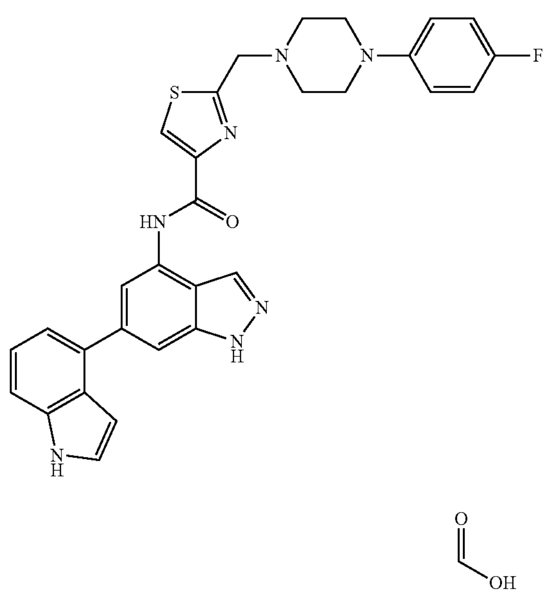 [SMILES: O=C(Nc1cc(-c2cccc3[nH]ccc23)cc2[nH]ncc12)c1csc(CN2CCN(c3ccc(F)cc3)CC2)n1 ; O=CO] | formic acid-2-{[4-(4-fluorophenyl)-1-piperazinyl]-methyl}-N-[6-(1H-indol-4-yl)-1H-indazol-4-yl]-1,3-thiazole-4-carboxamide (1:1) | 1-(4-fluorophenyl)-piperazine hydrochloride (available from Aldrich) | 552 | 2.21 |

| Example Number | Structure | Name | Precursor Amine | MH+ | LCMS Rt (min) |
|---|---|---|---|---|---|
| 151 | 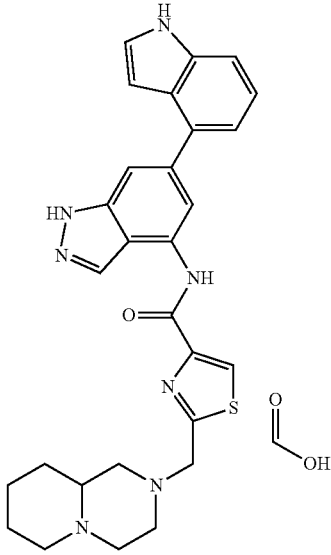 | formic acid-N-[6-(1H-indol-4-yl)-1H-indazol-4-yl]-2-(octahydro-2H-pyrido[1,2-a]pyrazin-2-ylmethyl)-1,3-thiazole-4-carboxamide (1:1) | octahydro-2H-pyrido[1,2-a]-pyrazine (available from Apollo Scientific) | 512 | 1.6 |
| 152 | 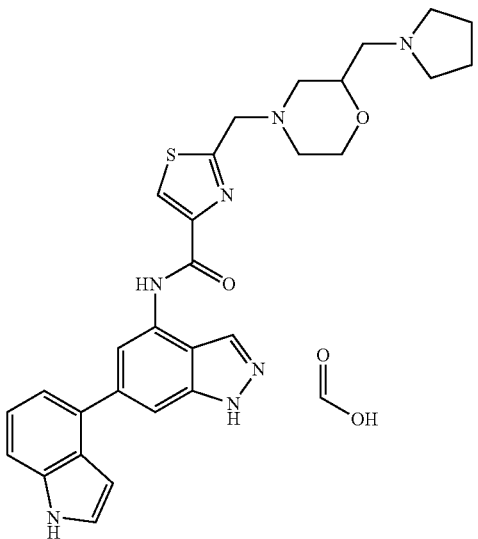 [SMILES: O=C(Nc1cc(-c2cccc3[nH]ccc23)cc2[nH]ncc12)c1csc(CN2CCOC(CN3CCCC3)C2)n1 ; O=CO] | formic acid-N-[6-(1H-indol-4-yl)-1H-indazol-4-yl]-2-{[2-(1-pyrrolidinyl-methyl)-4-morpholinyl]-methyl}-1,3-thiazole-4-carboxamide (1:1) | 2-(1-pyrrolidinyl-methyl)-morpholine (available from AB Chemicals Inc.) | 542 | 1.58 |

| Example Number | Structure | Name | Precursor Amine | MH+ | LCMS Rt (min) |
|---|---|---|---|---|---|
| 153 | 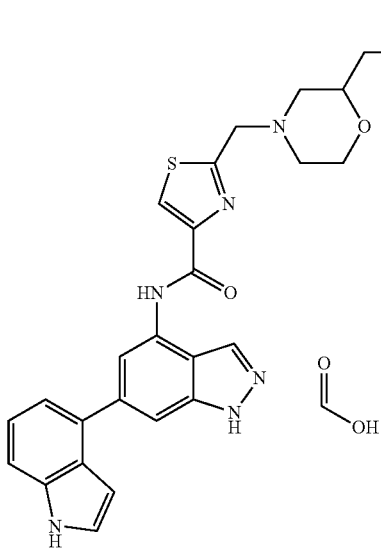 | formic acid-N-[6-(1H-indol-4-yl)-1H-indazol-4-yl]-2-{[2-(2-methylpropyl)-4-morpholinyl]-methyl}-1,3-thiazole-4-carboxamide (1:1) | 2-(2-methylpropyl)-morpholine (available from Chembridge) | 515 | 2.26 |
| 154 | 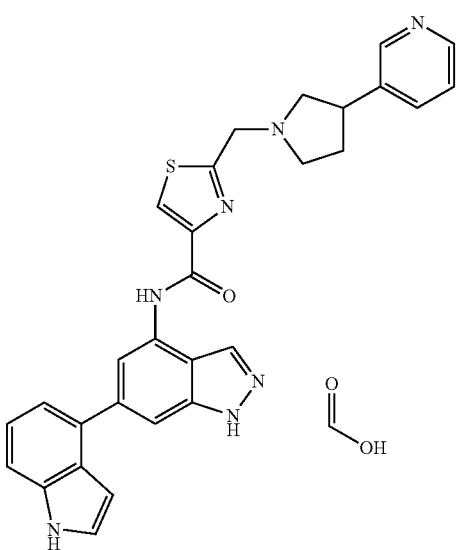 [SMILES: O=C(Nc1cc(-c2cccc3[nH]ccc23)cc2[nH]ncc12)c1csc(CN2CCC(c3cccnc3)C2)n1 ; O=CO] | formic acid-N-[6-(1H-indol-4-yl)-1H-indazol-4-yl]-2-{[3-(3-pyridinyl)-1-pyrrolidinyl]-methyl}-1,3-thiazole-4-carboxamide (1:1) | 3-(3-pyrrolidinyl)-pyridine (available from Apollo Scientific) | 520 | 1.34 |

| Example Number | Structure | Name | Precursor Amine | MH+ | LCMS Rt (min) |
|---|---|---|---|---|---|
| 155 | 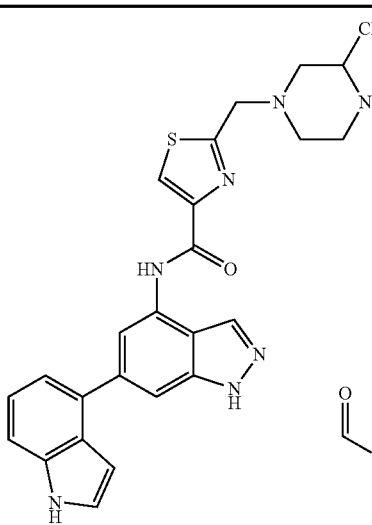 | formic acid-N-[6-(1H-indol-4-yl)-1H-indazol-4-yl]-2-{[3-methyl-4-(1-methylethyl)-1-piperazinyl]-methyl}-1,3-thiazole-4-carboxamide (1:1) | 2-methyl-1-(1-methylethyl)-piperazine (available from Fluorochem) | 514 | 1.64 |
| 156 | 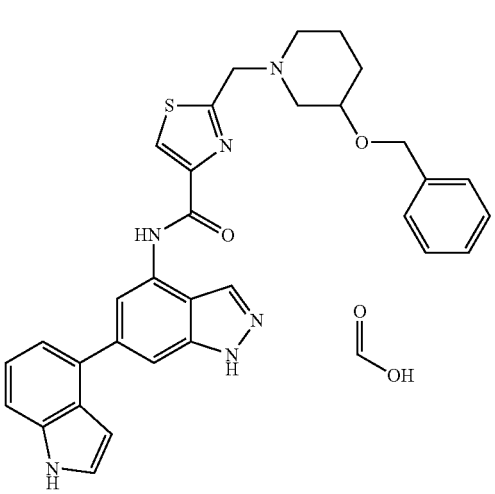 [SMILES: O=C(Nc1cc(-c2cccc3[nH]ccc23)cc2[nH]ncc12)c1csc(CN2CCCC(OCc3ccccc3)C2)n1 ; O=CO] | formic acid-N-[6-(1H-indol-4-yl)-1H-indazol-4-yl]-2-({3-[(phenylmethyl)-oxy]-1-piperidinyl}-methyl)-1,3-thiazole-4-carboxamide (1:1) | 3-[(phenylmethyl)-oxy]piperidine (available from ASDI International) | 563 | 1.91 |

-continued

| Example Number | Structure | Name | Precursor Amine | MH+ | LCMS Rt (min) |
|---|---|---|---|---|---|
| 157 | 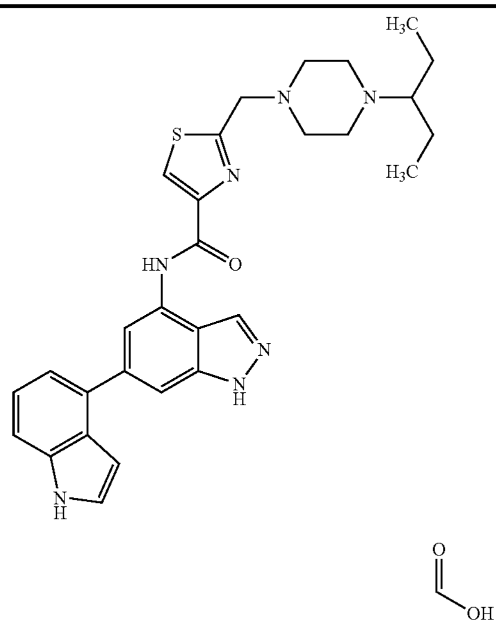 | formic acid-2-{[4-(1-ethylpropyl)-1-piperazinyl]-methyl}-N-[6-(1H-indol-4-yl)-1H-indazol-4-yl]-1,3-thiazole-4-carboxamide (1:1) | 1-(1-ethylpropyl)-piperazine (available from Fluorochem) | 528 | 1.7 |
| 158 | 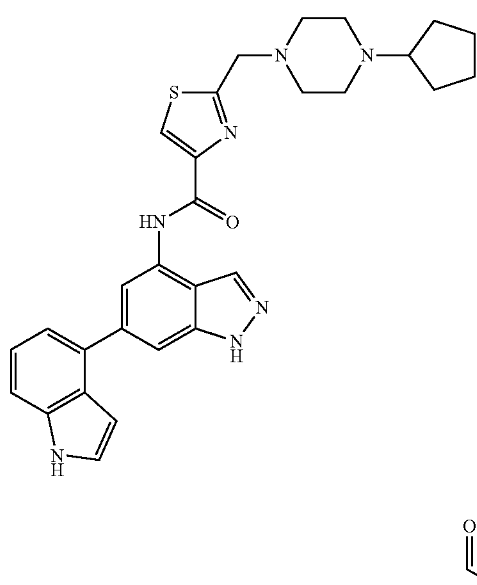 | formic acid-2-[(4-cyclopentyl-1-piperazinyl)-methyl]-N-[6-(1H-indol-4-yl)-1H-indazol-4-yl]-1,3-thiazole-4-carboxamide (1:1) | 1-cyclopentyl-piperazine (available from Fluorochem) | 526 | 1.66 |

Example 159

2-Methyl-N-[6-(2-methyl-1H-indol-4-yl)-1H-indazol-4-yl]-1,3-thiazole-4-carboxamide

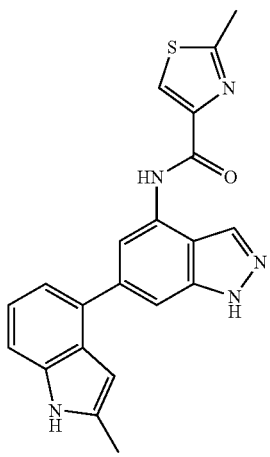 [SMILES: Cc1cc2c(-c3cc(NC(=O)c4csc(C)n4)c4cn[nH]c4c3)cccc2[nH]1]

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (50 mg, 0.104 mmol), 4-bromo-2-methyl-1H-indole (22 mg, 0.104 mmol), Pd(dppf)Cl$_2$ (8 mg, 0.01 mmol) and sodium carbonate (44 mg, 0.415 mmol) were added to a 0.5-2 ml microwave vial and suspended in 1,4-dioxane (0.5 mL) and water (0.5 mL). The mixture was heated in the microwave at 140° C. for 20 min, then cooled and passed through a 1 g silica cartridge which was washed with DCM:methanol. The solvent was evaporated by blow down. The residue was dissolved in 1.6 ml DMSO:methanol (1:1, v/v), passed through a 1 g C18 cartridge washing with acetonitrile and evaporated by blow down. The residue was dissolved in 1.6 ml DMSO:methanol (1:1, v/v) and purified by Mass Directed Auto Preparative HPLC (Method G). Pure fractions were combined, evaporated to dryness, the residue suspended in 3 ml dioxane:water (1:1, v/v) and freeze dried to afford the title compound as an off-white solid (17 mg).

LCMS (Method D) R$_t$=1.01 min, MH$^+$=388.

Similarly prepared was:

| Example Number | Structure | Name | Biaryl monomer | MH$^+$ | LCMS Rt (min) |
|---|---|---|---|---|---|
| 160 | 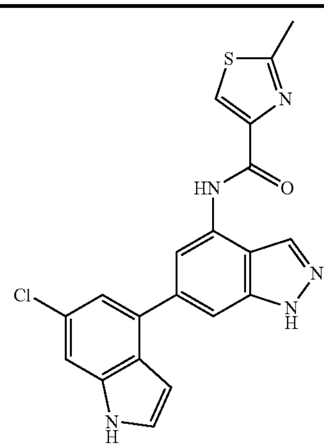 | N-[6-(6-chloro-1H-indol-4-yl)-1H-indazol-4-yl]-2-methyl-1,3-thiazole-4-carboxamide | 4-bromo-6-chloro-1H-indole | 408 | 1.01 |
| 161 | 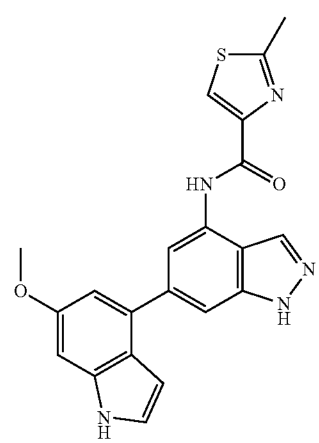 [SMILES: COc1cc(-c2cc(NC(=O)c3csc(C)n3)c3cn[nH]c3c2)c2cc[nH]c2c1] | 2-methyl-N-{6-[6-(methyloxy)-1H-indol-4-yl]-1H-indazol-4-yl}-1,3-thiazole-4-carboxamide | 4-bromo-6-(methyloxy)-1H-indole | 404 | 0.97 |

Example 162

N-[6-(6-Cyano-1H-indol-4-yl)-1H-indazol-4-yl]-2-methyl-1,3-thiazole-4-carboxamide

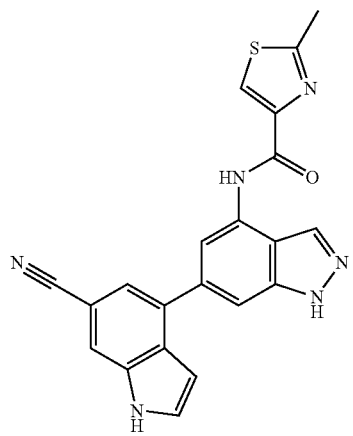 [SMILES: Cc1nc(C(=O)Nc2cc(-c3cc(C#N)cc4[nH]ccc34)cc3[nH]ncc23)cs1]

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (50 mg, 0.104 mmol), 4-bromo-1H-indole-6-carbonitrile (252 mg, 0.114 mmol), Pd(dppf)Cl$_2$ (8 mg, 0.01 mmol) and sodium carbonate (44 mg, 0.415 mmol) were added to a 0.5-2 ml microwave vial and suspended in 1,4-dioxane (0.5 mL) and water (0.5 mL). The mixture was heated in the microwave at 140° C. for 20 min, then cooled and passed through a 1 g silica cartridge which was washed with methanol. The solvent was evaporated by blow down. The residue was dissolved in 1.6 ml DMSO:methanol (1:1, v/v) and purified by Mass Directed Auto Preparative HPLC (Method F). To the sample-containing fractions 2M HCl (aq) (ca. 1 ml) was added and the fractions were blown down. The residue was dissolved in DCM:methanol (ca. 50:50, v/v) and passed through a 1 g PS—NH2 cartridge, washing with DCM:methanol. Solvent was removed by blow down then the residue was suspended in 2 ml dioxane:water (1:1, v/v) and freeze dried to afford the title compound as a white solid (22 mg).

LCMS (Method D) R$_f$=0.96 min, MH$^+$=399.

Example 163

N-[6-(6-Fluoro-1H-indol-4-yl)-1H-indazol-4-yl]-2-methyl-1,3-thiazole-4-carboxamide

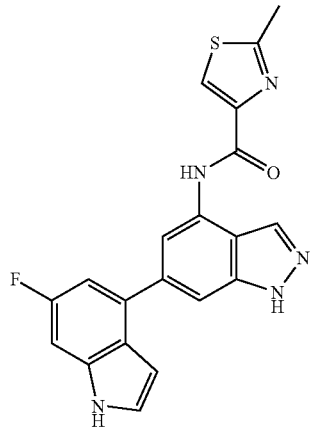

HATU (0.1 mmol) was dissolved in N,N-dimethylformamide (DMF) (0.2 ml) and added to 2-methyl-1,3-thiazole-4-carboxylic acid (0.1 mmol) also in DMF (0.2 ml). DIPEA (0.05 ml 0.3 mmol) was added and the mixture was left to stand for 5 mins. 3-Fluoro-6-{6-fluoro-1-[(4-nitrophenyl)sulfonyl]-1H-indol-4-yl}-1-(phenylsulfonyl)-1H-indazol-4-amine (0.1 mmol) was dissolved in DMF (0.2 ml) and to this was added the acid containing mixture. The solution was shaken for 5 minutes and left to stand at room temperature overnight. A further portion of HATU (0.1 mmol) was dissolved in N,N-dimethylformamide (DMF) (0.2 mL) and added to further 2-methyl-1,3-thiazole-4-carboxylic acid (0.1 mmol), also in N,N-Dimethylformamide (DMF) (0.2 mL). DIPEA (0.3 mmol) was added and the mixture left to stand for 5 mins, then the resultant solution was added to the vessel containing the reaction mixture. Solutions were shaken for 5 minutes and then placed in the oven at 40° C. for 1 hour. DMF was removed by vacuum centrifugation (not to dryness) and the residue was dissolved in chloroform (0.3 ml). The solution was loaded onto aminopropyl SPE cartridge (500 mg) that had been preconditioned with MeOH followed by chloroform (2 ml each). The column was eluted with 10% MeOH in EtOAc (5 ml) and the fractions obtained were blown down under a stream of nitrogen. The residue was dissolved in DMSO (0.5 ml) and purified by Mass Directed AutoPrep on an Xbridge column using Acetonitrile/Water as eluent with an ammonium carbonate modifier. The solvent was evaporated in vacuo using the Genevac. The residue was dissolved in isopropanol (0.3 ml) and NaOH (2M, aqueous, 0.3 ml) was added. The solution was left for 32 hours at room temperature, then heated at 40° C. overnight. The reaction mixture was neutralised using 2 M, aqueous HCl and then blown down under a stream of nitrogen. The residue was dissolved in DMSO (0.5 ml) and purified by Mass Directed AutoPrep on an Xbridge column using Acetonitrile/Water with a formic acid modifier. The solvent was evaporated by vacuum centrifugation to give the title compound (4 mg).

LCMS (Method D) R$_f$=0.97 min, MH$^+$=392.

Similarly prepared was:

| Example Number | Structure | Name | Monomer | MH+ | LCMS Rt (min) |
|---|---|---|---|---|---|
| 164 | 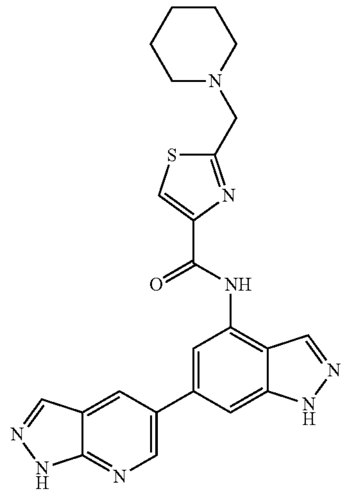 [SMILES: O=C(Nc1cc(-c2cnc3[nH]ncc3c2)cc2[nH]ncc12)c1csc(CN2CCCCC2)n1] | 2-(1-piperidinyl-methyl)-N-[6-(1H-pyrazolo[3,4-b]pyridin-5-yl)-1H-indazol-4-yl]-1,3-thiazole-4-carboxamide | 2-{[ethyl(propyl)-amino]-methyl}-1,3-thiazole-4-carboxylic acid | 459 | 0.52 min |

Example 165

N-[6-(6-Fluoro-1H-indol-4-yl)-1H-indazol-4-yl]-2-(1-piperidinylmethyl)-1,3-thiazole-4-carboxamide

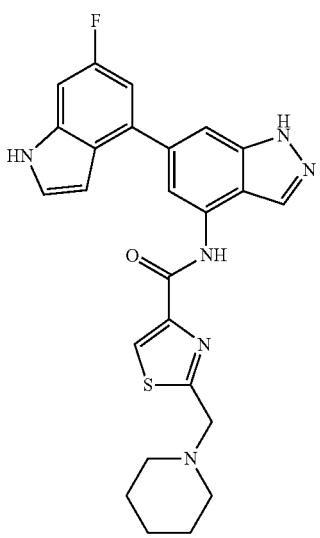 [SMILES: O=C(Nc1cc(-c2cc(F)cc3[nH]ccc23)cc2[nH]ncc12)c1csc(CN2CCCCC2)n1]

To a suspension of 2-(chloromethyl)-N-[6-(6-fluoro-1H-indol-4-yl)-1-(phenylsulfonyl)-1H-indazol-4-yl]-1,3-thiazole-4-carboxamide (50 mg, 0.088 mmol) in acetonitrile (2 ml) was added piperidine (0.02 ml, 0.18 mmol) and the mixture was heated to 80° C. for 2 hours. Further piperidine (0.02 ml, 0.18 mmol) was added and heating was continued at 80° C. for 30 mins. The mixture was cooled to room temperature and the solvent was removed in vacuo. The residue was taken up in MeOH and 2M aqueous NaOH (5 ml, 1:1, v.v) and stirred at room temperature for 1 hour, then neutralised with 2M aqueous HCl to ~pH=5 and extracted with DCM (3×5 ml). The extracts were combined and the solvent removed under a stream of nitrogen. The residue was taken up again in MeOH and 2M aqueous NaOH (5 ml, 1:1, v/v) and stirred at room temperature for 3 hours. The mixture was neutralised with 2M aqueous HCl to ~pH=7 and the MeOH was blown off under a stream of nitrogen. A precipitate was observed which was collected by filtration, then dissolved in 1 ml DMSO/MeOH (1:1) and purified by MDAP (Method B). The product-containing fractions were blown down under a stream of nitrogen to give a clear oil which was dissolved in dioxane/water (2 ml, 1:1, v/v) and freeze dried to give the title compound as a white solid (10 mg).

LCMS (Method D) $R_t$=0.76 min, MH+=475.

Example 166

2-Methyl-N-(6-{6-[(phenylsulfonyl)amino]-1H-indol-4-yl}-1H-indazol-4-yl)-1,3-thiazole-4-carboxamide

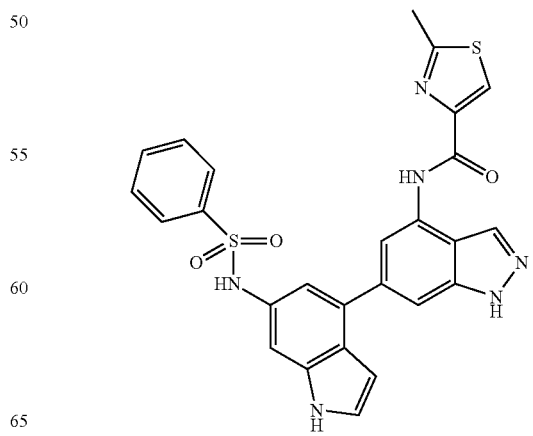

2-Methyl-N-[2-(tetrahydro-2H-pyran-2-yl)-6-(4,4,6,6-tetramethyl-1,3,2-dioxaborinan-2-yl)-2H-indazol-4-yl]-1,3-thiazole-4-carboxamide (50 mg, 0.104 mmol) was placed in 1,4-Dioxane (3 mL) and Water (1 mL). Tripotassium phosphate (66.0 mg, 0.311 mmol), Pd(dppf)Cl$_2$ (15.17 mg, 0.021 mmol) and (4-bromo-1H-indol-6-yl)benzenesulfonamide (30.0 mg, 0.104 mmol) was added and the mixture heated at 80° C. for 10 mins. The solvent was removed by blow down and the residue dissolved in a mixture of methanol and DCM. 2M aqueous HCl (5 drops) was added and the mixture stirred for 5 hours The solvent was removed and the residue purified by MDAP to afford the title compound as an off-white solid (15 mg). LCMS (Method D) R$_t$=0.89 min, MH$^+$=467.

Similarly prepared were:

| Example Number | Structure | Name | Monomer | MH$^+$ | LCMS Rt (min) |
|---|---|---|---|---|---|
| 167 | 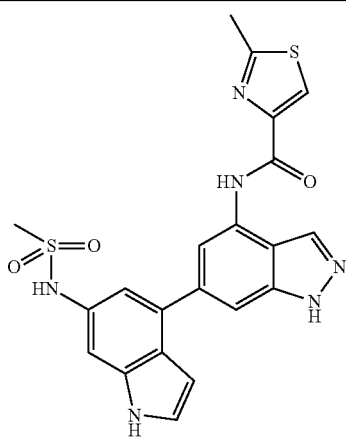 | 2-methyl-N-(6-{6-[(methylsulfonyl)amino]-1H-indol-4-yl}-1H-indazol-4-yl)-1,3-thiazole-4-carboxamide | N-(4-bromo-1H-indol-6-yl)methanesulfonamide | 529 | 1.02 |
| 168 | 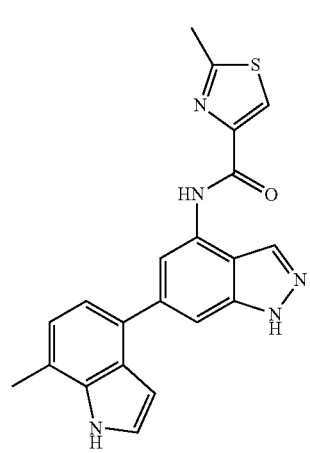 [SMILES: Cc1nc(C(=O)Nc2cc(-c3ccc(C)c4[nH]ccc34)cc3[nH]ncc23)cs1] | 2-methyl-N-[6-(7-methyl-1H-indol-4-yl)-1H-indazol-4-yl]-1,3-thiazole-4-carboxamide | 4-bromo-7-methyl-1H-indole (available from Sinova Laboratories) | 388 | 1.04 |

Example 169

2-(4-Morpholinylmethyl)-N-[6-(1H-pyrazolo[3,4-b]pyridin-5-yl)-1H-indazol-4-yl]-1,3-thiazole-4-carboxamide

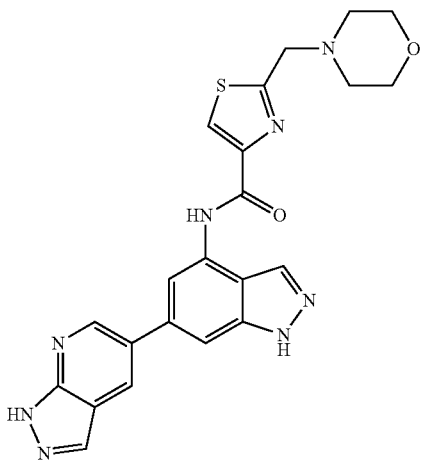 [SMILES: O=C(Nc1cc(-c2cnc3[nH]ncc3c2)cc2[nH]ncc12)c1csc(CN2CCOCC2)n1]

2-(4-Morpholinylmethyl)-N-{1-(phenylsulfonyl)-6-[1-(phenylsulfonyl)-1H-pyrazolo[3,4-b]pyridin-5-yl]-1H-indazol-4-yl}-1,3-thiazole-4-carboxamide (124 mg, 0.167 mmol) was suspended in Isopropanol (1 mL) and Sodium hydroxide (1 ml, 2.0 mmol) was added. The mixture was stirred at room temperature for 18 h. The mixture was neutralised with 2 M HCl (aq.) and the solvent was removed under a stream of nitrogen. The residue was dissolved in DMSO (2 ml) (insoluble salt was filtered off through a filter tube) and the samples (2×1 ml injections) were purified by mass directed autoprep HPLC (Method F). The product-containing fractions were concentrated under a stream of nitrogen to give the title compound as a cream solid (23 mg).

LCMS (Method D) Rt=0.53 min, MH+ 461.

Example 170

Formic acid-2-{[(2R,6S)-2,6-dimethyl-4-morpholinyl]methyl}-N-[6-(1H-pyrazolo[3,4-b]pyridin-5-yl)-1H-indazol-4-yl]-1,3-thiazole-4-carboxamide (1:1)

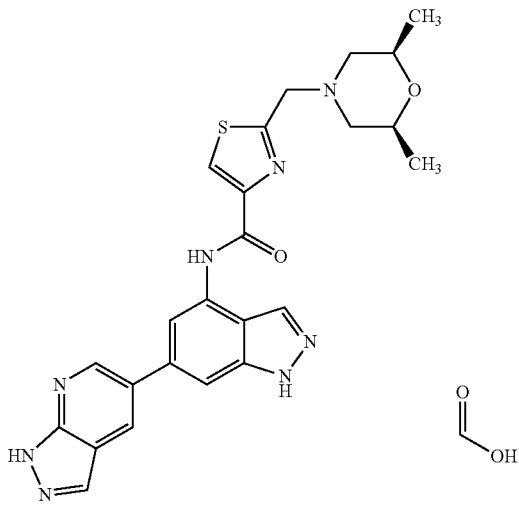 [SMILES: C[C@@H]1CN(Cc2nc(C(=O)Nc3cc(-c4cnc5[nH]ncc5c4)cc4[nH]ncc34)cs2)C[C@H](C)O1 ; O=CO]

2-{[(2R,6S)-2,6-Dimethyl-4-morpholinyl]methyl}-N-{1-(phenylsulfonyl)-6-[1-(phenylsulfonyl)-1H-pyrazolo[3,4-b]pyridin-5-yl]-1H-indazol-4-yl}-1,3-thiazole-4-carboxamide (99 mg, 0.129 mmol) was suspended in Isopropanol (1 mL) and Sodium hydroxide (1 ml, 2.0 mmol) was added. The mixture was stirred at room temperature for 18 h then neutralised with 2 M HCl (aq.) and the solvent was removed under a stream of nitrogen. The residue was dissolved in DMSO (2 ml) (insoluble salt was filtered off through a filter tube) and the samples (2×1 ml injections) were purified by mass directed autoprep HPLC (Method F). The product-containing fractions were concentrated under a stream of nitrogen to give the title compound as a white solid (18 mg).

LCMS (Method D) $R_f$=0.62 min, MH+=489.

Example 171

2-(4-Morpholinylmethyl)-N-[6-(1H-pyrrolo[2,3-b]pyridin-4-yl)-1H-indazol-4-yl]-1,3-thiazole-4-carboxamide

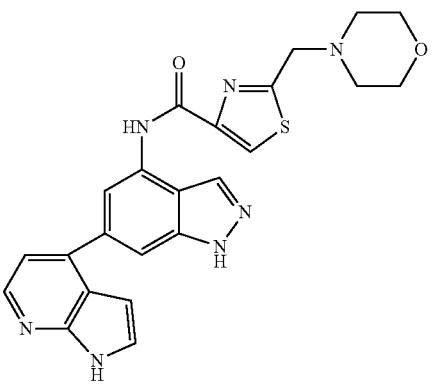 [SMILES: O=C(Nc1cc(-c2ccnc3[nH]ccc23)cc2[nH]ncc12)c1csc(CN2CCOCC2)n1]

2-(Chloromethyl)-N-{1-(phenylsulfonyl)-6-[1-(phenylsulfonyl)-1H-pyrrolo[2,3-b]pyridin-4-yl]-1H-indazol-4-yl}-1,3-thiazole-4-carboxamide (30 mg, 0.044 mmol) and morpholine (0.5 ml, 5.74 mmol) were mixed then heated in the microwave for 15 min at 90° C. The solvent was blown off under nitrogen. Isopropanol (1.5 mL) and 2M NaOH (1.500 ml) were added. The reaction mixture was stirred for 1.5 h. Further Isopropanol (1.5 mL) and 2M NaOH (1.5 mL) were added to the mixture which was stirred for 26 hours. The solvent was blown off under nitrogen. The resultant solid was dissolved in DMSO (2 mL). The salts were removed by filtration and the mixture was purified by MDAP to afford the title compound (4 mg).

LCMS (Method D) $R_f$=0.54 min, MH+=460.

Example 172

N-[6-(1H-Indol-4-yl)-1H-indazol-4-yl]-2-[(2-methyl-4-morpholinyl)methyl]-1,3-thiazole-4-carboxamide

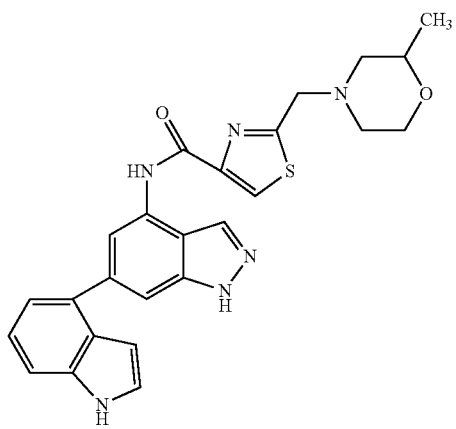 [SMILES: CC1CN(Cc2nc(C(=O)Nc3cc(-c4cccc5[nH]ccc45)cc4[nH]ncc34)cs2)CCO1]

2-(Chloromethyl)-N-[6-(1H-indol-4-yl)-1-(phenylsulfonyl)-1H-indazol-4-yl]-1,3-thiazole-4-carboxamide (50 mg, 0.091 mmol) and 2-methylmorpholine (0.5 mL, 0.091 mmol) were put in a 0.5-2 mL vial then heated in the microwave at 90° C. for 15 min. The solvent was blown down under nitrogen. Isopropanol (2 mL) and 2M NaOH (2.000 mL) were added and the reaction mixture was stirred for 3 hr at 25° C., then neutralised with 2M HCl aqueous solution until pH=7 (checking with pH paper). The solvent was removed under nitrogen. The mixture was dissolved in 2 mL of DMSO and passed through a hydrophobic frit. Purification was carried out by MDAP to afford the title compound (10 mg).

LCMS (Method D) 0.74 min, MH+ 473.

Similarly prepared were:

| Example Number | Structure | Name | Monomer | MH+ | LCMS Rt (min) |
|---|---|---|---|---|---|
| 173 | 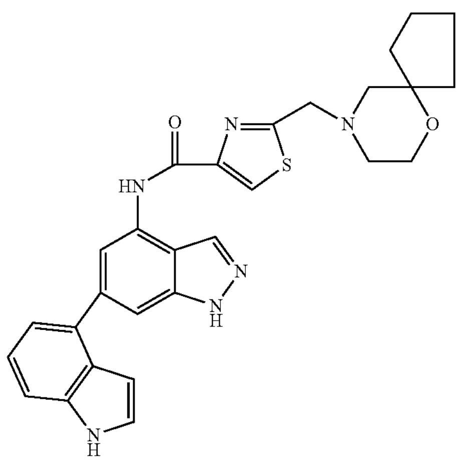 [SMILES: O=C(Nc1cc(-c2cccc3[nH]ccc23)cc2[nH]ncc12)c1csc(CN2CCOC3(CCCC3)C2)n1] | N-[6-(1H-indol-4-yl)-1H-indazol-4-yl]-2-(6-oxa-9-azaspiro[4.5]dec-9-ylmethyl)-1,3-thiazole-4-carboxamide | 6-oxa-9-azaspiro[4.5]decane | 653 | 1.25 |
| 174 | 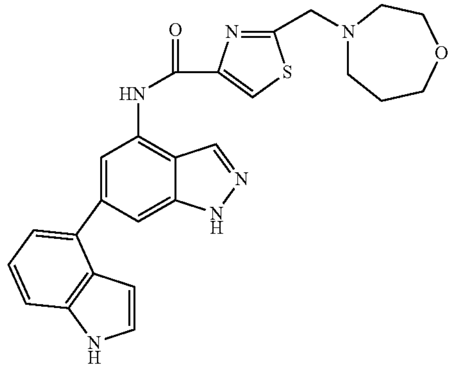 [SMILES: O=C(Nc1cc(-c2cccc3[nH]ccc23)cc2[nH]ncc12)c1csc(CN2CCCOCC2)n1] | N-[6-(1H-indol-4-yl)-1H-indazol-4-yl]-2-(tetrahydro-1,4-oxazepin-4(5H)-ylmethyl)-1,3-thiazole-4-carboxamide | hexahydro-1,4-oxazepine | 473 | 0.56 |

-continued

| Example Number | Structure | Name | Monomer | MH+ | LCMS Rt (min) |
|---|---|---|---|---|---|
| 175 | 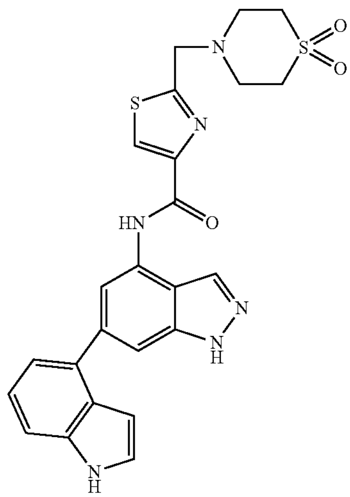 [SMILES: O=C(Nc1cc(-c2cccc3[nH]ccc23)cc2[nH]ncc12)c1csc(CN2CCS(=O)(=O)CC2)n1] | 2-[(1,1-dioxido-4-thiomorpholinyl)methyl]-N-[6-(1H-indol-4-yl)-1H-indazol-4-yl]-1,3-thiazole-4-carboxamide | thiomorpholine 1,1-dioxide | 507 | 0.81 |
| 176 | 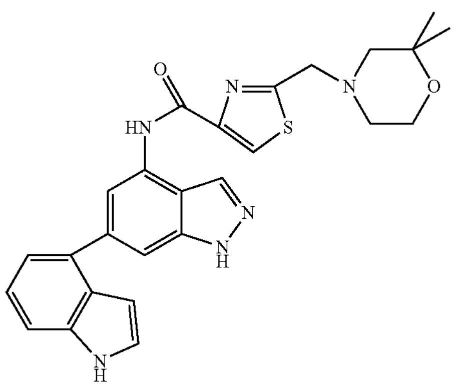 [SMILES: CC1(C)CN(Cc2nc(C(=O)Nc3cc(-c4cccc5[nH]ccc45)cc4[nH]ncc34)cs2)CCO1] | 2-[(2,2-dimethyl-4-morpholinyl)methyl]-N-[6-(1H-indol-4-yl)-1H-indazol-4-yl]-1,3-thiazole-4-carboxamide | 2,2-dimethyl-morpholine | 487 | 0.82 |

Example 177

2-{[(2R,6S)-2,6-Dimethyl-4-morpholinyl]methyl}-N-[6-(1H-indol-4-yl)-1-methyl-1H-indazol-4-yl]-1,3-thiazole-4-carboxamide

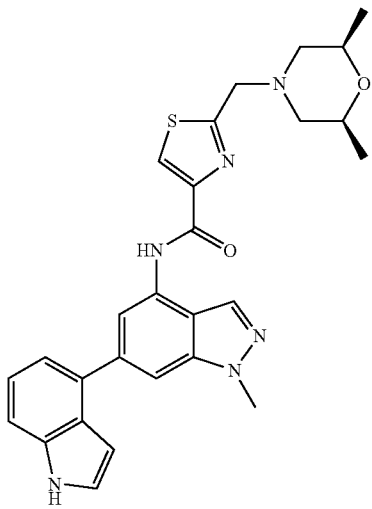 [SMILES: C[C@@H]1CN(Cc2nc(C(=O)Nc3cc(-c4cccc5[nH]ccc45)cc4c3cnn4C)cs2)C[C@H](C)O1]

N-(6-Bromo-1-methyl-1H-indazol-4-yl)-2-{[(2R,6S)-2,6-dimethyl-4-morpholinyl]methyl}-1,3-thiazole-4-carboxamide (100 mg, 0.215 mmol), 1H-indol-4-ylboronic acid (38.1 mg, 0.237 mmol), Pd(dppf)Cl₂ (15.76 mg, 0.022 mmol) and tripotassium phosphate (137 mg, 0.646 mmol) were placed into a microwave vial with water (0.300 mL) and 1,4-dioxane (1.5 mL) and the mixture heated at 100° C. in a microwave for 10 mins. The solvent was blown off and the residue partitioned between water (10 ml) and DCM (10 ml). The organic layer was collected using a hydrophobic frit and the solvent blown off. The residue was purified by chromatography on silica eluting with 0-100% ethyl acetate in cyclohexane followed by 0-25% methanol to give the title compound.

LCMS (Method D) Rt 0.89 min, MH+ 501.

Biological Data
Determination of AKT Phosphorylation in Expanded T Cells Using Flow Cytometry
Assay Principle The assay measures the single cell phosphorylation of AKT in response to co stimulation of CD3/CD28 on expanded T cells with anti CD3 and anti CD28. Intracellular protein phosphorylation is analysed using a Beckman Coulter FC500 microplate loading (MPL) flow cytometer, after labelling with fluorochrome conjugated phospho protein specific antibodies. In this case intracellular phosphorylated AKT was labelled with monoclonal antibodies to phospho-AKT S473 directly conjugated to Alexa 488. Light scatter versus fluorescence scatter plots are made and AKT phosphorylation is detected as an increase in % of activated (pAKT) cells.

Assay Protocol

Cell Plating

Remove expanded T cells from flasks (See appendix below). Centrifuge and remove supernatant. Re-suspend pellet in warm (37 C) stimulation buffer (RPMI containing pen/strep/glutamine and 5% FCS) and centrifuge again. Re-suspend pellet in 10-20 mls of warm stimulation buffer and count. Adjust cell concentration to $1 \times 10^6$ cells/ml. Add 45 ul of cell suspension to wells of v bottomed polystyrene plates and incubate at 37 C for 90 minutes.

Prepare stimulant plate containing anti CD3 (BDBiosciences #555329) and anti CD28 (BD Biosiences # 555725). Require 1-0.7 ug of each antibody per well. Stock antibody solutions are at 1000 ug/ml. Add an appropriate volume of diluted antibody solution to each well. Addition of 5 ul of this stock solution to cells results in a final concentration of 1-0.7 ug of each antibody per well.

Compound Plate Preparation and Stimulant Addition

Add serial (1/3) diluted compounds in wells A1-H10 (columns 11 and 12 contained stimulated and un-stimulated cells respectively). Top concentration is 10 uM and resulting final DMSO concentration is 0.15% DMSO. These steps are usually automated using a Beckman Coulter Biomek FX. Positive control is also included in plate sets (as a bundle). Positive control used in this assay is GW450853X (LY294002). Make up stock solutions of compounds at 6.66M and serially dilute it by 1 in 3 with 100% DMSO (8-span Biomek FX). Make plate replicates (stamp out) required number of plates. Each well contains 0.75 ul of compound at 6.666M in 100% DMSO (Use Biomek automation protocol). Dilute serially diluted stock compounds to 100 uM by adding 49.25 ul of stimulation buffer.

A further 1/10 dilution will result in a top concentration of 10 uM containing 0.15% DMSO. In this case 5 ul of each diluted compound is added to plates containing 50 ul of rested cell suspension. Columns 11 and 12 contain stimulation buffer and DMSO only.

Cell Treatments

Set up Biomek deck with compound plates and tip boxes as required. Place cell plates in appropriate deck locations on the Biomek FX. Start Biomek Program transfer 5 ul of each compound to cell plates. Following addition of compounds each plate is shaken gently (600 rpm) for 5 seconds. Once finished, place lids on plates and transfer them to a carbon dioxide incubator. Incubate in the presence of compound for 30 mins.

Cell Stimulation

Set up Biomek FX as per automation protocol. Place stimulation plate on deck.

Place cell plates in position and add stimulant. Remove plates and place back in incubator for 19.25 minutes (total stimulation time is 20 mins)

Cell Fixation

Set up Biomek deck as per Cell fixation protocol. Pour pre warmed fixative (4% buffered paraformaldehyde solution or BD Cytofix reagent) into reservoir and place on heated deck (temperature maintained at 37 deg C.). Centrifuge plates for 5 mins at 1000 g. Remove fixative supernatant by pipetting using Biomek FX. Break up pellets by vortexing wells. This is performed by simply sweeping the bottom on the plates over a whirlmixer. Arrange a large tray of ice (capable of holding several pates). Arrange plates on the ice and add 200 ul of ice-cold 90% methanol to each well. Cover and leave on ice for 30 minutes. Centrifuge plates at 1000 g for 5 minutes and remove methanol solution. Vortex plates and wash with 100 ul of PBS. Centrifuge again for 5 mins at 1000 g. Remove supernatant and vortex pellet Add 50 ul of Alexa fluor 488 Phospho-Akt (Ser 473) phospho specific rabbit monoclonal antibody (CST #2336) solution (1/100 dilution of stock anti body in stain solution). Cover plates and incubate in the dark for 60 minutes. Centrifuge plates (1000 g for 5 mins), remove supernatant and wash once using stain buffer. Re-suspend pellet in 180 ul of stain buffer (PBS, 2.5% FCS, 0.02% NaN3) Analyze plates using the FC500 MPL flow cytometer.

Appendix:

T Cell Expansion

Coating of Tissue Culture Plates for Stimulation

Add 1.5 ml of PBS containing 1 mM MgCl2, 1 mM CaCl2, anti CD3 5 ug/ml and anti CD28 5 ug/ml to each well of 6 well Costar Tissue culture plate and incubate overnight at 37 deg C. in a CO2 incubator. This will coat the plate with the mAb's.

Wash the wells of the Costar plates once with 3 ml/well of PBS.

Re-suspend the PBMCs at $2 \times 10^6$ cells/ml in the growth media with IL-2 (10 ng/ml, R&D Systems # 202-IL) and PHA (2 ug/ml, Sigma # L2769). Add 3 mls of the cell suspension to each well of a six well culture dish (Costar). Incubate the plate at 37 deg C. in a CO2 incubator until they are confluent i.e. the medium turns yellow.

After four days, wash the stimulated lymphocytes from culture wells using growth media. Culture lymphocytes in growth media (RPMI GIBCO CT 5615 10% Heat inactivated FCS, Hyclone, 2 mM Glutamine GIBCO, 1% Pen/Strep GIBCO, 1% Non essential amino acids, GIBCO, 1% Sodium Pyruvate, GIBCO, 20 uM Hepes GIBCO, 1.75 ul/500 mls 2-mercaptoethanol, Sigmal) in a medium size flask (T75) at a concentration of $\sim 10^6$/ml with IL-2 (10 ng/ml) and IL-7 (1 ng/ml, R&D Systems # 207-IL). Allow the cells to expand in resting phase at 37° C. in a CO2 incubator for 4-7 days. During this period of expansion, check cell growth every day and top up with 10 to 15 ml of resting media with IL-2 (10 ng/ml) and IL-7 (1 ng/ml) depending on how confluent the growth is. If required transfer cells to larger flask (T175). $1 \times 10^6$/ml cells are stained with Propidium Iodide and analysed by flow cytometry. Apoptotic cells are excluded from viable cell counts for subsequent experiments. Cells should be >80% viable for use.

PI3K Alpha, Beta, Delta and Gamma Assays

Assay Principle

The assay readout exploits the specific and high affinity binding of PIP3 to an isolated pleckstrin homology (PH) domain in the generation of a signal. Briefly, the PIP3 product is detected by displacement of biotinylated PIP3 from an energy transfer complex consisting of Europium (Eu)-labelled anti-GST monoclonal antibody, a GST-tagged PH domain, biotin-PIP3 and Streptavidin-APC. Excitation of Eu leads to a transfer of energy to APC and a sensitized fluorescence emission at 665 nm. PIP3 formed by PI3kinase activity competes for the binding site on the PH domain, resulting in a loss of energy transfer and a decrease in signal.

Assay Protocol

Solid compounds are typically plated with 0.1 μl of 100% DMSO in all wells (except column 6 and 18) of a 384-well, v bottom, low volume Greiner plate. The compounds are serially diluted (4-fold in 100% DMSO) across the plate from column 1 to column 12 and column 13 to column 24 and leave column 6 and 18 containing only DMSO to yield 11 concentrations for each test compound.

The assays are run using specific PI3 kinase kits from Millipore (Cat# 33-001)

The assay kit consist of the following:

4×PI3K reaction buffer (Contains 200 mM Hepes pH 7, 600 mM NaCl, 40 mM Mgcl$_2$, <1% Cholate (w/v), <1% Chaps (w/v), 0.05% Sodium Azide (w/v))

PIP2 (1 mM)

3× Biotin PIP3 (50 μM)

Detection Mix C (Contains 267 mM KF)

Detection Mix A (Contains 60 μg/ml streptavadin-APC)

Detection Mix B (Contains 36 μg/ml Europium-anti-GST (Anti-GST-K) and 90 μg/ml GST-GRP1-PH-Domain and 1 mM DTT)

Stop Solution (Contains 150 mM EDTA)

Manually add 3 μl of Reaction buffer (contains 1 mM DTT) to column 18 only for 100% inhibition control (no activity)

Manually add 3 μl of 2× Enzyme solution to all wells except column 18. Preincubate with compound for 15 minutes.

Manually add 3 μl of 2× Substrate solution to all wells. (column 6 represents 0% inhibition control)

Leave plate for 1 hr (cover from light) (In the case of Gamma only a 50 min incubation is required)

Manually add 3 μl Stop/Detection solution to all wells

Leave plate for 1 hour (cover from light)

The assay is read upon the BMG Rubystar and the ratio data is utilised to calculate 11 point curves.

NB The substrate solution (concentrations) differ with each isoform (see below)

Alpha

2× substrate solution containing 500 μM ATP, 16 μM PIP2 and 0.030 μM 3× biotin-PIP3.

Beta

2× substrate solution containing 800 μM ATP, 16 μM PIP2 and 0.030 μM 3× biotin-PIP3.

Delta

2× substrate solution containing 160 μM ATP, 10 μM PIP2 and 0.030 μM 3× biotin-PIP3.

Gamma

2× substrate solution containing 30 μM ATP, 16 μM PIP2 and 0.030 μM 3× biotin-PIP3.

Analysis Method

Data processed through the XC50 4-parameter logistic curve fit algorithm in Activity Base.

Normalise to % inhibition between the high and low controls (0% and 100% inhibition respectively)

Primary Module fit: Slope, Min and Max asymptotes varies

Secondary Module fits: (1) Fix Min asymptote, (2) Fix Max asymptote, (3) Fix Min and Max Asymptotes Curve Fit QC: pXC50 95% CL ratio>1

−20<Min asymptote<20

80<Max asymptote<120

The compounds of Examples 1 to 177 were tested in one or more of the PI3K Alpha, Beta, Delta and/or Gamma assays above or similar assays and were found to have a mean pIC$_{50}$ of 5 or greater. Certain compounds were also tested in the T cell assay above or a similar assay and were found to have a mean pIC$_{50}$ of 6 or greater.

What is claimed is:
1. A compound of formula (I):

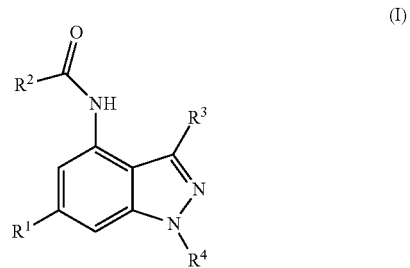

wherein
$R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN, —OR$^{13}$ or —NHSO$_2$R$^{14}$; or phenyl fused to a 5-membered heterocyclyl wherein the 5-membered heterocyclyl contains one or two heteroatoms independently selected from oxygen and nitrogen and is substituted by oxo;
$R^2$ is 5-membered heteroaryl wherein the 5-membered heteroaryl contains from one to three heteroatoms independently selected from oxygen, nitrogen and sulphur and is optionally substituted by from one to three substituents independently selected from $C_{1-6}$alkyl optionally substituted by from one to three fluorine atoms; $C_{2-6}$alkenyl; $C_{3-6}$cycloalkyl; —OR$^5$; halo; —COR$^6$; —CO$_2$R$^7$; —CONR$^8$R$^9$; —(CH$_2$)$_m$NR$^{10}$R$^{11}$; —CH(CH$_3$)NH-COphenyl; —NHCO$_2$R$^{12}$; —(CH$_2$)$_n$phenyl; and 5-membered heteroaryl wherein the second 5-membered heteroaryl contains one or two heteroatoms independently selected from oxygen, nitrogen and sulphur and is optionally substituted by $C_{1-6}$alkyl;
$R^3$ is hydrogen or fluoro;
$R^4$ is hydrogen or methyl;
$R^5$, $R^7$, $R^{12}$ and $R^{13}$ are each independently hydrogen or $C_{1-6}$alkyl;
$R^6$, $R^{18}$ and $R^{19}$ are each independently $C_{1-6}$alkyl;
$R^8$ and $R^9$ are each independently hydrogen or $C_{1-6}$alkyl, or $R^8$ and $R^9$, together with the nitrogen atom to which they are attached, are linked to form a 5- or 6-membered heterocyclyl optionally containing an oxygen atom;
$R^{10}$ and $R^{11}$ are each independently hydrogen or $C_{1-6}$alkyl, or $R^{10}$ and $R^{11}$, together with the nitrogen atom to which they are attached, are linked to form a 5-, 6- or 7-membered heterocyclyl or a 10-membered bicyclic heterocyclyl wherein the 5-, 6- or 7-membered heterocyclyl or the 10-membered bicyclic heterocyclyl optionally contains an oxygen atom, a sulphur atom or a further nitrogen atom and is optionally substituted by one or two substituents independently selected from $C_{1-6}$alkyl; $C_{3-6}$cycloalkyl; halo; oxo; phenyl optionally substituted by halo; pyridinyl; —(CH$_2$)$_p$OR$^{15}$; —(CH$_2$)$_q$NR$^{16}$R$^{17}$; —COR$^{18}$; and —SO$_2$R$^{19}$;
$R^{14}$ is $C_{1-6}$alkyl or phenyl;
$R^{15}$ is hydrogen, $C_{1-6}$alkyl or —(CH$_2$)$_r$phenyl;
$R^{16}$ and $R^{17}$, together with the nitrogen atom to which they are attached, are linked to form a 5- or 6-membered heterocyclyl optionally containing an oxygen atom; and
m, n, p, q, r are each independently 0, 1 or 2;
or a salt thereof.

2. A compound of formula (I) according to claim 1 or a salt thereof wherein $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo or —CN.

3. A compound of formula (I) according to claim 1 or a salt thereof wherein $R^1$ is 9-membered bicyclic heteroaryl wherein the 9-membered bicyclic heteroaryl contains one or two nitrogen atoms and is optionally substituted by $C_{1-6}$alkyl or halo.

4. A compound of formula (I) according to claim 1 or a salt thereof wherein $R^2$ is 5-membered heteroaryl wherein the 5-membered heteroaryl contains from one to three heteroatoms independently selected from oxygen, nitrogen and sulphur and is optionally substituted by from one to three substituents independently selected from $C_{1-6}$alkyl and —(CH$_2$)$_m$NR$^{10}$R$^{11}$.

5. A compound of formula (I) according to claim 1 or a salt thereof wherein $R^3$ is hydrogen.

6. A compound of formula (I) according to claim 1 or a salt thereof wherein $R^3$ is fluoro.

7. A compound of formula (I) according to claim 1 or a salt thereof wherein $R^4$ is hydrogen.

8. A compound of formula (I) according to claim 1 which is:

N-[6-(1H-indol-4-yl)-1H-indazol-4-yl]-5-methyl-1H-pyrazole-3-carboxamide;
N-[6-(1H-indol-4-yl)-1H-indazol-4-yl]-1-methyl-1H-imidazole-2-carboxamide;
N-[6-(1H-indol-4-yl)-1H-indazol-4-yl]-1-methyl-1H-pyrrole-2-carboxamide;
N-[6-(1H-indol-4-yl)-1H-indazol-4-yl]-1-methyl-1H-imidazole-4-carboxamide;
N-[6-(1H-indol-4-yl)-1H-indazol-4-yl]-1-methyl-1H-pyrazole-5-carboxamide;
N-[6-(1H-indol-4-yl)-1H-indazol-4-yl]-1,5-dimethyl-1H-pyrazole-3-carboxamide;
N-[6-(1H-indol-4-yl)-1H-indazol-4-yl]-2-(phenylmethyl)-1,3-thiazole-4-carboxamide;
1-ethyl-N-[6-(1H-indol-4-yl)-1H-indazol-4-yl]-1H-pyrazole-3-carboxamide;
N-[6-(1H-indol-4-yl)-1H-indazol-4-yl]-2-methyl-3-furancarboxamide;
N-[6-(1H-indol-4-yl)-1H-indazol-4-yl]-5-methyl-2-furancarboxamide;
N-[6-(1H-indol-4-yl)-1H-indazol-4-yl]-1-methyl-1H-pyrazole-3-carboxamide;
N-[6-(1H-indol-4-yl)-1H-indazol-4-yl]-3-furancarboxamide;
N-[6-(1H-indol-4-yl)-1H-indazol-4-yl]-3-thiophenecarboxamide;
N-[6-(1H-indol-4-yl)-1H-indazol-4-yl]-5-(1-pyrrolidinylmethyl)-2-furancarboxamide;
N-[6-(1H-indol-4-yl)-1H-indazol-4-yl]-2-phenyl-1,3-thiazole-4-carboxamide;
2-chloro-N-[6-(1H-indol-4-yl)-1H-indazol-4-yl]-3-furancarboxamide;
1-ethenyl-N-[6-(1H-indol-4-yl)-1H-indazol-4-yl]-1H-pyrazole-5-carboxamide;
1-ethyl-N-[6-(1H-indol-4-yl)-1H-indazol-4-yl]-1H-pyrazole-5-carboxamide;
N-[6-(1H-indol-4-yl)- 1H-indazol-4-yl]-2-(trifluoromethyl)-1,3-thiazole-4-carboxamide;
N-[6-(1H-indol-4-yl)-1H-indazol-4-yl]-2-{1-[(phenylcarbonyl)amino]ethyl}-1,3-thiazole-4-carboxamide;
N-[6-(1H-indol-4-yl)-1H-indazol-4-yl]-5-(trifluoromethyl)-2-furancarboxamide;
5-[(dimethylamino)methyl]-N-[6-(1H-indol-4-yl)-1H-indazol-4-yl]-2-furancarboxamide;
3-ethyl-N-[6-(1H-indol-4-yl)-1H-indazol-4-yl]-1H-pyrazole-5-carboxamide;
5-chloro-N-[6-(1H-indol-4-yl)-1H-indazol-4-yl]-2-furancarboxamide;
N-[6-(1H-indol-4-yl)-1H-indazol-4-yl]-4-methyl-2-thiophenecarboxamide;
N-[6-(1H-indol-4-yl)-1H-indazol-4-yl]-2-(4-morpholinylmethyl)-1,3-thiazole-4-carboxamide;
N-[6-(1H-indol-4-yl)-1H-indazol-4-yl]-1H-pyrazole-3-carboxamide;
N-[6-(1H-indol-4-yl)-1H-indazol-4-yl]-1,3-thiazole-5-carboxamide;
1-(1-methylethyl)-N-[6-(1H-pyrazolo[3,4-b]pyridin-4-yl)-1H-indazol-4-yl]-1H-pyrazole-5-carboxamide;
N-[6-(1H-indol-4-yl)-1H-indazol-4-yl]-1H-imidazole-4-carboxamide;
N-[6-(1H-indol-4-yl)-1H-indazol-4-yl]-1,3-thiazole-4-carboxamide;
N-[6-(1H-indol-4-yl)-1H-indazol-4-yl]-5-methyl-3-isoxazolecarboxamide;
N-[6-(1H-indol-4-yl)-1H-indazol-4-yl]-1,2,3-thiadiazole-4-carboxamide;
N-[6-(1H-indol-4-yl)-1H-indazol-4-yl]-2,5-dimethyl-1,3-oxazole-4-carboxamide;
N-[6-(1H-indol-4-yl)-1H-indazol-4-yl]-2-methyl-1,3-oxazole-4-carboxamide;
N-[6-(1H-indol-4-yl)-1H-indazol-4-yl]-3-isoxazolecarboxamide;
N-[6-(1H-indol-4-yl)-1H-indazol-4-yl]-2-methyl-5-(trifluoromethyl)-1,3-oxazole-4-carboxamide;
N-[6-(1H-indol-4-yl)-1H-indazol-4-yl]-5-(2-methyl-1,3-thiazol-4-yl)-3-isoxazolecarboxamide;
4-[(dimethylamino)methyl]-N-[6-(1H-indol-4-yl)-1H-indazol-4-yl]-5-methyl-3-isoxazolecarboxamide;
N-[6-(1H-indol-4-yl)-1H-indazol-4-yl]-5-(4-morpholinylmethyl)-3-isoxazolecarboxamide;
N-[6-(1H-indol-4-yl)-1H-indazol-4-yl]-5-methyl-4-(1-piperidinylmethyl)-3-isoxazolecarboxamide;
N-[6-(1H-indol-4-yl)-1H-indazol-4-yl]-5-methyl-4-(4-morpholinylmethyl)-3-isoxazolecarboxamide;
N-[6-(1H-indol-4-yl)-1H-indazol-4-yl]-5-methyl-4-(1-pyrrolidinylmethyl)-3-isoxazolecarboxamide;
N-[6-(1H-indol-4-yl)-1H-indazol-4-yl]-2-(1-piperidinylmethyl)-1,3-thiazole-4-carboxamide;
N-[6-(1H-indol-4-yl)-1H-indazol-4-yl]-1H-imidazole-2-carboxamide;
N-1H,1'H-5,6'-biindazol-4'-yl-2-methyl-1,3-thiazole-4-carboxamide;
4-chloro-N-[6-(1H-indol-4-yl)-1H-indazol-4-yl]-1-methyl-1H-pyrazole-5-carboxamide;
N-[6-(1H-indol-4-yl)-1H-indazol-4-yl]-1,4-dimethyl-1H-pyrazole-5-carboxamide;
N-[6-(1H-indol-4-yl)-1H-indazol-4-yl]-5-(1-methylethyl)-2-(4-morpholinylmethyl)-1,3-thiazole-4-carboxamide;
4-chloro-N-[6-(1H-indol-4-yl)-1H-indazol-4-yl]-1H-pyrazole-5-carboxamide;
4-chloro-N-[6-(1H-indol-4-yl)-1H-indazol-4-yl]-1-(1-methylethyl)-1H-pyrazole-3-carboxamide;
2-chloro-N-[6-(1H-indol-4-yl)-1H-indazol-4-yl]-5-(1-methylethyl)-1,3-thiazole-4-carboxamide;
N-[6-(1H-indol-4-yl)-1H-indazol-4-yl]-2,5-dimethyl-1,3-thiazole-4-carboxamide;
4-chloro-N-[6-(1H-indol-4-yl)-1H-indazol-4-yl]-1-(1-methylethyl)-1H-pyrazole-5-carboxamide;
N-[6-(1H-indol-4-yl)-1H-indazol-4-yl]-1-methyl-4-(trifluoromethyl)-1H-pyrazole-5-carboxamide;

N-[6-(1H-indol-4-yl)-1H-indazol-4-yl]-2-methyl-5-(1-methylethyl)-1,3-thiazole-4-carboxamide;
N-[6-(1H-indol-4-yl)-1H-indazol-4-yl]-1-(1-methylethyl)-3-(4-morpholinylmethyl)-1H-pyrazole-5-carboxamide;
N-[6-(1H-indol-4-yl)-1H-indazol-4-yl]-1-(1-methylethyl)-5-(4-morpholinylmethyl)-1H-pyrazole-3-carboxamide;
N-[6-(1H-indol-4-yl)-1H-indazol-4-yl]-1-methyl-1H-1,2,4-triazole-5-carboxamide;
N-[6-(1H-indol-4-yl)-1H-indazol-4-yl]-1-(1-methylethyl)-1H-1,2,4-triazole-5-carboxamide;
1-(1,1-dimethylethyl)-N-[6-(1H-indol-4-yl)-1H-indazol-4-yl]-3-methyl-1H-pyrazole-5-carboxamide;
N-[6-(1H-indol-4-yl)-1H-indazol-4-yl]-1-(2,2,2-trifluoroethyl)-1H-pyrazole-5-carboxamide;
1-(difluoromethyl)-N-[6-(1H-indol-4-yl)-1H-indazol-4-yl]-1H-pyrazole-5-carboxamide;
1,1-dimethylethyl[4-({[6-(1H-indol-4-yl)-1H-indazol-4-yl]amino}carbonyl)-1,3-thiazol-2-yl]carbamate;
1,1-dimethylethyl 3-cyclopropyl-4-({[6-(1H-indol-4-yl)-1H-indazol-4-yl]amino}carbonyl)-1H-pyrazole-1-carboxylate;
4-fluoro-N-[6-(1H-indol-4-yl)-1H-indazol-4-yl]-1-(1-methylethyl)-1H-pyrazole-5-carboxamide;
2-amino-N-[6-(1H-indol-4-yl)-1H-indazol-4-yl]-1,3-thiazole-4-carboxamide;
1-ethyl-4-fluoro-N-[6-(1H-indol-4-yl)-1H-indazol-4-yl]-1H-pyrazole-5-carboxamide;
2-amino-N-[6-(1H-indol-4-yl)-1H-indazol-4-yl]-4-(trifluoromethyl)-1,3-thiazole-5-carboxamide;
2-amino-N-[6-(1H-indol-4-yl)-1H-indazol-4-yl]-5-(1-methylethyl)-1,3-thiazole-4-carboxamide;
N-[6-(1H-indol-4-yl)-1H-indazol-4-yl]-2-(1-methylethyl)-2H-1,2,3-triazole-4-carboxamide;
4-bromo-N-[6-(1H-indol-4-yl)-1H-indazol-4-yl]-1,3-dimethyl-1H-pyrazole-5-carboxamide;
N-[6-(1H-indol-4-yl)-1H-indazol-4-yl]-5-(1-methylethyl)-1,3-thiazole-4-carboxamide;
1-(2-fluoroethyl)-N-[6-(1H-indol-4-yl)-1H-indazol-4-yl]-1H-pyrazole-5-carboxamide;
1-(2-fluoroethyl)-N-[6-(1H-indol-4-yl)-1H-indazol-4-yl]-1H-pyrazole-3-carboxamide;
5-acetyl-N-[6-(1H-indol-4-yl)-1H-indazol-4-yl]-2-methyl-1,3-thiazole-4-carboxamide;
N-[6-(1H-indol-4-yl)-1H-indazol-4-yl]-5-(1-methylethyl)-1,3-oxazole-4-carboxamide;
N-[6-(1H-indol-4-yl)-1H-indazol-4-yl]-1-(1-methylethyl)-1H-1,2,3-triazole-5-carboxamide;
N-[6-(1H-indol-4-yl)-1H-indazol-4-yl]-2-methyl-1,3-thiazole-4-carboxamide;
N-[6-(1H-indol-4-yl)-1H-indazol-4-yl]-1-methyl-1H-1,2,4-triazole-3-carboxamide;
N-[6-(1H-indol-5-yl)-1H-indazol-4-yl]-2-methyl-1,3-thiazole-4-carboxamide;
N-[6-(1H-benzimidazol-4-yl)-1H-indazol-4-yl]-2-methyl-1,3-thiazole-4-carboxamide;
2-methyl-N-[6-(2-methyl-1H-pyrrolo[2,3-b]pyridin-4-yl)-1H-indazol-4-yl]-1,3-thiazole-4-carboxamide;
N-[6-(2-cyclopropyl-1H-pyrrolo[2,3-b]pyridin-4-yl)-1H-indazol-4-yl]-2-methyl-1,3-thiazole-4-carboxamide;
N-1H,1'H-4,6'-biindazol-4'-yl-1-(1-methylethyl)-1H-pyrazole-5-carboxamide;
N-[3-fluoro-6-(1H-indol-4-yl)-1H-indazol-4-yl]-2-methyl-1,3-thiazole-4-carboxamide;
4-chloro-1-ethyl-N-[3-fluoro-6-(1H-indol-4-yl)-1H-indazol-4-yl]-1H-pyrazole-5-carboxamide;
N-[3-fluoro-6-(1H-indol-4-yl)-1H-indazol-4-yl]-1-(1-methylethyl)-1H-pyrazole-5-carboxamide;
N-[6-(6-fluoro-1H-indol-4-yl)-1H-indazol-4-yl]-2-methyl-1,3-thiazole-4-carboxamide;
N-[6-(1H-indol-4-yl)-1H-indazol-4-yl]-1-(1-methylethyl)-1H-imidazole-2-carboxamide;
4-fluoro-N-[6-(1H-indol-4-yl)-1H-indazol-4-yl]-1-methyl-1H-pyrazole-3-carboxamide;
ethyl-N-[6-(1H-indol-4-yl)-1H-indazol-4-yl]-3-methyl-1H-pyrazole-5-carboxamide;
N-[6-(1H-indol-4-yl)-1H-indazol-4-yl]-1,3-dimethyl-1H-pyrazole-5-carboxamide;
3-(1,1-dimethylethyl)-N-[6-(1H-indol-4-yl)-1H-indazol-4-yl]-1-methyl-1H-pyrazole-5-carboxamide;
4-chloro-1-ethyl-N-[6-(1H-indol-4-yl)-1H-indazol-4-yl]-1H-pyrazole-5-carboxamide;
N-[6-(1H-indol-4-yl)-1H-indazol-4-yl]-1-methyl-3-(trifluoromethyl)-1H-pyrazole-5-carboxamide;
N-[6-(1H-indol-4-yl)-1H-indazol-4-yl]-1-methyl-3-(1-methylethyl)-1H-pyrazole-5-carboxamide;
3-cyclopropyl-N-[6-(1H-indol-4-yl)-1H-indazol-4-yl]-1-methyl-1H-pyrazole-5-carboxamide;
1-ethyl-N-[6-(1H-indol-4-yl)-1H-indazol-4-yl]-3-(1-methylethyl)-1H-pyrazole-5-carboxamide;
N-[6-(1H-indol-4-yl)-1H-indazol-4-yl]-1-methyl-3-(2-methylpropyl)-1H-pyrazole-5-carboxamide;
N-[6-(1H-indol-4-yl)-1H-indazol-4-yl]-4-(methyloxy)-3-thiophenecarboxamide;
N-[6-(1H-indol-4-yl)-1H-indazol-4-yl]-1-methyl-3-(4-morpholinylcarbonyl)-1H-pyrazole-5-carboxamide;
N-[6-(1H-indol-4-yl)-1H-indazol-4-yl]-1,4-dimethyl-1H-pyrazole-3-carboxamide;
1-ethyl-N-[6-(1H-indol-4-yl)-1H-indazol-4-yl]-3-(2-methylpropyl)-1H-pyrazole-5-carboxamide;
N-[6-(1H-indol-4-yl)-1H-indazol-4-yl]-1-methyl-5-(4-morpholinylmethyl)-1H-pyrazole-3-carboxamide;
N-[6-(1H-indol-4-yl)-1H-indazol-4-yl]-1-methyl-3-(4-morpholinylmethyl)-1H-pyrazole-5-carboxamide;
2-acetyl-N-[6-(1H-indol-4-yl)-1H-indazol-4-yl]-1,3-thiazole-4-carboxamide;
N-[6-(5-isoquinolinyl)-1H-indazol-4-yl]-2-methyl-1,3-thiazole-4-carboxamide;
2-methyl-N-[6-(1-methyl-1H-indol-4-yl)-1H-indazol-4-yl]-1,3-thiazole-4-carboxamide;
N-[6-(4-isoquinolinyl)-1H-indazol-4-yl]-2-methyl-1,3-thiazole-4-carboxamide;
N-[6-(1H-indol-3-yl)-1H-indazol-4-yl]-2-methyl-1,3-thiazole-4-carboxamide;
N-[6-(1H-indol-6-yl)-1H-indazol-4-yl]-2-methyl-1,3-thiazole-4-carboxamide;
2-methyl-N-[6-(1-methyl-1H-indol-6-yl)-1H-indazol-4-yl]-1,3-thiazole-4-carboxamide;
N-[6-(1H-indol-4-yl)-1H-indazol-4-yl]-2-furancarboxamide;
N-[6-(1-benzofuran-2-yl)-1H-indazol-4-yl]-2-methyl-1,3-thiazole-4-carboxamide;
N-[6-(6-cyano-1H-indol-4-yl)-1H-indazol-4-yl]-1-(1-methylethyl)-1H-pyrazole-5-carboxamide;
1-(1-methylethyl)-N-[6-(6-methyl-1H-indol-4-yl)-1H-indazol-4-yl]-1H-pyrazole-5-carboxamide;
N-[6-(1-benzofuran-5-yl)-1H-indazol-4-yl]-1-(1-methylethyl)-1H-pyrazole-5-carboxamide;
5-bromo-N-[6-(1H-indol-4-yl)-1H-indazol-4-yl]-1,3-thiazole-4-carboxamide;
N-[6-(1H-indol-4-yl)-1H-indazol-4-yl]-5-(1-methylethyl)-4-isoxazolecarboxamide;

N-[6-(1-benzofuran-5-yl)-1H-indazol-4-yl]-2-methyl-1,3-thiazole-4-carboxamide;

N-{6-[2-(1,1-dimethylethyl)-1H-pyrrolo[2,3-b]pyridin-4-yl]-1H-indazol-4-yl}1-2-methyl-1,3-thiazole-4-carboxamide;

1-(1-methylethyl)-N-[6-(2-methyl-1H-pyrrolo[2,3-b]pyridin-4-yl)-1H-indazol-4-yl]-1H-pyrazole-5-carboxamide;

1-(1-methylethyl)-N-[6-(1H-pyrrolo[2,3-b]pyridin-4-yl)-1H-indazol-4-yl]-1H -pyrazole-5-carboxamide;

1-(1-methylethyl)-N-[6-(1H-pyrrolo[2,3-c]pyridin-4-yl)-1H-indazol-4-yl]-1H -pyrazole-5-carboxamide;

1-(1-methylethyl)-N-[6-(2-oxo-2,3-dihydro-1H-indol-4-yl)-1H-indazol-4-yl]-1H -pyrazole-5-carboxamide;

1-(1-methylethyl)-N-[6-(2-oxo-2,3-dihydro-1,3-benzoxazol-7-yl)-1H-indazol-4-yl]-1H -pyrazole-5-carboxamide;

1-(1-methylethyl)-N-[6-(7H-pyrrolo[2,3-d]pyrimidin-4-yl)-1H-indazol-4-yl]-1H -pyrazole-5-carboxamide;

N-[6-(6-fluoro-1H-indol-4-yl)-1H-indazol-4-yl]-1-(1-methylethyl)-1H-pyrazole-5-carboxamide;

N-1H,1'H-4,6'-biindazol-4'-yl-2-methyl-1,3-thiazole-4-carboxamide;

2-methyl-N-[6-(1H-pyrrolo[2,3-b]pyridin-4-yl)-1H-indazol-4-yl]-1,3-thiazole-4-carboxamide;

2-methyl-N-[6-(1H-pyrrolo[2,3-c]pyridin-4-yl)-1H-indazol-4-yl]-1,3-thiazole-4-carboxamide;

1,4-dimethyl-N-[6-(2-methyl-1H-pyrrolo[2,3-b]pyridin-4-yl)-1H-indazol-4-yl]-1H -pyrazole-3-carboxamide;

1,4-dimethyl-N-[6-(1H-pyrrolo[2,3-c]pyridin-4-yl)-1H-indazol-4-yl]-1H-pyrazole-3-carboxamide;

1,4-dimethyl-N-[6-(1H-pyrrolo[2,3-b]pyridin-4-yl)-1H-indazol-4-yl]-1H-pyrazole-3-carboxamide;

N-1H,1'H-4,6'-biindazol-4'-yl-1,4-dimethyl-1H-pyrazole-3-carboxamide;

4-chloro-1-ethyl-N-[6-(2-methyl-1H-pyrrolo[2,3-b]pyridin-4-yl)-1H-indazol-4-yl]-1H-pyrazole-5-carboxamide;

4-chloro-1-ethyl-N-[6-(1H-pyrrolo[2,3-c]pyridin-4-yl)-1H-indazol-4-yl]-1H-pyrazole-5-carboxamide;

4-chloro-1-ethyl-N-[6-(1H-pyrrolo[2,3-b]pyridin-4-yl)-1H-indazol-4-yl]-1H -pyrazole-5-carboxamide;

N-1H,1'H-4,6'-biindazol-4'-yl-4-chloro-1-ethyl-1H-pyrazole-5-carboxamide;

4-chloro-1-ethyl-N-[6-(1H-pyrazolo[3,4-b]pyridin-4-yl)-1H-indazol-4-yl]-1H -pyrazole-5-carboxamide;

N-[3-fluoro-6-(6-fluoro-1H-indol-4-yl)-1H-indazol-4-yl]-2-methyl-1,3-thiazole-4-carboxamide;

2-[(4,4-dimethyl-1-piperidinyl)methyl]-N-[6-(1H-indol-4-yl)-1H-indazol-4-yl]-1,3-thiazole-4-carboxamide;

2-[(3,3-dimethyl-1-piperidinyl)methyl]-N-[6-(1H-indol-4-yl)-1H-indazol-4-yl]-1,3-thiazole-4-carboxamide;

N-[6-(1H-indol-4-yl)-1H-indazol-4-yl]-2-{[4-(2-methylpropyl)-1-piperazinyl]methyl}-1,3-thiazole-4-carboxamide;

N-[6-(1H-indol-4-yl)-1H-indazol-4-yl]-2-{[4-(1-methylethyl)-1-piperazinyl]methyl}1-1,3-thiazole-4-carboxamide;

N-[6-(1H-indol-4-yl)-1H-indazol-4-yl]-2-({4-[2-(4-morpholinyl)ethyl]-1-piperazinyl}methyl)-1,3-thiazole-4-carboxamide;

N-[6-(1H-indol-4-yl)-1H-indazol-4-yl]-2-(octahydro-4H-1,4-benzoxazin-4-ylmethyl)-1,3-thiazole-4-carboxamide;

2-{[(2R,6S)-2,6-dimethyl-4-morpholinyl]methyl}-N-[6-(1H-indol-4-yl)-1H-indazol-4-yl]-1,3-thiazole-4-carboxamide;

2-{[4-(4-fluorophenyl)-1-piperazinyl]methyl}-N-[6-(1H-indol-4-yl)-1H-indazol-4-yl]-1,3-thiazole-4-carboxamide;

N-[6-(1H-indol-4-yl)-1H-indazol-4-yl]-2-(octahydro-2H-pyrido[1,2-α]pyrazin-2-ylmethyl)-1,3-thiazole-4-carboxamide;

N-[6-(1H-indol-4-yl)-1H-indazol-4-yl]-2-{[2-(1-pyrrolidinylmethyl)-4-morpholinyl]methyl}-1,3-thiazole-4-carboxamide;

N-[6-(1H-indol-4-yl)-1H-indazol-4-yl]-2-{[2-(2-methylpropyl)-4-morpholinyl]methyl}-1,3-thiazole-4-carboxamide;

N-[6-(1H-indol-4-yl)-1H-indazol-4-yl]-2-{[3-(3-pyridinyl)-1-pyrrolidinyl]methyl}1-1,3-thiazole-4-carboxamide;

N-[6-(1H-indol-4-yl)-1H-indazol-4-yl]-2-{[3-methyl-4-(1-methylethyl)-1-piperazinyl]methyl}-1,3-thiazole-4-carboxamide;

N-[6-(1H-indol-4-yl)-1H-indazol-4-yl]-2-({3-[(phenylmethyl)oxy]-1-piperidinyl}methyl)-1,3-thiazole-4-carboxamide;

2-{[4-(1-ethylpropyl)-1-piperazinyl]methyl}-N-[6-(1H-indol-4-yl)-1H-indazol-4-yl]-1,3-thiazole-4-carboxamide;

2-[(4-cyclopentyl-1-piperazinyl)methyl]-N-[6-(1H-indol-4-yl)-1H-indazol-4-yl]-1,3-thiazole-4-carboxamide;

2-methyl-N-[6-(2-methyl-1H-indol-4-yl)-1H-indazol-4-yl]-1,3-thiazole-4-carboxamide;

N-[6-(6-chloro-1H-indol-4-yl)-1H-indazol-4-yl]-2-methyl-1,3-thiazole-4-carboxamide;

2-methyl-N-{6-[6-(methyloxy)-1H-indol-4-yl]-1H-indazol-4-yl}-1,3-thiazole-4-carboxamide;

N-[6-(6-cyano-1H-indol-4-yl)-1H-indazol-4-yl]-2-methyl-1,3-thiazole-4-carboxamide;

N-[6-(6-fluoro-1H-indol-4-yl)-1H-indazol-4-yl]-2-methyl-1,3-thiazole-4-carboxamide;

2-(1-piperidinylmethyl)-N-[6-(1H-pyrazolo[3,4-b]pyridin-5-yl)-1H-indazol-4-yl]-1,3-thiazole-4-carboxamide;

N-[6-(6-fluoro-1H-indol-4-yl)-1H-indazol-4-yl]-2-(1-piperidinylmethyl)-1,3-thiazole-4-carboxamide;

2-methyl-N-(6-{6-[(phenylsulfonyl)amino]-1H-indol-4-yl}-1H-indazol-4-yl)-1,3-thiazole-4-carboxamide;

2-methyl-N-(6-{6-[(methylsulfonyl)amino]-1H-indol-4-yl}-1H-indazol-4-yl)-1,3-thiazole-4-carboxamide;

2-methyl-N-[6-(7-methyl-1H-indol-4-yl)-1H-indazol-4-yl]-1,3-thiazole-4-carboxamide;

2-(4-morpholinylmethyl)-N-[6-(1H-pyrazolo[3,4-b]pyridin-5-yl)-1H-indazol-4-yl]-1,3-thiazole-4-carboxamide;

2-{[(2R,6S)-2,6-dimethyl-4-morpholinyl]methyl}-N-[6-(1H-pyrazolo[3,4-b]pyridin-5-yl)-1H-indazol-4-yl]-1,3-thiazole-4-carboxamide;

2-(4-morpholinylmethyl)-N-[6-(1H-pyrrolo[2,3-b]pyridin-4-yl)-1H-indazol-4-yl]-1,3-thiazole-4-carboxamide;

N-[6-(1H-indol-4-yl)-1H-indazol-4-yl]-2-[(2-methyl-4-morpholinyl)methyl]-1,3-thiazole-4-carboxamide;

N-[6-(1H-indol-4-yl)-1H-indazol-4-yl]-2-(6-oxa-9-azaspiro[4.5]dec-9-ylmethyl) thiazole-4-carboxamide;

N-[6-(1H-indol-4-yl)-1H-indazol-4-yl]-2-(tetrahydro-1,4-oxazepin-4(5H)-ylmeth 1,3-thiazole-4-carboxamide;

2-[(1,1-dioxido-4-thiomorpholinyl)methyl]-N-[6-(1H-indol-4-yl)-1H-indazol-4-yl]-1,3-thiazole-4-carboxamide;

2-[(2,2-dimethyl-4-morpholinyl)methyl]-N-[6-(1H-indol-4-yl)-1H-indazol-4-yl]-1,3-thiazole-4-carboxamide;

2-{[(2R,6S)-2,6-dimethyl-4-morpholinyl]methyl}-N-[6-(1H-indol-4-yl)-1-methyl-1H-indazol-4-yl]-1,3-thiazole-4-carboxamide; or a salt thereof.

9. A compound of formula (I) according to claim 2 in the form of a pharmaceutically acceptable salt thereof.

10. A pharmaceutical composition comprising a compound of formula (I) as defined in claim 1, or a pharmaceutically acceptable salt thereof, and one or more pharmaceutically acceptable excipients.

11. A method of alleviating one or more symptoms or effects associated with asthma or COPD in a patient suffering from said diseases comprising administering an effective amount of a compound of formula (I) according to claim 2, or a pharmaceutically acceptable salt thereof, either neat or admixed with a pharmaceutically acceptable excipient.

* * * * *